(12) United States Patent
Kan et al.

(10) Patent No.: US 9,896,730 B2
(45) Date of Patent: Feb. 20, 2018

(54) USE OF EMT GENE SIGNATURES IN CANCER DRUG DISCOVERY, DIAGNOSTICS, AND TREATMENT

(75) Inventors: Julie Kan, San Diego, CA (US); Stuart Thomson, Port Washington, NY (US); Gretchen M. Argast, Farmingdale, NY (US); Matthew E. O'Connor, Massapequa Park, NY (US); Murray Robinson, Boston, MA (US); Bin Feng, North Reading, MA (US); Joerg Heyer, Newton, MA (US); Maria I. Chiu, Newton Centre, MA (US); Richard Nicoletti, South Borough, MA (US)

(73) Assignees: OSI Pharmaceuticals, LLC, Farmingdale, NY (US); AVEO PHARMACEUTICALS, INC., Cambridge, MA (US)

( * ) Notice: Subject to any disclaimer, the term of this patent is extended or adjusted under 35 U.S.C. 154(b) by 0 days.

(21) Appl. No.: 13/455,972

(22) Filed: Apr. 25, 2012

(65) Prior Publication Data

US 2012/0302572 A1 Nov. 29, 2012

Related U.S. Application Data

(60) Provisional application No. 61/517,789, filed on Apr. 25, 2011, provisional application No. 61/632,894, filed on Jan. 31, 2012.

(51) Int. Cl.
*C12Q 1/68* (2006.01)

(52) U.S. Cl.
CPC ..... *C12Q 1/6886* (2013.01); *C12Q 2600/106* (2013.01); *C12Q 2600/112* (2013.01); *C12Q 2600/158* (2013.01)

(58) Field of Classification Search
CPC .................................................. C12Q 1/6886
See application file for complete search history.

(56) References Cited

U.S. PATENT DOCUMENTS

| | | | |
|---|---|---|---|
| 5,367,064 A | 11/1994 | Rubin | |
| 6,171,779 B1 | 1/2001 | Chada | |
| 6,251,628 B1 | 6/2001 | Nakao | |
| 6,271,363 B1 | 8/2001 | Ingham | |
| 6,413,730 B1 | 7/2002 | Holland | |
| 6,448,086 B1 | 9/2002 | Khosravi | |
| 6,617,121 B1 | 9/2003 | Garcia | |
| 7,081,340 B2 | 7/2006 | Baker | |
| 7,241,444 B2 | 7/2007 | Goetsch | |
| 7,342,108 B2 | 3/2008 | Li | |
| 7,368,551 B2 | 5/2008 | Li | |
| 7,526,387 B2 | 4/2009 | Baker | |
| 7,569,349 B2 | 8/2009 | Gocke | |
| 2002/0169562 A1 | 11/2002 | Stephanopoulos et al. | |
| 2003/0053995 A1 | 3/2003 | Hung | |
| 2003/0165954 A1 | 9/2003 | Katagiri | |
| 2004/0018191 A1 | 1/2004 | Wang | |
| 2004/0018528 A1 | 1/2004 | Morimoto | |
| 2004/0048254 A1 | 3/2004 | Olek | |
| 2004/0063120 A1 | 4/2004 | Beer | |
| 2004/0106605 A1 | 6/2004 | Carboni | |
| 2004/0132097 A1 | 7/2004 | Bacus | |
| 2004/0209930 A1 | 10/2004 | Carboni | |
| 2004/0214203 A1 | 10/2004 | Fruehauf | |
| 2005/0019785 A1 | 1/2005 | Baker | |
| 2005/0136063 A1 | 6/2005 | Wang | |
| 2005/0164218 A1 | 7/2005 | Agus | |
| 2005/0170386 A1 | 8/2005 | Takahashi | |
| 2005/0249730 A1 | 11/2005 | Goetsch | |
| 2005/0260664 A1 | 11/2005 | Shaughnessy | |
| 2005/0266496 A1 | 12/2005 | Gilon | |
| 2006/0003365 A1 | 1/2006 | Shaughnessy | |
| 2006/0018910 A1 | 1/2006 | Gualberto | |
| 2006/0019268 A1 | 1/2006 | Cheng | |
| 2006/0046249 A1 | 3/2006 | Huang | |
| 2006/0078941 A1 | 4/2006 | Santin | |
| 2006/0121539 A1 | 6/2006 | Debinski | |
| 2006/0140960 A1 | 6/2006 | Wang | |
| 2006/0211060 A1 | 9/2006 | Haley | |
| 2006/0234259 A1 | 10/2006 | Rubin | |

(Continued)

FOREIGN PATENT DOCUMENTS

| WO | 2003078662 A1 | 9/2003 |
|---|---|---|
| WO | 2004046386 A1 | 6/2004 |

(Continued)

OTHER PUBLICATIONS

Yauch et al. (2005) Epithelial versusMesenchymal Phenotype Determines In vitro Sensitivity and Predicts Clinical Activity of Erlotinib in Lung Cancer Patients. Clinical Cancer Research, 11(24):8686-8698.*
Whitehead et al. (2005) Variation in tissue-specific gene expression among natural populations. Genome Biology, 6:R13.*
Michiels et al. (2005) Prediction of cancer outcome with microarrays: a multiple random validation strategy. Lancet, 365:488-492.*
Chabert et al. (1993) Cell Culture of Tumors Alters Endogenous Poly(ADPR)Polymerase Expression and Activity. International Journal of Cancer, 53:837-842.*
Bissell et al. (1999) Tissue Structure, Nuclear Organization, and Gene Expression in Normal and Malignant Breast. Cancer Research (Suppl.) 59:1757s-1764s.*
Balko et al. (2006) Gene expression patterns that predict sensitivity to epidermal growth factor receptor tyrosine kinase inhibitors in lung cancer cell lines and human lung tumors. BMC Genomics, 7:289, pp. 1-14.*

(Continued)

*Primary Examiner* — Neil P Hammell
(74) *Attorney, Agent, or Firm* — McCarter & English, LLP; Maria Laccotripe Zacharakis; Sai Venkatesh Seetharaman

(57) ABSTRACT

The present invention provides diagnostic methods for assessing the EMT status of tumor cells, and for predicting the effectiveness of treatment of a cancer patient with an EGFR or IGF-1R kinase inhibitor, utilizing an EMT gene signature index score. The present invention further provides methods for treating patients with cancer that incorporate these methods.

16 Claims, 84 Drawing Sheets

(56) References Cited

U.S. PATENT DOCUMENTS

Figure 1:
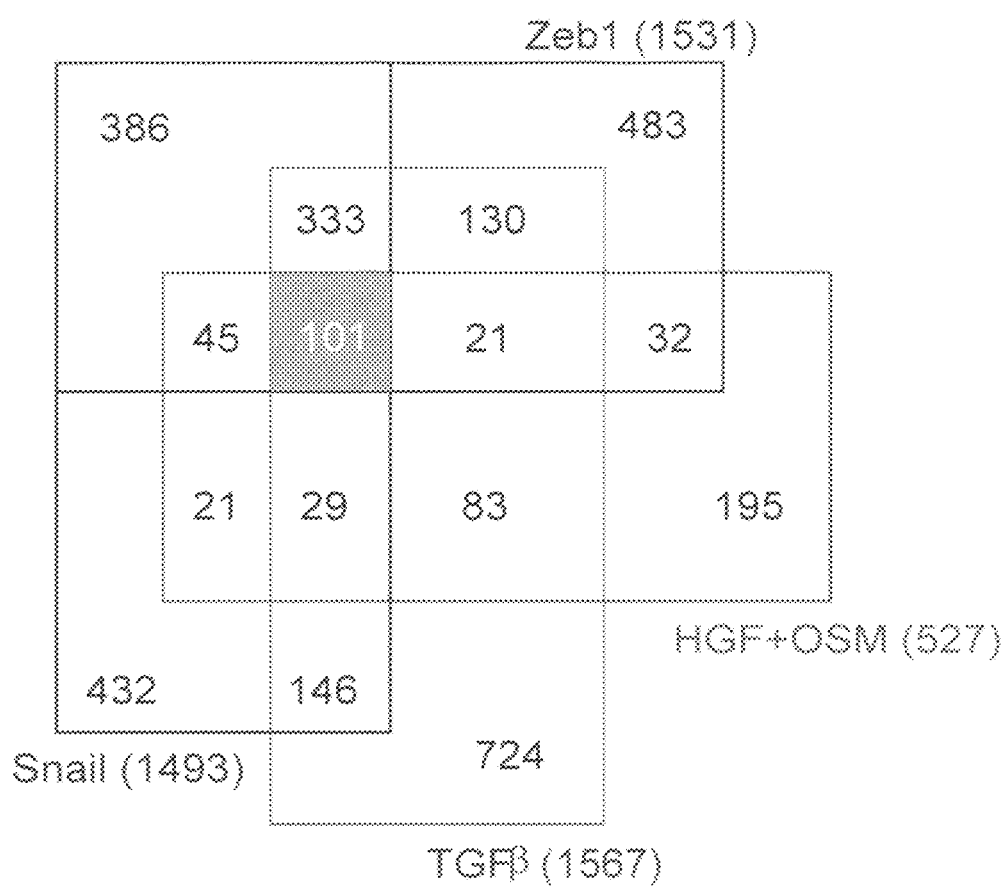

| | | |
|---|---|---|
| 2006/0263775 A1 | 11/2006 | Kaplan |
| 2006/0263806 A1 | 11/2006 | Ma |
| 2007/0031871 A1 | 2/2007 | Jove |
| 2007/0059785 A1 | 3/2007 | Bacus |
| 2007/0065858 A1 | 3/2007 | Haley |
| 2007/0077577 A1 | 4/2007 | Almouzni |
| 2007/0092881 A1 | 4/2007 | Ohnishi |
| 2007/0128636 A1 | 6/2007 | Baker |
| 2007/0141621 A1 | 6/2007 | Agus |
| 2007/0154915 A1 | 7/2007 | Inazawa |
| 2007/0172857 A1 | 7/2007 | Daito |
| 2007/0196352 A1 | 8/2007 | Zachary |
| 2007/0212738 A1* | 9/2007 | Haley ............... G01N 33/5011 435/7.23 |
| 2007/0218512 A1 | 9/2007 | Strongin |
| 2007/0231822 A1 | 10/2007 | Mitas |
| 2007/0237770 A1 | 10/2007 | Lai |
| 2007/0243194 A1 | 10/2007 | Hariharan |
| 2007/0265185 A1 | 11/2007 | Bouamrani |
| 2007/0270505 A1 | 11/2007 | Bunn |
| 2008/0015160 A1 | 1/2008 | Inazawa |
| 2008/0019961 A1 | 1/2008 | Wicha |
| 2008/0026481 A1 | 1/2008 | Mitas |
| 2008/0085519 A1 | 4/2008 | Gabrin |
| 2008/0090233 A1 | 4/2008 | Garcia |
| 2008/0112888 A1 | 5/2008 | Wang |
| 2008/0131885 A1 | 6/2008 | Pratilas |
| 2008/0167532 A1 | 7/2008 | Smallridge |
| 2008/0176229 A1 | 7/2008 | Agus |
| 2008/0187930 A1 | 8/2008 | Shaughnessy |
| 2008/0234138 A1 | 9/2008 | Shaughnessy |
| 2008/0312093 A1 | 12/2008 | Inazawa |
| 2008/0312260 A1 | 12/2008 | Haley |
| 2009/0023149 A1 | 1/2009 | Knudsen |
| 2009/0029354 A1 | 1/2009 | Chang |
| 2009/0061422 A1 | 3/2009 | Linke |
| 2009/0061454 A1 | 3/2009 | Brody |
| 2009/0092596 A1 | 4/2009 | Haley |
| 2009/0092983 A1 | 4/2009 | Birnbaum |
| 2009/0093488 A1 | 4/2009 | Buck |
| 2009/0118175 A1 | 5/2009 | Macina |
| 2009/0123374 A1 | 5/2009 | Buggy |
| 2009/0136945 A1 | 5/2009 | Loberg |
| 2009/0155786 A1 | 6/2009 | Marsit |
| 2009/0286850 A1 | 11/2009 | Shaaban |
| 2011/0143960 A1 | 6/2011 | LaBarbera |
| 2012/0101084 A1 | 4/2012 | Haley |
| 2014/0030255 A1* | 1/2014 | Loboda et al. ............ 424/133.1 |

FOREIGN PATENT DOCUMENTS

| | | | |
|---|---|---|---|
| WO | | 2004063709 A2 | 7/2004 |
| WO | | 2004065602 A1 | 8/2004 |
| WO | | 2004071572 A2 | 8/2004 |
| WO | | 2004111273 A2 | 12/2004 |
| WO | | 2005017493 A2 | 2/2005 |
| WO | | 2005037836 A2 | 4/2005 |
| WO | | 2005052005 A1 | 6/2005 |
| WO | | 2005061541 A1 | 7/2005 |
| WO | | 2005067667 A2 | 7/2005 |
| WO | | 2005070020 A2 | 8/2005 |
| WO | | 2005094332 A2 | 10/2005 |
| WO | | 2005097800 A1 | 10/2005 |
| WO | | 2005099363 A2 | 10/2005 |
| WO | | 2005107803 A2 | 11/2005 |
| WO | | 2005117553 A2 | 12/2005 |
| WO | | 2006099396 A2 | 9/2006 |
| WO | | 2006101925 A2 | 9/2006 |
| WO | | 2007001868 A1 | 1/2007 |
| WO | | 2007028146 A2 | 3/2007 |
| WO | | 2007035744 A1 | 3/2007 |
| WO | | 2007067500 A3 | 6/2007 |
| WO | | 2007075554 A2 | 7/2007 |
| WO | | 2007141626 A1 | 12/2007 |
| WO | | 2008070460 A2 | 6/2008 |
| WO | | 2008104344 A1 | 9/2008 |
| WO | | 2008108986 A2 | 9/2008 |
| WO | | 2008115470 A2 | 9/2008 |
| WO | | 2008144345 A2 | 11/2008 |
| WO | | 2009015233 A3 | 1/2009 |
| WO | | 2009023172 A2 | 2/2009 |
| WO | WO | 2009075799 A2 * | 6/2009 |
| WO | | 2010022268 A2 | 2/2010 |
| WO | | 2010120966 A1 | 10/2010 |
| WO | | 2012061510 A2 | 5/2012 |

OTHER PUBLICATIONS

Tan et al. (2010) A multicentre phase II gene expression profiling study of putative relationships between tumour biomarkers and clinical response with erlotinib in non-small-cell lung cancer. Annals of Oncology, 21:217-222.*
Laasko, M. et al. (2006) Clinical Cancer Research: An official Journal of the American Association for Cancer Research 12: 14 part 1, 4185-4191.
Lan, M. et al. (2004) Carcinogenesis 25(12): 2385-2395.
Larrson, O. et al. (2005) British Journal of Cancer 92, 2097-2101.
Lee, J. M. et al. (2006) Journal of Cell Biology 172:7, 973-981.
Lemoine, N.R. et al. (1992) Br. J. Cancer 66:1116-11121.
Letters to Journal (2005) J of Clin. Onco. 23, No. 4,Feb. 1, 2005; pp. 923-924.
Lippman, S.M. et al. (2005) Clin. Cancer Res. 11(17):6097-6099.
Locascio, A. et al. (2002) The Journal of Biological Chemistry 277(41): 38803-38809.
Lu, Z., et al., (2003) Cancer Cell. 4(6):499-515.
Markl, J. (1991) Journal of Cell Science 98: 261-264.
Matar, P. et al. (2004) Clin. Cancer Res. 10:6487-6501.
Matei, D. et al. (2006) Oncogene 25: 2060-2069.
Mitsiades, C.S., et al. (2006) Cancer Cell 5, 221-230.
Modern Pharmacology, 1990, Eds. Craig and Stitzel, Publishers, Little, Brown and Company, Chapter 60, pp. 776-778.
Moll, R. et al. (1982) Cell 31: 11-24.
Moody, S.E. (2005) Cancer Cell vol. 8, Sep. 2005, pp. 197-209.
Moon, H. et al (2001) Gynecologic Oncology 81:355-359.
Mulvihill, M.J. et al. (2009) Future Med. Chem. 1(6): 1153-1171.
Natalwala, A. et al. (2008) World J. Gastroenterol 14(24): 3792-3797.
Nolan, G.P. (2007) Nature Chemical Biology 3(4): 187-191.
Nunes, M. et al; (2004) Molecular Cancer Therapeutics, 3(1):21-27.
Ohira, T. et al. (2003) PNAS 100(18):10429-10434.
Osbourne, R. (2008) Nature Biotechnology 26(7):719-720.
Oshima, RG (2002) Cell Death and Differentiation 9: 486-492.
Pece, S. et al. (275) J Biol Chem 275 (52): 41227-41233.
Perez-Solar, R. et al. (2003) Lung Cancer 41 (Suppl. 2), p. S72, Abstract O247.
Peinado, H. et al, (2007) Nature Rev. Cancer, 7:415-428.
Pena, C. et al. (2005) Human Molecular Genetics 4(22): 3361-3370.
Pollack, M.N., et al. (2004) Nature Reviews/Cancer 4, 505-518.
Pollack, M. (2009) Nature Reviews Cancer 8: 915-928.
Qian, X. et al (2004) EMBO 23:1739-1748.
Ramaekers, F.C.S. et al. (1987) Acta Histochemica Suppl. 34: 45-56.
Ramaekers, F.C.S. et al. (1983) Proc. Natl. Acad. Sci. USA 80: 2618-2622, May 1983, Cell Biology.
Ransohoff, D.F. (2003) Science 299, 1679-1680, downloaded from www.Sciencemag.org on Mar. 11, 2009.
Rasmussen, A., et al. (1998) Breast Cancer Research and Treatment 47(3): 219-233.
Richardson, F. et al. (2009) International Association for the Study of Lung Cancer, 13th World Conference on Lung Cancer, Jul. 31-Aug. 4, 2009, Moscone West, San Francisco, USA. "Comparison of E-cadherin IHC Status with Clinical Outcomes from Erlotinib in the Non Small Cell Lung Cancer (NSCLC) Clinical Trial NCIC CTG BR.21" e-Poster: PD7.2.5. Congress: WCLC 2009; 29 pages.
Riedemann, J. et al. (2006) Endocrine-Related Cancer 13, s33-s43.
Rosivatz, E. et al. (2002) American Journal of Pathology 161(5): 1881-1891.
Rukstalis, J.M. et al. (2006) Endocrinology 147(6): 2997-3006.

(56) References Cited

OTHER PUBLICATIONS

Ryan, P.D., et al. (2008) The Oncologist 13, 16-24 *downloaded from www.TheOncologist.com on May 29, 2008.
Sabatini, P. et al. (2009) Clin Cancer Res 15(9): 3058-3067.
Sakurai, H. et al.; (1997) Proc. Natl. Acad. Sci. USA, 94:6279-6284.
Samani, A.A. et al. (2007) Endocrine Reviews 28(1): 20-47.
Sarrio, D. et al. (2008) Cancer Research 68:4, 989-997.
Savagner, P. (2001) Bioessays 23:912-923.
Schaafsma, HE (May 1993) J. Pathol. 170(1): 77-86.
Schlessinger, K. et al. (2004) Nature Cell Biology 6(10):913-915.
Schussler, M.N. et al. (Mar. 1992) Am. J. Pathol. 140(3): 559-568.
Shrader, M. et al. (2007) Mol Cancer Ther 6(1): 277-285.
Shen, X. et al. (2004) Amer J Path 165 (4): 1315-1329.
Jimeno, A. et al. (2009) Cancer J. 15 (2) pp. 110-113.
Jones, R.J., et al., (2003) Proc. Am. Soc. Clin. Oncol. 22:45a, abstract 180.
Kokkinos, M.L, et al., (2007) Cells Tissues Organs 185 (No. 1-3), pp. 191-203.
Lynch, T. J., et al., (2004) N. Engl. J. Med. 350 (21), pp. 2129-2139.
Manara, M.G., et al. (2005) Int. J. Oncol. 27, pp. 1605-1616.
Mani, S.A. et al (2007) Proceedings of the National Academy of Sciences of the United States of America 104, pp. 10069-10074.
Matsumura, T., et al., (2001) Clin Cancer Res 7, pp. 594-599.
Miyamoto, S., et al. (2005) Clin Cancer Res. 11(9) pp. 3494-3502.
Moyer, J.D. et al., (1997) Cancer Res. 57, p. 4838-4848.
Nakamura, M., et al. (2004) Clin Cancer Res. 10 (24) pp. 8434-8441.
Oft, M. et al., (1996) Genes & Development 10, pp. 2462-2477.
Oza, M, et al. (2003) Proc. Am. Soc. Clin. Oncol. 22: 196a, abstract 785.
Paez, J.G., et al. (2004) Science 304, pp. 1497-1500.
Perez-Soler R. et al., (2001) Proc. Am. Soc. Clin. Oncol 20:310a, abstract 1235.
Perl, A.K., et al., (1998) Nature 392, pp. 190-193.
Pitts, T.M. (2009) Mol Cancer Ther vol. 8 (12 Suppl):A39.
Pollack, V.A. et al., (1999) J. Pharmacol. Exp. Ther. 291, pp. 739-748.
Riely, G.J. and Ladanyi, M. (2008) J Mol Diagnostics 10(6) pp. 493-495.
Rodon, J., et al. (2008) Mol Cancer Ther. 7 (9) pp. 2575-2588.
Sachdev, D. and Yee, D. (2007) Mol Cancer Ther. 6 (1) pp. 1-12.
Saltz, L.B., et al. (2007) J. Clin. Oncol. 25 (30) pp. 4793-4799.
Shepherd, F. et al. (Jul. 14, 2005) N Engl J Med vol. 353 No. 2 pp. 123-132.
Siena, S. et al. (2009) JNCI 101(19) pp. 1308-1324.
Soulieres, D., et al., (2004) J. Clin. Oncol. 22 (1), pp. 77-85.
Tolcher, A.W. et al. Journal of Clinical Oncology, 2007 ASCO Annual Meeting Proceedings Part 1 vol. 25 No. 18S (June 20 Supplement), 2007: 3002.
Tripkovic, I. et al. (2007) Med. Res. Jul; 38 (5) pp. 519-525 E pub Apr. 26, 2007.
Willipinski-Stapelfeldt, B., et al., (2005) Clin Cancer Res 11 (22), pp. 8006-8014.
Winer, E., et al., (2002) Breast Cancer Res. Treat. 76:5115a, abstract 445.
Yoshiura, K., et al., (1995) Proceedings of the National Academy of Sciences of the United States of America 92, pp. 7416-7419.
International Search Report and the Written Opinion of the International Searching Authority in PCT/US2012/034989 dated Aug. 17, 2012.
International Preliminary Report on Patentability and Written Opinion of the International Searching Authority in PCT/US2012/034989.
Blick, T., et al., (2010) J Mannary Gland Biol Neoplasis vol. 15, No. 2, pp. 235-252.
Byers, L. et al., (2010) European Journal of Cancer vol. 8., No. 7 p. 21.
Choi, R.J., et al., (2007) "P78" Journal of Surgical Research, Vol 137, No. 2, p. 268.
Glinsky et al., (2004) J Clin Invest, 113: 913-923.
Loboda, A., et al. (2011) BMC Medical Genomics vol. 4, No. 1, p. 9.
Polyak, K., et al., (2009) Nature Reviews Cancer vol. 9 No. 4, pp. 265-273.
Ritchie et al., (2001) Am J. Hum Genet 69 pp. 138-147.
Sabbah, M. et al. (2008) Drug Resistance Updates vol. 11, No. 4-5, pp. 123-151.
Taube, J.H., et al. (2010) PNAS vol. 107, No. 35, pp. 15449-15454.
Vandesompele J. et al. (2003) Oncogene 22(3) pp. 456-460.
Voulgari, A. et al., (2009) Biochimica et Biophysica Act 1796 (BBA—Reviews on Cancer), pp. 75-90.
Joyce, T., et al., (2009) Clin Exp Metastasis vol. 26, No. 6, pp. 569-587.
Moreno-Bueno, G., et al. (2006) Cancer Research 66(19) pp. 9543-9556.
Oesterreich, S. et al. (1996) Clin Cancer Res. 2: pp. 1199-1206.
Aigner, K. et al. (2007) Oncogene pp. 1-10, Nature Publishing Group 2.
Alberts, B. et al. (1994) Molecular Biology of the Cell, 3rd edition, p. 465.
Amann, J. et al. (2005) Cancer Res. 65(1):226-235.
Andl, C. D., et al (2005) Cancer Biology and Therapy 4(1): 28-31.
Andl, C. D., et al (2003) J Biol Chem, 278 (No. 3):1824-1830.
Answers.com definition for "tumor", p. 1 (Apr. 17, 2009).
Arumugam, T. et al. (2009) Cancer Res 2009; 69(14): 5820-5828.
ATCC search Calu 6 (pp. 1-3; Mar. 10, 2010).
ATCC search H1703 (pp. 1-3; Mar. 10, 2010).
ATCC search H292 (pp. 1-3; Mar. 10, 2010).
ATCC search H358 (pp. 1-3; Mar. 10, 2010).
Auersberg, N. et al (1999) Proc Natl Acad Sci 96:6249-6254.
Babiychuk, E B et al. (2002) Bichimica ET Biophysica ACTA (BBA)—Proteins & Proteomics, Elsevier 1600, No. 1-2: 154-161.
Bailey, L.R. et al. (2003) Proc. Am. Assoc. Res. 44:1362. abst. LB-170.
Bankfalvi, Agnes, et al (2002) J Oral Pathol Med 31: 450-457.
Barrallo-Gimeno, A. et al. (2005) Development 132:3151-3161.
Baserga, R. (1999) Experimental Cell Research 253:1-6.
Bates, R.C. et al. (2003) Current Biology 13.1721-1727.
Batlle, E. et al. (2000) Nature Cell Biology 2:84-89.
Bergh, J. (1984) "Expression of intermediate filaments in established human lung cancer cell lines. An indicator of differentiation and derivation" Lab Invest 51(3): 307-316.
Berx, G. et al. (2009) Cold Spring Harb Perspect Biol 2009; 1: a003129 * published online Sep. 23, 2009.
Blanco, M.J. (2002) Oncogene 21: 3241-3246.
Bianco, R. et al. (2005) Endocrine-related cancer 12:S159-S171.
Biowww.net; "BRK gene" definition; pp. 1-3; Mar. 9, 2010.
Bolos, V. et al. (2003) Journal of Cell 116:499-511.
Brehmer, D. et al; (2005) Cancer Res. 65(2):379-382.
Broers, J.L.V. et al. (1988) Journal of Cell Science 83: 37-60.
Broers, J.L.V. et al. (1988) Journal of Cell Science 91: 91-108.
Buck, E. et al. (2007) Molecular Cancer Therapeutics 6(2): 532-541.
Buck, E. et al. (2006) Molecular Cancer Therapeutics 5(8): 2051-2059.
Buck, E. et al. (2008) Cancer Res 68(20): 8322-8332.
Burtrum, et al. (2003) American Association for Cancer Research 53(24): 8912-8921.
Camirand, A., et al. (2005) Breast Cancer Research 7:R570-R579.
Camp, E.R. et al; (2005) Clinical Cancer Research (1):397-405.
Cano, A. et al; (2000) Nature Cell Biology 2: 76-83.
Castillo, L. et al. (2004) Annals of Oncology 15:1007-1012.
Chaffer, C. L. et al. (2006) Cancer Research 66(23): 11271-11278.
Chandler, L.A. (1999) Int. J. Cancer 82: 451-458.
Christofori, G. (2006) Nature 441(7092): 444-450.
Chung, L.W.K. et al. (2005) The Journal of Urology 173:10-20.
Ciruna, B. et al. (2001) Developmental Cell 1: 37-49.
Clara, et al. (2007) European Journal of Cancer Supplement 5:4, 366-367.
Clark, D M et al. (1991) Histochemistry 96:5, 405-412.
Coltrera, M.D. (1995) Cancer Research 55: 2703-2708.
D'Souza, B et al (1994) Proc Natl Acad Sci 91:7202-7206.
Dai, Q. et al: (2005) Clinical Cancer Research 11:1572-1578.
Dancey, J. et al. (2003) Nature Rev. Drug Discovery 2:296-313.

(56) References Cited

OTHER PUBLICATIONS

Dandachi, N. et al. (2001) J. Pathology; 193:181-189.
De Bono, J.S. and Rowinsky, E.K. (2002) Trends in Mol. Medicine 8:S19-S26.
De Craene, B. et al. (2005) Cancer Res. 65(14): 6237-6244.
Derwent/ Delphion record for WO 2004065602.
Dumstrei, Karin et al (2002) Development 129: 3983-3994.
Ei-Deiry, W.S. et al. (2005) Cancer Res. 65(11):4475-4484.
Fedor-Chaiken, M et al (2003) Cell Communication and Adhesion 10:105-118.
Feng, Y., et al. (2008) Current Opinion in Drug Discovery & Development 11(2):178-185.
Frederick, B.A. et al. (2007) Mol Cancer Ther 6(6): 1683-1691.
Garber, K. (2009) JNCI 101(1): 6-8 *downloaded from http://jnci.oxfordjournals.org at OSI Pharmaceuticals, Inc. on Apr. 28, 2010.
Garcia-Echeverri, C., et al. (2004) Cancer Cell 5:231-239.
Giaccone, G. (2005) Annals of Oncology 16: 538-548.
Gotlieb, W.H., et al. (2000) Gynecologic Oncology 100, 389-396.
Grande, M. el al. (2202) J. Cell Science 115:4227-4236.
Greenbaum, D. et al. (2003) Genome Biology 4(9): 117.1-117.8.
Grille, S.J. et al. (2003) Cancer Res. 63: 2172-2178.
Gualberto, A. et al. (2009) Current Drug Targets 10: 923-936.
Gualberto, A. et al. (2009) Oncogene 28: 3009-3021.
Gura, T. (1997) Science 278: 1041-1042.
Hajra, K.M. (2002) Cancer Research 62: 1613-1618.
Haluska, P., et al. (2006) Cancer Research 66(1): 362-371.
Hazan, R. B. (1998) J Biol Chem 273 (15), 9078-9084.
Hirsch, F.R. (2005) Curr. Opin. Oncol. 17:118-122.
Hong, R. et al. (2008) The Korean Journal of Pathology 42: 351-357.
Hoorens, A. et al. (May 1998) J. Pathol. 185(1): 53-60.
Hopfner, M., et al. (2006) Endocrine-Related Cancer 13, 135-149.
Hotz,B. et al. (2007) Clin cancer Res 13(16):4769-4776.
Huang, F. et al. (2009) Cancer Res 69(1):161-170 with 9 page supplement.
Huber, M. et al. (2005) Current Opinion in Cell Biology 17:548-558.
Ibrahim, Y.H., et al. (2005) Clinical cancer Research 11, 944s-950s.
Imamichi, Y.(2007) Oncogene 26: 2381-2385.
International Search Report of the International Search Authority in PCT/US2008/011299 dated May 14, 2009.
International Preliminary Report on Patentability in PCT/US2008/011299 dated Apr. 7, 2010.
Jain, A. et al. (2005) PNAS 102(33): 11858-11863.
Janda, E. et al; (2002) J. Cell Biology 156(2):299-313.
Janne, P.A. et al. (2009) Nature Reviews: Drug Discovery Sep. 2009, vol. 8:709-723.
Jawhari, Aida U. et al (1999) J Pathol 187: 155-157.
Jechlinger, M. et al. (2006) The Journal of Clinical Investigation, http: www.jci.org, vol. 16(6): 1561-1570.
Jechlinger, M. et al. (2003) Oncogene 22: 7155-7169.
Ji, Q. et al.(2007) Molecular Cancer Therapeutics 6(8):2158-2167.
Ji, Q. et al. (2007) Proceeding of the Annual Meeting of the American Association for Cancer Research vol. 48, Apr. 14, 2007, Abstract #2373.
Ji, Q., et al. (2007) Poster—Proceeding of the Annual Meeting of the American Association for Cancer Research vol. 48, Apr. 14, 2007—Abstract #2373.
Jiao, W. et al. (2002) British of Journal Cancer 86: 98-101.
Kamalati, T. et al. (2000) Oncogene 19:5471-5476.
Kamalati, T. et al. (1996) J. Biol. Chemistry 271(48):30956-30963.
Kang, Y. et al. (2004) Cell 118(3):277-279.
Kassouf, W. et al. (2005) Cancer Res. 65(2):10524-10535.
Kiermer,A.K. et al. (2001) Oncogene 20:6679-6688.
Kim, K.S. et al. (2005) Clinical Cancer Research, 11:2244-2251.
Kobayashi, S. et al; (2005) New England Journal of Medicine 352:786-792.
Kokubo, Y. et al. (2005) British J. Cancer 92:1711-1719.
Kris, M. et al. (2003) JAMA 290 (16):2149-2158.
Adams, T.E., et al. (2000) Cell Mol Life Sci 57 pp. 1050-1093.
Spaderna, S. et al. (2008) Cancer Res 68(2): 537-544.
"Sternberg, D., TAT Meeting, 8th International Symposium on Targeted Anticancer Therapies, Mar. 4-6, 2010. Bethesda, MD, USA, ""The Development and Application of EMT Biomarkers in the Therapy of Solid Tumors""; 37 slides."
Struz, F. et al. (2002) Kidney Interantional 61:1714-1728.
Suggitt, M. et al. (2005) Clinical Cancer Res 11: 971-981.
Sun, T.T. (1984) Cancer Cell 1, The Transformed Phonotype vol. 1; 169-176, Levine, A. et al. eds.; Cold Spring Harbor Laboratory.
Suto, K. et al. (1999) J. Can.Res.Clin. Oncol. 125:83-88.
Takenaka, K. et al. (2005) Cancer Epidemiology Biomakers & Prevention 14(8) :1972-1975.
Takkunen, M. (2006) Journal of Histochemistry & Cytochemistry 54(11): 1263-1275.
Tejeda, M.L. et al. (2006) Clinical Cancer Research 12(9): 2676-2688, May 1, 2006.
Thiery, J.P. (2002) Nat. Rev. Cancer 2:442-454.
Thomas, P.A. et al. (1999) Clinical Cancer Research 5: 2698-2703.
Thomson, S. et al. (2005) Cancer Res. 65(20):9455-9462.
Tockman, M.S. et al. (1992) Cancer Res 52:2711s-2718s.
Tsutsumi, S. et al. (2004) Clin Cancer Res 10: 7775-7784.
Tuma, R.S. et al. (2007) AACR-NCI-EORTC Molecular Targets Conference, Dec. 25, 2007; pp. 54-55.
Tuma, R.S. et al. (2005) J. Natl. Cancer Institute, 97(14):1028-1029.
Turley, E.A. et al. (2008) Nature Clinical Practice 5(5): 280-290.
Umemoto, M. et al. (2001) Brit. J. Can. 85:1032-1036.
Valdes, F. et al. (2002) Molecular Cancer Research, 1:68-78.
Valles, A. M. et al. (1990) Proc. Natl. Acad. Sci. USA 87:1124-1128, Feb. 1990, Cell Biology.
Van Roy, F. et al. (2008) Cell. Mol. Life Sci. 65: 3756-3788.
Warshamana-Greene, G. S., et al. (2003) Molecular Cancer Therapeutics, pp. 527-535.
Wellner, U. et al. (2010) Cancers 2: 1617-1628.
Wilding, J. et al. (1996) Cancer Res 56: 5285-5292.
Winter, J.M. et al. Clin Cancer Res 14(2): 412-418.
Witta S.E. et al. (2004) Proc. Amer. Assoc. Cancer Res. vol. 45 Abst. #3671, p. 1.
Witta S.E. et al. (2005) J. Clin. Oncol. vol. 23, No. 165 (June 1 Suppl.) Abst. #7083 (ASCO Proceedings).
Witta, S.E. et al. (2006) Cancer Res. 66(2):944-950.
Written Opinion of the International Search Authority in PCT/US2008/011299 dated May 14, 2009.
Xie, L. et al. (2004) Neoplasia 6(5): 603-610.
Yang, L. et al. (2006) Cell 127:139-155.
Yang, J. et al. (2008) Developmental Cell 14: 818-829.
Yano, S. et al. (2003) AntiCancer Res. 23(5A):3639-3650.
Yausch, R. L. et al. (2005) Clin. Cancer Res. 11:8686-8698.
Yin, T. et al. (2007) Journal of Surgical Research 141: 196-203.
Younes, M. (2005) J. Clinical Oncology 23(4): 923-924.
Zavadil, J. et al. (2005) Oncogene 24:5764-5774.
De Craene, B., et al. (2005) Cellular Signalling, 17 (5) pp. 535-547.
Baumgart, E., et al., (2007) Clin Cancer Res 13 (6), pp. 1685-1694.
Brabletz, T. et al. (2005) Nat Rev Cancer 5, pp. 744-749.
Brugger, W. et al. (2009) J Clin Oncol ASCO Annual Meeting Proceedings (Post-Meeting Edition) 27: 15s, (suppl; abstr 8020).
Camirand, A., et al. (2004) Brit J Cancer 90:1825-1829.
Chakravarti, A., et al. (2002) Cancer Res 62: 200-207.
Choi, Y.L. et al., (2010) Cancer Research 70(6) pp. 2296-2306.
Chung, C.H. et al. (2006) Cancer Research 66 (16) pp. 8210-8218.
Engelman, J.A., et al., (2007) Science 316, pp. 1039-1043.
Grothey, A., et al. (1999) J Cancer Res Clin Oncol. 125 pp. 166-173.
Gupta, G.P. and Massague, J. (2006) Cell, 127, pp. 679-695.
Hofmann, F. and Garcia-Echeverria, C. (2005) Drug Discov Today 10 (15) pp. 1041-1047.
Office Action dated Aug. 24, 2016 in corresponding Japanese Application No. 2014-508515 (with English translation).
Office Action dated Jul. 8, 2016 in corresponding European Application No. 12725171.8.

* cited by examiner

Figure 8A

E-Cadherin Vimentin DNA

| | Untreated | HGF | OSM | TGFβ | HGF+OSM | OSM+TGFβ |
|---|---|---|---|---|---|---|
| Morphology change | | + | + | ++ | +++ | ++++ |
| Marker change | | + | + | ++ | +++ | ++++ |
| Phenotype change | | + | + | ++ | +++ | ++++ |
| Reversibility | | + | + | +/- | + | +/- |
| Erlotinib EC50 (µM) | 1.06 | >20 | 2.06 | >10 | >20 | >20 |
| EMT index | 2.13 | 2.44 | 2.24 | 4.16 | 3.25 | 5.11 |

Figure 8B

E-Cadherin Vimentin DNA

|  | Vector | Snail | Zeb1 |
|---|---|---|---|
| -Dox | | | |
| +Dox | | | |

| | | | |
|---|---|---|---|
| Morphology change | | ++ | ++ |
| Marker change | | +++ | +++ |
| Phenotype change | | ++ | ++ |
| Reversibility | | + | + |
| Erlotinib EC50 (μM) (-/+Dox) | 1.63/1.53 | 0.86/>10 | 1.12/1.26 |
| EMT index (-/+Dox) | ND | 2.69/4.72 | 2.0/3.65 |

Figure 9
GeneLogic Lung U133 Plus 2.0
Version 1
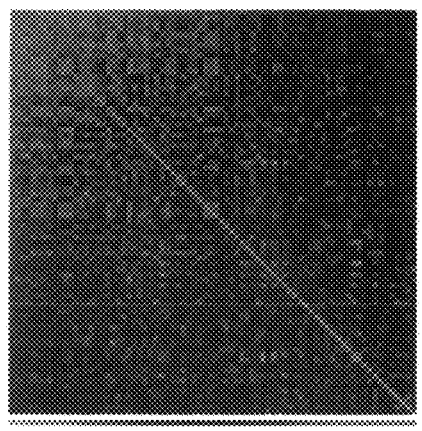
-1　　Correlation　　+1
Version 2
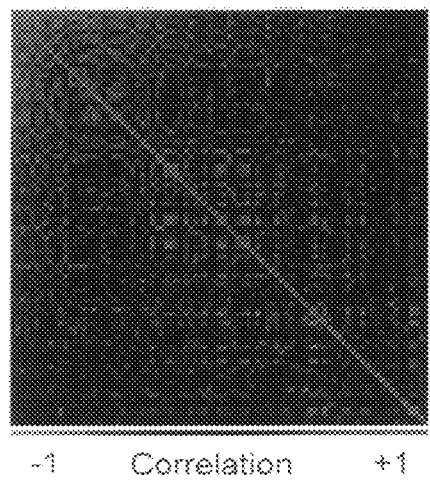
-1　　Correlation　　+1
Version 3
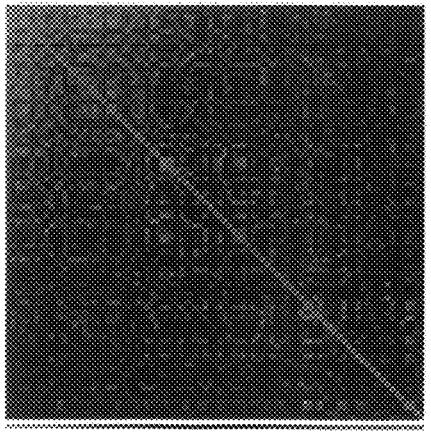
-1　　Correlation　　+1
Version 4
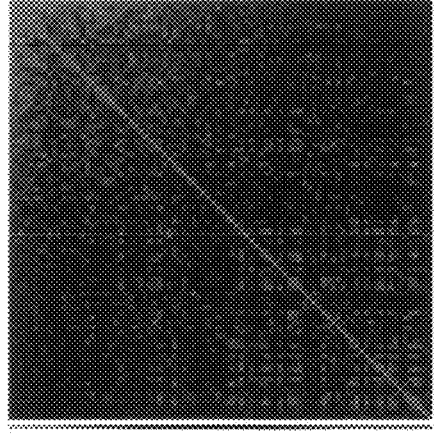
-1　　Correlation　　+1

Figure 10
GeneLogic Pancreas U133 Plus 2.0
Version 1
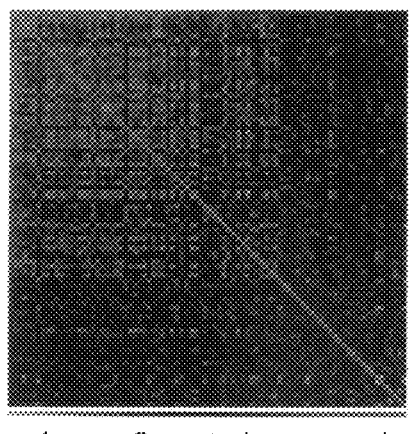
-1    Correlation    +1
Version 2
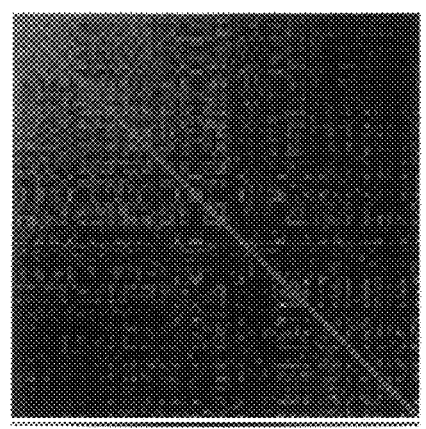
-1    Correlation    +1
Version 3
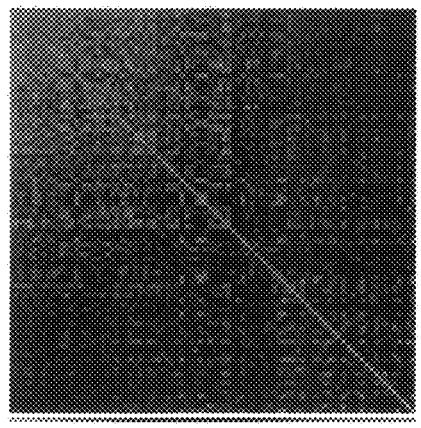
-1    Correlation    +1
Version 4
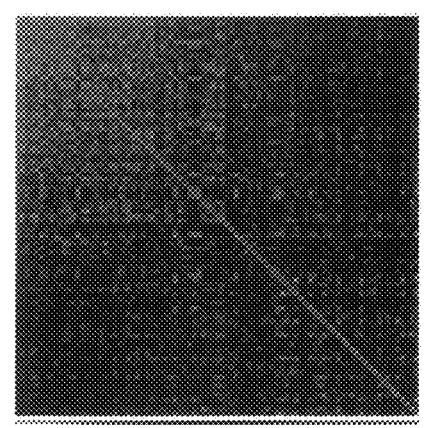
-1    Correlation    +1

88 gene index

GeneLogic Lung AB
Anchor: CLDN3

88 Gene — ITGA5

GeneLogic Lung AB
Anchor: CLDN3

Figure 11A:
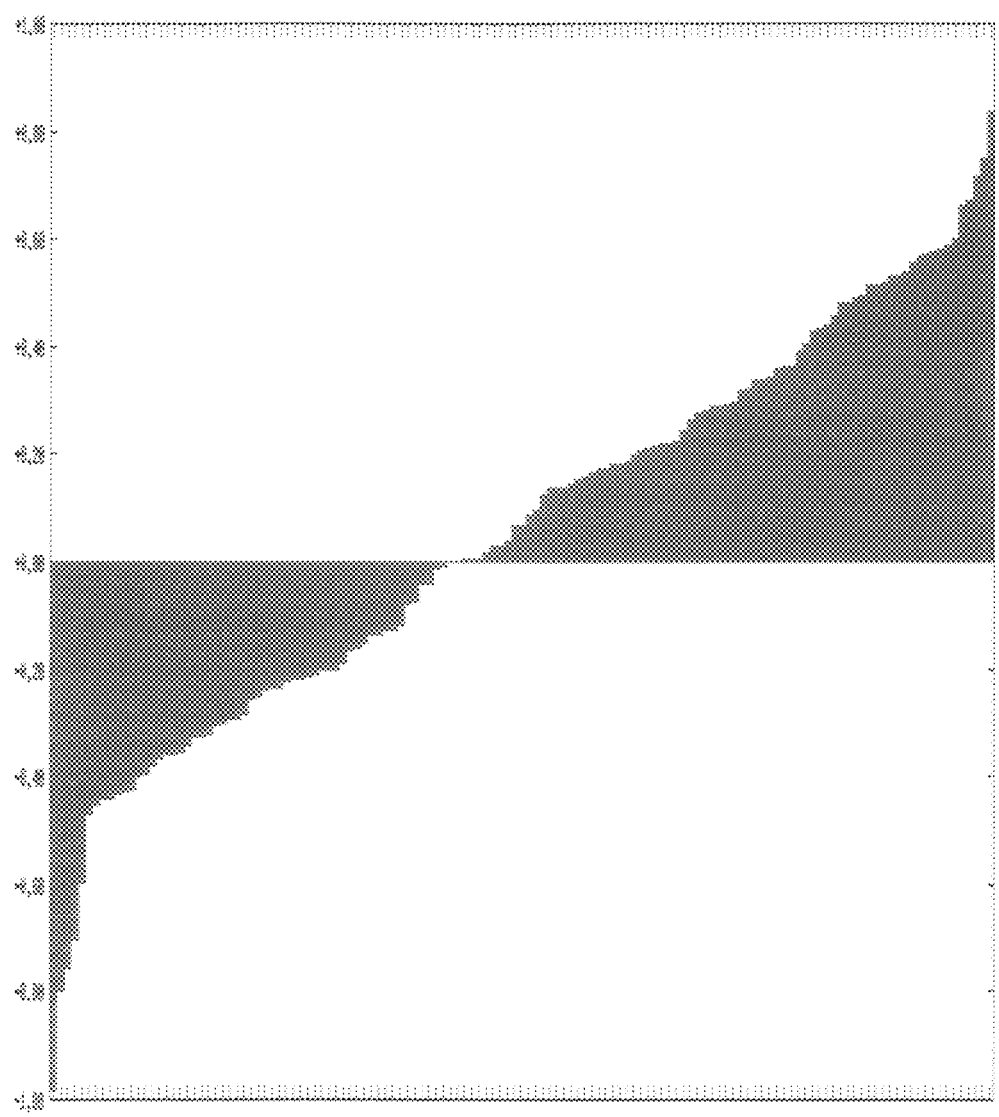
Figure 11B:
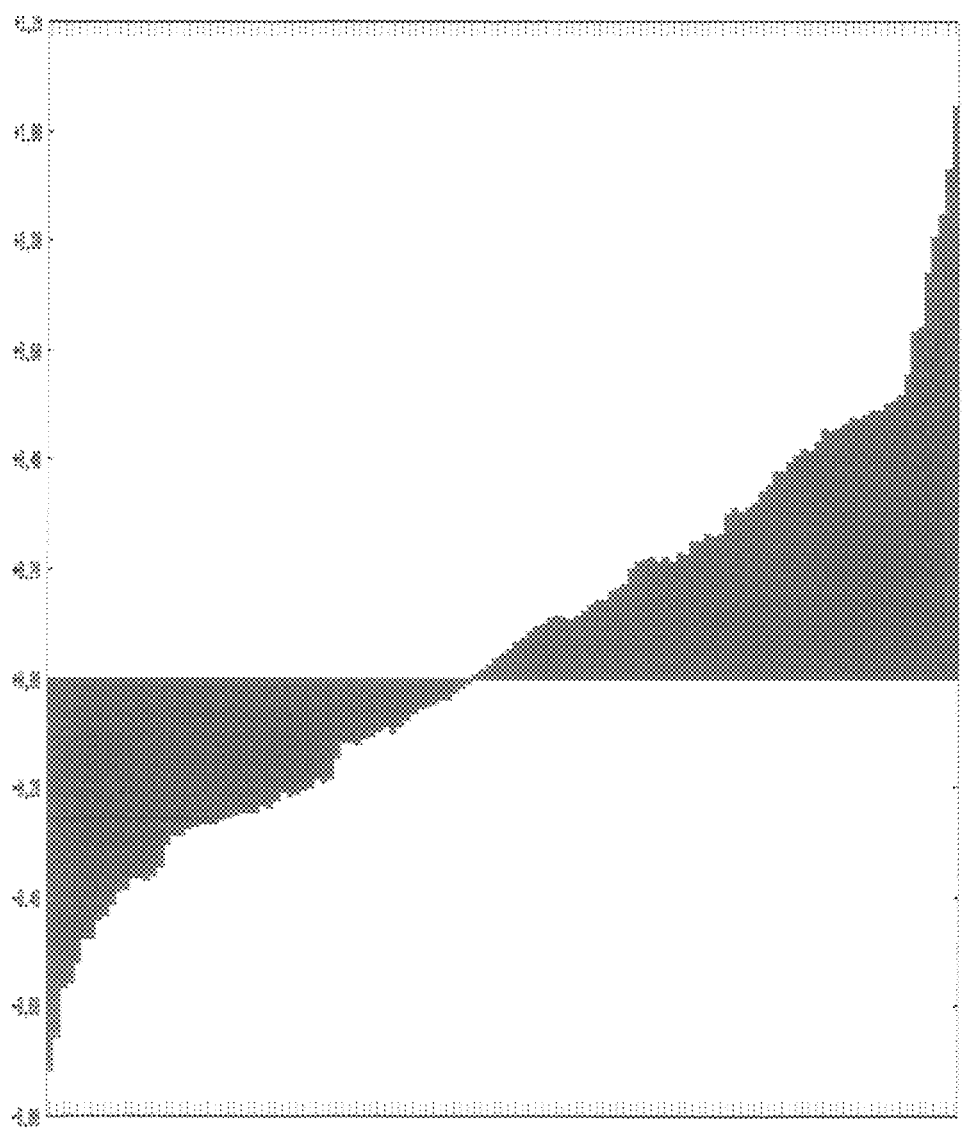
Figure 11D:
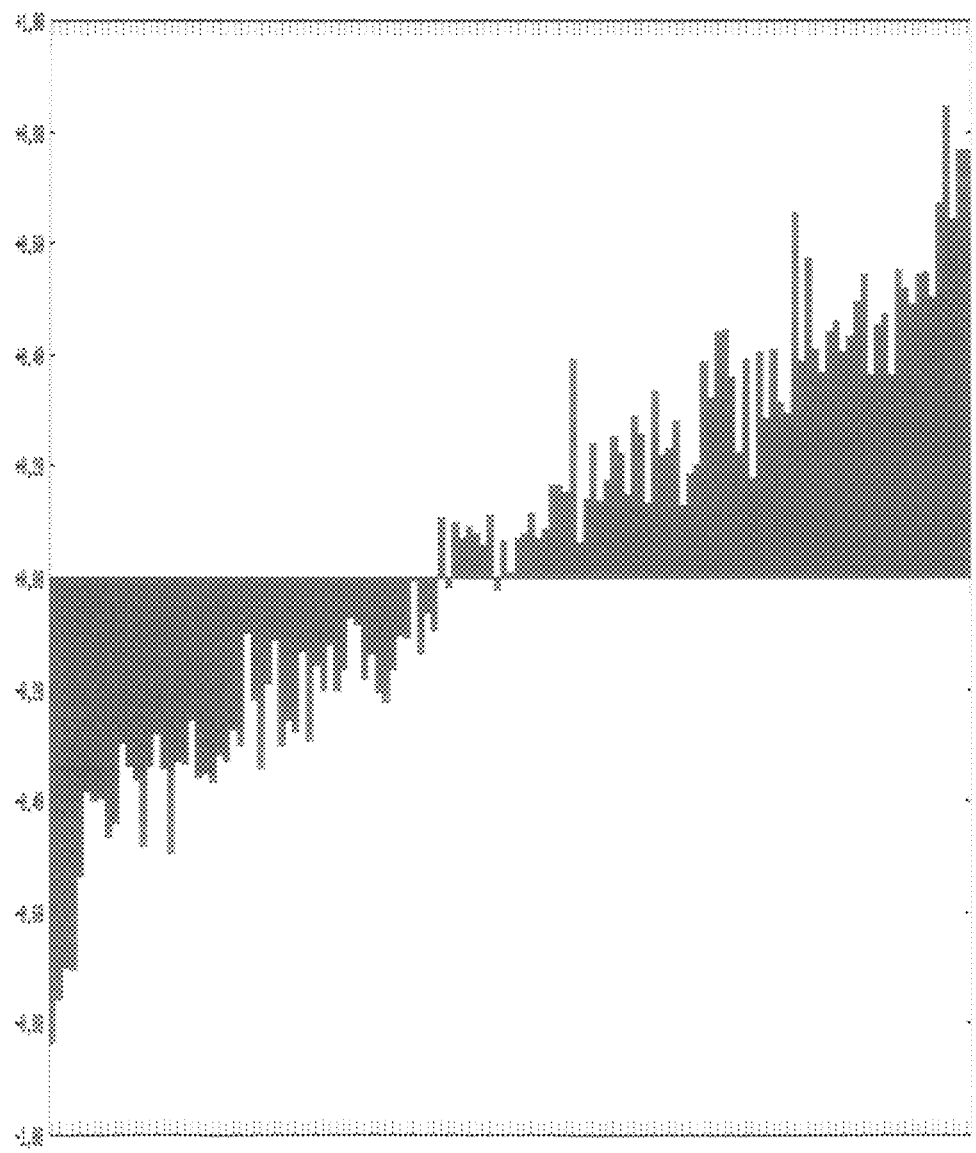
Figure 11E:
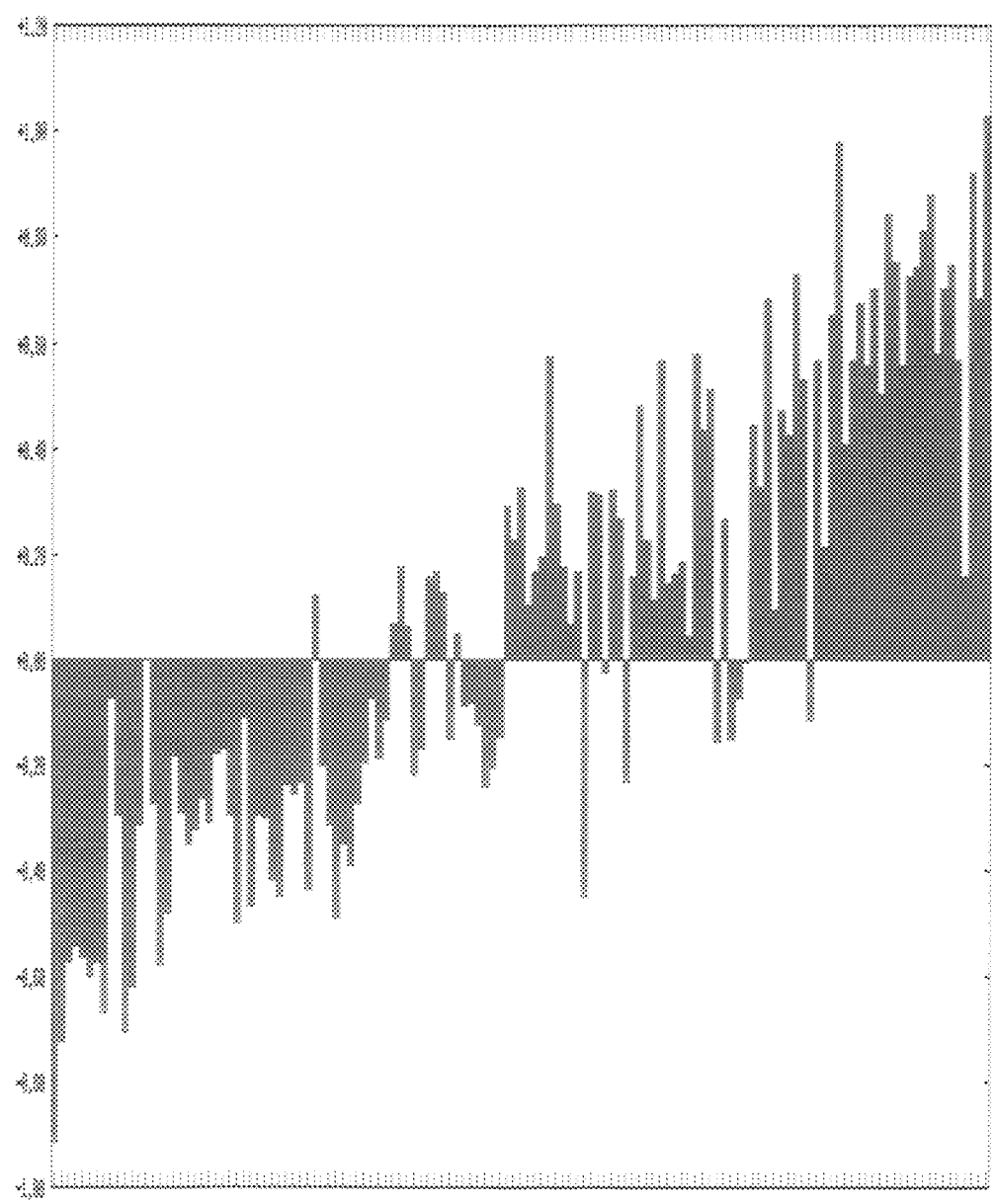

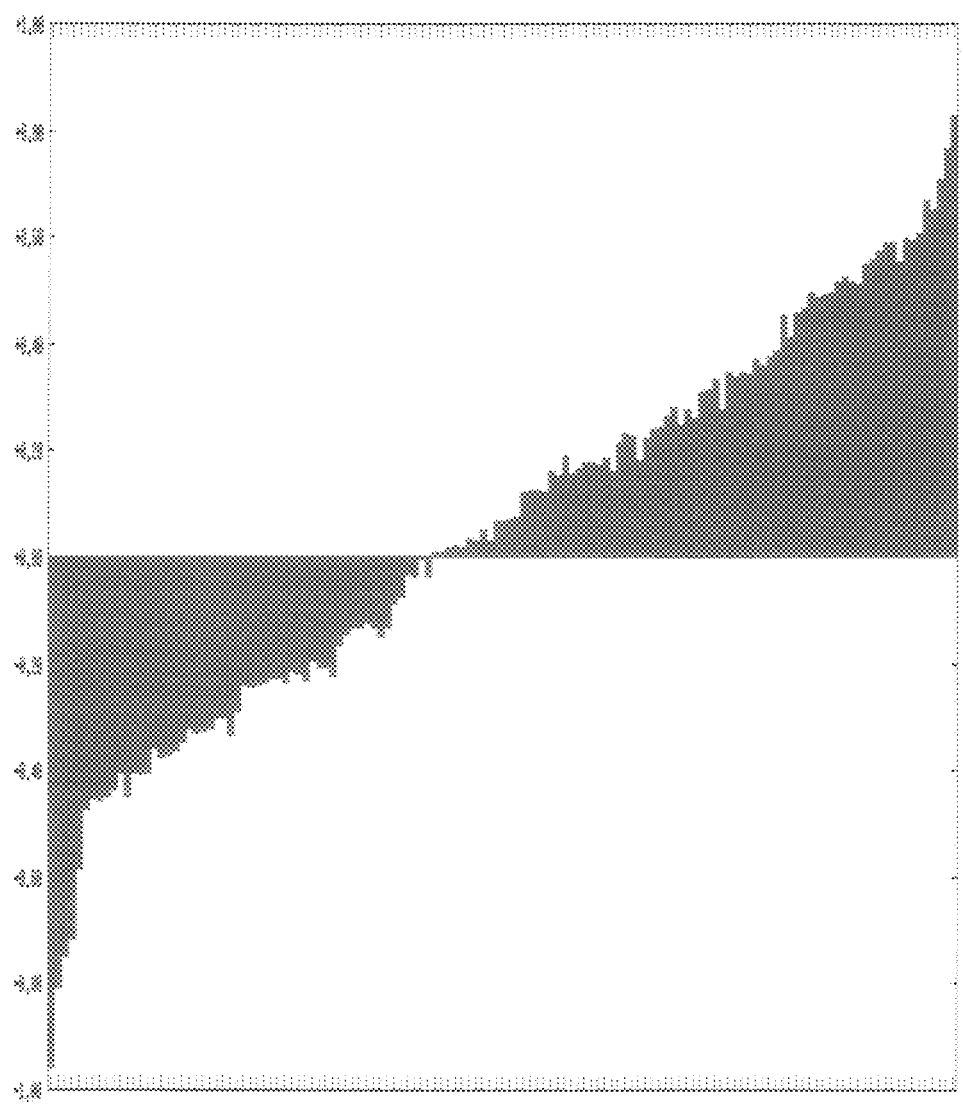
Figure 11C — 88 Gene – CDH1 — GeneLogic Lung AB — Anchor: CLDN3

80 gene index

GeneLogic Lung AB  
Anchor: CLDN3

E-only index (44)

GeneLogic Lung A8
Anchor: CLDN3

GeneLogic Lung AB
Anchor: CLDN3

Figure 12A:
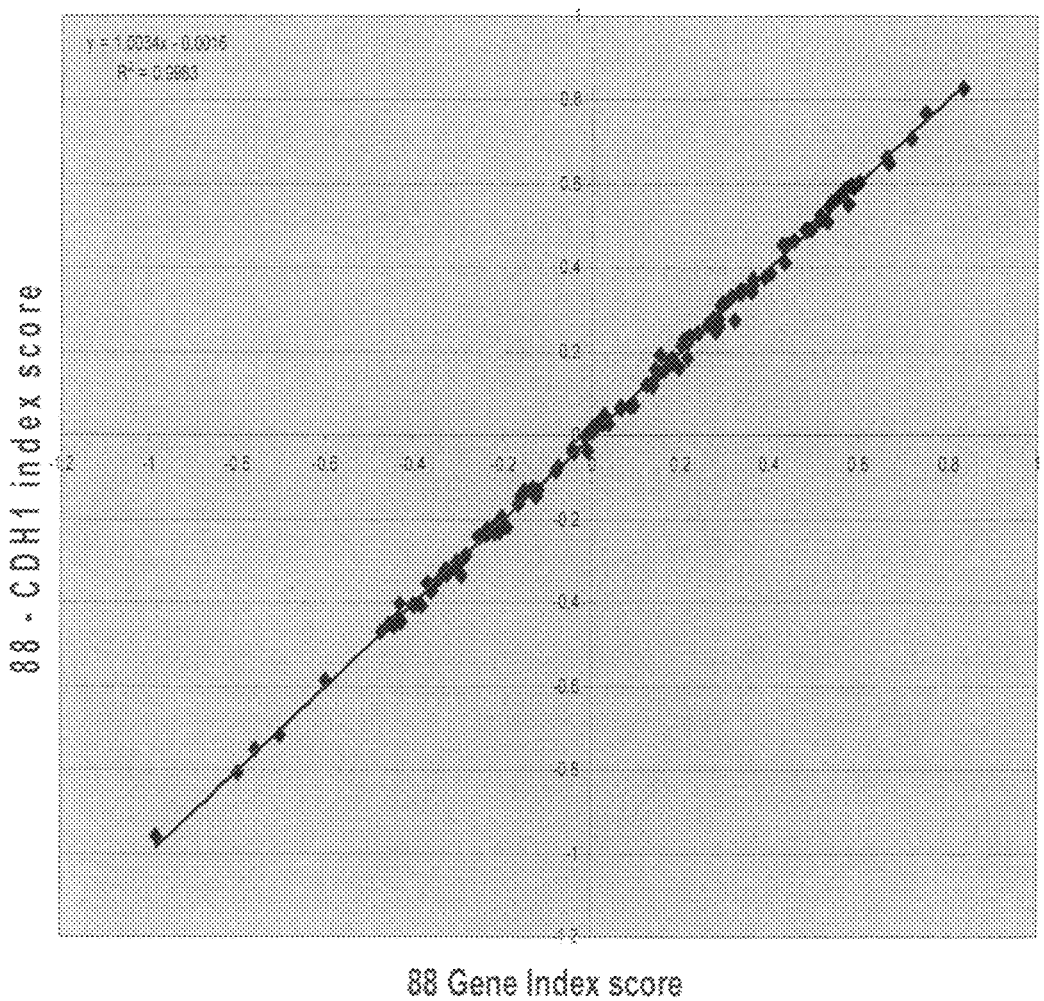

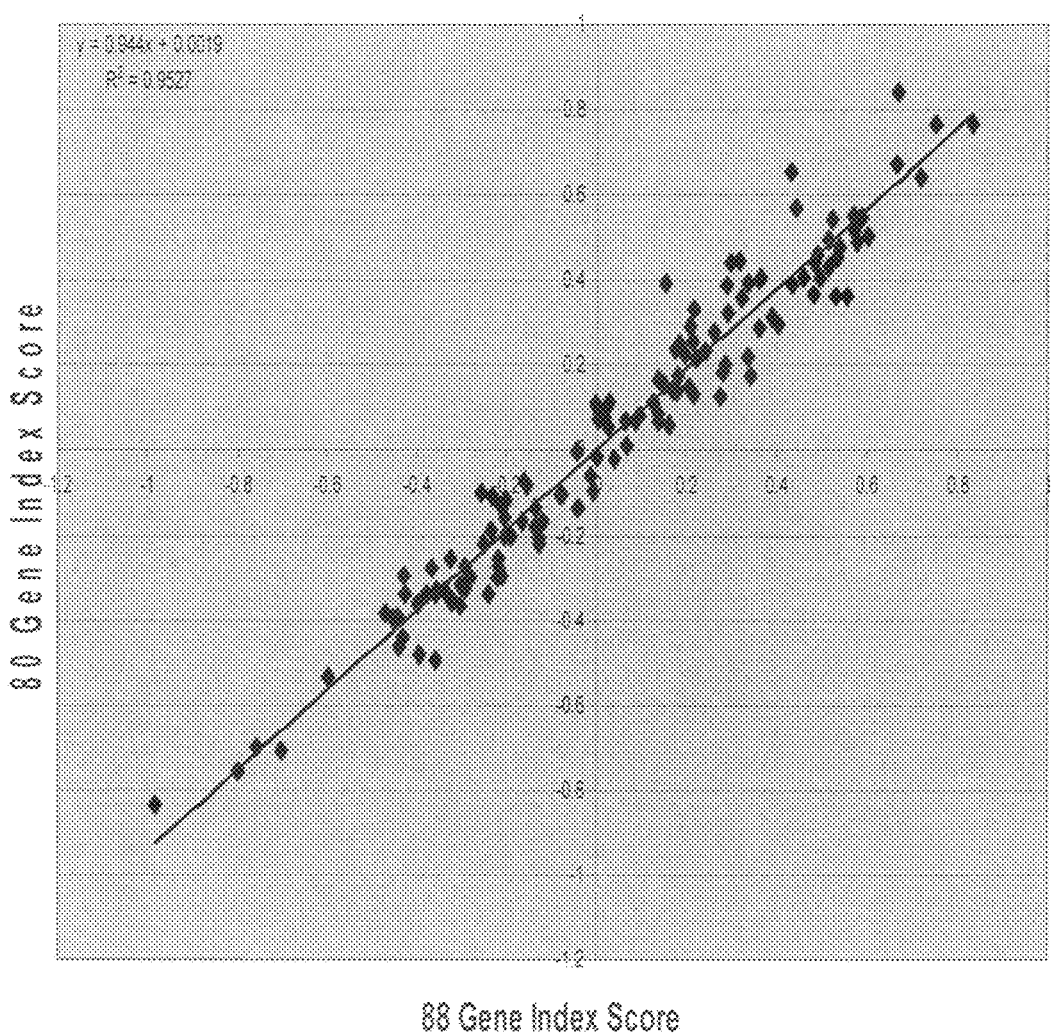
Figure 12B    GeneLogic Lung AB
              Anchor: CLDN3

Figure 12C — GeneLogic Lung AB
Anchor: CLDN3
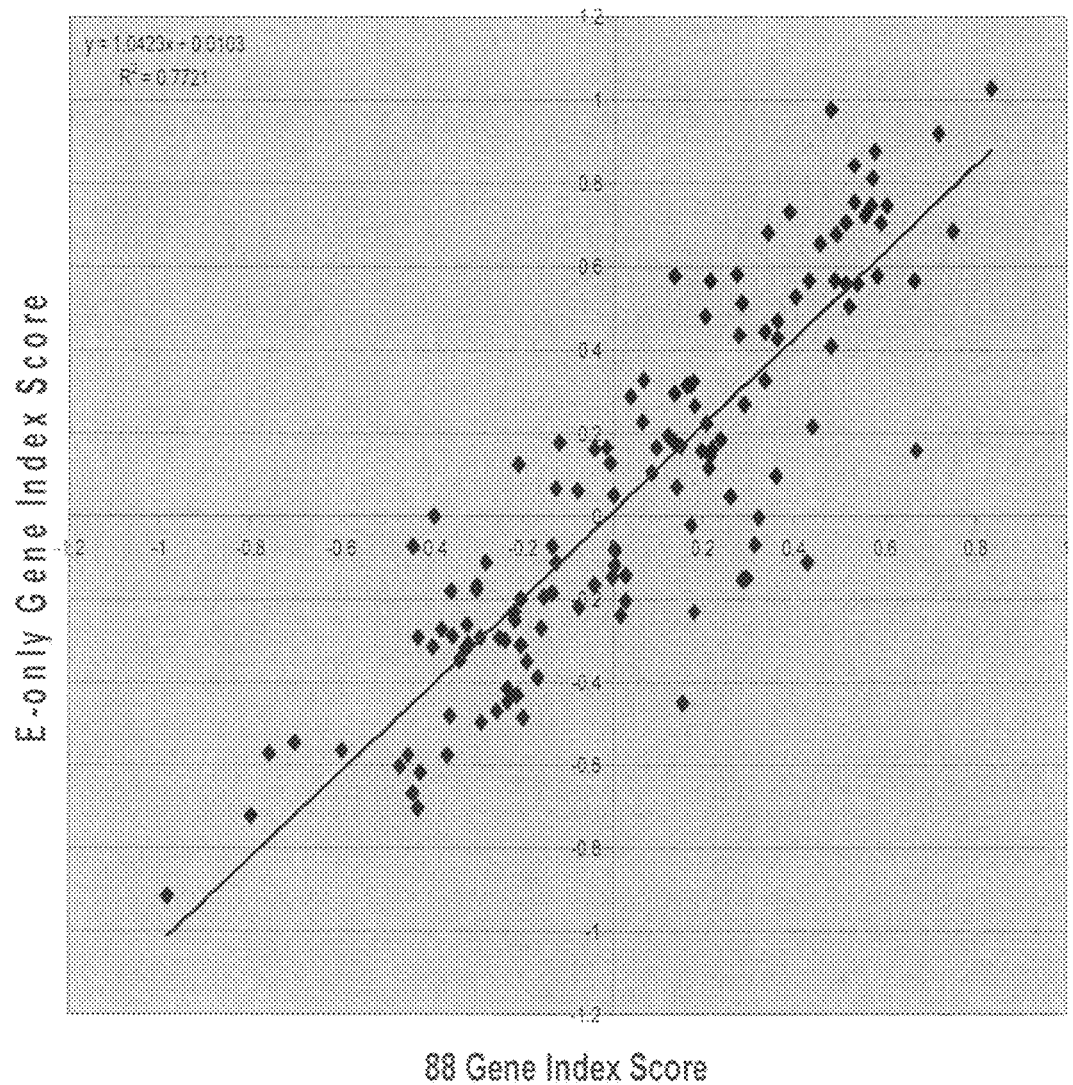

88 EMT Gene Signature

Pancreas Plus2

Anchor: RASSF8

E-only Gene Signature

Pancreas Plus2

Anchor:
RASSF8

88 EMT vs E-only gene index score

Figure 24B:
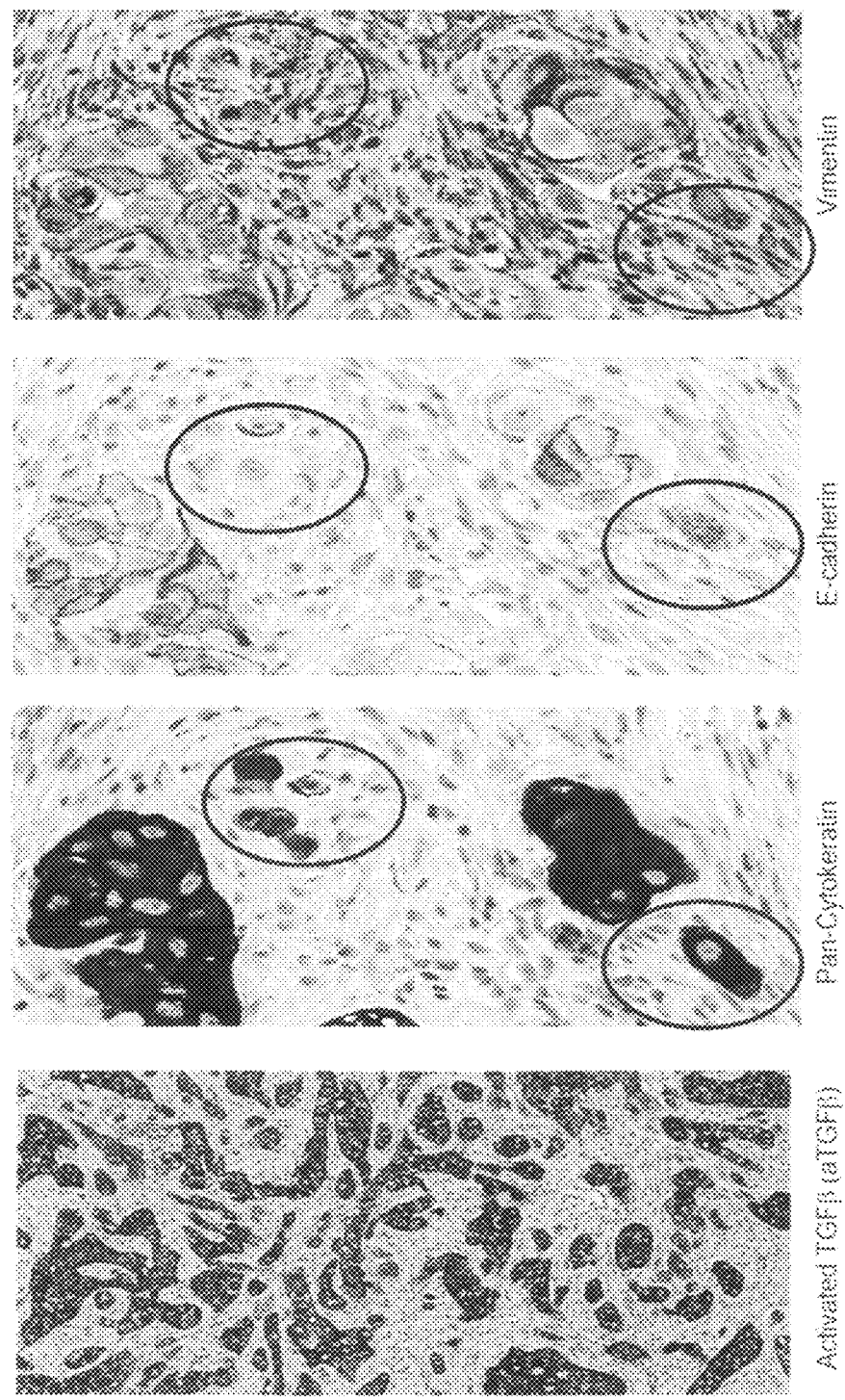

Figure 24A    aTGFb model: IHC
Activated TGFβ (aTGFβ)
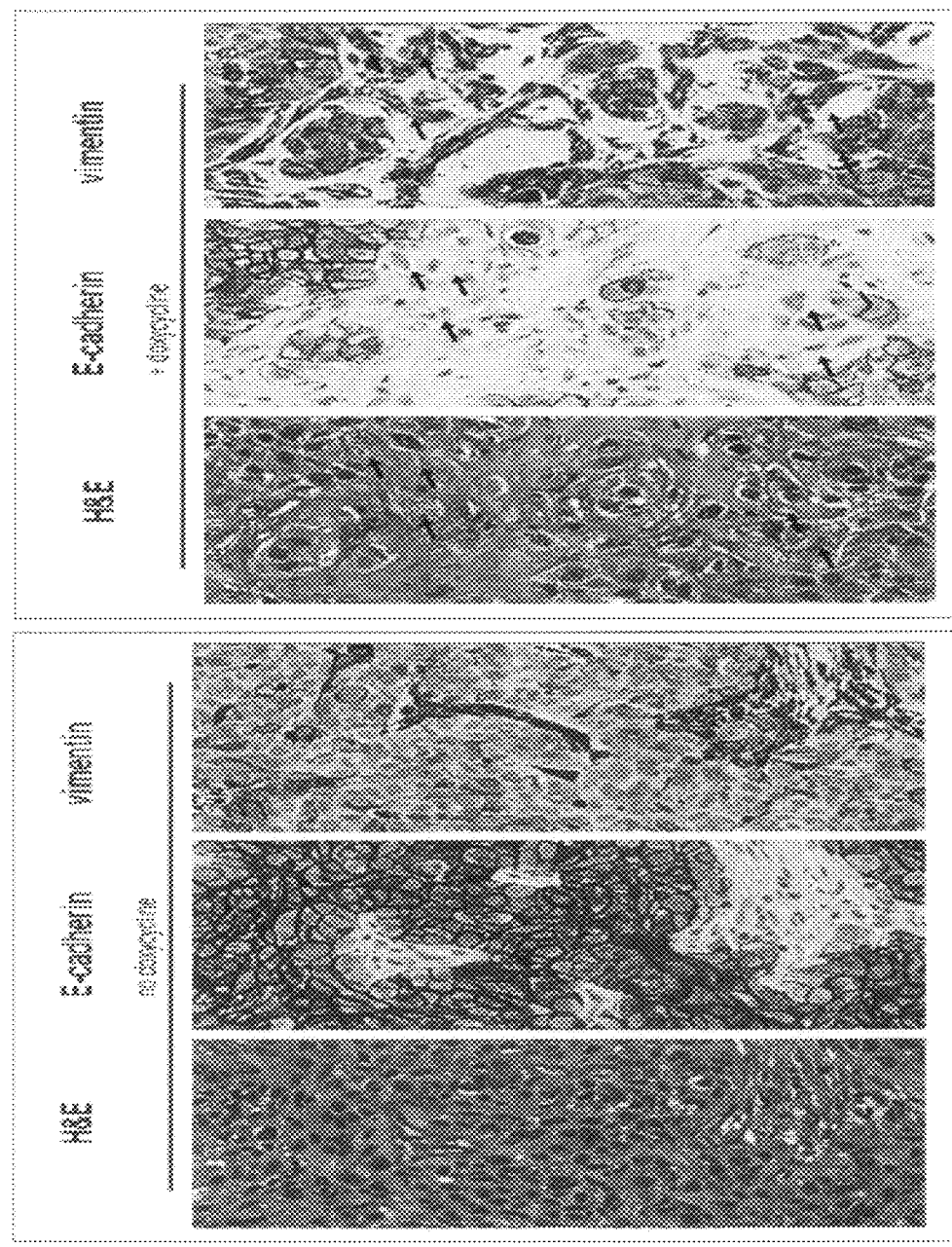

In vivo models of EMT: Growth rate after transgene induction

Figure 26B

| EMT model | Erlotinib EC50 (μM) | | EMT index | |
| --- | --- | --- | --- | --- |
| | Uninduced | Induced | Uninduced | Induced |
| Vector *in vitro* | 1.63 | 1.53 | ND | ND |
| TGFb *in vitro* | 0.93 | >20 | 2.82 | 5.80 |
| Snail *in vitro* | 0.86 | >20 | 2.69 | 4.72 |
| Zeb1 *in vitro* | 1.12 | 1.26 | 2.00 | 3.64 |

3D culture of H358 engineered EMT models

CFPAC1

CFPAC1

CFPAC1

H1650

H292

H292

H292

Figure 31

| EMT model | In vitro only | Common | In vivo only |
|---|---|---|---|
| TGFb | 25 | 33 | 9 |
| Snail | 34 | 21 | 20 |
| Zeb1 | 27 | 4 | 13 |

EMT Index with E-cadherin IHC score overlay

BH Archive

Figure 36    Mesenchymal genes

Figure 37    Epithelial genes

Figure 38

| Cell Line | EMT Index Score | % Max Inhibition @1um Erlotinib | EC50 (uM) |
|---|---|---|---|
| H322 | 3.07 | 80 | 0.4 |
| CALU3 | 6.38 | 78 | 0.6 |
| H358 | 3.40 | 75 | 0.6 |
| H292 | 3.68 | 72 | 0.1 |
| BxPC3 | 3.32 | 69.38 | 0.693 |
| HCT15 | 2.98 | 67 | 3.3 |
| HCT8 | 2.33 | 64 | 1.6 |
| GEO | 2.05 | 63.308 | 0.5 |
| SKBr3 | 1.84 | 63.29 | 3.91 |
| A427 | 6.21 | 62 | 3 |
| DLD-1 | 1.45 | 61 | 3 |
| HPAC | 1.88 | 58 | |
| H441 | 2.82 | 55 | 2 |
| BT474 | 1.72 | 53.59 | 1.91 |
| FET | 2.09 | 50 | 1 |
| Capan1 | 2.57 | 50 | |
| CBS | 2.28 | 50 | 0.5 |
| CFPAC | 3.13 | 50 | 4.88 |
| H2122 | 3.57 | 45 | 5 |
| T47D | 1.94 | 41.4 | 4.09 |
| H1703 | 7.72 | 30 | 7 |
| H23 | 7.21 | 30 | 5 |
| H460 | 6.95 | 29 | 5 |
| H1299 | 7.66 | 25 | 5 |
| HT29 | 1.83 | 25 | >10 |
| SW1573 | 7.39 | 25 | 9 |
| HOP92 | 7.37 | 22 | 5 |
| MiaPaCa2 | 7.36 | 18.19 | 3.37 |
| ZR75.1 | 1.80 | 17.7 | >10 |
| MDA-468 | 6.11 | 17.19 | >10 |
| MDA 435 | 9.43 | 16.78 | >10 |
| Colo205 | 1.45 | 15 | >10 |
| PANC1 | 6.57 | 11.35 | >10 |
| RKO | 6.20 | 10 | >10 |
| Sw620 | 4.61 | 10 | >10 |
| HCT116 | 3.99 | 8 | >10 |
| MDA 231 | 6.03 | 7.963 | >10 |
| DU4445 | 3.48 | 4.06 | >10 |
| A1165 | 6.75 | 1.49 | 3.48 |

Figure 39

| Cell Line | % Max Inhibition @ 10uM Erlotinib | Erlotinib sensitivity | EMT Signature Used EMT 88 Index Score | EMT88 ITGA5 Index Score | EMT88 VIM Index Score | EMT88 CDH1 Index Score | EMT88 ErbB3 Index Score | EMT E only Index Score | EMT E only minus CDH1 Index Score | EMT E only minus ErbB3 Index Score |
|---|---|---|---|---|---|---|---|---|---|---|
| A1165 | 1.49 | Insensitive | 6.05 | 6.07 | 6.02 | 6.06 | 6.03 | | | |
| DU4445 | 4.06 | Insensitive | 3.43 | 3.70 | 3.63 | 3.44 | 3.41 | | | |
| MDA231 | 7.63 | Insensitive | 6.01 | 6.06 | 5.97 | 5.90 | 6.08 | 7.56 | 7.44 | 7.58 |
| HCT15 | 8 | Insensitive | 3.02 | 3.10 | 3.23 | 3.06 | 3.05 | 4.77 | 4.93 | 4.95 |
| BKO | 10 | Insensitive | 6.18 | 6.24 | 6.34 | 6.08 | 6.25 | 7.97 | 7.86 | 8.14 |
| SW620 | 10 | Insensitive | 4.57 | 4.68 | 4.57 | 4.57 | 4.59 | 6.44 | 6.49 | 6.54 |
| Panc1 | 11.36 | Insensitive | 6.65 | 6.73 | 6.60 | 6.69 | 6.61 | 7.77 | 7.89 | 7.73 |
| Colo205 | 15 | Insensitive | 1.49 | 1.53 | 1.71 | 1.52 | 1.47 | 3.10 | 3.22 | 3.12 |
| MDA435 | 15.78 | Insensitive | 9.47 | 9.60 | 9.51 | 9.35 | 9.52 | 11.91 | 11.79 | 12.24 |
| MDA468 | 17.19 | Insensitive | 6.11 | 6.16 | 6.08 | 6.02 | 6.08 | 7.62 | 7.41 | 7.51 |
| ZR751 | 17.7 | Insensitive | 1.77 | 1.82 | 1.67 | 1.66 | 1.77 | 3.23 | 3.37 | 3.27 |
| MiaPaca2 | 19.19 | Insensitive | 7.35 | 7.49 | 7.33 | 7.23 | 7.35 | 9.54 | 9.40 | 9.60 |
| Hop92 | 22 | Insensitive | 7.46 | 7.54 | 7.45 | 7.37 | 7.45 | 8.80 | 8.69 | 8.84 |
| H1299 | 25 | Insensitive | 7.66 | 7.76 | 7.67 | 7.55 | 7.67 | 9.31 | 9.19 | 9.38 |
| HT29 | 25 | Insensitive | 1.91 | 1.97 | 1.97 | 1.85 | 1.91 | 2.92 | 2.91 | 2.95 |
| SW1573 | 25 | Insensitive | 7.43 | 7.59 | 7.45 | 7.38 | 7.40 | 9.75 | 9.74 | 9.77 |
| H460 | 27 | Insensitive | 6.95 | 7.04 | 6.93 | 6.82 | 6.94 | 9.26 | 9.13 | 9.35 |
| H1703 | 30 | Insensitive | 7.73 | 7.85 | 7.75 | 7.68 | 7.72 | 10.09 | 10.09 | 10.15 |
| H23_C | 30 | Insensitive | 7.11 | 7.22 | 7.12 | 7.17 | 7.10 | 9.02 | 9.20 | 9.07 |
| T47D | 41.4 | Insensitive | 2.95 | 3.03 | 2.93 | 2.93 | 2.96 | 3.89 | 3.81 | 3.76 |
| H2122 | 45 | Insensitive | 4.05 | 4.17 | 4.03 | 3.99 | 4.01 | | | |
| Capan1 | 50 | Sensitive | 2.57 | 2.63 | 2.65 | 2.60 | 2.58 | 3.34 | 3.44 | 3.39 |
| CBS | 50 | Sensitive | 2.17 | 2.24 | 2.39 | 2.23 | 2.19 | 3.68 | 3.62 | 3.76 |
| CFPAC | 50 | Sensitive | 3.19 | 3.28 | 3.14 | 3.25 | 3.19 | 4.23 | 4.30 | 4.36 |
| FET | 50 | Sensitive | 2.17 | 2.36 | 2.54 | 2.23 | 2.18 | 3.86 | 3.81 | 3.74 |
| BT474 | 53.89 | Sensitive | 1.72 | 1.81 | 1.71 | 1.77 | 1.72 | 3.04 | 3.15 | 3.10 |
| H441 | 55 | Sensitive | 2.73 | 2.80 | 2.50 | 2.86 | 2.75 | 4.37 | 4.53 | 4.42 |
| HPAC | 55 | Sensitive | 1.97 | 1.99 | 2.02 | 1.98 | 1.95 | 3.60 | 3.71 | 3.65 |
| DLD-1 | 61 | Sensitive | 2.98 | 2.99 | 3.10 | 2.91 | 2.95 | 4.72 | 4.67 | 4.76 |
| A427 | 63 | Sensitive | 6.25 | 6.38 | 6.09 | 6.26 | 6.28 | 8.71 | 8.61 | 8.87 |
| SKBR3 | 63.29 | Sensitive | 1.71 | 1.77 | 1.66 | 1.63 | 1.71 | 3.19 | 3.08 | 3.25 |
| GEO | 65.98 | Sensitive | 2.13 | 2.22 | 2.34 | 2.19 | 2.13 | 3.36 | 3.39 | 3.30 |
| HCT116 | 66 | Sensitive | 3.98 | 4.08 | 4.13 | 4.00 | 3.95 | 6.09 | 6.19 | 6.15 |
| HCT8 | 67 | Sensitive | 6.68 | 6.76 | 6.65 | 6.78 | 6.64 | 7.66 | 7.61 | 7.62 |
| BxPC3 | 69.39 | Sensitive | 2.95 | 2.99 | 3.01 | 3.03 | 2.94 | 4.02 | 4.05 | 4.06 |
| H292 | 72 | Sensitive | 3.67 | 3.70 | 3.66 | 3.72 | 3.67 | 5.68 | 5.61 | 5.74 |
| H358 | 75 | Sensitive | 3.42 | 3.55 | 3.44 | 3.47 | 3.41 | 4.57 | 4.70 | 4.60 |
| CALU3 | 78 | Sensitive | 6.47 | 6.59 | 6.48 | 6.55 | 6.45 | 7.78 | 7.87 | 7.79 |
| H322 | 91 | Sensitive | 2.71 | 2.78 | 2.84 | 2.79 | 2.67 | 4.66 | 4.67 | 4.82 |

Figure 40

| Signature Index | EMT 88 | | | | | | | |
|---|---|---|---|---|---|---|---|---|
| | All 88 | All 88 Minus ITGA5 | All 88 Minus Vim | All 88 Minus CDH1 | All 88 Minus ErbB3 | E only | E only minus CDH1 | E only minus ErbB3 |
| Anchor Gene | TMEM125 | TMEM125 | TMEM125 | TMEM125 | TMEM125 | TMEM125 | TMEM125 | TMEM125 |
| 2 | BSPRY | BSPRY | BSPRY | BSPRY | BSPRY | BSPRY | BSPRY | BSPRY |
| 3 | EVA1 | EVA1 | EVA1 | EVA1 | EVA1 | EVA1 | EVA1 | EVA1 |
| 4 | TJP3 | TJP3 | TJP3 | TJP3 | TJP3 | TJP3 | TJP3 | TJP3 |
| 5 | EHF | EHF | EHF | EHF | EHF | EHF | EHF | EHF |
| 6 | ERBB3 | ERBB3 | ERBB3 | ERBB3 | VIM | ERBB3 | ERBB3 | TMEM45B |
| 7 | VIM | VIM | ZEB1 | VIM | ZEB1 | TMEM45B | TMEM45B | CDH1 |
| 8 | ZEB1 | ZEB1 | TMEM45B | ZEB1 | TMEM45B | CDH1 | SCNN1A | SCNN1A |
| 9 | TMEM45B | TMEM45B | CDH1 | TMEM45B | CDH1 | SCNN1A | ELF3 | ELF3 |
| 10 | CDH1 | CDH1 | SCNN1A | SCNN1A | SCNN1A | ELF3 | CLDN3 | CLDN3 |
| 11 | SCNN1A | SCNN1A | ELF3 | ELF3 | ELF3 | CLDN3 | MAP7 | MAP7 |
| 12 | ELF3 | ELF3 | CLDN3 | CLDN3 | CLDN3 | MAP7 | LCN2 | LCN2 |
| 13 | CLDN3 | CLDN3 | MAP7 | MAP7 | MAP7 | LCN2 | PPL | PPL |
| 14 | MAP7 | MAP7 | ZEB2 | ZEB2 | ZEB2 | PPL | SLC27A2 | SLC27A2 |
| 15 | ZEB2 | ZEB2 | LCN2 | LCN2 | LCN2 | SLC27A2 | AP1M2 | AP1M2 |
| 16 | LCN2 | LCN2 | PPL | PPL | PPL | AP1M2 | PLXNB1 | PLXNB1 |
| 17 | PPL | PPL | SLC27A2 | SLC27A2 | SLC27A2 | PLXNB1 | DSP | DSP |
| 18 | SLC27A2 | SLC27A2 | SPARC | SPARC | SPARC | DSP | AGR2 | AGR2 |
| 19 | SPARC | SPARC | AP1M2 | AP1M2 | AP1M2 | AGR2 | OCLN | OCLN |
| 20 | AP1M2 | AP1M2 | EFNB2 | EFNB2 | EFNB2 | OCLN | CLDN4 | CLDN4 |
| 21 | EFNB2 | EFNB2 | SERPINE1 | SERPINE1 | SERPINE1 | CLDN4 | AKAP12 | AKAP12 |
| 22 | SERPINE1 | SERPINE1 | PLXNB1 | PLXNB1 | PLXNB1 | AKAP12 | ETV6 | ETV6 |
| 23 | PLXNB1 | PLXNB1 | ITGB3 | ITGB3 | ITGB3 | ETV6 | SFRP1 | SFRP1 |
| 24 | ITGB3 | ITGB3 | DSP | DSP | DSP | SFRP1 | TBX2 | TBX2 |
| 25 | DSP | DSP | RASSF6 | RASSF6 | RASSF6 | TBX2 | ELF5 | ELF5 |
| 26 | RASSF6 | RASSF6 | AGR2 | AGR2 | AGR2 | ELF5 | MB | MB |
| 27 | AGR2 | AGR2 | OCLN | OCLN | OCLN | MB | VWF | VWF |
| 28 | OCLN | OCLN | ITGA5 | ITGA5 | ITGA5 | VWF | SPDEF | SPDEF |
| 29 | ITGA5 | CLDN4 | CLDN4 | CLDN4 | CLDN4 | SPDEF | MMP7 | MMP7 |
| 30 | CLDN4 | MSLN | MSLN | MSLN | MSLN | MMP7 | XBP1 | XBP1 |
| 31 | MSLN | SRPX | SRPX | SRPX | SRPX | XBP1 | | |
| 32 | SRPX | AXL | AXL | AXL | AXL | | | |
| 33 | AXL | IHH | IHH | IHH | IHH | | | |
| 34 | IHH | COL9 | COL9 | COL9 | COL9 | | | |
| 35 | COL9 | AKAP12 | AKAP12 | AKAP12 | AKAP12 | | | |
| 36 | AKAP12 | ETV6 | ETV6 | ETV6 | ETV6 | | | |
| 37 | ETV6 | SFRP1 | SFRP1 | SFRP1 | SFRP1 | | | |
| 38 | SFRP1 | TBX2 | TBX2 | TBX2 | TBX2 | | | |
| 39 | TBX2 | ELF5 | ELF5 | ELF5 | ELF5 | | | |
| 40 | ELF5 | MB | MB | MB | MB | | | |
| 41 | MB | ALCAM | ALCAM | ALCAM | ALCAM | | | |
| 42 | ALCAM | CDH2 | CDH2 | CDH2 | CDH2 | | | |
| 43 | CDH2 | VWF | VWF | VWF | VWF | | | |
| 44 | VWF | FOSL1 | FOSL1 | FOSL1 | FOSL1 | | | |
| 45 | FOSL1 | FLRT3 | FLRT3 | FLRT3 | FLRT3 | | | |
| 46 | FLRT3 | PCOLCE2 | PCOLCE2 | PCOLCE2 | PCOLCE2 | | | |
| 47 | PCOLCE2 | IL18 | IL18 | IL18 | IL18 | | | |
| 48 | IL18 | SPDEF | SPDEF | SPDEF | SPDEF | | | |
| 49 | SPDEF | MMP7 | MMP7 | MMP7 | MMP7 | | | |
| 50 | MMP7 | XBP1 | XBP1 | XBP1 | XBP1 | | | |
| 51 | XBP1 | | | | | | | |

88EMTGS index:
BH archive, ERBB3 anchor

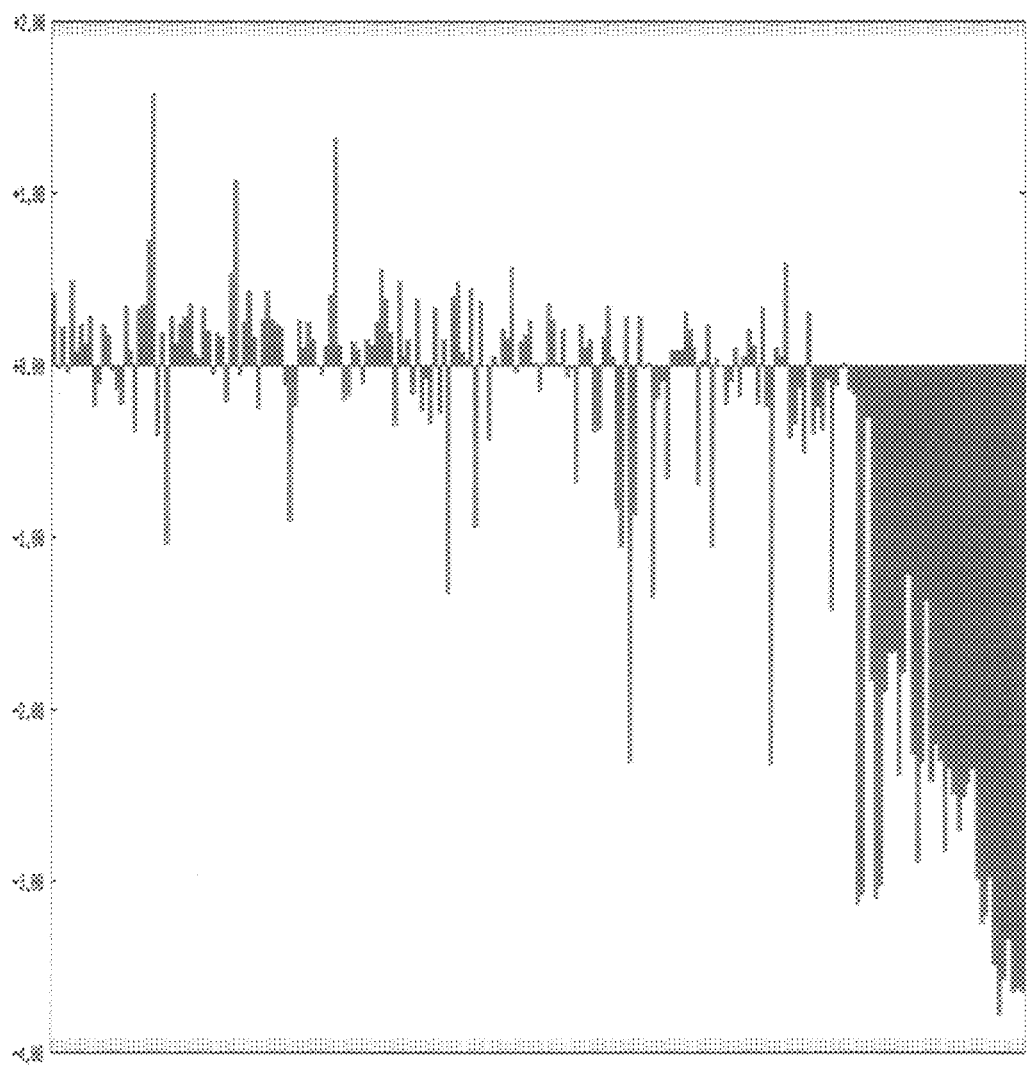

Figure 49B

| EMT model | Erlotinib EC50 (µM) | | EMT index | |
|---|---|---|---|---|
| | Uninduced | Induced | Uninduced | Induced |
| Vector *in vitro* | 1.63 | 1.53 | ND | ND |
| TGFb *in vitro* | 0.93 | >20 | 4.57 | 8.03 |
| Snail *in vitro* | 0.86 | >20 | 4.18 | 6.85 |
| Zeb1 *in vitro* | 1.12 | 1.26 | 3.45 | 4.23 |

Figure 51

| Cell Line | EMT Index Score | % Max Inhibition @ 1uM Erlotinib | EC50 (uM) |
|---|---|---|---|
| H322 | 5.65 | 80 | 0.4 |
| CALU3 | 9.16 | 78 | 0.6 |
| H358 | 6.18 | 75 | 0.6 |
| H292 | 6.45 | 72 | 0.1 |
| BxPC3 | 6.09 | 69.38 | 0.693 |
| HCT15 | 5.76 | 67 | 3.3 |
| HCT8 | 7.28 | 64 | 1.6 |
| GEO | 4.82 | 63.308 | 0.5 |
| SKBR3 | 4.62 | 63.29 | 3.91 |
| A427 | 8.99 | 62 | 3 |
| DLD-1 | 5.59 | 61 | 3 |
| HPAC | 4.65 | 58 | |
| H441 | 5.59 | 55 | 2 |
| BT474 | 4.49 | 53.59 | 1.91 |
| FET | 4.87 | 50 | 1 |
| Capan1 | 5.35 | 50 | |
| CBS | 5.05 | 50 | 0.5 |
| CFPAC | 5.90 | 50 | 4.88 |
| H2122 | 6.35 | 45 | 5 |
| T47D | 4.71 | 41.4 | 4.09 |
| H1703 | 10.49 | 30 | 7 |
| H23 | 9.98 | 30 | 5 |
| H460 | 9.72 | 29 | 5 |
| H1299 | 10.43 | 25 | 5 |
| HT29 | 4.60 | 25 | >10 |
| SW1573 | 10.16 | 25 | 9 |
| Hop92 | 10.14 | 22 | 5 |
| MiaPaca2 | 10.14 | 18.19 | 3.37 |
| ZR75-1 | 4.58 | 17.7 | >10 |
| MDA-468 | 8.88 | 17.19 | >10 |
| MDA-435 | 12.21 | 16.78 | >10 |
| Colo205 | 4.23 | 15 | >10 |
| Panc1 | 9.34 | 11.35 | >10 |
| RKO | 8.97 | 10 | >10 |
| SW620 | 7.38 | 10 | >10 |
| HCT116 | 6.77 | 8 | >10 |
| MDA-231 | 8.81 | 7.963 | >10 |
| DU4445 | 6.26 | 4.06 | >10 |
| A1165 | 9.53 | 1.49 | 3.48 |

Figure 52

| Cell Line | % Max Inhibition @ 1uM Erlotinib | Erlotinib Sensitivity | EMT Signature Used EMT 88 Index Score | EMT88 ITGA5 Index Score | EMT88 VIM Index Score | EMT88 CDH1 Index Score | EMT88 ErbB3 Index Score | EMT E only Index Score | EMT E only minus CDH1 Index Score | EMT E only minus ErbB3 Index Score |
|---|---|---|---|---|---|---|---|---|---|---|
| A1165 | 1.9 | Insensitive | 9.53 | 9.55 | 9.45 | 9.62 | 9.56 | 8.91 | 8.94 | 8.94 |
| OV445 | 4.06 | Insensitive | 6.26 | 6.47 | 6.44 | 6.54 | 6.31 | 7.06 | 7.21 | 7.15 |
| MDA-231 | 7.963 | Insensitive | 8.81 | 8.82 | 8.76 | 8.76 | 8.83 | 8.50 | 8.40 | 8.65 |
| HCT15 | 8.7 | Insensitive | 5.76 | 5.79 | 5.93 | 5.97 | 5.82 | 6.67 | 6.75 | 6.67 |
| RKO | 10 | Insensitive | 8.97 | 8.98 | 9.10 | 8.92 | 9.10 | 8.87 | 8.78 | 9.07 |
| SW620 | 10 | Insensitive | 7.36 | 7.45 | 7.37 | 7.43 | 7.45 | 7.45 | 7.54 | 7.53 |
| Panc1 | 11.35 | Insensitive | 9.34 | 9.38 | 9.30 | 9.45 | 9.34 | 8.50 | 8.57 | 8.48 |
| Colo205 | 15 | Insensitive | 4.23 | 4.23 | 4.43 | 4.32 | 4.27 | 3.94 | 4.09 | 3.99 |
| MDA-435 | 16.79 | Insensitive | 12.21 | 12.30 | 12.22 | 12.15 | 12.41 | 12.94 | 12.76 | 13.20 |
| MDA-468 | 17.19 | Insensitive | 8.80 | 8.88 | 8.83 | 8.85 | 8.81 | 8.40 | 8.03 | 8.43 |
| IM-51 | 17.7 | Insensitive | 4.58 | 4.59 | 4.68 | 4.69 | 4.63 | 4.13 | 4.31 | 4.23 |
| MiaPacO2 | 18.19 | Insensitive | 10.14 | 10.23 | 10.10 | 10.07 | 10.19 | 10.41 | 10.30 | 10.50 |
| Hs95 | 22 | Insensitive | 10.14 | 10.17 | 10.10 | 10.10 | 10.20 | 9.41 | 9.32 | 9.47 |
| H358 | 25 | Insensitive | 10.43 | 10.49 | 10.42 | 10.40 | 10.50 | 9.95 | 9.88 | 10.05 |
| H28 | 25 | Insensitive | 4.60 | 4.72 | 4.74 | 4.70 | 4.66 | 3.72 | 3.84 | 3.73 |
| SW1573 | 25 | Insensitive | 10.16 | 10.27 | 10.15 | 10.16 | 10.19 | 10.55 | 10.58 | 10.61 |
| H460 | 29 | Insensitive | 9.72 | 9.77 | 9.73 | 9.65 | 9.73 | 10.15 | 10.04 | 10.19 |
| H1703 | 30 | Insensitive | 10.43 | 10.57 | 10.49 | 10.46 | 10.55 | 11.00 | 11.00 | 11.11 |
| H23 | 30 | Insensitive | 9.96 | 10.06 | 9.97 | 10.10 | 10.02 | 10.12 | 10.02 | 10.19 |
| T47D | 41.4 | Insensitive | 4.71 | 4.70 | 4.83 | 4.81 | 4.78 | 4.31 | 4.46 | 4.40 |
| H322 | 45 | Insensitive | 6.35 | 6.37 | 6.60 | 6.36 | 6.39 | 7.41 | 7.46 | 7.49 |
| Calu1 | 50 | Sensitive | 5.35 | 5.35 | 5.40 | 5.45 | 5.41 | 4.22 | 4.35 | 4.31 |
| U87 | 50 | Sensitive | 5.05 | 5.03 | 5.25 | 5.17 | 5.13 | 4.81 | 5.01 | 4.93 |
| MPAC | 50 | Sensitive | 5.90 | 5.92 | 5.85 | 6.02 | 5.95 | 4.79 | 4.94 | 4.85 |
| FEF | 50 | Sensitive | 4.87 | 4.98 | 5.01 | 4.99 | 4.95 | 4.39 | 4.47 | 4.41 |
| BT474 | 50.59 | Sensitive | 4.90 | 4.80 | 4.95 | 4.90 | 4.95 | 3.88 | 4.01 | 3.94 |
| H441 | 55 | Sensitive | 5.50 | 5.52 | 5.64 | 5.71 | 5.55 | 5.19 | 5.36 | 5.28 |
| HPAC | 59 | Sensitive | 4.65 | 4.67 | 4.75 | 4.73 | 4.68 | 4.48 | 4.59 | 4.53 |
| SUD1 | 61 | Sensitive | 5.59 | 5.61 | 5.74 | 5.70 | 5.63 | 5.51 | 5.69 | 5.58 |
| A431 | 62 | Sensitive | 8.99 | 9.01 | 8.94 | 9.04 | 9.05 | 9.58 | 9.65 | 9.77 |
| SKBR3 | 62.29 | Sensitive | 4.52 | 4.54 | 4.75 | 4.46 | 4.57 | 4.29 | 4.50 | 4.37 |
| GEO | 62.36 | Sensitive | 4.90 | 4.96 | 5.01 | 4.99 | 4.97 | 4.07 | 4.23 | 4.13 |
| HCT116 | 64 | Sensitive | 6.77 | 6.80 | 6.85 | 6.89 | 6.82 | 7.02 | 7.10 | 7.11 |
| HCT8 | 64 | Sensitive | 7.28 | 7.28 | 7.34 | 7.41 | 7.32 | 6.50 | 6.69 | 6.55 |
| BxPC3 | 69.39 | Sensitive | 6.06 | 6.09 | 6.13 | 6.20 | 6.14 | 5.63 | 5.79 | 5.68 |
| H292 | 70 | Sensitive | 6.46 | 6.47 | 6.50 | 6.56 | 6.51 | 6.40 | 6.55 | 6.57 |
| H358 | 75 | Sensitive | 6.10 | 6.09 | 6.17 | 6.26 | 6.23 | 5.58 | 5.83 | 5.73 |
| CALU3 | 75 | Sensitive | 9.18 | 9.20 | 9.15 | 9.26 | 9.19 | 9.54 | 9.66 | 9.65 |
| H322 | 80 | Sensitive | 5.85 | 5.87 | 5.94 | 5.95 | 5.96 | 5.98 | 6.11 | 5.99 |

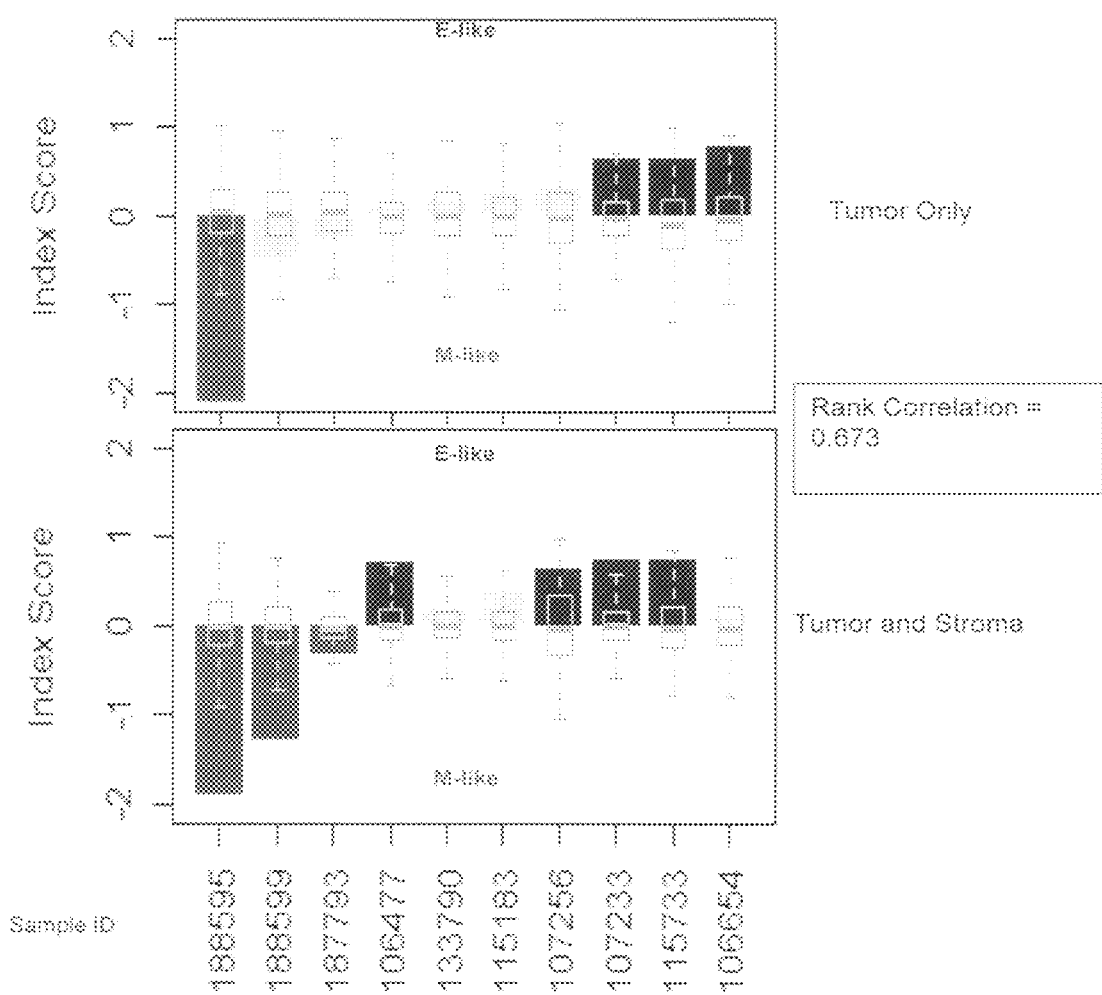

USE OF EMT GENE SIGNATURES IN CANCER DRUG DISCOVERY, DIAGNOSTICS, AND TREATMENT

CROSS-REFERENCE TO RELATED APPLICATIONS

This application claims the benefit of U.S. Provisional Application No. 61/517,789, filed Apr. 25, 2011, and U.S. Provisional Application No. 61/632,894, filed Jan. 31, 2012, both of which are herein incorporated by reference in their entirety.

BACKGROUND OF THE INVENTION

Cancer is a generic name for a wide range of cellular dysfunctions and dysregulations characterized by unregulated growth, lack of differentiation, and the potential to invade local tissues and metastasize to distant sites. These neoplastic malignancies may affect, with various degrees of prevalence, every tissue and organ in the body. The present invention is directed to methods for diagnosing and treating cancer patients. In particular, the present invention is directed to methods for determining which patients will most benefit from treatment with anti-cancer agents that are inhibitors of protein kinases, e.g. epidermal growth factor receptor (EGFR) kinase inhibitors (e.g. erlotinib), or IGF-1R kinase inhibitors (e.g. OSI-906), and methods of identifying and characterising new anti-cancer agents.

It has been recognized that inhibitors of protein kinases are useful as selective inhibitors of the growth of mammalian cancer cells. For example, Gleevec™ (also known as imatinib mesylate), a 2-phenylpyrimidine tyrosine kinase inhibitor that inhibits the kinase activity of the BCR-ABL fusion gene product, has been approved by the U.S. Food and Drug Administration for the treatment of CML. The 4-anilinoquinazoline compound Tarceva™ (erlotinib HCl) has also been approved by the FDA, and selectively inhibits EGF receptor kinase with high potency. The development for use as anti-tumor agents of compounds that directly inhibit the kinase activity of IGF-1R, as well as antibodies that reduce IGF-1R kinase activity by blocking IGF-1R activation or antisense oligonucleotides that block IGF-1R expression, are areas of intense research effort (e.g. see Larsson, O. et al (2005) Brit. J. Cancer 92:2097-2101; Ibrahim, Y. H. and Yee, D. (2005) Clin. Cancer Res. 11:944s-950s; Mitsiades, C. S. et al. (2004) Cancer Cell 5:221-230; Camirand, A. et al. (2005) Breast Cancer Research 7:R570-R579 (DOI 10.1186/bcr1028); Camirand, A. and Pollak, M. (2004) Brit. J. Cancer 90:1825-1829; Garcia-Echeverria, C. et al. (2004) Cancer Cell 5:231-239; Sachdev D, and Yee D., Mol Cancer Ther. 2007 January; 6(1):1-12; Hofmann F., and Garcia-Echeverria C., Drug Discov Today 2005 10:1041-7). Agents inhibiting the IGF-1R pathway have demonstrated anti-tumor efficacy in multiple human cancer models both in vitro and in vivo, particularly in pediatric models of Ewing's sarcoma and rhabdomyosarcoma (Manara M C, et al. Int J Oncol 2005 27:1605-16). Despite early hints of efficacy in patients with sarcoma, results to date of IGF-1R inhibitors in early clinical trials have not been impressive, indicating that patient selection strategies and rational combinations may be needed to move forward with this approach (Tolcher A. W., et al. Journal of Clinical Oncology, 2007 ASCO Annual Meeting Proceedings Part I. Vol 25, No. 18S (June 20 Supplement), 2007: 3002). Data acquired this far, has not indicated that activation, overexpression, or amplification of members of the IGF-1R pathway will predict responsiveness.

The epidermal growth factor receptor (EGFR) family comprises four closely related receptors (HER1/EGFR, HER2, HER3 and HER4) involved in cellular responses such as differentiation and proliferation. Over-expression of the EGFR kinase, or its ligand transforming growth factor-alpha (TGF-alpha), is frequently associated with many cancers, including breast, lung, colorectal, ovarian, renal cell, bladder, head and neck cancers, glioblastomas, and astrocytomas, and is believed to contribute to the malignant growth of these tumors. A specific deletion-mutation in the EGFR gene (EGFRvIII) has also been found to increase cellular tumorigenicity. Activation of EGFR stimulated signaling pathways promote multiple processes that are potentially cancer-promoting, e.g. proliferation, angiogenesis, cell motility and invasion, decreased apoptosis (programmed cell death) and induction of drug resistance. Increased HER1/EGFR expression is frequently linked to advanced disease, metastases and poor prognosis. For example, in non small cell lung cancer (NSCLC) and gastric cancer, increased HER1/EGFR expression has been shown to correlate with a high metastatic rate, poor tumor differentiation and increased tumor proliferation.

Mutations which activate the EGF receptor's intrinsic protein tyrosine kinase activity and/or increase downstream signaling have been observed in NSCLC and glioblastoma. However the role of mutations as a principle mechanism in conferring sensitivity to EGFR kinase inhibitors, for example erlotinib (TARCEVA®) or gefitinib (IRESSA™), has been controversial. Recently, a mutant form of the full length EGFR has been reported to predict responsiveness to the EGFR tyrosine kinase inhibitor gefitinib (Paez, J. G. et al. (2004) Science 304:1497-1500; Lynch, T. J. et al. (2004) N. Engl. J. Med. 350:2129-2139). Cell culture studies have shown that cell lines which express the mutant form of EGFR (i.e. H3255) were more sensitive to growth inhibition by the EGFR tyrosine kinase inhibitor gefitinib, and that much higher concentrations of gefitinib was required to inhibit the tumor cell lines expressing wild type EGFR. These observations suggests that specific mutant forms of EGFR may reflect a greater sensitivity to EGFR kinase inhibitors, but do not identify a completely non-responsive phenotype.

The development for use as anti-tumor agents of compounds that directly inhibit the kinase activity of EGFR, as well as antibodies that reduce EGFR kinase activity by blocking EGFR activation, are areas of intense research effort (de Bono J. S. and Rowinsky, E. K. (2002) Trends in Mol. Medicine. 8:S19-S26; Dancey, J. and Sausville, E. A. (2003) Nature Rev. Drug Discovery 2:92-313). Erlotinib (e.g. erlotinib HCl, also known as TARCEVA® or OSI-774) is an orally available inhibitor of EGFR kinase. In vitro, erlotinib has demonstrated substantial inhibitory activity against EGFR kinase in a number of human tumor cell lines, including colorectal and breast cancer (Moyer J. D. et al. (1997) Cancer Res. 57:4838), and preclinical evaluation has demonstrated activity against a number of EGFR-expressing human tumor xenografts (Pollack, V. A. et al (1999) J. Pharmacol. Exp. Ther. 291:739). More recently, erlotinib has demonstrated promising activity in Phase I and II trials in a number of indications, including head and neck cancer (Soulieres, D., et al. (2004) J. Clin. Oncol. 22:77), NSCLC (Perez-Soler R, et al. (2001) Proc. Am. Soc. Clin. Oncol. 20:310a, abstract 1235), colorectal cancer (CRC) (Oza, M., et al. (2003) Proc. Am. Soc. Clin. Oncol. 22:196a, abstract 785) and metastatic breast cancer (MBC) (Winer, E., et al. (2002) Breast Cancer Res. Treat. 76:5115a, abstract 445). In a Phase III trial, erlotinib monotherapy significantly prolonged survival, delayed disease progression and delayed worsening of lung cancer-related symptoms in patients with advanced, treatment-refractory NSCLC (Shepherd, F. et al. (2004) J. Clin. Oncology, 22:14 S (July 15 Supplement), Abstract 7022). While most of the clinical trial data for erlotinib relate to its use in NSCLC, preliminary results from Phase I/II studies have demonstrated promising activity for erlotinib and capecitabine/erlotinib combination therapy in patients with wide range of human solid tumor types, including CRC (Oza, M., et al. (2003) Proc. Am. Soc. Clin. Oncol. 22:196a, abstract 785) and MBC (Jones, R. J., et al. (2003) Proc. Am. Soc. Clin. Oncol. 22:45a, abstract 180). In November 2004 the U.S. Food and Drug Administration (FDA) approved TARCEVA® for the treatment of patients with locally advanced or metastatic NSCLC after failure of at least one prior chemotherapy regimen. TARCEVA® is the only drug in EGFR class to demonstrate in a Phase III clinical trial an increase in survival in advanced NSCLC patients.

IGF-1R belongs to the insulin receptor family that includes the Insulin Receptor (IR), IGF-1R (homodimer), IGF-1R/IR (hybrid receptor), and IGF-2R (mannose 6-phosphate receptor). IGF-1R/IR hybrids act as homodimers, preferentially binding and signaling with IGFs. IR exists in two isoforms: IR-B (traditional insulin receptor) and IR-A (a fetal form which is re-expressed in selected tumors and preferentially binds IGF-II). IGF-2R is a non-signaling receptor that acts as a "sink" for IGF-II (Pollak M. N., et al. Nat Rev Cancer 2004 4:505-18). Six well-characterized insulin-like growth factor binding proteins (IGFBP-1 through -6) associate with IGF ligands to stabilize the IGFs and modulate their ability to bind the IGF-1R.

IGF-1R is a transmembrane RTK that binds primarily to IGF-1 but also to IGF-II and insulin with lower affinity. Binding of IGF-1 to its receptor results in activation of it's tyrosine kinase activity, intermolecular receptor autophosphorylation, and phosphorylation of cellular substrates, including IRS1 and Shc, leading to activation of the PI3K/Akt and mitogen-activated protein kinase (MAPK) pathways (Adams T. E., et al. Cell Mol Life Sci 2000 57:1050-93; Pollak M. N., et al. Nat Rev Cancer 2004 4:505-18; Baserga R., Exp Cell Res 1999 253:1-6). The ligand-activated IGF-1R induces mitogenic activity in normal cells and plays an important role in abnormal growth. A major physiological role of the IGF-1 system is the promotion of normal growth and regeneration. Overexpressed IGF-1R (type 1 insulin-like growth factor receptor) can initiate mitogenesis and promote ligand-dependent neoplastic transformation. Furthermore, IGF-1R plays an important role in the establishment and maintenance of the malignant phenotype. Unlike the epidermal growth factor (EGF) receptor, no mutant oncogenic forms of the IGF-1R have been identified. However, several oncogenes have been demonstrated to affect IGF-1 and IGF-1R expression. A correlation between a reduction of IGF-1R expression and resistance to transformation has been seen. Exposure of cells to mRNA antisense to IGF-1R RNA prevents soft agar growth of several human tumor cell lines. IGF-1R abrogates progression into apoptosis, both in vivo and in vitro. It has also been shown that a decrease in the level of IGF-1R below wild-type levels causes apoptosis of tumor cells in vivo. The ability of IGF-1R disruption to cause apoptosis appears to be diminished in normal, non-tumorigenic cells.

The IGF-1 pathway has an important role in human tumor development. IGF-1R overexpression is frequently found in various tumors (breast, colon, lung, sarcoma) and is often associated with an aggressive phenotype. High circulating IGF1 concentrations are strongly correlated with prostate, lung and breast cancer risk. Furthermore, IGF-1R is required for establishment and maintenance of the transformed phenotype in vitro and in vivo (Baserga R. *Exp. Cell. Res.,* 1999, 253, 1-6). The kinase activity of IGF-1R is essential for the transforming activity of several oncogenes: EGFR, PDGFR, SV40 T antigen, activated Ras, Raf, and v-Src. The expression of IGF-1R in normal fibroblasts induces neoplastic phenotypes, which can then form tumors in vivo. IGF-1R expression plays an important role in anchorage-independent growth. IGF-1R has also been shown to protect cells from chemotherapy-, radiation-, and cytokine-induced apoptosis. Conversely, inhibition of endogenous IGF-1R by dominant negative IGF-1R, triple helix formation or antisense expression vector has been shown to repress transforming activity in vitro and tumor growth in animal models. The IGF-1R signaling pathway also appears to be a robust target in colorectal cancer (CRC), based upon data demonstrating overexpress ion of the receptor and ligands in CRC, association with a more malignant phenotype, chemotherapy resistance, and correlation with a poor prognosis (Saltz, L. B., et al. J Clin Oncol 2007; 25(30): 4793-4799; Tripkovic I., et al. Med. Res. 2007 July; 38(5):519-25. Epub 2007 Apr. 26; Miyamoto S., et al. Clin Cancer Res. 2005 May 1; 11(9):3494-502; Nakamura M., et al. Clin Cancer Res. 2004 Dec. 15; 10(24):8434-41; Grothey A, et al. J Cancer Res Clin Oncol. 1999; 125(3-4):166-73).

There is a need for both more efficacious treatment for neoplasia and other proliferative disorders, and for more effective means for determining which tumors will respond to which treatment. Several groups have investigated or disclosed potential biomarkers to predict a patient's response to protein-tyrosine kinase inhibitors (see for example, PCT publications: WO 2004/063709, WO 2005/017493, WO 2004/111273, WO 2008/108986, WO 2007/001868, WO 2004/071572, WO 2003/078662, WO 2007/067500, WO 2005/070020, WO 2009/015233, WO 2009/023172, WO 2004/046386, WO 2008/070460, and WO 2010/022268; US published patent applications: US 2005/0019785, US 2007/0065858, US 2005/0164218, US 2009/0092596, US 2009/0093488, US 2009/0093488, US 2006/0140960, US 2009/0118175, US 2004/0132097, US 2003/0165954, US 2007/0218512, US 2007/0265185, US 2007/0270505, US 2007/0128636, US 2009/0092596, US 2007/0212738, US 2007/0237770, US 2009/0029354, US 2009/0092526, US 2006/0263775, US 2004/0018528, US 2006/0121539, US 2008/0131885, US 2005/0019785, US 2006/0263806, US 2007/0172857, US 2004/0048254, US 2009/0061454, US 2009/0123374, US 2007/0196352, US 2006/0078941, US 2008/0234138, US 2005/0170386, US 2002/0169562, US 2003/0053995, US 2007/0077577, US 2008/0187930, US 2006/0003365, US 2005/0260664, US 2008/0112888, US 2008/0019961, US 2008/0167532, US 2006/0234259, US 2004/0063120, US 2007/0092881, US 2008/0026481, US 2009/0092983, US 2004/0214203, US 2009/0136945, US 2007/0154915, US 2009/0155786, US 2008/0015160, US 2008/0312093, US 2008/0176229, US 2004/0157255, US 2007/0031871, US 2009/0061422, US 2008/0113874, US 2006/0019268, US 2007/0065858, US 2007/0231822, and US 2009/0023149, and U.S. Pat. Nos. 5,367,064, 7,368,551, 6,171,779, 7,342,108, 6,413,730, 7,526,387, 6,271,363, 6,251,628, and 7,569,349). Several biomarkers have been proposed for predicting the response to EGFR kinase inhibitors, including mutant KRAS as a predictor of non-responsiveness in colorectal cancer (e.g. see Brugger, W. et al. (2009) J Clin Oncol 27:15s, (suppl; abstr 8020); Siena, S et al (2009) JNCI 101(19):1308-1324; Riely and Ladanyi (2008) J Mol Diagnostics 10(6):493; Jimeno, A. et al. (2009) Cancer J. 15(2):110-13). In addition, several biomarkers, including mutant KRAS, have been disclosed that have potential in predicting a patient's response to IGF-1R kinase inhibitors (e.g. see Rodon, J. et al (2008) Mol Cancer Ther. 7:2575-2588; T. Pitts et al. (2009) EORTC Conference, Boston, Mass., abstract #2141; Huang, F. et al. (2009) Cancer Res. 69(1):161-170; Rodon, J. et al., (2008) Mol. Cancer. Ther. 7:2575-2588). However, in most instances no FDA-approved diagnostic tests have yet emerged that can effectively guide practicing physicians in the treatment of their patients with such inhibitors, or can indicate to the physician which tumors will respond most favorably to a combination of such an inhibitor with a standard chemotherapy agent.

During most cancer metastases, an important change occurs in a tumor cell known as the epithelial-mesenchymal transition (EMT) (Thiery, J.P. (2002) Nat. Rev. Cancer 2:442-454; Savagner, P. (2001) Bioessays 23:912-923; Kang Y. and Massague, J. (2004) Cell 118:277-279; Julien-Grille, S., et al. Cancer Research 63:2172-2178; Bates, R. C. et al. (2003) Current Biology 13:1721-1727; Lu Z., et al. (2003) Cancer Cell. 4(6):499-515)). EMT does not normally occur in healthy cells except during embryogenesis, though a transient EMT state is induced in epithelial wound healing to aid in the reconstruction of epithelial tissue. Epithelial cells, which are bound together tightly and exhibit polarity, change to a more mesenchymal cellular phenotype, in which these mesenchymal cells are held together more loosely, exhibit a loss of polarity, and have the ability to move within tissues. These mesenchymal-like cells can spread into tissues surrounding the original tumor, as well as separate from the tumor, invade blood and lymph vessels, and travel to new locations where they divide and form additional tumors. Recent research has demonstrated that epithelial cells respond well to EGFR and insulin-like growth factor-1 receptor (IGF-1R) kinase inhibitors, but that after an EMT the resulting mesenchymal-like tumor cells are much less sensitive to such inhibitors. (e.g. see Thompson, S. et al. (2005) Cancer Res. 65(20):9455-9462; U.S. Patent Application 60/997,514). Thus there is a pressing need for anti-cancer agents that can prevent or reverse tumor cell EMT events (e.g. stimulate a mesenchymal to epithelial transition (MET)), or inhibit the growth of the mesenchymal-like tumor cells resulting from EMT. Such agents should be particularly useful when used in conjunction with other anti-cancer drugs such as EGFR and IGF-1R kinase inhibitors. The present invention provides new methods for identification and characterization of compounds that modulate EMT.

As human cancers progress to a more invasive, metastatic state, multiple signaling programs regulating cell survival and migration are observed depending on cell and tissue contexts (Gupta, G. P., and Massague, J. (2006) Cell 127, 679-695). Recent data highlight the transdifferentiation of epithelial cancer cells to a more mesenchymal-like state, a process resembling epithelial-mesenchymal transition (EMT; (Oft, M., et al. (1996). Genes & development 10, 2462-2477; Perl, A. K., et al. (1998). Nature 392, 190-193), to facilitate cell invasion and metastasis (Brabletz, T. et al. (2005) Nat Rev Cancer 5, 744-749; Christofori, G. (2006) Nature 441, 444-450). Through EMT-like transitions mesenchymal-like tumor cells are thought to gain migratory capacity at the expense of proliferative potential. A mesenchymal-epithelial transition (MET) has been postulated to regenerate a more proliferative state and allow macrometastases resembling the primary tumor to form at distant sites (Thiery, J. P. (2002) Nat Rev Cancer 2, 442-454). EMT-like transitions in tumor cells result from transcriptional reprogramming over considerable periods of time (weeks to months) via transcription factors harboring zinc finger, forkhead, bHLH and HMG-box domains (Mani, S. A. et al. (2007) Proceedings of the National Academy of Sciences of the United States of America 104, 10069-10074; Peinado, H. et al. (2007) Nat Rev Cancer 7, 415-428). The loss of E-cadherin and transition to a more mesenchymal-like state, with increased expression of mesenchymal proteins such as vimentin or fibronectin, likely serves a major role in the progression of cancer (Matsumura, T. et al. (2001) Clin Cancer Res 7, 594-599; Yoshiura, K. et al. (1995). Proceedings of the National Academy of Sciences of the United States of America 92, 7416-7419) and the acquisition of a mesenchymal phenotype has been correlated with poor prognosis (Baumgart, E. et al. (2007) Clin Cancer Res 13, 1685-1694; Kokkinos, M. I. Et al. (2007) Cells, tissues, organs 185, 191-203; Willipinski-Stapelfeldt, B. et al. (2005) Clin Cancer Res 11, 8006-8014.). Targeting tumor-derived and/or tumor-associated stromal cells provides a unique mechanism to block EMT-like transitions and inhibit the survival of invading cells.

The cellular changes associated with EMT-like transitions alter the dependence of carcinoma cells on EGFR signaling networks for survival. It has been observed that an EMT-like transition was associated with cellular insensitivity to the EGFR kinase inhibitor erlotinib (Thomson, S. et al. (2005) Cancer Research 65, 9455-9462; Witta, S. E., et al. (2006) Cancer Research 66, 944-950; Yauch, R. L., et al. (2005) Clin Cancer Res 11, 8686-8698), in part from EGFR independent activation of either or both the PI3-kinase or Mek-Erk pathways (Buck, E. et al. (2007). Molecular Cancer Therapeutics 6, 532-541). Similar data correlating EMT status to sensitivity to EGFR kinase inhibitors have been reported in pancreatic, CRC (Buck, E. et al. (2007) Molecular Cancer Therapeutics 6, 532-541) bladder (Shrader, M. et al. (2007) Molecular Cancer Therapeutics 6, 277-285) and HNSCC (Frederick et al. (2007) Molecular Cancer Therapeutics 6, 1683-1691) cell lines, xenografts and in patients (Yauch, R. L., et al. (2005) Clin Cancer Res 11, 8686-8698). The molecular determinants to alternative routes of activation of the PI3-kinase and Erk pathways, which can bypass cellular sensitivity to EGFR kinase inhibitors, have been actively investigated (Chakravarti, A. et al. (2002) Cancer research 62, 200-207; Engelman, J. A. et al. (2007) Science 316:1039-1043).

Although considerable progress has been made in recent years in elucidating factors that influence tumor cell sensitivity to EGFR or IGF-1R kinase inhibitors, there remains a critical need for improved methods for determining the best mode of treatment for any given cancer patient and for the incorporation of such determinations into more effective treatment regimens for cancer patients, whether such inhibitors are used as single agents or combined with other anti-cancer agents. The present invention provides new methods for determining which tumors will respond most effectively to treatment with such inhibitors.

SUMMARY OF THE INVENTION

The present invention provides a method of determining the EMT status of tumor cells, comprising: measuring in a sample of the tumor cells the relative expression level of each gene of an EMT gene signature (EMTGS); wherein the EMTGS consists of a group of genes that have been determined to be coordinately regulated during EMT; calculating an EMTGS index score for said tumor cells by applying an algorithm (e.g. algorithm A or algorithm $A^1$, as described herein) to the measured expression level values that incorporates the contributions of co-correlated genes; and determining if said EMTGS index score is more similar to an EMTGS index score from a reference epithelial tumor cell or an EMTGS index score from a reference mesenchymal-like tumor cell, and thus determining the EMT status of the sample tumor cells. This method may be utilized as part of a number of methods to identify new anticancer compounds that inhibit EMT or that function optimally in a particular phase of EMT.

The present invention also provides a method of determining whether a group of genes are coordinately regulated during EMT by a process including the steps (a) selection of an initial group of genes that are coordinately regulated in multiple tumor cell models of EMT; and (b) repeated addition or removal of genes from said group to maximize the number of genes whose expression is co-correlated in multiple human tumor datasets.

The present invention further provides a method of determining the EMT status of tumor cells, comprising: measuring in a sample of the tumor cells the relative expression level of each gene of an EMT gene signature (EMTGS), wherein the EMTGS consists essentially of the following genes: SERPINA3, ACTN1, AGR2, AKAP12, ALCAM, AP1M2, AXL, BSPRY, CCL2, CDH1, CDH2, CEP170, CLDN3, CLDN4, CNN3, CYP4X1, DNMT3A, DSG3, DSP, EFNB2, EHF, ELF3, ELF5, ERBB3, ETV5, FLRT3, FOSB, FOSL1, FOXC1, FXYD5, GPD1L, HMGA1, FIMGA2, HOPX, IFI16, IGFBP2, IHH, IKBIP, IL-11, IL-18, IL6, IL8, ITGA5, ITGB3, LAMB1, LCN2, MAP7, MB, MMP7, MMP9, MPZL2, MSLN, MTA3, MTSS1, OCLN, PCOLCE2, PECAM1, PLAUR, PLXNB1, PPL, PPP1R9A, RASSF8, SCNN1A, SERPINB2, SERPINE1, SFRP1, SH3YL1, SLC27A2, SMAD7, SNAI1, SNAI2, SPARC, SPDEF, SRPX, STAT5A, TBX2, TJP3, TMEM125, TMEM45B, TWIST1, VCAN, VIM, VWF, XBP1, YBX1, ZBTB10, ZEB1, ZEB2; calculating an EMTGS index score for said tumor cells by applying an algorithm (e.g. algorithm A or algorithm $A^1$) to the measured expression level values that incorporates the contributions of co-correlated genes; and determining if said EMTGS index score is more similar to an EMTGS index score from a reference epithelial tumor cell or an EMTGS index score from a reference mesenchymal-like tumor cell, and thus determining the EMT status of the sample tumor cells.

The present invention further provides a method of identifying a human tumor as likely to be responsive or non-responsive to treatment with an EGFR kinase inhibitor, comprising: measuring in a sample of the tumor cells the relative expression level of each gene of an EMT gene signature (EMTGS), wherein the EMTGS consists essentially of the following genes: SERPINA3, ACTN1, AGR2, AKAP12, ALCAM, AP1M2, AXL, BSPRY, CCL2, CDH1, CDH2, CEP170, CLDN3, CLDN4, CNN3, CYP4X1, DNMT3A, DSG3, DSP, EFNB2, EHF, ELF3, ELF5, ERBB3, ETV5, FLRT3, FOSB, FOSL1, FOXC1, FXYD5, GPD1L, HMGA1, HMGA2, HOPX, IFI16, IGFBP2, IHH, IKBIP, IL-11, IL-18, IL6, IL8, ITGA5, ITGB3, LAMB1, LCN2, MAP7, MB, MMP7, MMP9, MPZL2, MSLN, MTA3, MTSS1, OCLN, PCOLCE2, PECAM1, PLAUR, PLXNB1, PPL, PPP1R9A, RASSF8, SCNN1A, SERPINB2, SERPINE1, SFRP1, SH3YL1, SLC27A2, SMAD7, SNAI1, SNAI2, SPARC, SPDEF, SRPX, STAT5A, TBX2, TJP3, TMEM125, TMEM45B, TWIST1, VCAN, VIM, VWF, XBP1, YBX1, ZBTB10, ZEB1, ZEB2; calculating an EMTGS index score for said tumor cells by applying an algorithm (e.g. algorithm A or algorithm $A^1$) to the measured expression level values that incorporates the contributions of co-correlated genes; and determining if the EMTGS index score is above a defined threshold that indicates that the tumor is likely to be responsive to an EGFR kinase inhibitor, or below said threshold and thus likely to be non-responsive to an EGFR kinase inhibitor.

The present invention further provides a method of identifying a human tumor as likely to be responsive or non-responsive to treatment with an IGF-1R kinase inhibitor, comprising: measuring in a sample of the tumor cells the relative expression level of each gene of an EMT gene signature (EMTGS), wherein the EMTGS consists essentially of the following genes: SERPINA3, ACTN1, AGR2, AKAP12, ALCAM, AP1M2, AXL, BSPRY, CCL2, CDH1, CDH2, CEP170, CLDN3, CLDN4, CNN3, CYP4X1, DNMT3A, DSG3, DSP, EFNB2, EHF, ELF3, ELF5, ERBB3, ETV5, FLRT3, FOSB, FOSL1, FOXC1, FXYD5, GPD1L, HMGA1, HMGA2, HOPX, IFI16, IGFBP2, IHH, IKBIP, IL-11, IL-18, IL6, IL8, ITGA5, ITGB3, LAMB1, LCN2, MAP7, MB, MMP7, MMP9, MPZL2, MSLN, MTA3, MTSS1, OCLN, PCOLCE2, PECAM1, PLAUR, PLXNB1, PPL, PPP1R9A, RASSF8, SCNN1A, SERPINB2, SERPINE1, SFRP1, SH3YL1, SLC27A2, SMAD7, SNAI1, SNAI2, SPARC, SPDEF, SRPX, STAT5A, TBX2, TJP3, TMEM125, TMEM45B, TWIST1, VCAN, VIM, VWF, XBP1, YBX1, ZBTB10, ZEB1, ZEB2; calculating an EMTGS index score for said tumor cells by applying an algorithm (e.g. algorithm A or algorithm $A^1$) to the measured expression level values that incorporates the contributions of co-correlated genes; and determining if the EMTGS index score is above a defined threshold that indicates that the tumor is likely to be responsive to an IGF-1R kinase inhibitor, or below said threshold and thus likely to be non-responsive to an IGF-1R kinase inhibitor.

The present invention further provides methods for treatment of cancer patients incorporating these diagnostic methods.

The present invention further provides additional related methods wherein the 88 gene EMTGS described above is substituted by a subset of the genes of this signature, or by an alternative signature.

FIG. 1: 4-Way Venn Analysis of H358 EMT cell models. Significant genes identified by Affymetrix microarray analysis that were up regulated or down regulated in H358 tumor cells treated with 1] dual ligands HGF+OSM, 2] TGFβ, 3] doxycycline to induce expression of snai1, or 4] doxycycline to induce expression of zeb1 were compared by Venn analysis using the 4-way Venn diagram generator (http://www.panglossom/seidl/Protocols/venn4.cgi). 101 genes were identified that were common in all 4 cell models induced to undergo an epithelial to mesenchymal transition.

Figure 2:
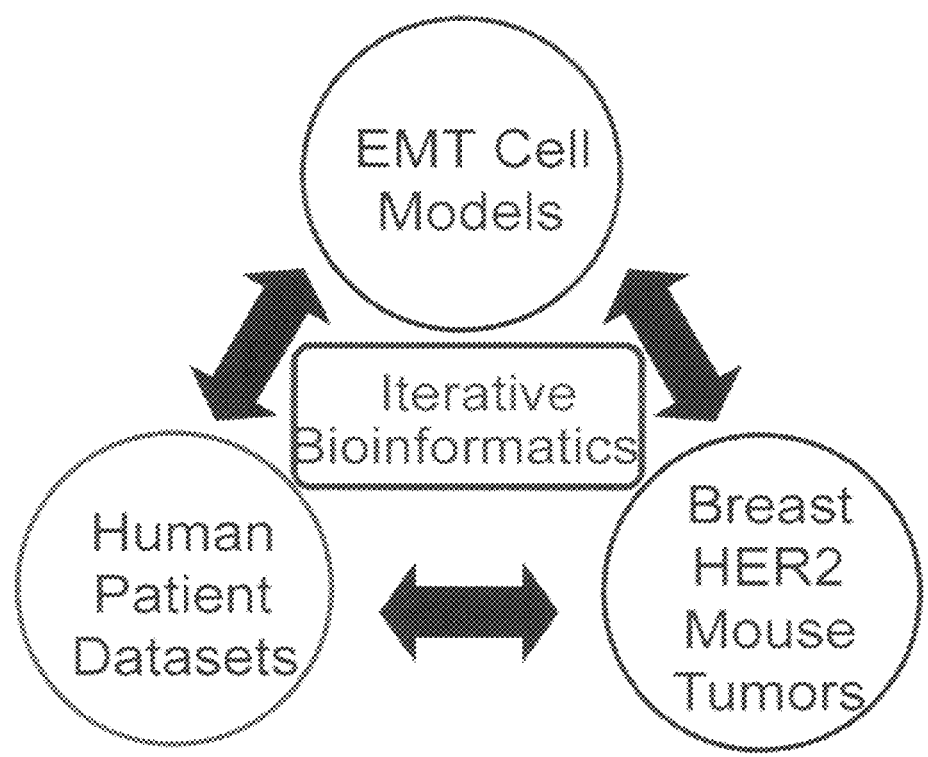

FIG. 2: Process for Generation of 88 gene EMT Gene Signature.

Figure 3A:
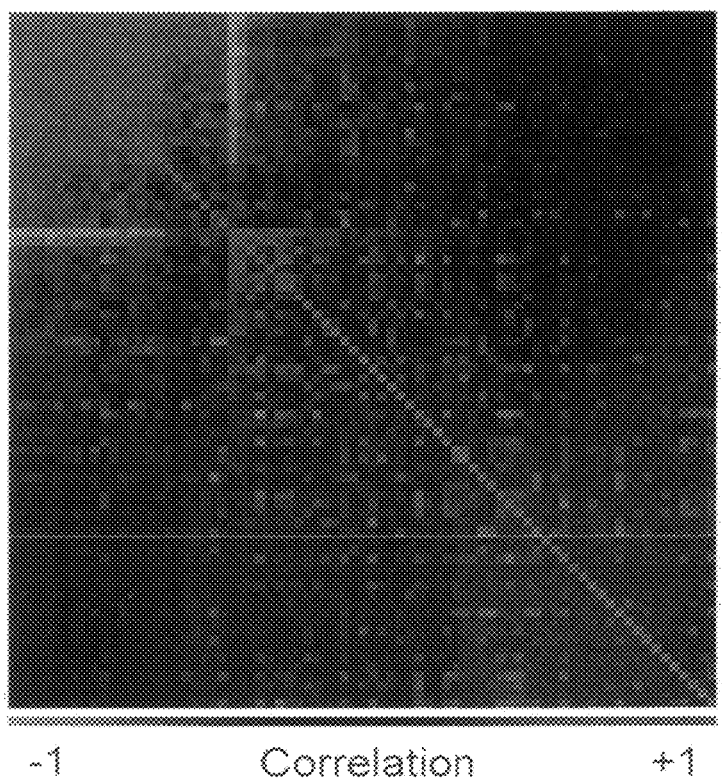
Figure 3B:
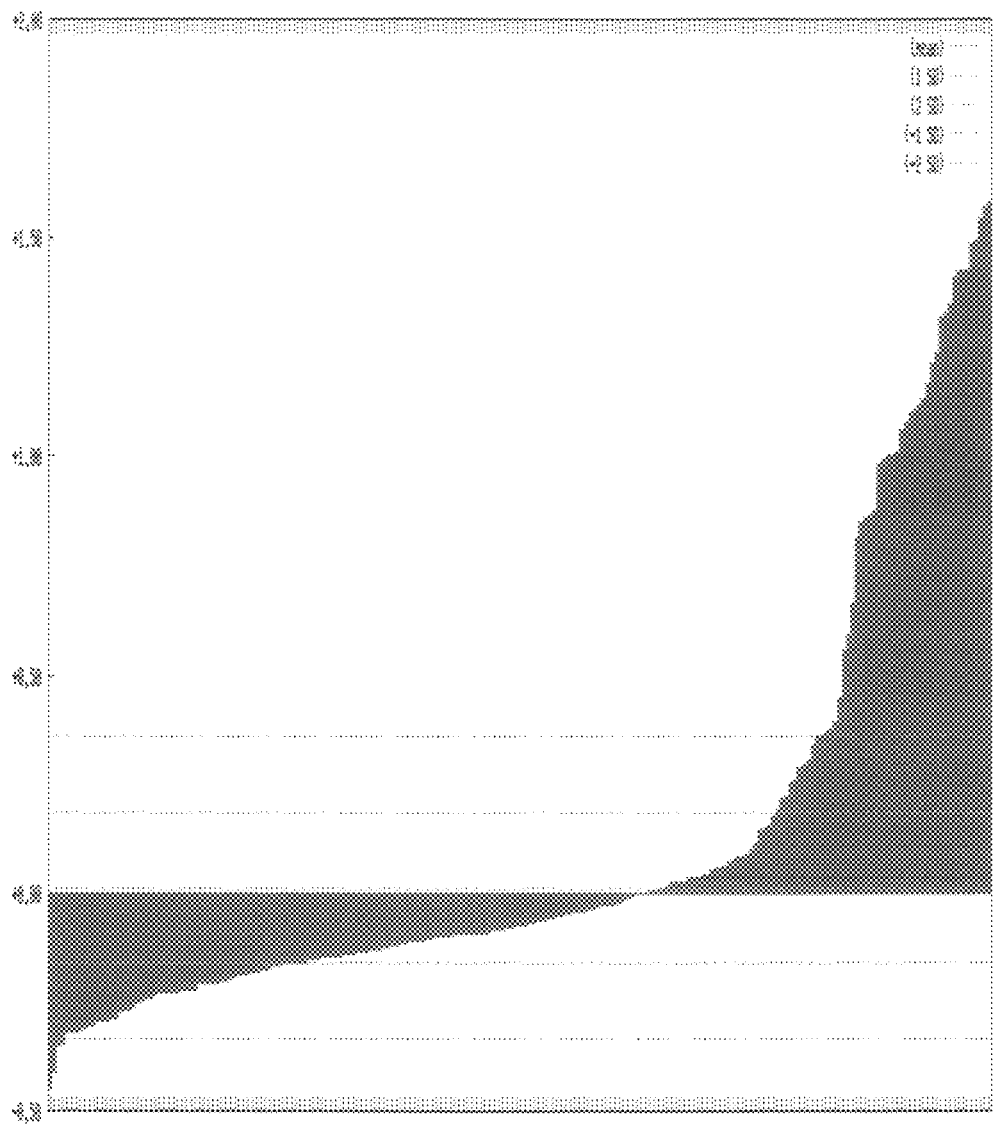

FIG. 3: Gene Correlations in breast HER2 archive samples. The 91 genes identified from analysis of epithelial to mesenchymal transition in H358 cells were analyzed for co-correlation using proprietary custom software running algorithm A. [A] Correlation map with ErbB3 as the anchor gene. Genes above the yellow line are those that have passed a P-value cutoff for correlation to the anchor gene. [B] Waterfall plot of gene index values for the correlations of the 91 genes.

Figure 4A:
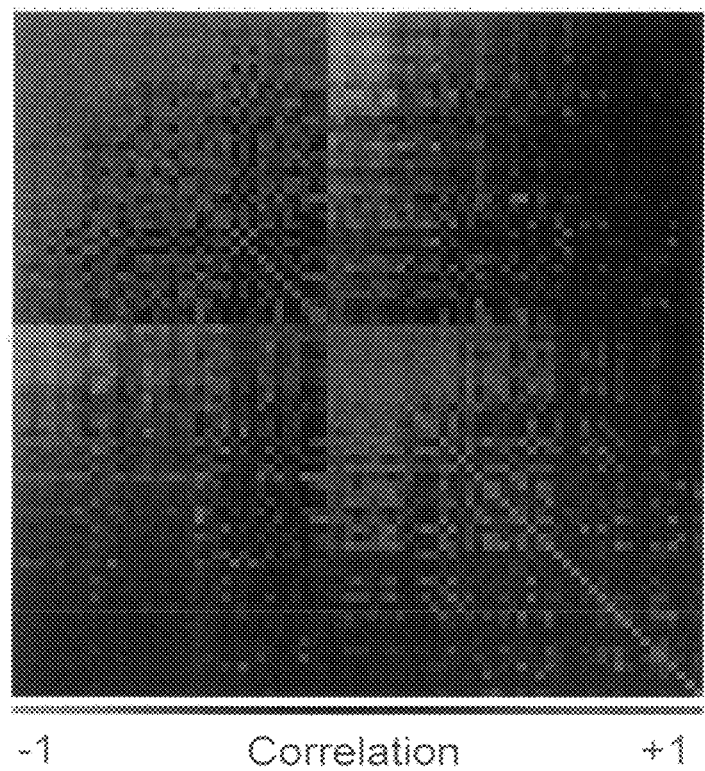

FIG. 4: 88 EMT Gene Signature Gene Correlations with Breast HER2 Archive Dataset. EMT gene signature (Table 1) was used for co-correlation analysis using proprietary custom software running algorithm A. [A] Breast HER2 archive microarray dataset co-correlation map with ERBB3 as anchor gene. [B] Waterfall plot of gene index values in Breast HER2 archive dataset.

FIG. 5: 88 EMT Gene Signature Gene Correlations with human tumor datasets (Genelogic) demonstrates broad applicability of the 88 gene EMTGS. The 88 gene EMT gene signature (Table 1) was used for co-correlation analysis using algorithm A with AVEO software. A. Co-correlation map of 88 gene EMTGS in human solid tumor combined GeneLogic dataset (breast, colon, kidney, liver, lung, pancreas, prostate and stomach/esophagus tumors; U133 Plus 2.0 platform) with vimentin as anchor gene. B. Waterfall plots of EMT index scores in GeneLogic solid tumor datasets (The tumors are, left to right, breast, colon, kidney, liver, lung, pancreatic, prostate and stomach). C. Heat map of expression values of the 88 genes in each of the tumors, arranged by index score. D. Co-correlation plots of the 88 gene EMTGS in each of 6 GeneLogic tumor datasets (breast, colon, kidney, lung, pancreas and stomach/esophagus) run independently.

FIG. 6: Molecular characterization of EMT models and reversion using 88 gene EMT gene signature. A) Induction of EMT with indicated ligands in H358, CFPAC1, H1650, and H292 tumor cells in vitro. B) Induction of EMT by doxycycline induction of Zeb1, Snai1 or activated TGF-beta (aTGFβ) proteins in H358 tumor cell models. N.B. Green=down-regulated genes; Red=up-regulated genes.

Figure 7:
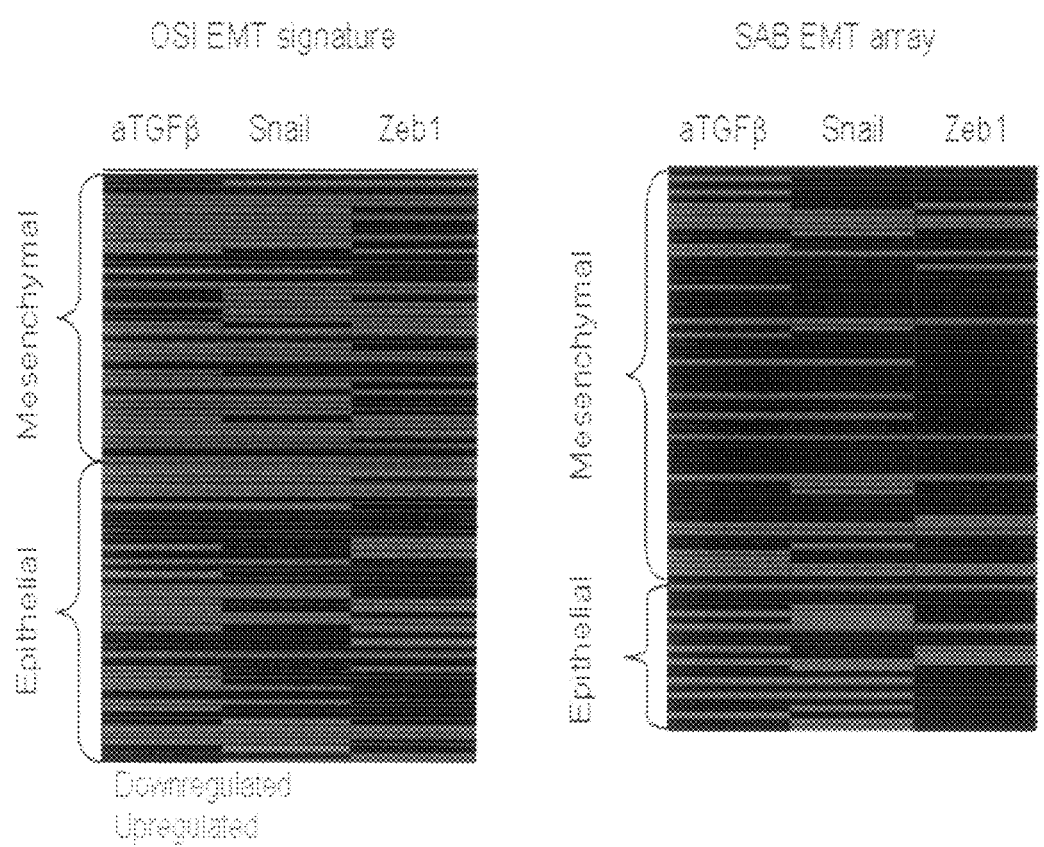

FIG. 7: Comparison of OSI EMT gene signature and SABiosciences EMT Array. H358 cells were stimulated to undergo EMT with ectopic expression of three drivers, aTGFb, Snai1, and Zeb1. After 7 days, cells were harvested for RNA which was processed to cDNA and run on the two individual qPCR plates. Fold changes for each gene were calculated relative to untreated cells.

FIG. 8: Summary of EMT morphologic, marker and phenotypic changes and corresponding changes to erlotinib sensitivity and EMT index score. (A.) Changes induced in H358 ligand driven models in vitro. Cells were incubated for 7 days with the ligands indicated. For immunofluorescence, cells were fixed and stained for immunoreactivity for E-cadherin (green), vimentin (red) and counterstained with TOPRO-3 to visualize nuclei. In separate experiments, cells were also evaluated for protein abundance by western blot for well-characterized EMT markers, and qPCR quantification of changes to the 88 gene EMTGS. Finally, cells were examined for proliferative and invasive capacity in vitro as indicators of phenotypic changes. Qualitative results of all experiments are indicated as follows: Mild change (+), moderate change (++) and robust change (+++). (B.) Changes induced in H358 engineered models of Snai1 and Zeb1 driven by Doxycycline (Dox).

FIG. 9: Co-correlation maps of progressive versions of the 88 gene EMTGS (Table 5) in GeneLogic Lung U133 Plus 2.0 dataset.

FIG. 10: Co-correlation maps of progressive versions of the 88 gene EMTGS (Table 5) in GeneLogic Pancreas U133 Plus 2.0 dataset.

FIG. 11: Influence of individual genes and gene sets on EMT index scores. Waterfall plots of index scores in GeneLogic Lung AB dataset. Plots are of index scores in the same tumor for the full 88 gene signature, the 88 gene signature excluding ITGA5 or CDH1, the 88 gene signature excluding 8 genes found in common with the Choi EMT signature and the Bunn gefitinib resistance signature (80 gene index), and finally, only the 44 epithelial genes of the 88 gene EMTGS (E-only index).

FIG. 12: Influence of individual genes and gene sets on EMT index scores. For each tumor, index scores from two lists as described for FIG. 11 were plotted against each other to evaluate the impact of subtracting genes from the signature.

Figure 13A:
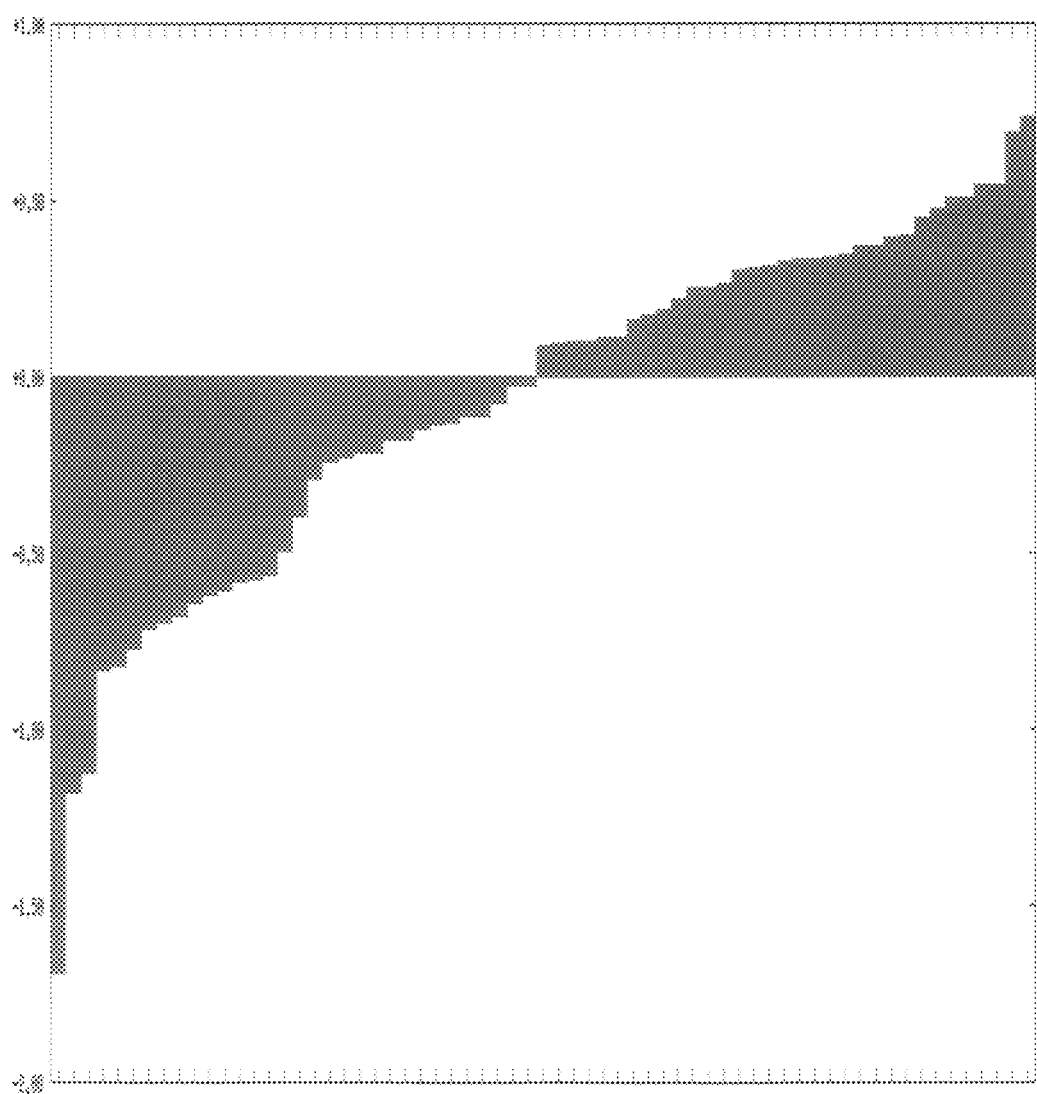
Figure 13B:
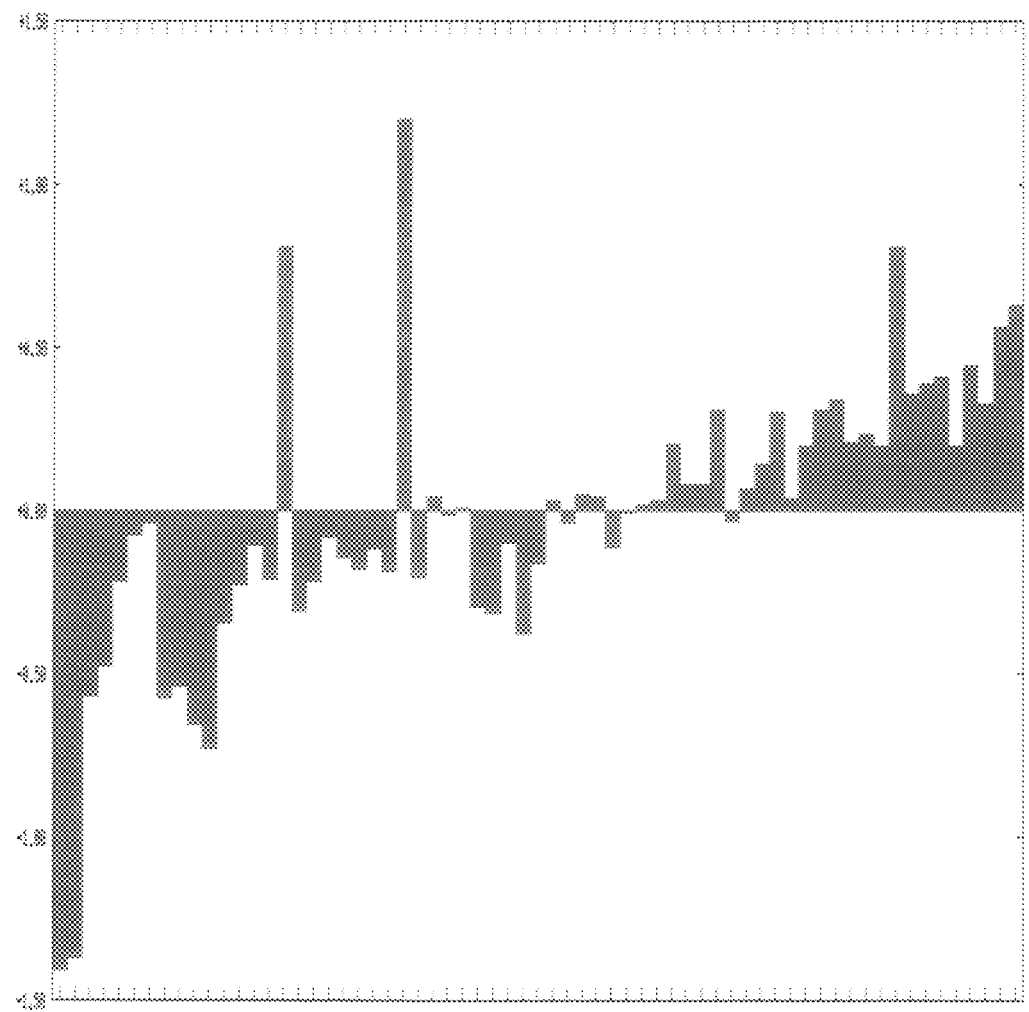
Figure 13C:
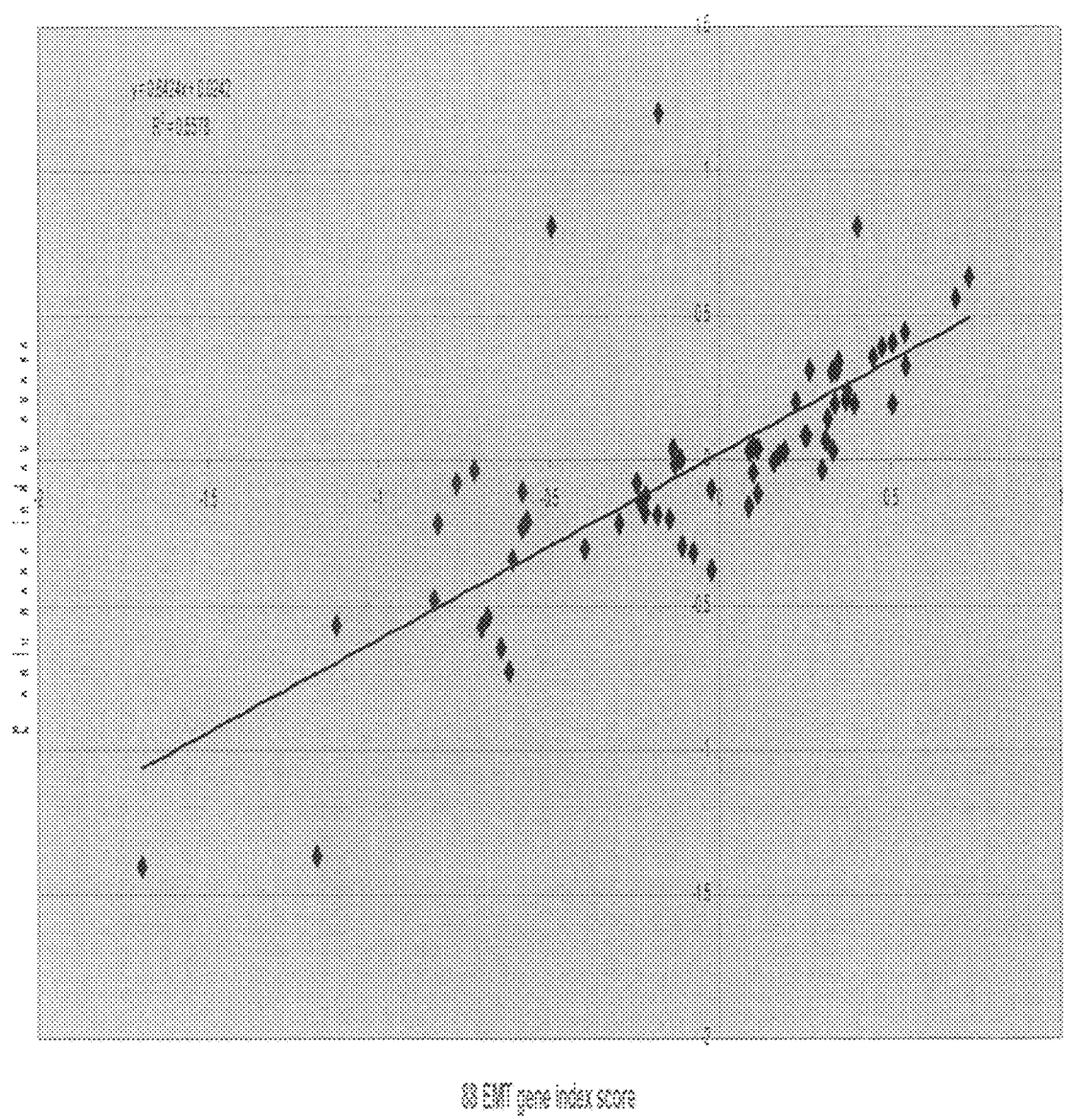

FIG. 13: (A.) Waterfall plot of EMT index scores for the full 88 gene signature in the GeneLogic Pancreas Plus 2.0 dataset. (B) Waterfall plot of EMT index scores for the epithelial-only signature in the GeneLogic Pancreas Plus 2.0 dataset. (C.) For each tumor, index scores from the 88 gene signature and the epithelial-only signature were plotted against each other.

Figure 14:
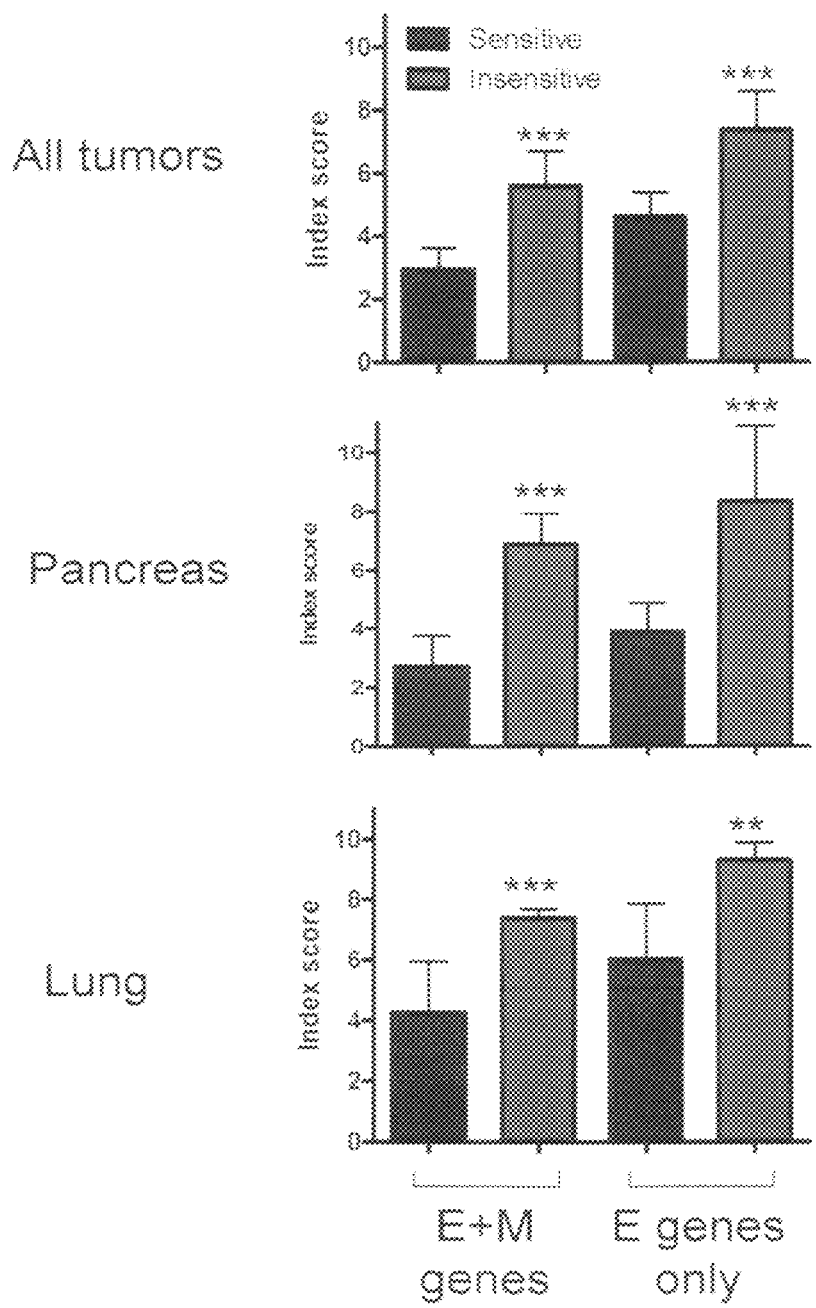

FIG. 14: Comparison of EMT index scores calculated from qPCR data from erlotinib-sensitive and -insensitive cell lines. Index scores in the left two columns are from the full 88 gene EMTGS. Index scores in the right two columns are from the epithelial-only gene signature. Cell lines from lung, pancreas, colon and breast tumors were evaluated together (All Tumors) and compared to cell lines from pancreatic tumors and lung tumors separately.

Figure 15:
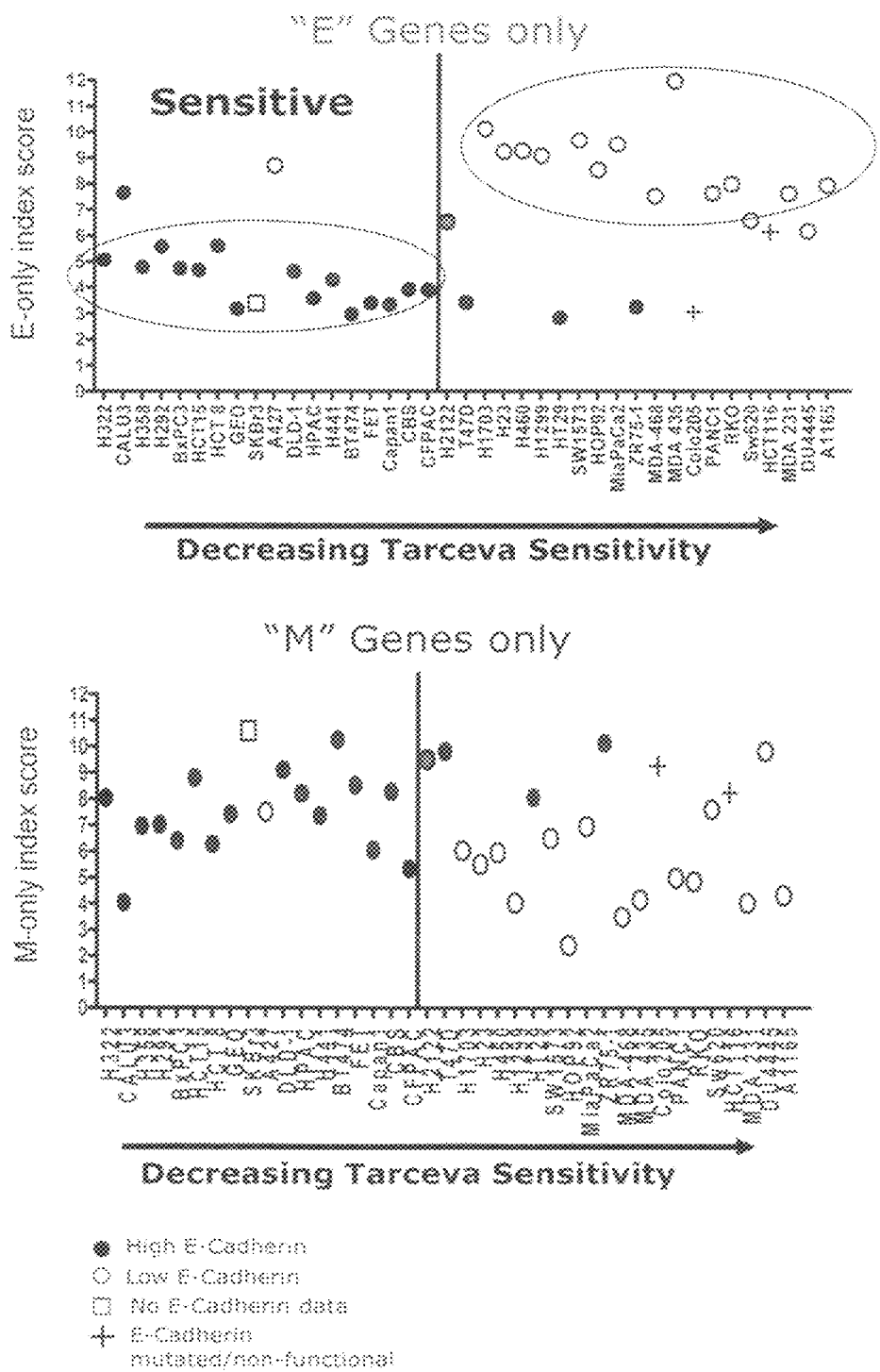

FIG. 15: Predictive value of epithelial and mesenchymal genes for erlotinib sensitivity in cell lines. Index scores were calculated using the 44 epithelial genes or the 44 mesenchymal genes in the EMT signature and plotted for each cell line, arranged according to erlotinib sensitivity (calculated with Algorithm A).

Figure 16:
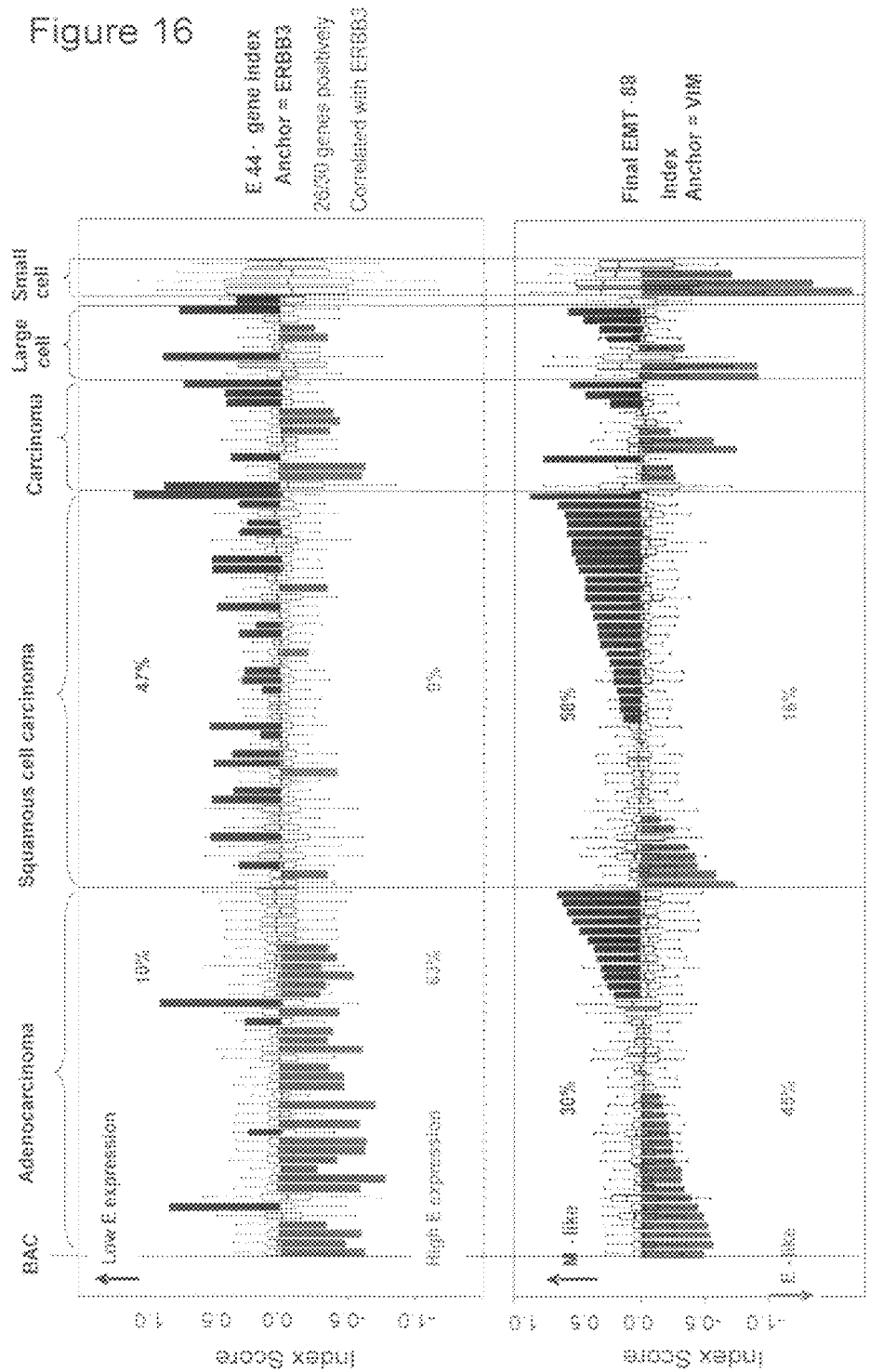

FIG. 16: Comparison of index scores in GeneLogic Lung AB dataset calculated from the full 88 gene EMTGS and the epithelial-only gene signature. Tumors are arranged according to the 88 gene EMTGS index scores and categorized by tumor subtype. The boxplot in each sample shows the distribution of 1000 index scores based on random genelists, each having the same size as the signature. The red and blue bars indicate the signature index scores of samples that are significantly low and high (P=0.05), respectively, based on the distribution of 1000 index scores from random genelists in each sample. For samples with index scores that are neither significantly low nor high, their index scores are depicted in yellow.

Figure 17:
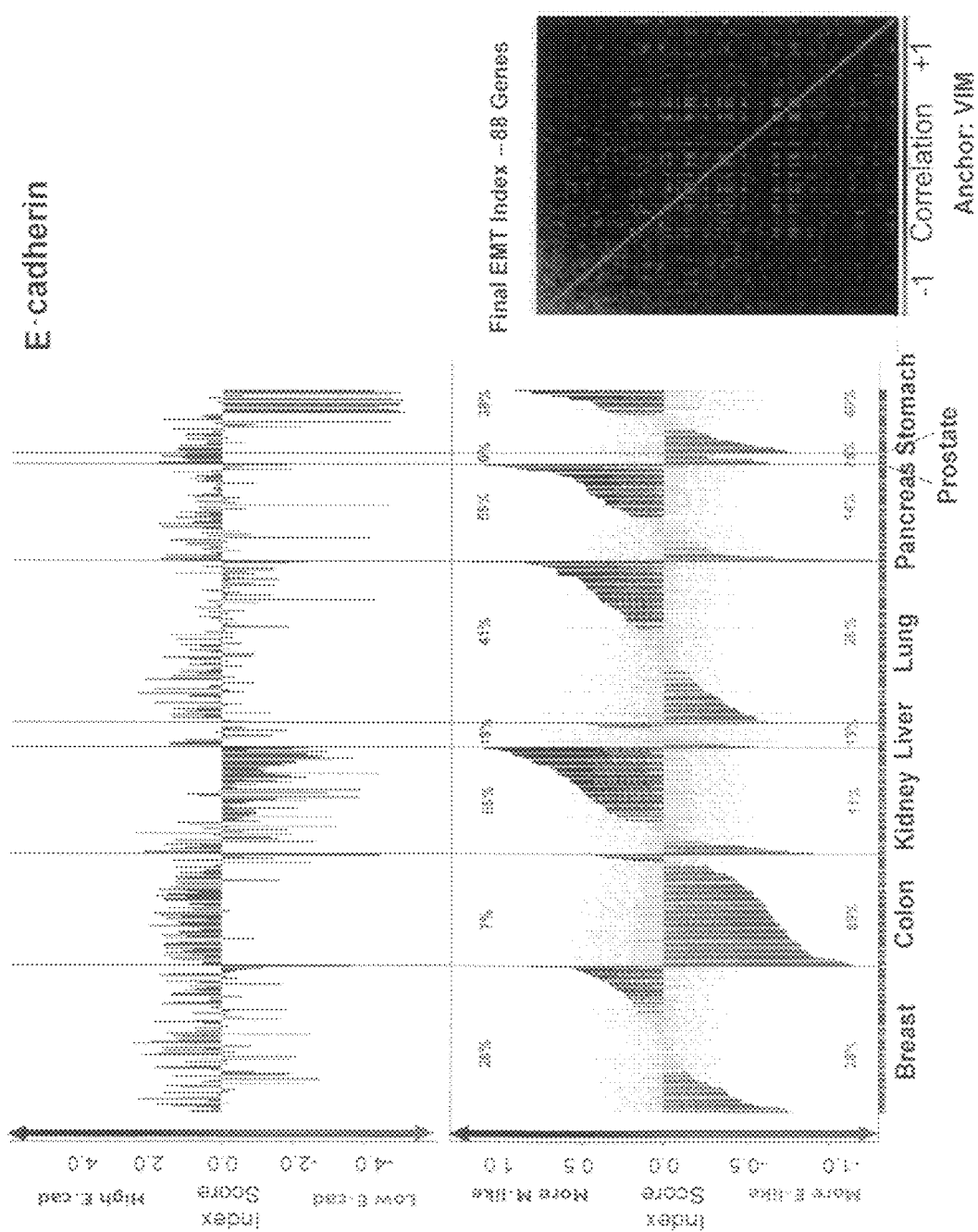

FIG. 17: Comparison of 88 EMTGS index scores with E-cadherin index score (microarray signal intensity) in GeneLogic solid tumor dataset. The boxplot in each sample shows the distribution of 1000 index scores based on random genelists, each having the same size as the signature. The red and blue bars indicate the signature index scores of samples that are significantly low and high (P=0.05), respectively, based on the distribution of 1000 index scores from random genelists in each sample. For samples with index scores that are neither significantly low nor high, their index scores are depicted in yellow.

Figure 18:
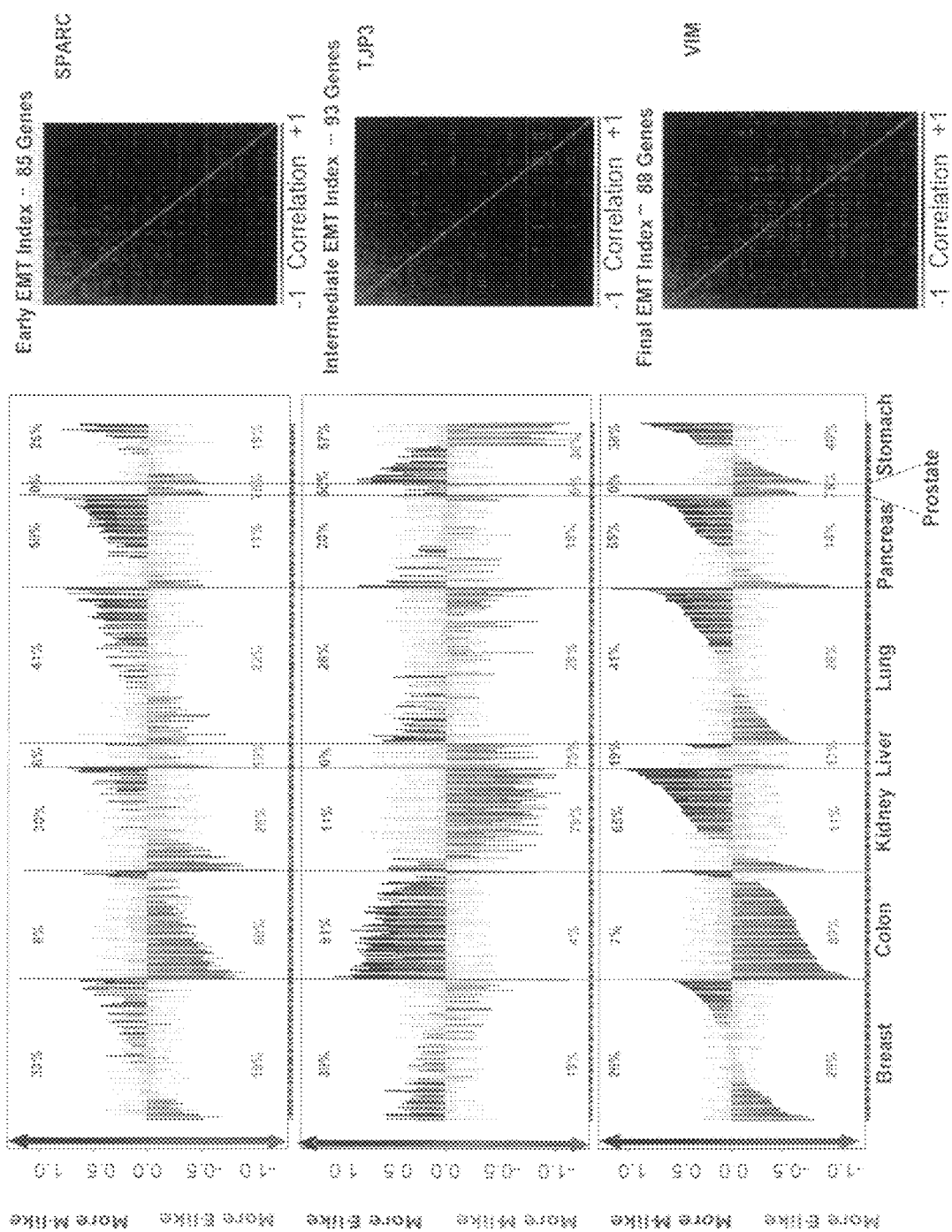

FIG. 18: Comparison of index scores from 3 progressive versions of the EMT gene signature in GeneLogic solid tumor dataset. The boxplot in each sample shows the distribution of 1000 index scores based on random genelists, each having the same size as the signature. The red and blue bars indicate the signature index scores of samples that are significantly low and high (P=0.05), respectively, based on the distribution of 1000 index scores from random genelists in each sample. For samples with index scores that are neither significantly low nor high, their index scores are depicted in yellow.

Figure 19:
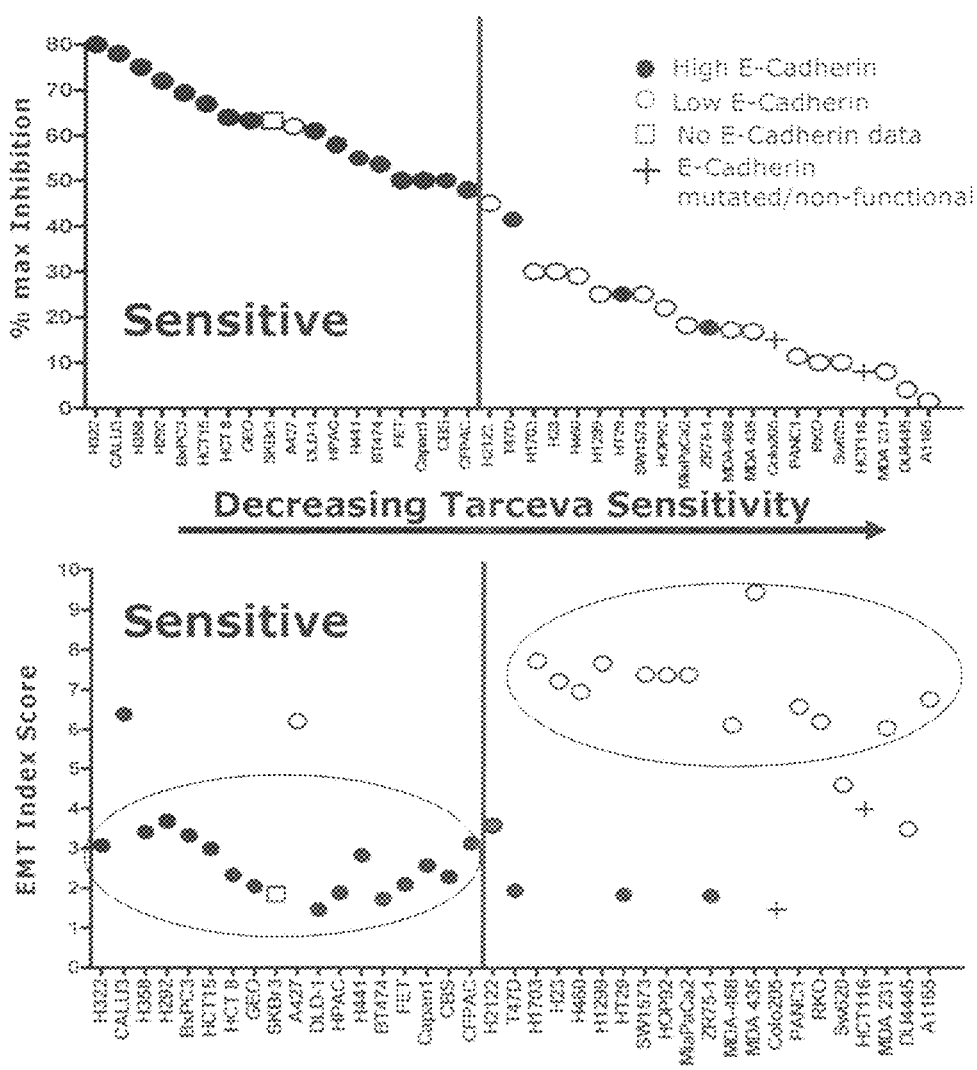

FIG. 19: EMT index score correlates with E-cadherin status and sensitivity to erlotinib. In the top panel, cell lines from breast, colon, pancreas, and lung tumors were scored for E-cadherin status and ordered according to % maximum growth inhibition by erlotinib. In the lower panel, index scores for the same cell lines were were calculated using the 88 gene EMTGS (calculated with Algorithm A) and plotted in the same order.

Figure 20:
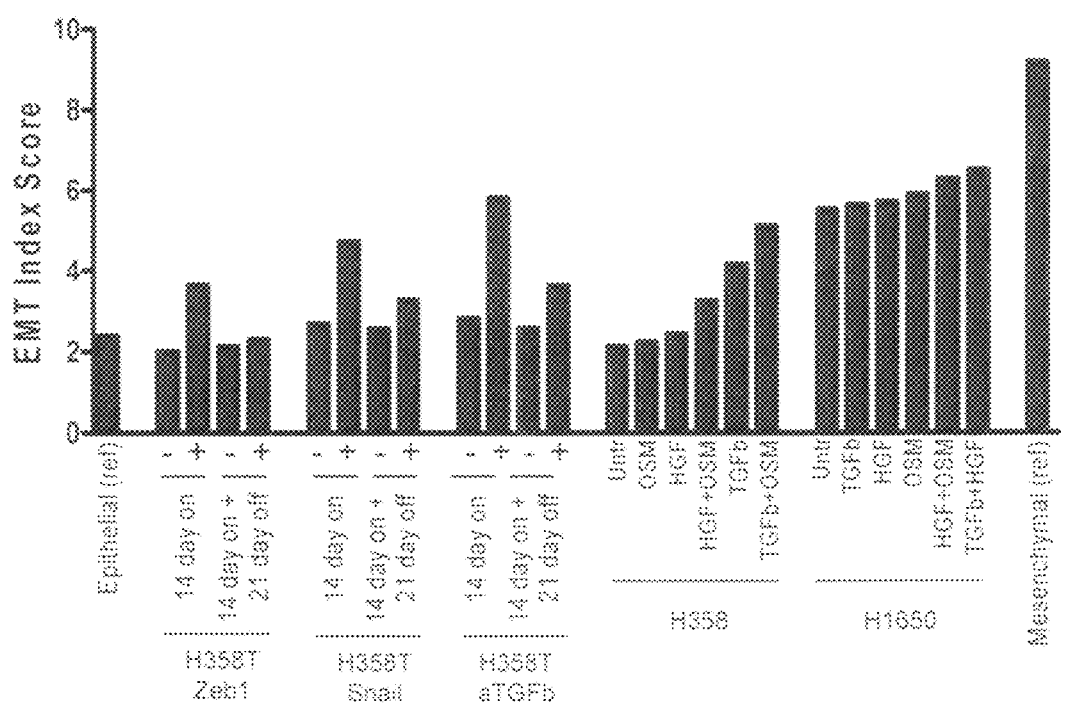

FIG. 20: 88 gene EMTGS index scores were calculated for H358 and H1650 EMT models and plotted with index scores from known reference Epithelial cell (NCI-H441) and Mesenchymal (NCI-H1703) cell lines (all calculated with Algorithm A). Induction of the transgenes in the H358T-Zeb1, Snai1 and aTGFb models for 14 days induced increases in (i.e. more mesenchymal) EMT index scores which were partially or completely reversed 21 days after withdrawal of doxycycline. In the H358 ligand driven models, changes to index scores after 7 day ligand treatment reflected more mesenchymal states that correlated with morphological and phenotypic changes previously characterized. In the H1650 model, index scores did not change after incubation with ligand, but correctly indicated insensitivity to erlotinib in all conditions.

Figure 21A:
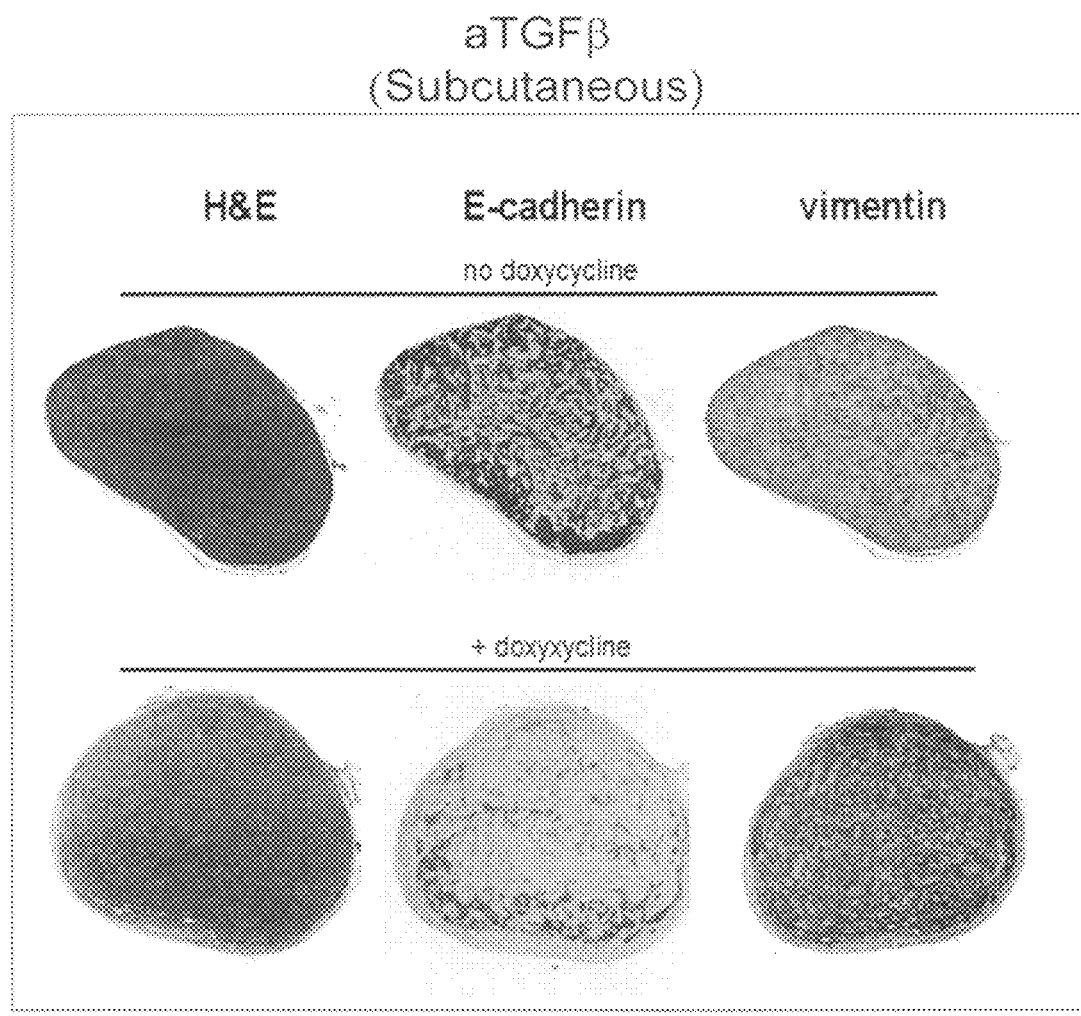
Figure 21B:
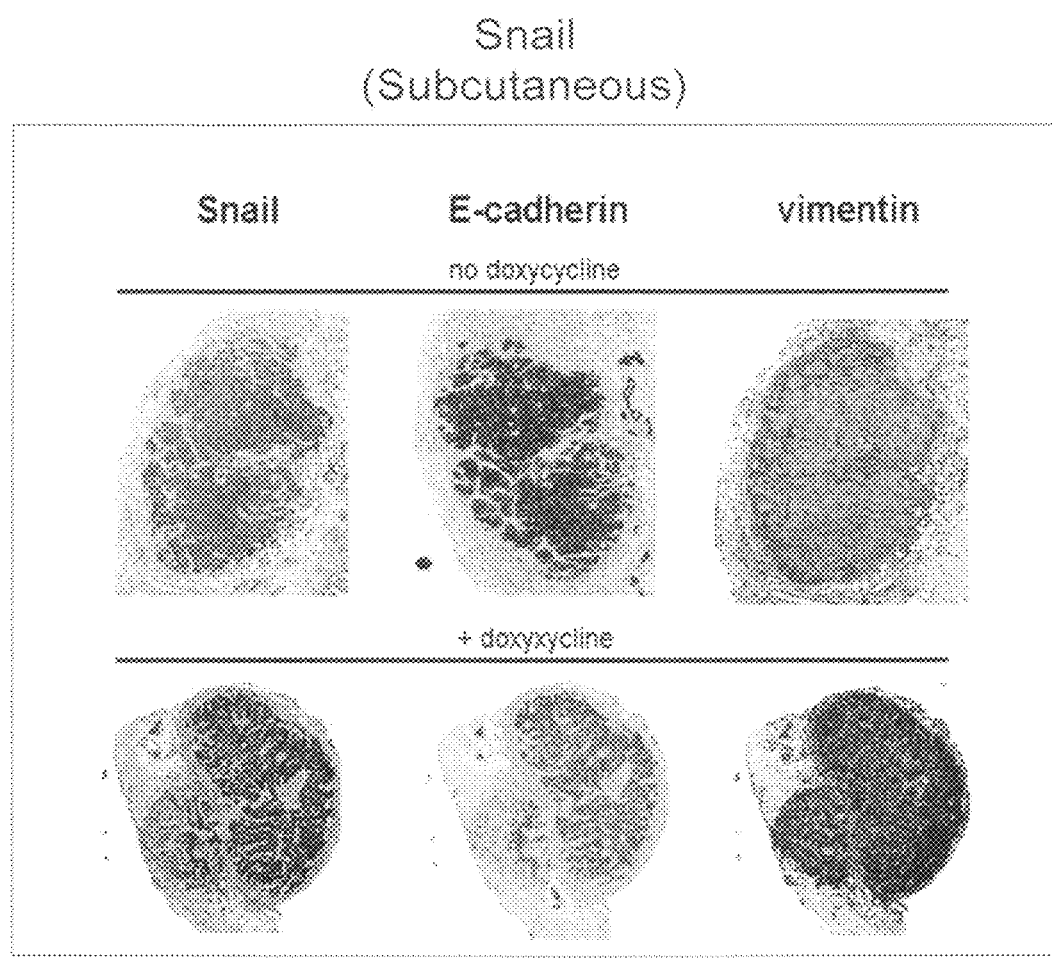
Figure 21C:
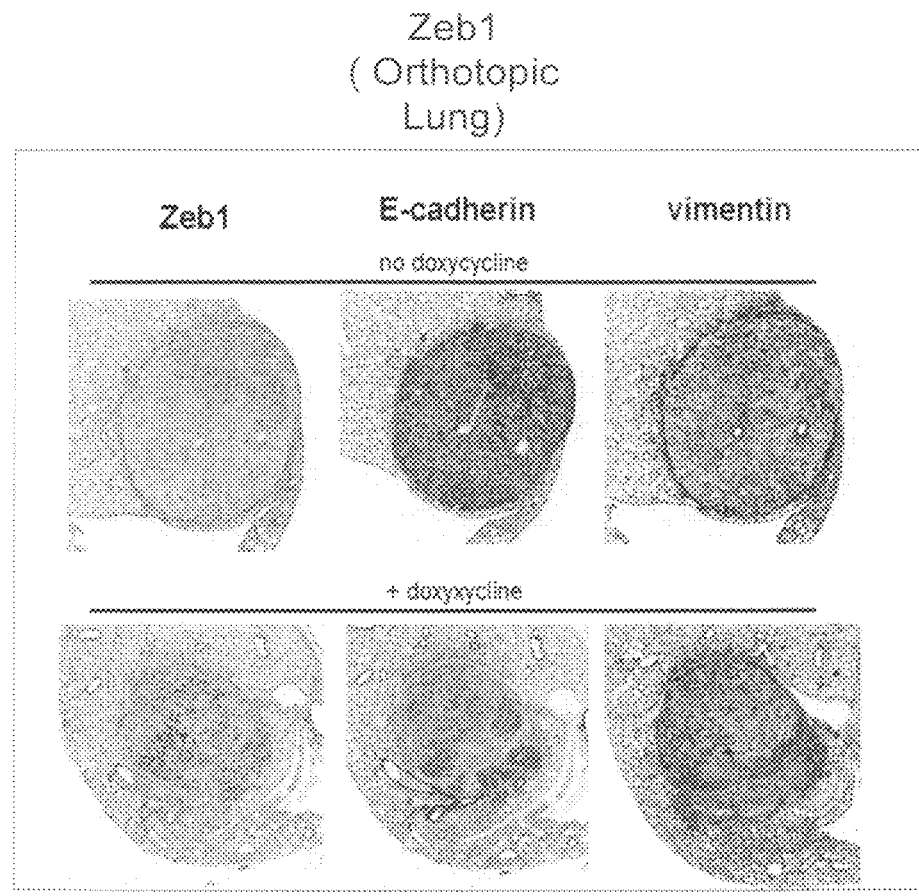

FIG. 21: Induction of aTGFb, Snai1 or Zeb in H358 engineered models of EMT resulted in down regulation of E-cadherin and up regulation of vimentin in vivo. Tumors were grown either in the subcutaneous or orthotopic settings for 7 days post implantation. Mice were administered doxycycline from day 14 to 21 post-implantation to induce transgene expression. Tumors were harvested and evaluated for induction of Snai1, Zeb1, E-cadherin or vimentin by IHC (low power magnification).

Figure 22:
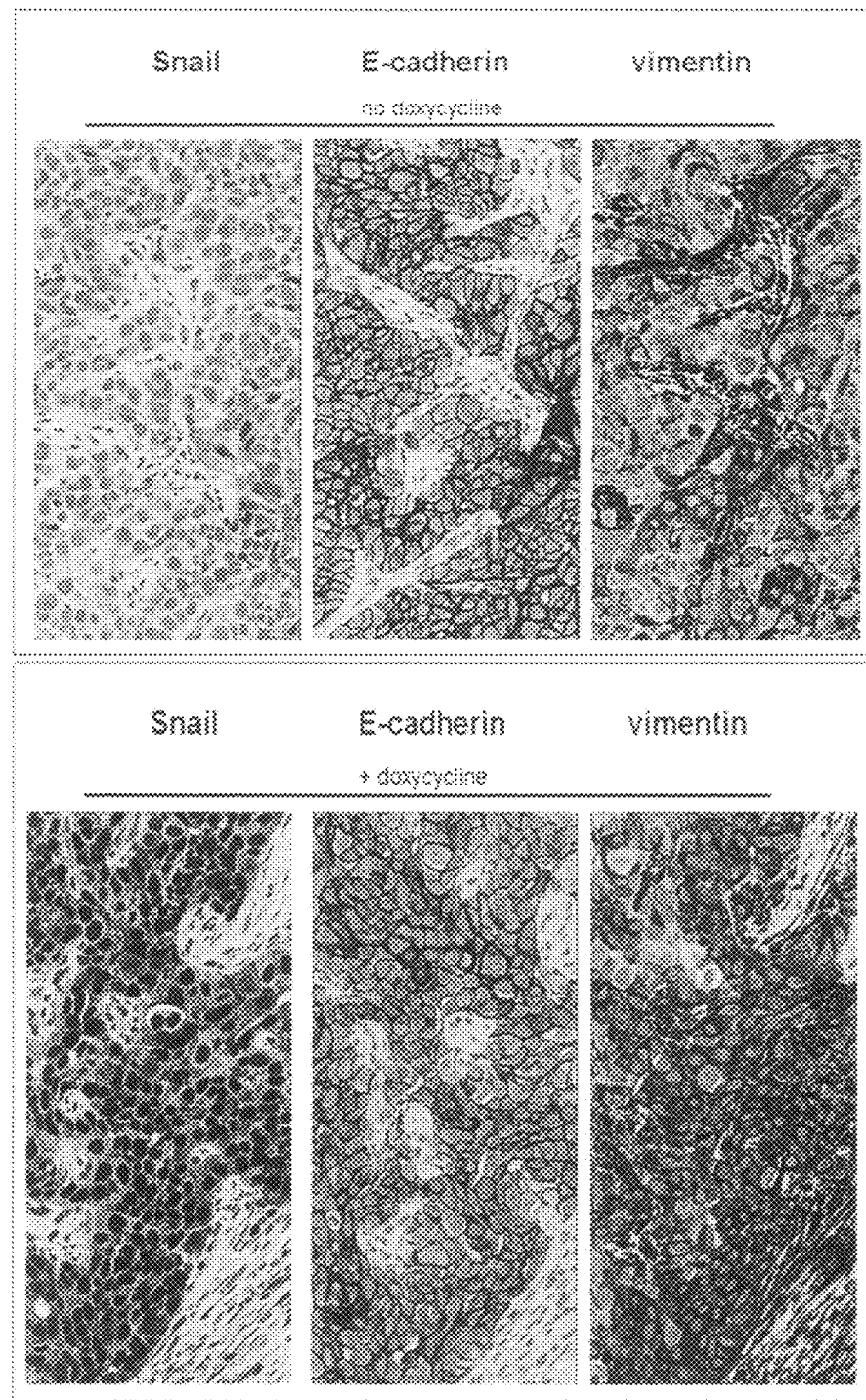

FIG. 22: Evaluation of architectural and histological changes after induction of Snai1 in H358T model of EMT. Higher magnification of IHC sections shown in FIG. 21 shows no architectural changes to tumors after expression of Snai1. E-cadherin is modestly down regulated and vimentin is robustly up regulated.

Figure 23:
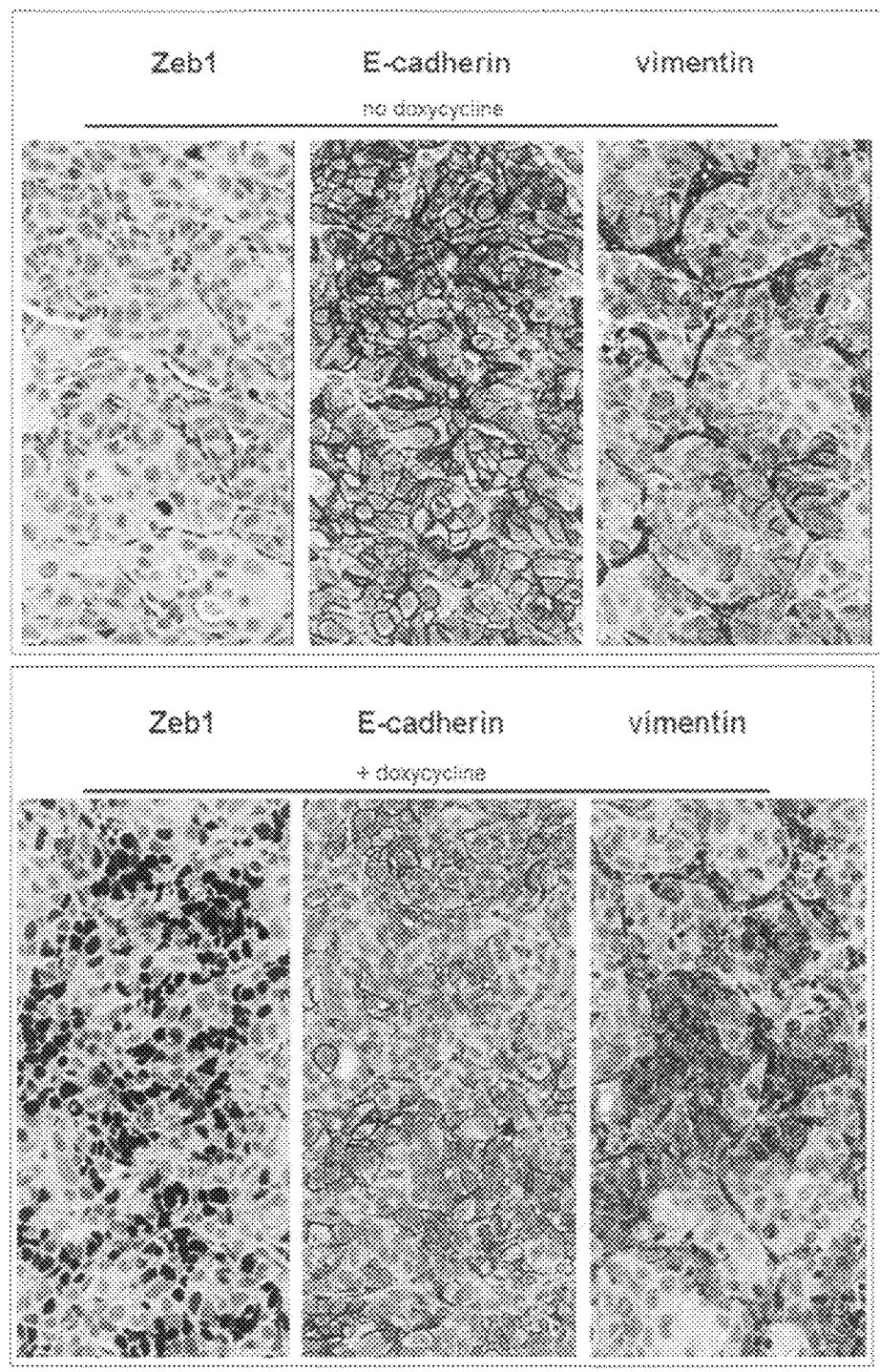

FIG. 23: Evaluation of architectural and histological changes after induction of Zeb1 in H358T model of EMT. Higher magnification of IHC sections shown in FIG. 21 shows no architectural changes to tumors after expression of Zeb1. E-cadherin is strongly down regulated and vimentin is modestly up regulated.

FIG. 24: Evaluation of architectural and histological changes after induction of aTGFb in H358T model of EMT. (A) Higher magnification of IHC sections shown in FIG. 21 shows increased stromal infiltration after induction of aTGFb (H&E stain). E-cadherin is down regulated and vimentin is robustly up regulated. Arrows indicate cells in the stroma which have a nuclear size consistent with human tumor cells, not mouse stromal cells. (B) Evaluation of infiltrating cells for EMT status. aTGFb IHC was performed to verify expression of the transgene in epithelial nests of the tumor. Cells were evaluated for multiple markers by IHC on serial sections. Infiltrating cells expressed high levels of cytokeratin, low levels of E-cadherin and high levels of vimentin.

Figure 25:
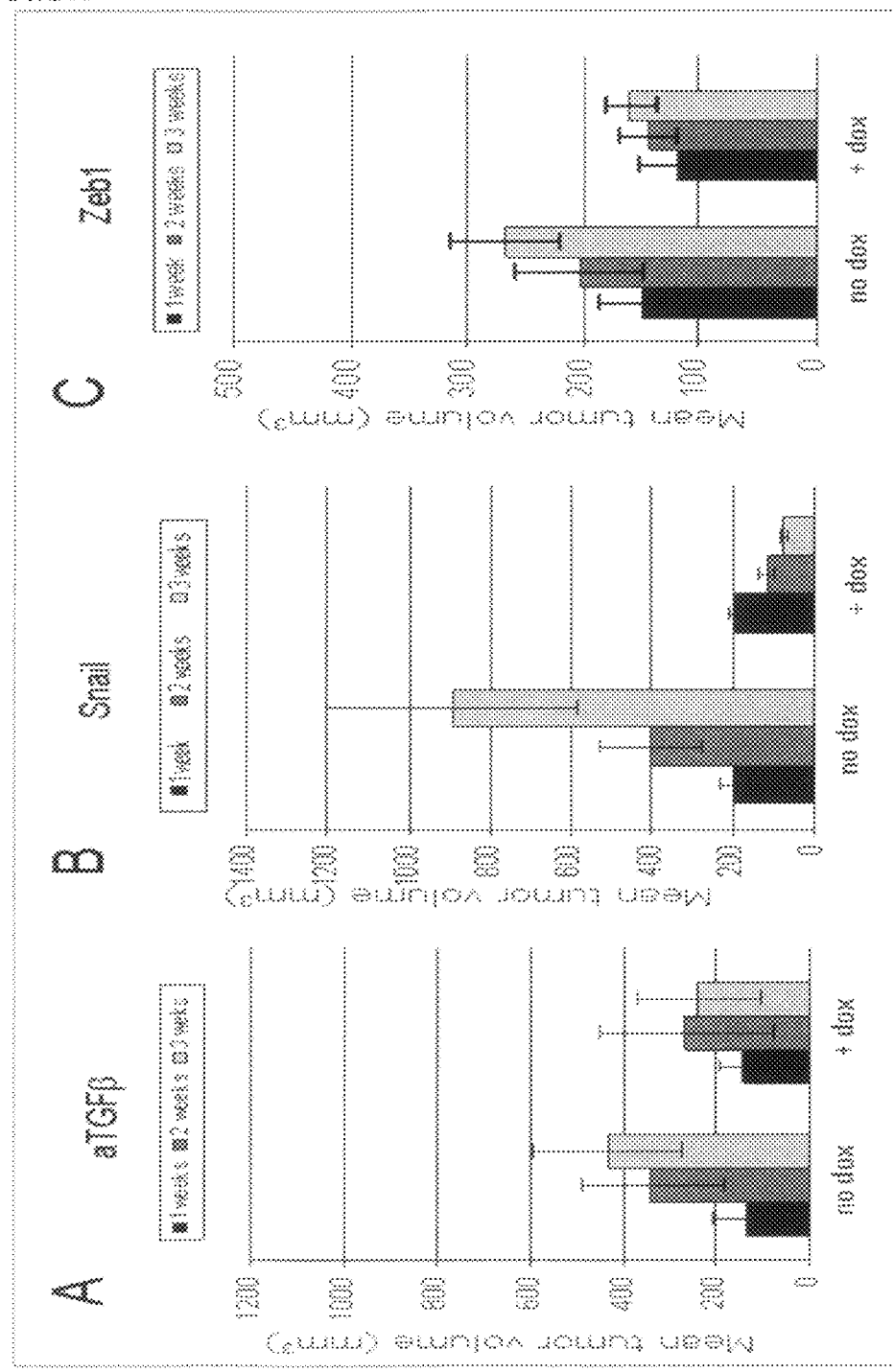

FIG. 25: Growth of H358T-aTGFb, Snai1 and Zeb1 xenografts after induction of transgenes. Tumors grew for 1 week after implantation without doxycycline. For weeks 2 and 3, mice were divided to two groups: one was administered doxycycline, the control group was not. Tumors were measured at week 2 and 3 to evaluate changes in growth rate.

Figure 26A:
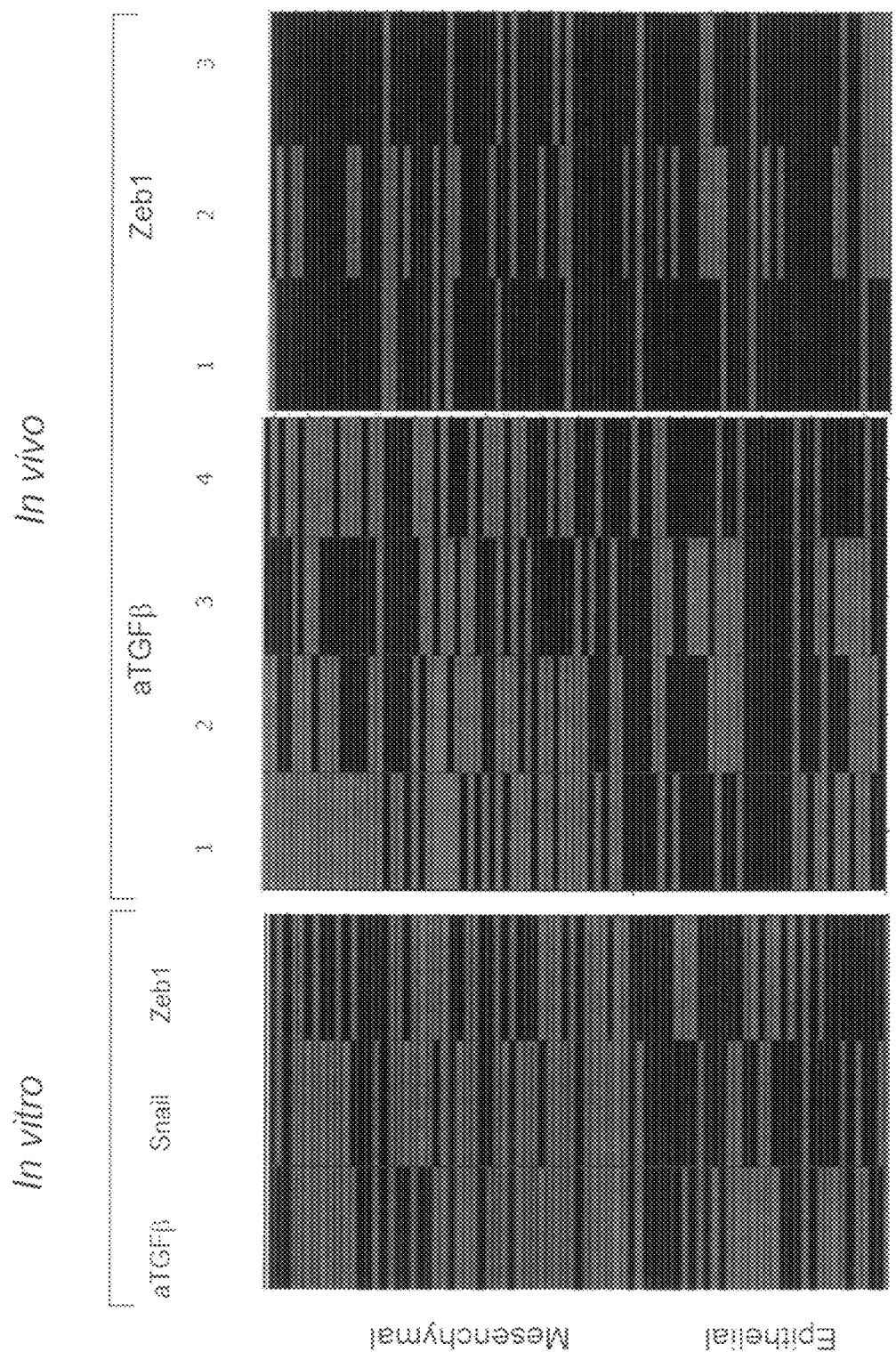

FIG. 26: Comparison of 88 gene EMTGS in H358T aTGFb, Snai1 and Zeb1 models in vitro and in vivo. (A.) In vitro: Cells were grown in vitro for 7 days with doxycycline and profiled by qPCR for changes to the 88 gene EMTGS relative to untreated cells. In vivo: Xenografts were induced to express transgenes for 2 weeks and harvested for RNA which was used to profile changes to the 88 gene EMTGS relative to tumors that were not treated with doxycycline. Profiles from tumors from replicate mice are indicated. (B.) Changes to erlotinib EC50 values and corresponding changes to the EMT index scores are shown for uninduced and induced models in vitro (calculated with Algorithm A).

Figure 27:
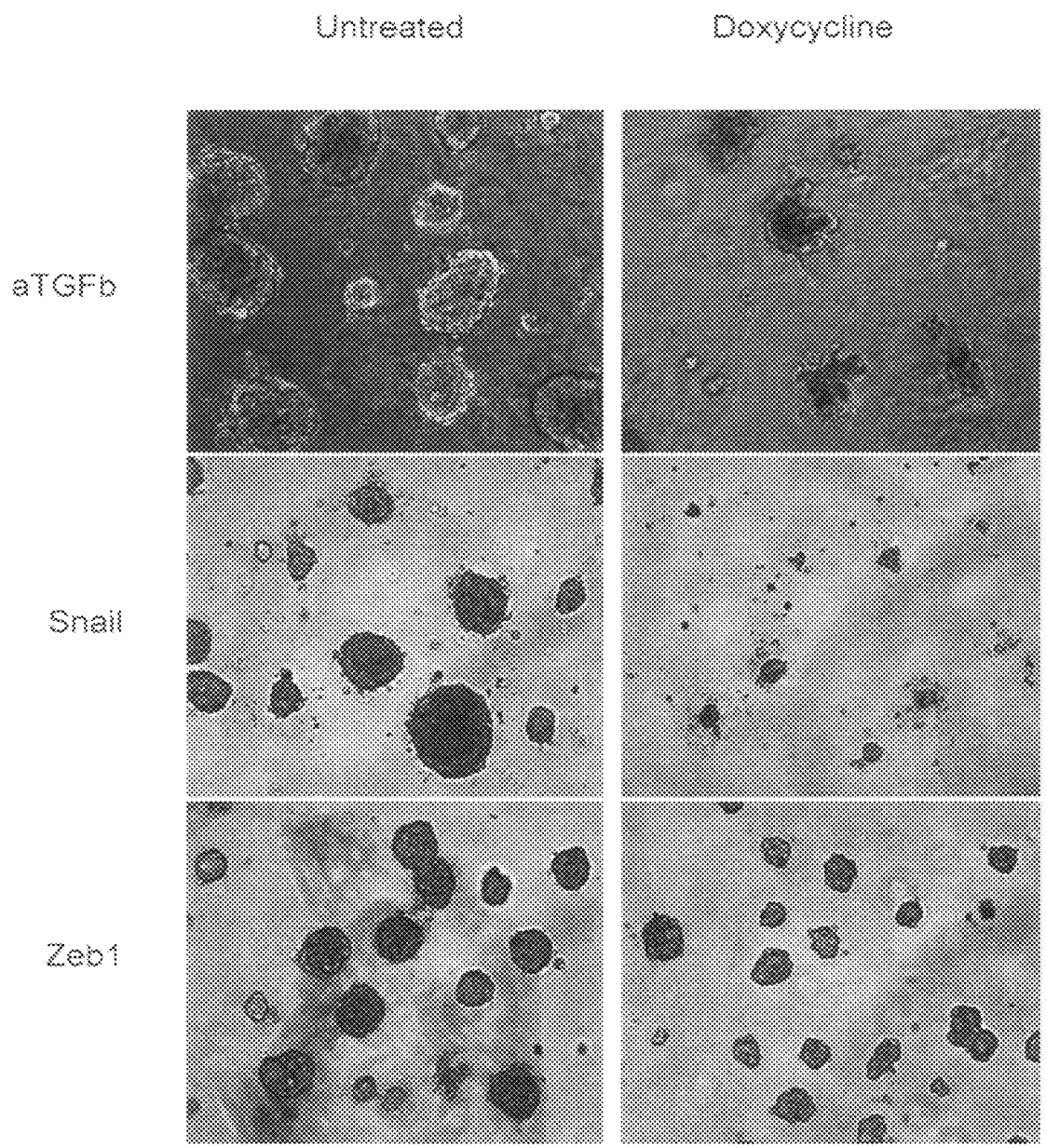

FIG. 27: Induction of EMT in 3D culture results in growth changes to H358 engineered models. H358T-aTGFb, Snai1 and Zeb1 cells were grown in Matrigel with or without doxycycline for 14 days and evaluated for differences in growth and architecture of the colonies.

Figure 28A:
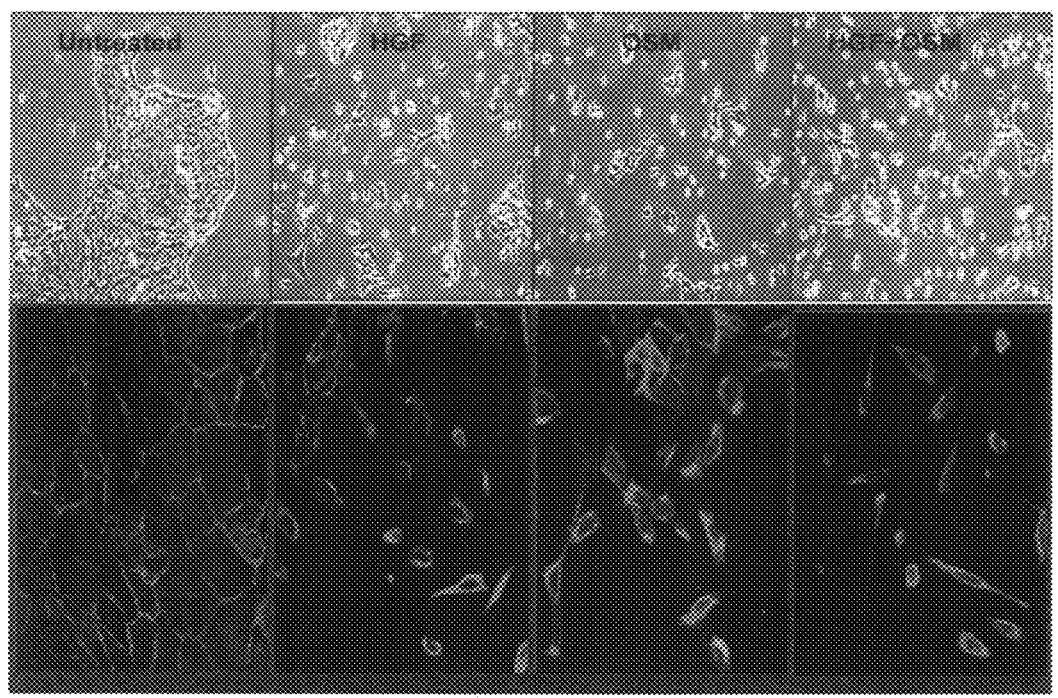
Figure 28B:
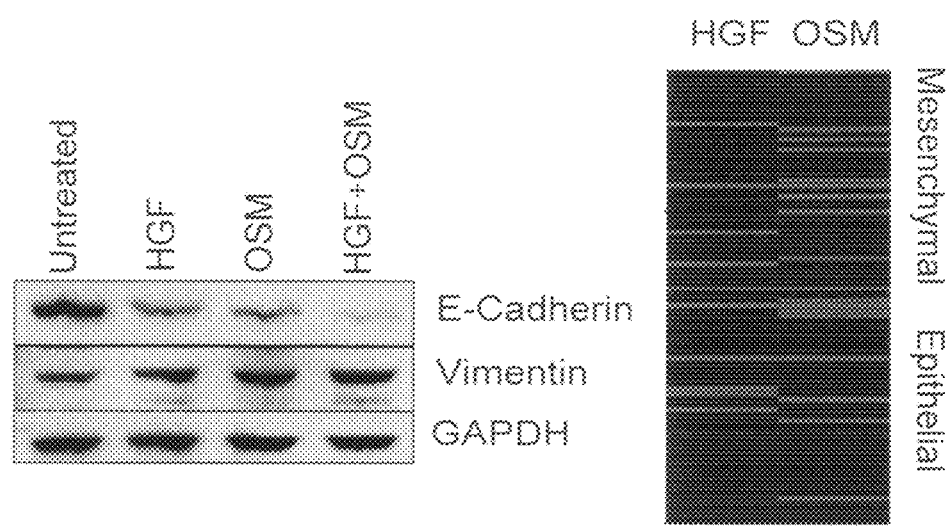
Figure 28C:
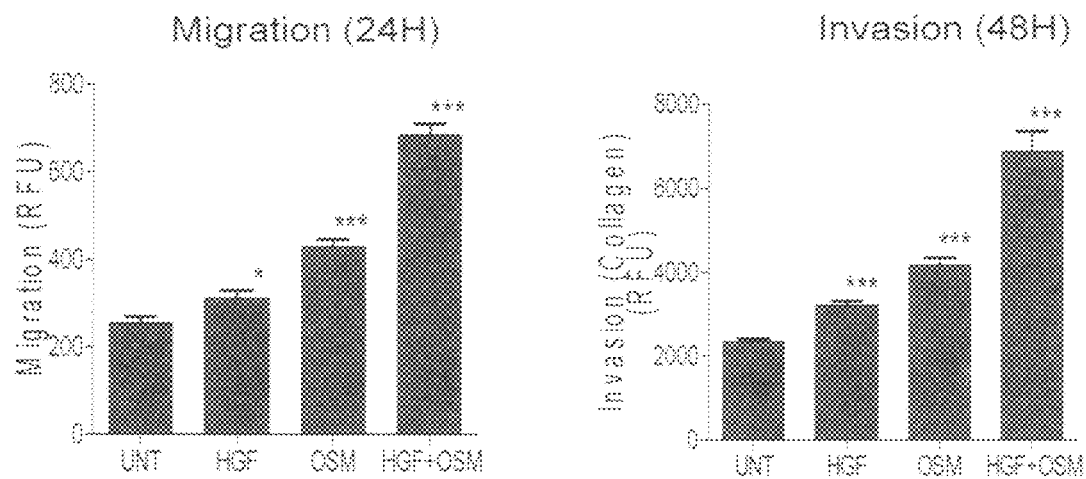

FIG. 28: EMT changes induced by HGF and OSM in CFPAC1 pancreatic tumor model. Morphological changes (A) are illustrated by increased scattering and acquisition of a more fibroblast-like morphology. Marker changes (B) are indicated by western blot and heat map of changes to the 88 gene EMTGS. Phenotypic changes (C) are indicated by increased cell migration and invasion capacity after 7 day incubation with ligands.

Figure 29A:
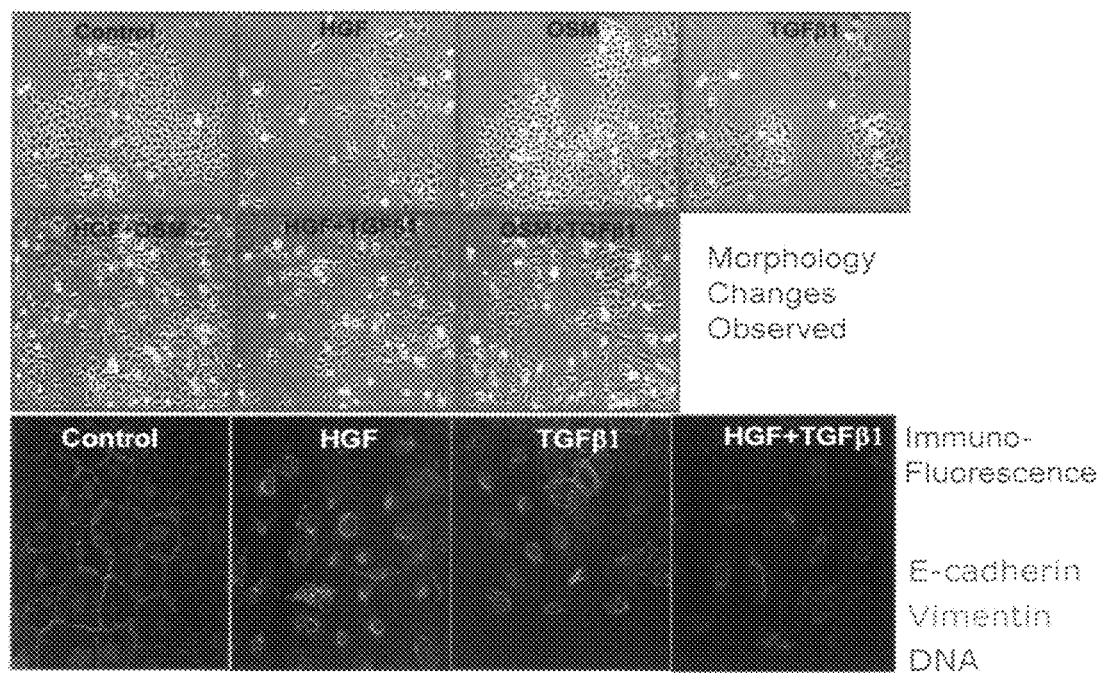
Figure 29B:
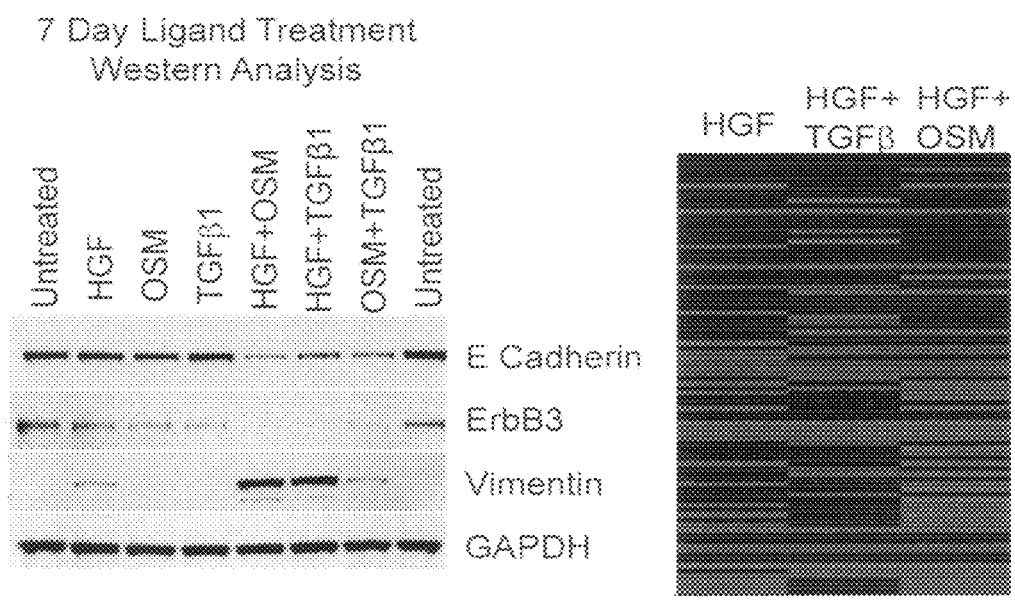

FIG. 29: EMT changes induced by HGF, OSM, and TGFb1 in H1650 NSCLC tumor model. Morphological (A), and biomarker (B) changes to cells induced by indicated ligands for 7 days.

Figure 30A:
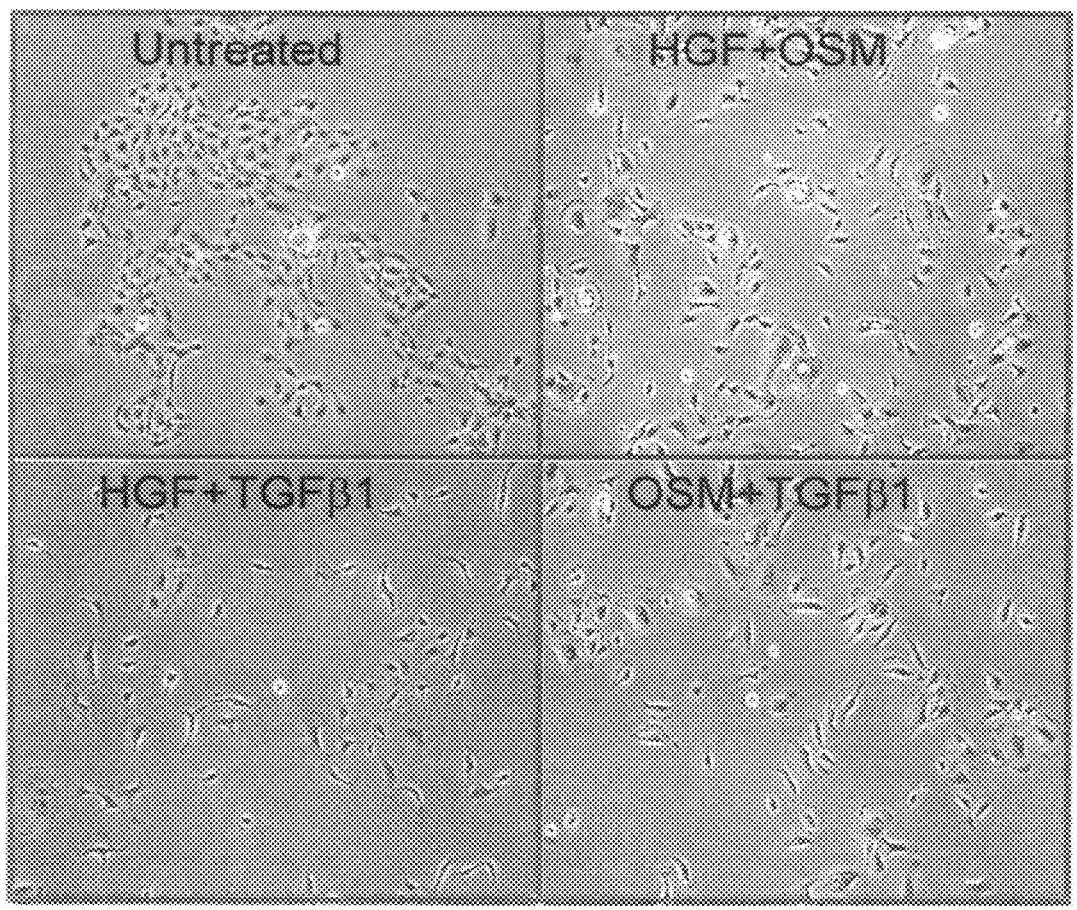
Figure 30B:
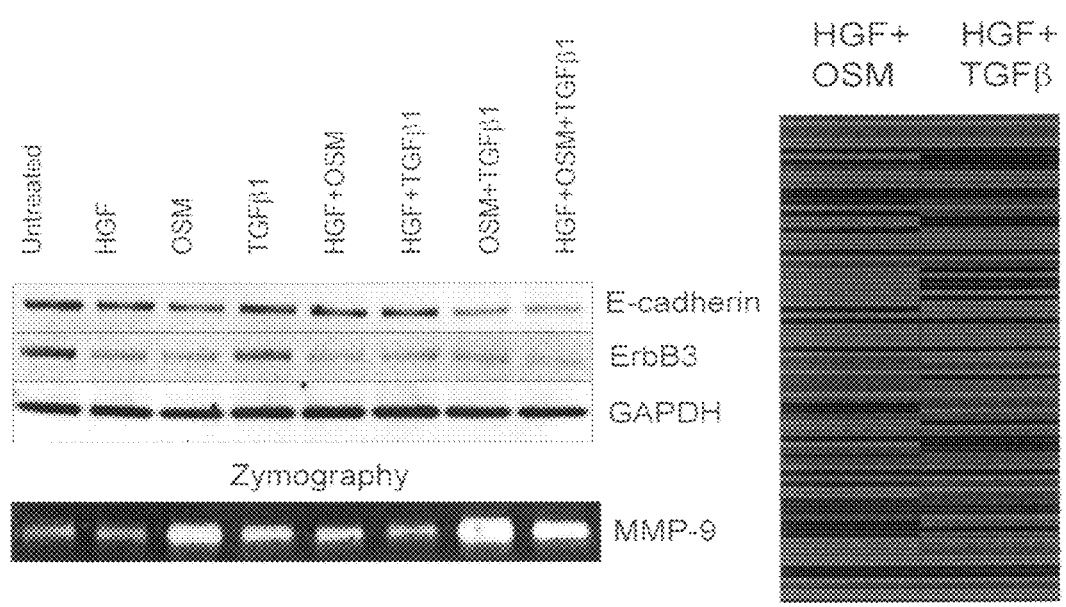
Figure 30C:
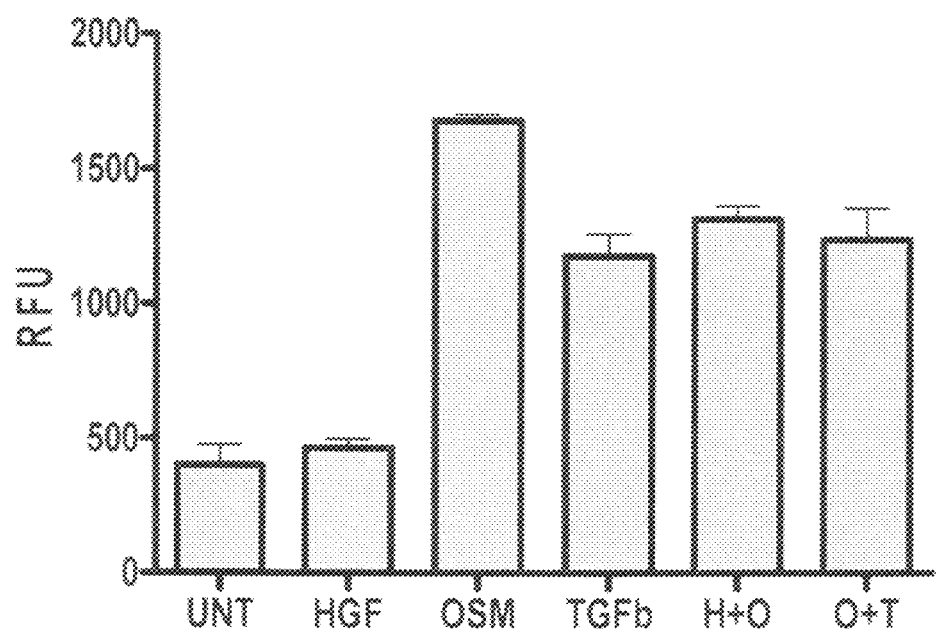

FIG. 30: EMT changes induced by HGF, OSM and TGFb1 in H292 NSCLC tumor model. Morphological (A), marker (B) and phenotypic (C) changes to cells induced by indicated ligands for 7 days.

FIG. 31: Comparison of genes in the 88 gene EMTGS that are regulated in vitro and in vivo in the H358 engineered models.

Figure 32:
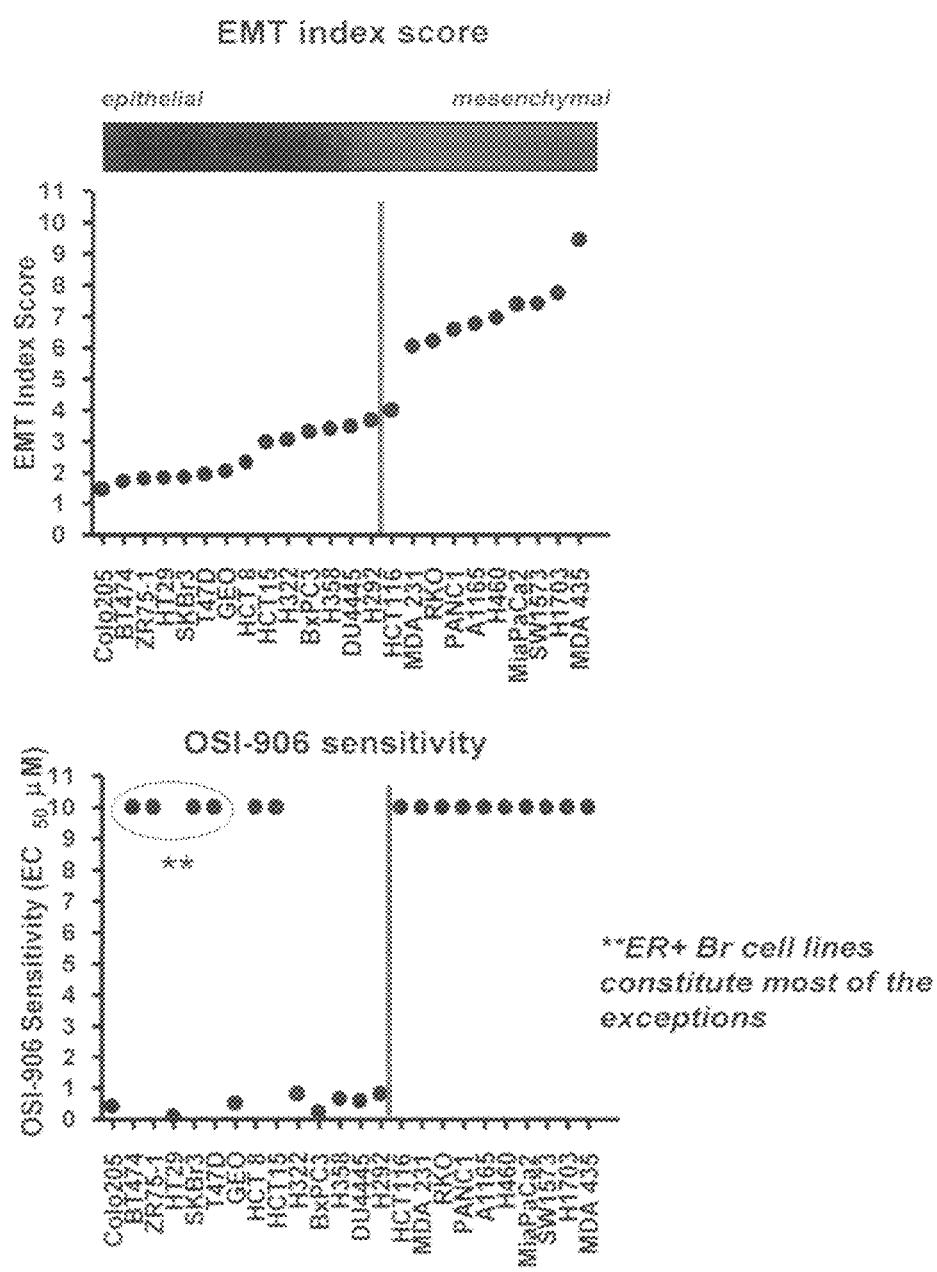

FIG. 32: Correlation of the 88 gene EMTGS index score with OSI-906 sensitivity. The 88 geneEMTGS index scores were calculated for OSI-906 sensitive and insensitive cell lines. The EC50 values for each of the cell lines is shown in the bottom panel and the EMT index scores are shown in the top panel (calculated with Algorithm A).

Figure 33:
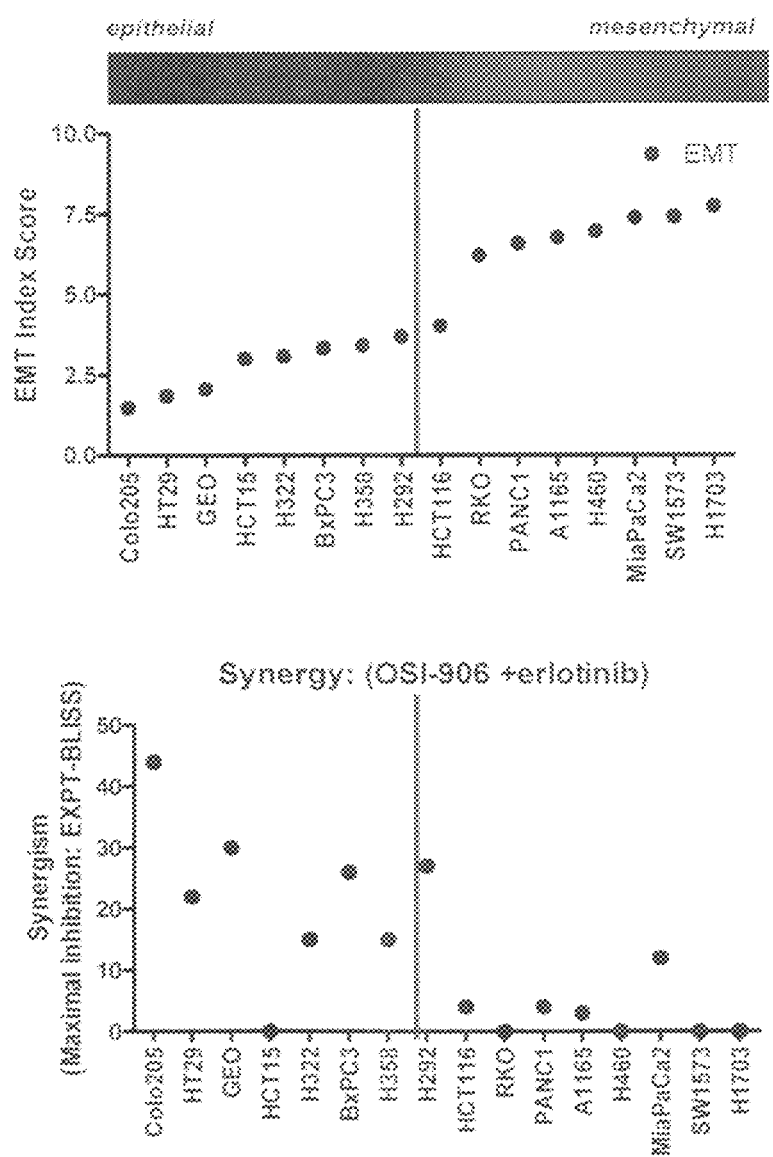

FIG. 33: Correlation of the 88 gene EMTGS index score with OSI906-erlotinib synergy. The 88 gene EMTGS index scores were calculated for cell lines and plotted in increasing order in the top panel (calculated with Algorithm A). In the bottom panel, synergy between OSI-906 and erlotinib was quantified as the ratio of maximal inhibition to experimental BLISS value.

Figure 34:
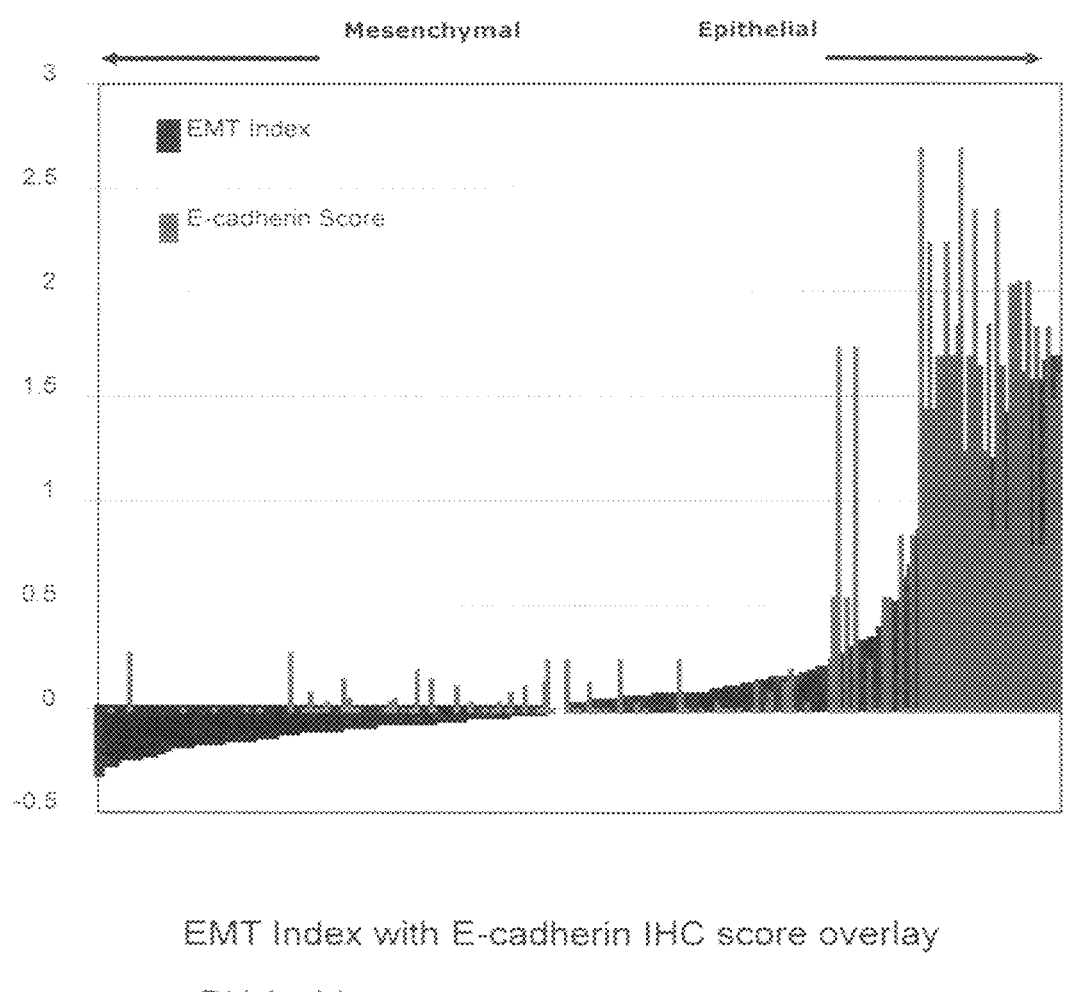

FIG. 34: Correlation of the 88 gene EMTGS index score with E-cadherin expression values. The 88EMTGS index scores were calculated for tumors in a mouse breast tumor archive. E-cadherin expression values (log microarray signal intensity) were overlaid on the EMT index scores for comparison.

Figure 35:
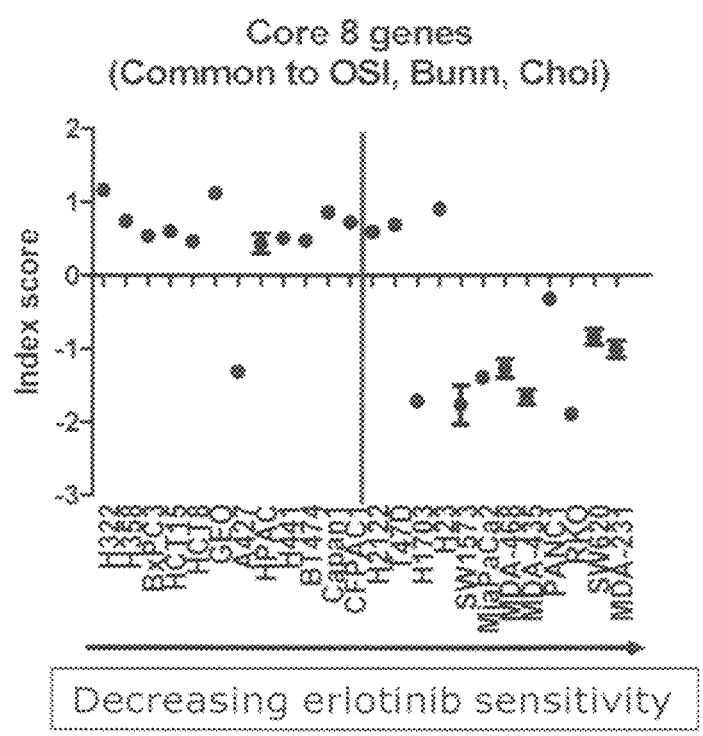

FIG. 35: Core 8 EMTGS index score correlates with erlotinib sensitivity. Index scores were calculated from microarray data for 24 cell lines of known erlotinib sensitivity using 8 genes in common to the 88 gene EMTGS, Choi EMTGS and the Bunn gefitinib sensitivity GS (i.e. AGR2, CDH1, CLDN4, ELF3, ERBB3, IKIP, OCLN, SH3YL1). Cell lines were arranged in order of decreasing erlotinib sensitivity.

FIG. 36: Annotation for 44 mesenchymal genes in the 88 gene EMTGS

FIG. 37: Annotation for 44 epithelial genes in 88 gene EMTGS

FIG. 38: Correlation of the 88 gene EMTGS index score and erlotinib sensitivity values (calculated with Algorithm A).

FIG. 39: Index scores in multiple tumor cell lines for the 88 gene EMTGS omitting selected genes (calculated with Algorithm A).

FIG. 40: Co-correlating genes that were used to generate index scores in FIG. 39.

Figure 41A:
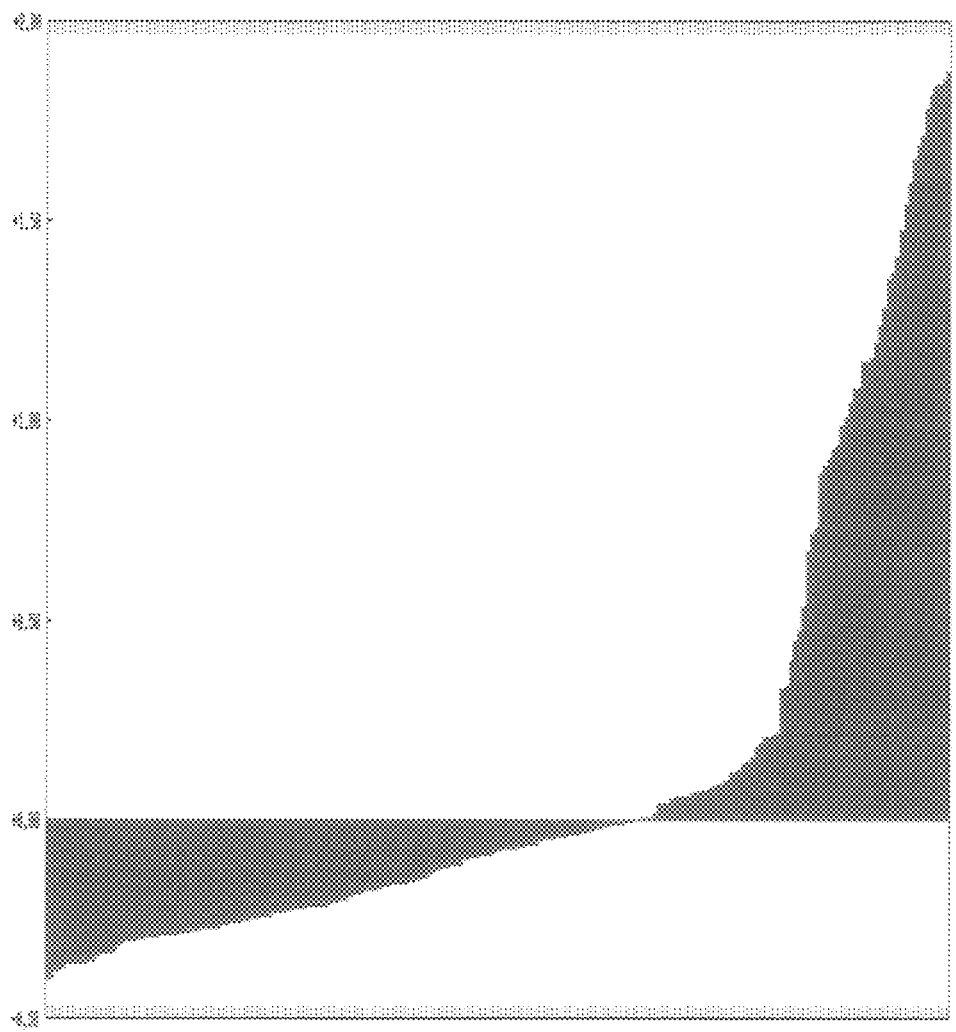

FIG. 41: In breast tumor BH archive cells, comparison of the 88 gene EMTGS index (upper panel) with AXL gene expression (lower panel) indicates that AXL has low expression in tumors that are more epithelial and is more highly expressed in tumors that are more mesenchymal-like, suggesting AXL as a potential gene that is important for mesenchymal tumors.

FIG. 42: Taq-man RT-PCR analysis with the 88 EMT gene signature has value in new target identification and discovery. (A) A549 cells were treated with TNF and either control or TAK1 siRNA. Changes to the 88EMTGS were quantified by qPCR as relative fold change. Changes induced by TNF+control siRNA are relative to no ligand+control siRNA. Changes induced by TNF+TAK1 siRNA are relative to TNF+control siRNA. (B) H358 cells were treated with HGF+OSM with or without c-MET inhibitor Compound M for 7 days. Fold changes for HGF+OSM samples are relative to untreated cells. Fold changes for HGF+OSM+Compound M are relative to HGF+OSM. Biological replicates are shown in paired columns. (C) H358T-aTGFb cells were treated for 7 days with doxycycline to induce TGFb expression with or without FAK inhibitor Compound F. Fold changes for doxycycline treated cells are relative to untreated cells. Fold changes for doxycycline+Compound F are relative to doxycycline alone.

Figure 43:
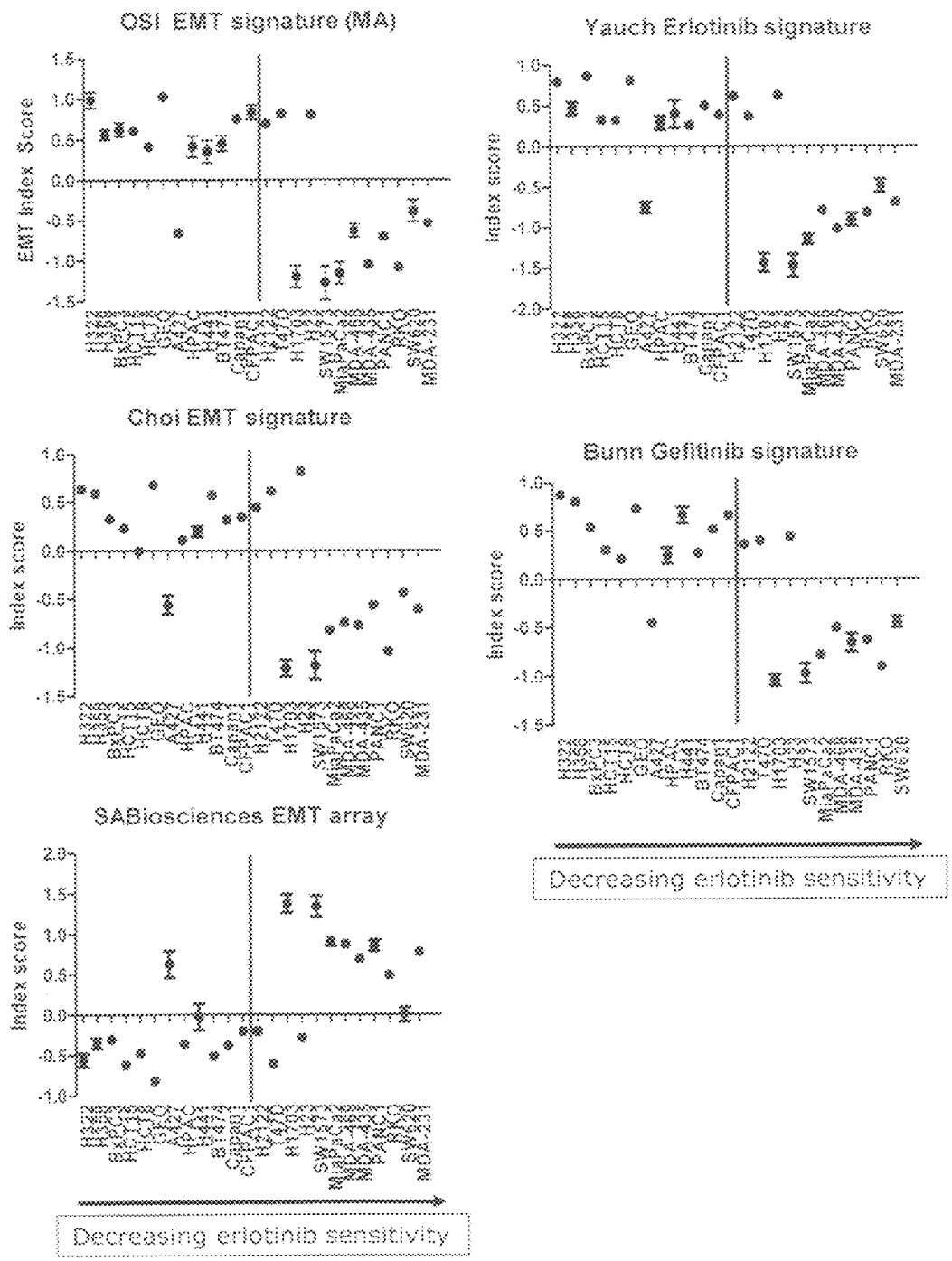

FIG. 43: Derivation of index scores from published gene signatures. Index scores for 5 signatures (88 gene EMTGS, Choi, SAbiosciences, Yauch, and Bunn) were calculated from microarray data from cell lines of known erlotinib sensitivity and plotted in order of decreasing sensitivity.

Figure 44:
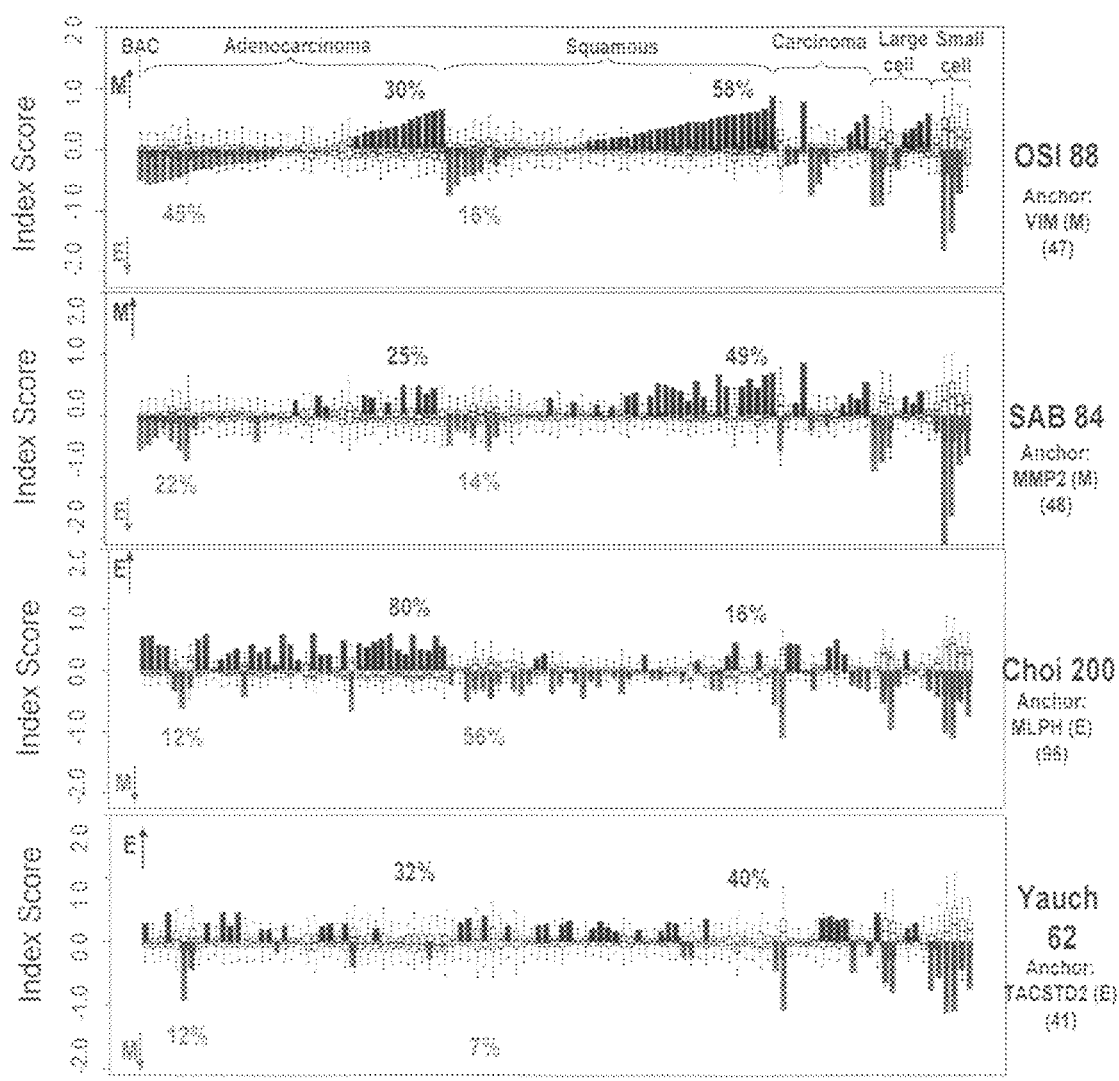

FIG. 44: Use of Index scores to analyse tumor cell populations. Index scores were calculated for the GeneLogic lung U133AB dataset using the 88 gene EMTGS, the SAbiosciences EMTGS, the Choi EMTGS, and the Yauch erlotinib sensitivity signature. Tumors were arranged in order of the 88EMTGS to compare index scores from the four signatures. The boxplot in each sample shows the distribution of 1000 index scores based on random genelists, each having the same size as the signature. The red and blue bars indicate the signature index scores of samples that are significantly low and high (P=0.05), respectively, based on the distribution of 1000 index scores from random genelists in each sample. For samples with index scores that are neither significantly low nor high, their index scores are depicted in yellow.

Figure 45:
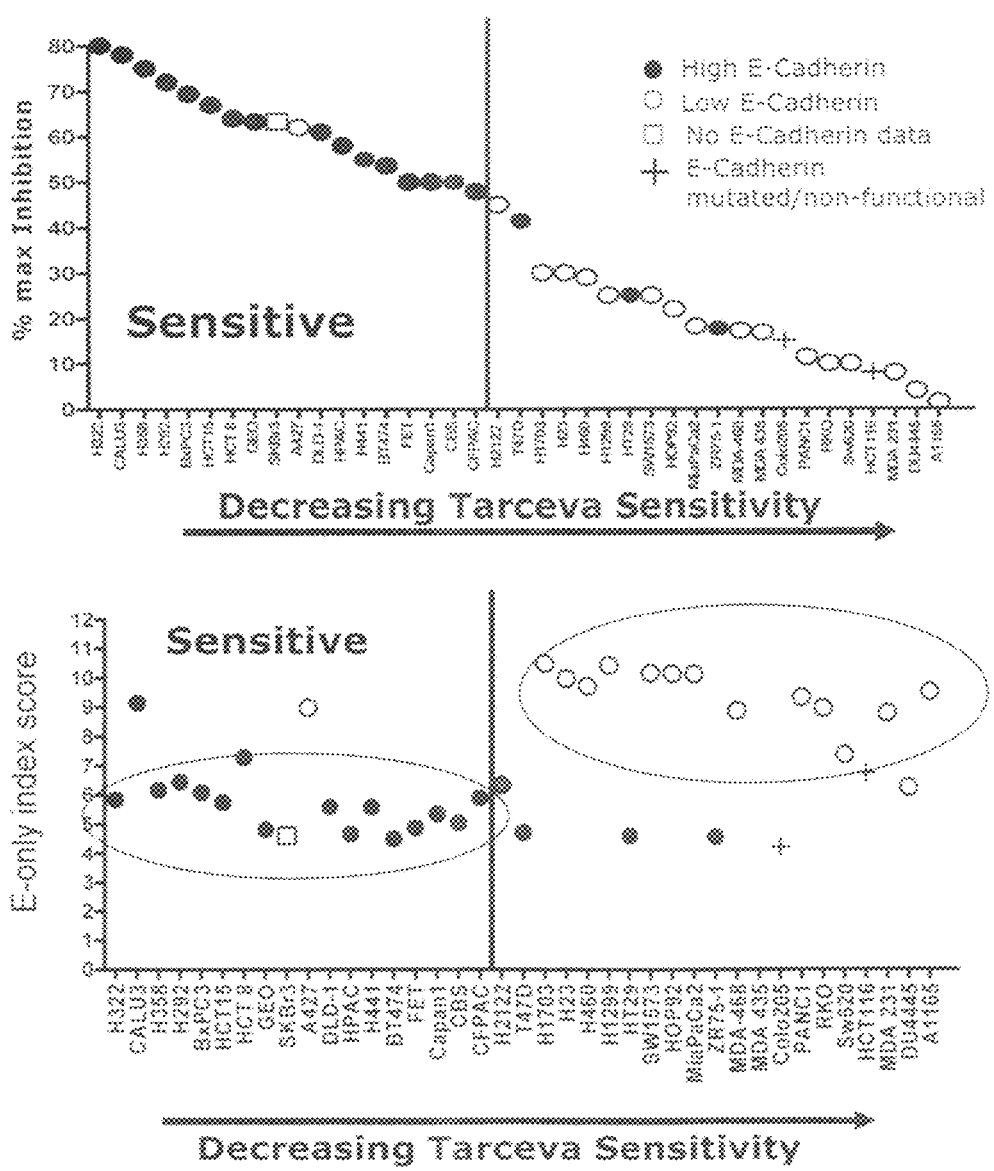

FIG. 45: EMT index score correlates with E-cadherin status and sensitivity to erlotinib. In the top panel, cell lines from breast, colon, pancreas, and lung tumors were scored for E-cadherin status and ordered according to % maximum growth inhibition by erlotinib. In the lower panel, index scores for the same cell lines were were calculated using the 88 gene EMTGS (with Algorithm $A^1$) and plotted in the same order.

Figure 46:
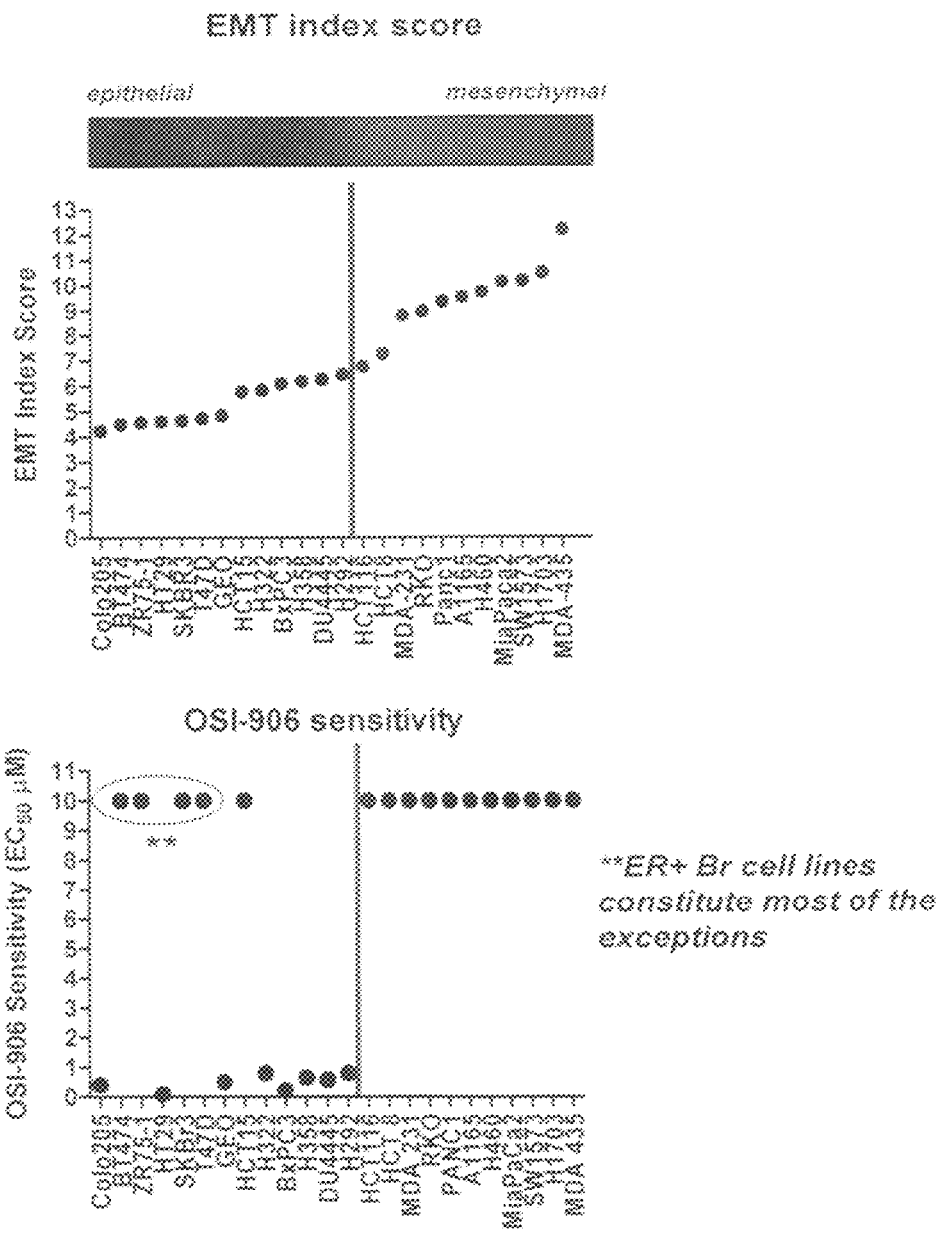

FIG. 46: Correlation of the 88 gene EMTGS index score with OSI-906 sensitivity. The 88 geneEMTGS index scores were calculated for OSI-906 sensitive and insensitive cell lines. The EC50 values for each of the cell lines is shown in the bottom panel and the EMT index scores are shown in the top panel (calculated with Algorithm $A^1$).

Figure 47:
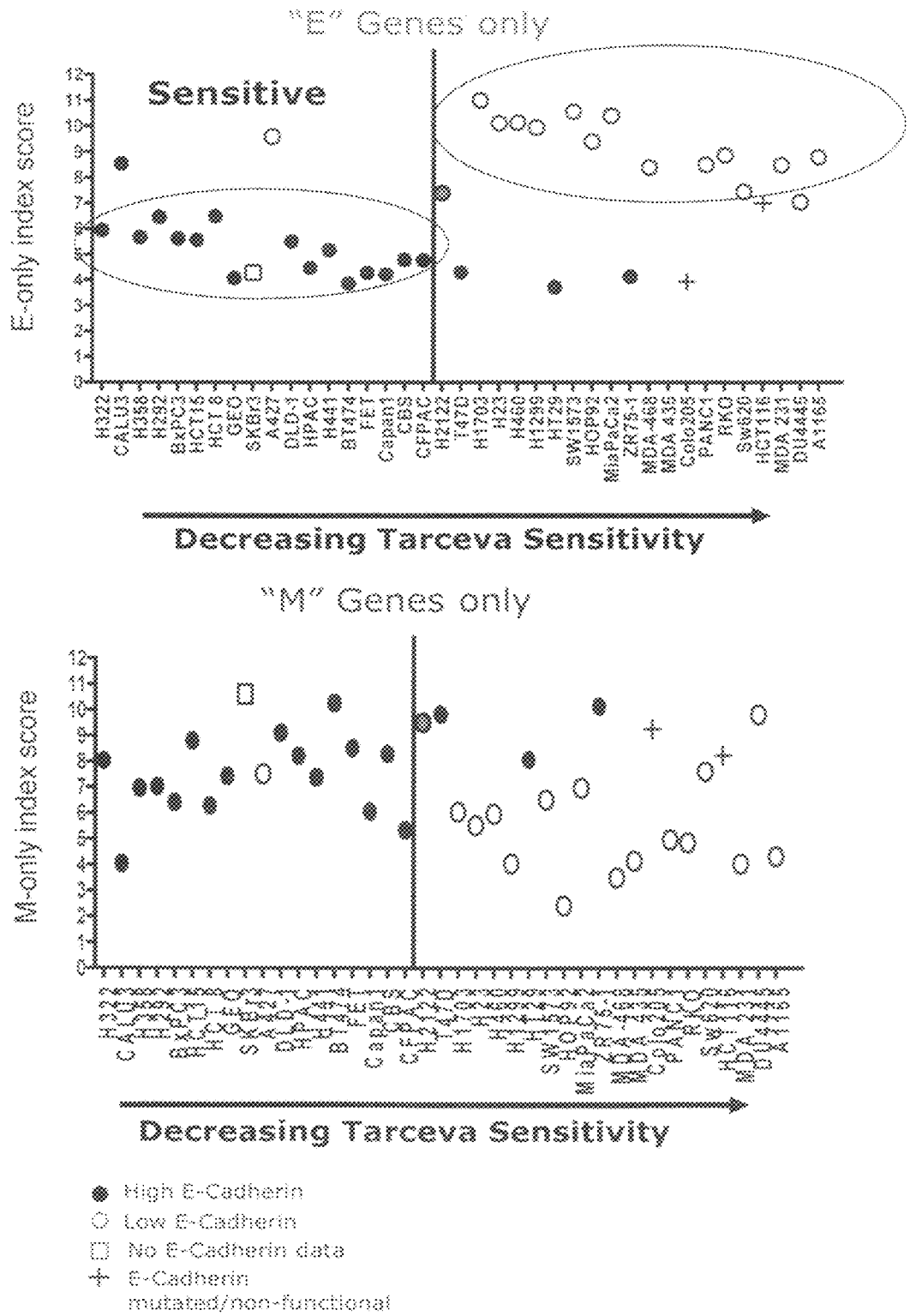

FIG. 47: Predictive value of epithelial and mesenchymal genes for erlotinib sensitivity in cell lines. Index scores were calculated using the 44 epithelial genes or the 44 mesenchymal genes in the EMT signature and plotted for each cell line, arranged according to erlotinib sensitivity (calculated with Algorithm $A^1$).

Figure 48:
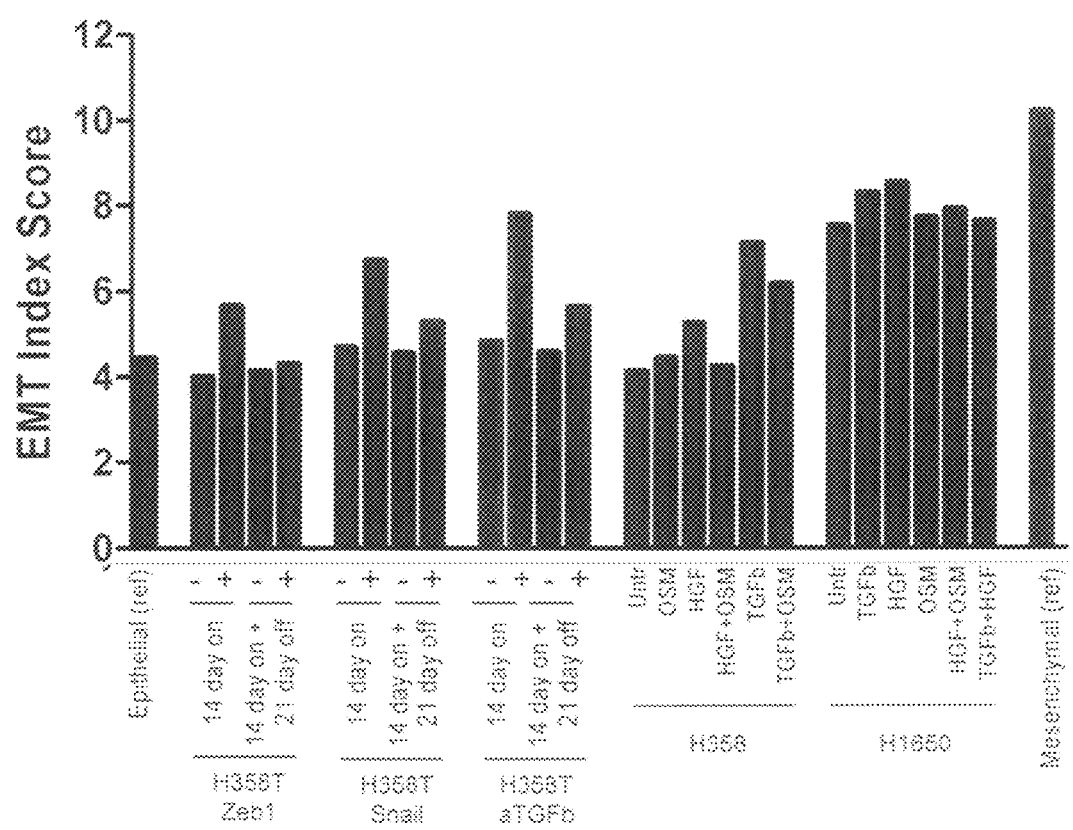

FIG. 48: 88 gene EMTGS index scores were calculated for H358 and H1650 EMT models and plotted with index scores from known reference Epithelial cell (NCI-H441) and Mesenchymal (NCI-H1703) cell lines (all calculated with Algorithm $A^1$). Induction of the transgenes in the H358T-Zeb1, Snai1 and aTGFb models for 14 days induced increases in (i.e. more mesenchymal) EMT index scores which were partially or completely reversed 21 days after withdrawal of doxycycline. In the H358 ligand driven models, changes to index scores after 7 day ligand treatment reflected more mesenchymal states that correlated with morphological and phenotypic changes previously characterized. In the H1650 model, index scores did not change after incubation with ligand, but correctly indicated insensitivity to erlotinib in all conditions.

Figure 49A:
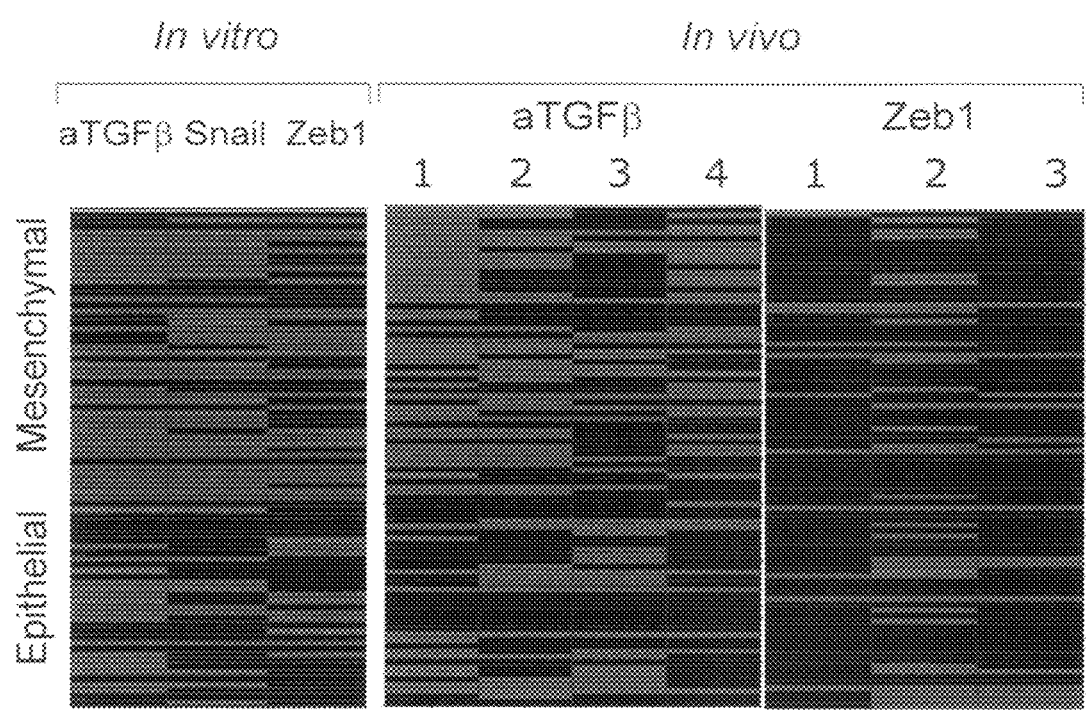

FIG. 49: Comparison of 88 gene EMTGS in H358T aTGFb, Snai1 and Zeb1 models in vitro and in vivo. (A.) In vitro: Cells were grown in vitro for 7 days with doxycycline and profiled by qPCR for changes to the 88 gene EMTGS relative to untreated cells. In vivo: Xenografts were induced to express transgenes for 2 weeks and harvested for RNA which was used to profile changes to the 88 gene EMTGS relative to tumors that were not treated with doxycycline. Profiles from tumors from replicate mice are indicated. (B.) Changes to erlotinib EC50 values and corresponding changes to the EMT index scores are shown for uninduced and induced models in vitro (calculated with Algorithm $A^1$).

Figure 50:
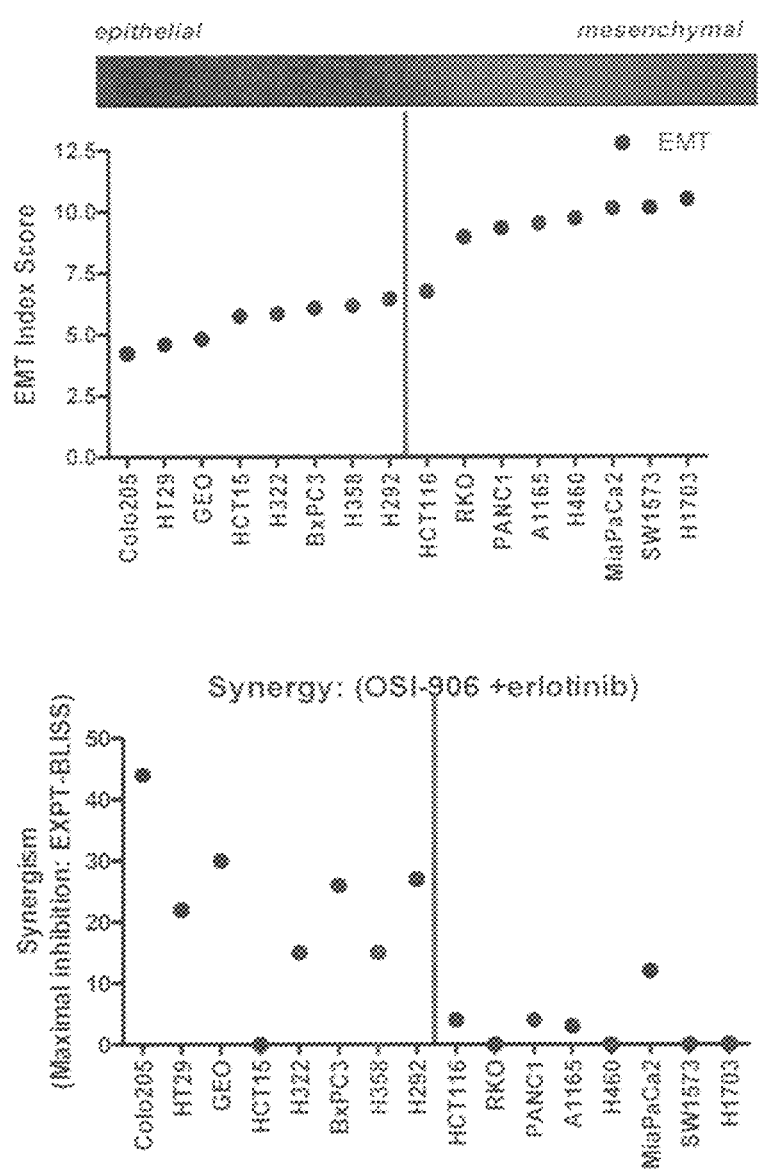

FIG. 50: Correlation of the 88 gene EMTGS index score with OS1906-erlotinib synergy. The 88 gene EMTGS index scores were calculated for cell lines and plotted in increasing order in the top panel (calculated with Algorithm $A^1$). In the bottom panel, synergy between OSI-906 and erlotinib was quantified as the ratio of maximal inhibition to experimental BLISS value.

FIG. 51: Correlation of the 88 gene EMTGS index score and erlotinib sensitivity values (calculated with Algorithm $A^1$).

FIG. 52: Index scores in multiple tumor cell lines for the 88 gene EMTGS omitting selected genes (calculated with Algorithm $A^1$).

Figure 53A:
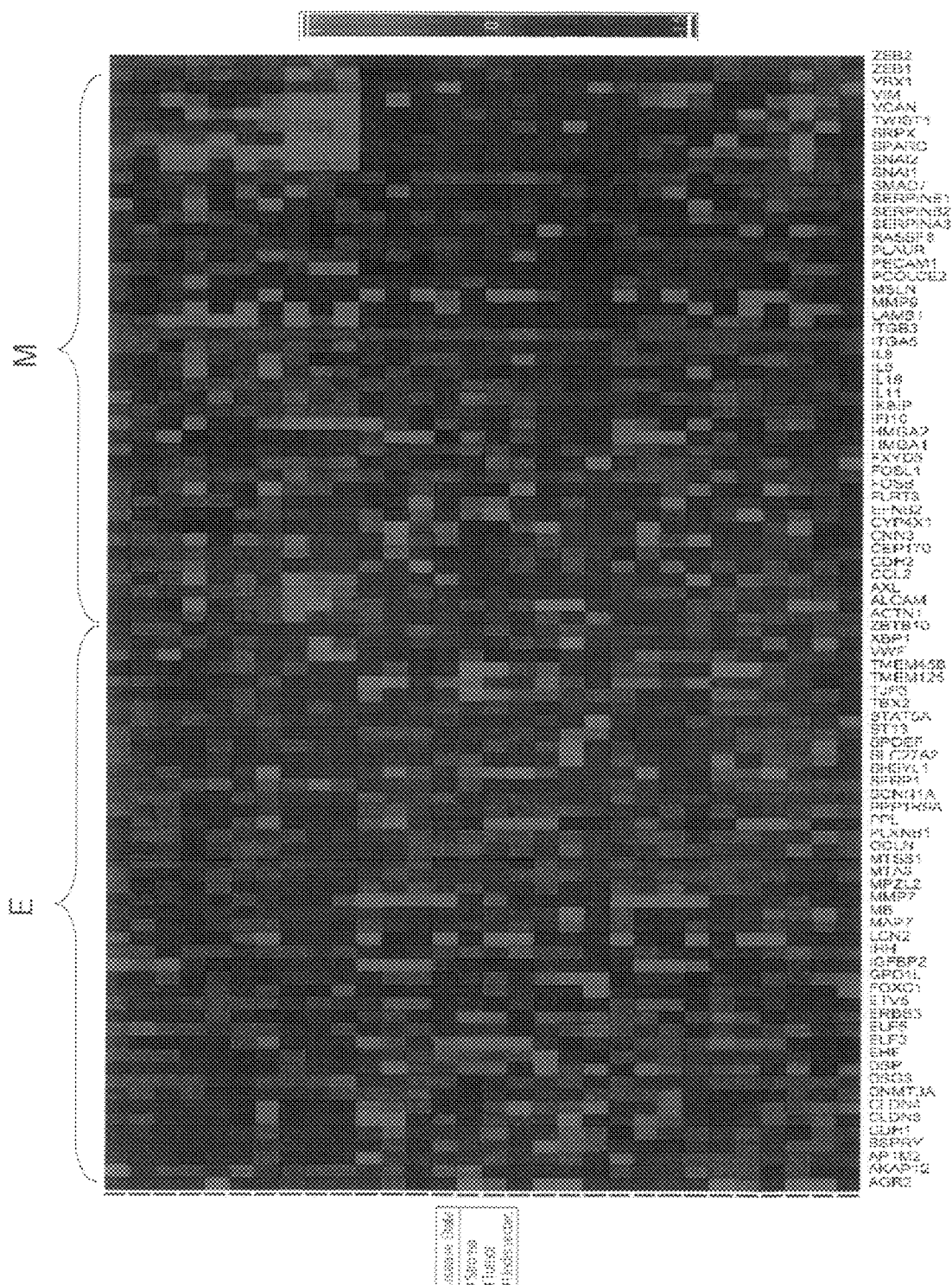
Figure 53B:
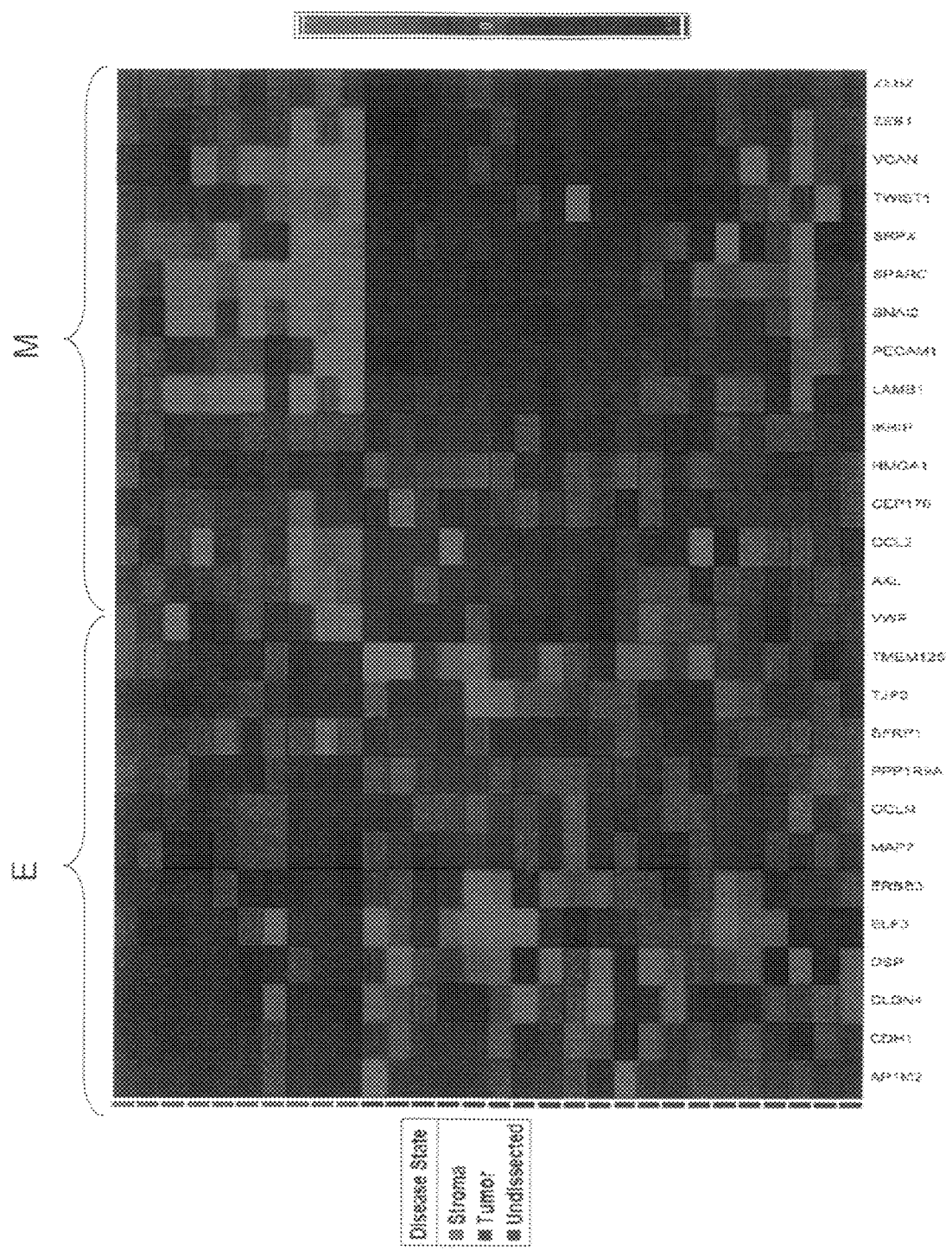

FIG. 53: Expression heatmaps for the 88-gene EMTGS in GeneLogic laser capture microdissection tumor dataset. (A) Mean-centered expression levels of each of the 88 genes in the EMTGS for matched stroma, tumor, and undissected patient samples are displayed on a red-blue color scale. (B) Mean-centered expression levels of a subset of 27 genes from the EMTGS that were statistically differentially expressed between matched tumor and stroma patient samples by a paired T-test with an FDR-corrected p-value <0.01.

FIG. 54: Comparison of 88-gene (A) and 44-epithelial-gene (B) EMTGS index scores from dissected tumors and matched tumors with infiltrating stromal tissue in GeneLogic laser capture microdissection tumor dataset. For each panel the matching samples are ordered by increasing index scores for the tumor-only set for direct comparison with the tumor plus stroma set. The boxplot in each sample shows the distribution of 1000 index scores based on random genelists, each having the same size as the signature. The red and blue bars indicate the signature index scores of samples that are significantly low and high (P=0.05), respectively, based on the distribution of 1000 index scores from random genelists in each sample. For samples with index scores that are neither significantly low nor high, their index scores are depicted in yellow. The Spearman rank correlation between the tumor-only and tumor plus stroma matched samples are shown for both the 88-gene and 44-epithelial-gene EMTGS index scores. Note that in (A) there is strong anti-correlation due to an E-gene being selected as the anchor gene by the software platform for the tumor-only samples while an M-gene was selected as the anchor gene for the tumor plus stroma samples.

DETAILED DESCRIPTION OF THE INVENTION

The term "cancer" in an individual refers to the presence of cells possessing characteristics typical of cancer-causing cells, such as uncontrolled proliferation, immortality, metastatic potential, rapid growth and proliferation rate, and certain characteristic morphological features. Often, cancer cells will be in the form of a tumor, but such cells may exist alone within an individual, or may circulate in the blood stream as independent cells, such as leukemic cells.

"Cell growth", as used herein, for example in the context of "tumor cell growth", unless otherwise indicated, is used as commonly used in oncology, where the term is principally associated with growth in cell numbers, which occurs by means of cell reproduction (i.e. proliferation) when the rate of the latter is greater than the rate of cell death (e.g. by apoptosis or necrosis), to produce an increase in the size of a population of cells, although a small component of that growth may in certain circumstances be due also to an increase in cell size or cytoplasmic volume of individual cells. An agent that inhibits cell growth can thus do so by either inhibiting proliferation or stimulating cell death, or both, such that the equilibrium between these two opposing processes is altered.

"Tumor growth" or "tumor metastases growth", as used herein, unless otherwise indicated, is used as commonly used in oncology, where the term is principally associated with an increased mass or volume of the tumor or tumor metastases, primarily as a result of tumor cell growth.

"Abnormal cell growth", as used herein, unless otherwise indicated, refers to cell growth that is independent of normal regulatory mechanisms (e.g., loss of contact inhibition). This includes the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (4) any tumors that proliferate by receptor tyrosine kinases; (5) any tumors that proliferate by aberrant serine/threonine kinase activation; and (6) benign and malignant cells of other proliferative diseases in which aberrant serine/threonine kinase activation occurs.

The term "treating" as used herein, unless otherwise indicated, means to give medical aid to counteract a disease or condition. The phrase "a method of treating" or its equivalent, when applied to cancer refers to a procedure or course of action that is designed to reduce or eliminate the number of cancer cells in a patient, or to alleviate the symptoms of a cancer. "A method of treating" cancer or another proliferative disorder does not necessarily mean that the cancer cells or other disorder will, in fact, be eliminated, that the number of cells or disorder will, in fact, be reduced, or that the symptoms of a cancer or other disorder will, in fact, be alleviated. Often, a method of treating cancer will be performed even with a low likelihood of success, but which, given the medical history and estimated survival expectancy of a patient, is nevertheless deemed an overall beneficial course of action.

The term "therapeutically effective agent" means a composition that will elicit the biological or medical response of a tissue, system, animal or human that is being sought by the researcher, veterinarian, medical doctor or other clinician.

The term "therapeutically effective amount" or "effective amount" means the amount of the subject compound or combination that will elicit the biological or medical response of a tissue, system, animal or human that is being sought by the researcher, veterinarian, medical doctor or other clinician.

The terms "responsive" or "responsiveness" when used herein in referring to a patient's reaction to administration of an IGF-1R kinase inhibitor or an EGFR kinase inhibitor, refer to a response that is positive or effective, from which the patient is likely to benefit. With regard to a treated tumor, responsiveness may for example be indicated by a tumor that displays: (a) slowing of growth, (b) cessation of growth, or (c) regression.

The term "dataset", as in for example "tumor dataset", means a collection or plurality of tumors or tumor cell lines that is used to derive gene expression data for a gene set or gene signature that may be used for the determination of a gene index as described herein.

The present invention derives from research that provided methods for determining which tumors will respond most effectively to treatment with protein-tyrosine kinase inhibitors (e.g. Thompson, S. et al. (2005) Cancer Res. 65(20): 9455-9462; U.S. Patent Application 60/997,514) based on whether the tumor cells have undergone an epithelial to mesenchymal transition ("EMT"; Thiery, J.P. (2002) Nat. Rev. Cancer 2:442-454; Savagner, P. (2001) Bioessays 23:912-923; Kang Y. and Massague, J. (2004) Cell 118:277-279; Julien-Grille, S., et al. Cancer Research 63:2172-2178; Bates, R. C. et al. (2003) Current Biology 13:1721-1727; Lu Z., et al. (2003) Cancer Cell. 4(6):499-515). This research demonstrated that epithelial carcinoma cells respond well to EGFR and IGF-1R kinase inhibitors, but that after an EMT the resulting mesenchymal-like cells are much less sensitive to such inhibitors. Biomarkers can be used to determine whether tumor cells have undergone an EMT (Thomson, S. et al. (2005) Cancer Res. 65(20):9455-9462). As a result of such work it became apparent that new therapeutic approaches would be required to find agents that were capable of inhibiting the formation, growth and/or function of such mesenchymal-like cells, which are thought to be an important element in the invasive and metastatic properties of tumors.

A considerable body of work is emerging that is beginning to delineate the biochemical pathways involved in regulating tumor EMT events, and to characterize the resultant mesenchymal-like tumor cells. For example, experiments using specific siRNA inhibitors of the expression of various protein products produced by mesenchymal-like tumor cells have demonstrated that reduced expression of the products of certain genes can specifically inhibit the growth of mesenchymal-like tumor cells. Thus pharmacological agents that also specifically inhibit the expression of the protein products encoded by these genes, or specifically inhibit the biological activity of the expressed proteins (e.g. phosphotransferase activity), such as specific antibodies to expressed proteins that possess an extracellular domain, antisense molecules, ribozymes, or small molecule enzyme inhibitors (e.g. protein kinase inhibitors), are similarly expected to be agents that will also specifically inhibit the growth of mesenchymal-like tumor cells. The anti-tumor effects of a combination of an EGFR or IGF-1R kinase inhibitor with such an agent should be superior to the anti-tumor effects of these kinase inhibitors by themselves, since such a combination should effectively inhibit both epithelial and mesenchymal-like tumor cells, and thus co-administration of such agents with EGFR or IGF-1R kinase inhibitors should be effective for treatment of patients with advanced cancers such as NSCL, pancreatic, colon or breast cancers.

Given the identification of key targets for the discovery and development of agents that will inhibit the growth of mesenchymal-like tumor cells, or the EMT process, there is thus a pressing need for quantitative, reliable and universally applicable methods to evaluate agents identified by in vitro screening methods to determine if they have the predicted effect of inhibiting the formation, growth and/or migration of mesenchymal-like tumor cells in vivo, both in animal model systems during drug development, and in human patients when evaluating drug efficacy. There is also a need for reliable diagnostic methods for determining the EMT status of cells in patients' tumors in order to predict which are likely to be susceptible or not to inhibition by EGFR or IGF-1R kinase inhibitors, and thus good candidates for such treatments, and also which would likely benefit from additional agents that inhibit EMT or the resulting mesenchymal tumor cells.

There are several potential shortcomings of current methods for determining EMT status in tumor cells, either in vitro or in vivo. These include, for example, the following: (1) Individual biomarker methods of determination of EMT status are not always reliably predictive of EMT status, and thus of sensitivity to inhibitors of EGFR or IGF-1R kinases. For example, E-cadherin expression, as a biomarker for epithelial status, does not always reliably predict tumor cell sensitivity to EGFR or IGF-1R kinase inhibitors (e.g. when E-Cadherin is mutated). Similarly, vimentin expression, as a biomarker for mesenchymal status, does not always reliably predict tumor cell sensitivity to EGFR kinase inhibitors (Richardson, F. et al. (2009) International Association for the Study of Lung Cancer, 13th World Conference on Lung Cancer, Jul. 31-Aug. 4, 2009, e-Poster: PD7.2.5. Congress: WCLC 2009; 29 pages); (2) Contamination of tumor samples with stromal tissue can complicate of confound analysis of tumor cell biomarker expression; (3) Quantitation of tumor cell biomarker expression and its correlation with EMT status can be unreliable; (4) It is difficult to use classical EMT biomarker analysis to differentiate different intermediate states during EMT; (5) There is great variability from tumor to tumor in the spectrum of genes whose expression is modulated (e.g. induced or inhibited) in response to EMT, in part due to the different effects of different EMT inducers, and in part due to different tissue-specific responses, which makes it difficult to choose biomarkers that will reliably predict EMT status across a broad spectrum of tumors; (6) The spectrum of genes whose expression is modulated in response to EMT in cell culture models used in drug discovery and development varies from in vitro culture to in vivo xenograft growth, making it difficult to choose individual biomarkers that will reliably predict EMT status in any given application of the cell model.

The data presented in the Examples herein below demonstrate that it is possible to derive an EMT gene signature (EMTGS) comprised of genes whose individual expression levels can be used collectively to formulate an EMTGS index score that can accurately quantify the degree of epithelial to mesenchymal transition (EMT) that a tumor cell has undergone (i.e. assess EMT status), and also effectively predict the responsiveness of tumor cells to certain anti-cancer drugs, such as EGFR kinase inhibitors or IGF-1R kinase inhibitors. These observations are the basis of valuable new diagnostic methods for predicting the effects of EGFR or IGF-1R kinase inhibitors on patient outcome, giving oncologists an additional tool to assist them in choosing the most appropriate treatment regimen for their patients. They also provide researchers with a powerful new tool to assist them in drug discovery and development of drugs that specifically inhibit EMT, or the resulting mesenchymal-like cells; or anti-cancer drugs whose action is influenced by EMT.

The present invention thus provides a method of determining the EMT status of tumor cells, comprising: measuring in a sample of the tumor cells the relative expression level of each gene of an EMT gene signature (EMTGS); wherein the EMTGS consists of a group of genes that have been determined to be coordinately regulated during EMT; calculating an EMTGS index score for said tumor cells by applying an algorithm to the measured expression level values that incorporates the contributions of co-correlated genes; and determining if said EMTGS index score is more similar to an EMTGS index score from a reference epithelial tumor cell or an EMTGS index score from a reference mesenchymal-like tumor cell, and thus determining the EMT status of the sample tumor cells.

The present invention further provides a method of determining the EMT status of tumor cells, comprising: measuring in a sample of the tumor cells the relative expression level of each gene of an EMT gene signature (EMTGS); wherein the EMTGS consists of a group of genes that have been determined to be coordinately regulated during EMT by a process including (a) selection of an initial group of genes that are coordinately regulated in multiple tumor cell models of EMT; and (b) repeated addition or removal of genes from said group to maximize the number of genes whose expression is co-correlated in multiple human tumor datasets; calculating an EMTGS index score for said tumor cells by applying an algorithm to the measured expression level values that incorporates the contributions of co-correlated genes; and determining if said EMTGS index score is more similar to an EMTGS index score from a reference epithelial tumor cell or an EMTGS index score from a reference mesenchymal-like tumor cell, and thus determining the EMT status of the sample tumor cells.

The present invention also provides a method of determining whether a group of genes are coordinately regulated during EMT by a process including the steps (a) selection of an initial group of genes that are coordinately regulated in multiple tumor cell models of EMT; and (b) repeated addition or removal of genes from said group to maximize the number of genes whose expression is co-correlated in multiple human tumor datasets.

The present invention further provides a method of determining the EMT status of tumor cells, comprising: measuring in a sample of the tumor cells the relative expression level of each gene of an EMT gene signature (EMTGS), wherein the EMTGS consists essentially of the following genes: SERPINA3, ACTN1, AGR2, AKAP12, ALCAM, AP1M2, AXL, BSPRY, CCL2, CDH1, CDH2, CEP170, CLDN3, CLDN4, CNN3, CYP4X1, DNMT3A, DSG3, DSP, EFNB2, EHF, ELF3, ELF5, ERBB3, ETV5, FLRT3, FOSB, FOSL1, FOXC1, FXYD5, GPD1L, HMGA1, HMGA2, HOPX, IFI16, IGFBP2, IHH, IKBIP, IL-11, IL-18, IL6, IL8, ITGA5, ITGB3, LAMB1, LCN2, MAP7, MB, MMP7, MMP9, MPZL2, MSLN, MTA3, MTSS1, OCLN, PCOLCE2, PECAM1, PLAUR, PLXNB1, PPL, PPP1R9A, RASSF8, SCNN1A, SERPINB2, SERPINE1, SFRP1, SH3YL1, SLC27A2, SMAD7, SNAI1, SNAI2, SPARC, SPDEF, SRPX, STAT5A, TBX2, TJP3, TMEM125, TMEM45B, TWIST1, VCAN, VIM, VWF, XBP1, YBX1, ZBTB10, ZEB1, ZEB2; calculating an EMTGS index score for said tumor cells by applying an algorithm to the measured expression level values that incorporates the contributions of co-correlated genes; and determining if said EMTGS index score is more similar to an EMTGS index score from a reference epithelial tumor cell or an EMTGS index score from a reference mesenchymal-like tumor cell, and thus determining the EMT status of the sample tumor cells.

As used herein, "co-correlated" means, when applied to a set of genes, that expression levels of the members of the set display a statistically significant tendency to increase or decrease in concert, within a given type of tissue, e.g. tumor tissue. Without intending to be bound by theory, it noted that co-correlation is likely to indicate that the co-correlated genes share a common involvement in one or more biological functions.

In an embodiment of any of the methods disclosed herein, the algorithm that incorporates the contributions of co-correlated genes that is applied to the measured expression level values is algorithm $A^1$, as defined herein below (see also Experimental Details section).

Algorithm $A^1$ consists of two main components: 1) a gene selection component based on correlation of expression and 2) an index score calculation component based on mean expression of selected genes. Specifically, given a genelist A (e.g. the 88 gene EMTGS) and dataset B, algorithm $A^1$ performs the following steps:

1) Define correlation-based anchor gene (AG) for A in B:
   a) Calculate Pearson or Spearman correlation (user-selected) of gene expression for every gene-gene pair in A across all samples in B.
   b) AG for AB is the gene x that maximizes the following:

$$AG_{AB} = \frac{\sum_{Nx} |R|}{n}$$

Where $AG_{AB}$ is the anchor gene for genelist A in dataset B, Nx is the set of all gene-gene pairs with gene x, n is the number of gene-gene pairs in Nx, and |R| is the absolute value of the Pearson (or Spearman) correlation coefficient for each gene-gene pair across all samples in B.

2) Select a subset of genes from the genelist ($A_{AG}$) that significantly correlate with AG:
   a) Rank all genes based on the Pvalue of their correlation to AG.
   b) $A_{AG}$ is defined as the subset of genes in A that correlate with AG across B, for which Pvalue≤c, where c is the user-specified significance cutoff (typically 0.01).

3) For each sample s in B, calculate a correlation-based expression index score (I) for genelist A:
   a) Define $I_{ABs}$ as:

$$I_{ABs} = \frac{\sum_{A_{AG}} e'_{sx}}{m}$$

Where $A_{AG}$ is the subset of genes in A that significantly correlate with the anchor gene AG, m is the number of genes in $A_{AG}$, and $e_{sx}'$ defined as the expression of gene x (from subset $A_{AG}$) in sample s of dataset B as follows:

$e_{sx}' = e_{sx}$ if $R_x > 0$ or $e_{sx}' = 2\mu_{Bx} - e_{sx}$ if $R_x < 0$

Where $e_{sx}$ is the expression of gene x in sample s, $\mu_{Bx}$ is the mean expression of gene x is dataset B, and $R_x$ is the correlation coefficient of gene x with the anchor gene AG.

In an alternative embodiment of any of the methods disclosed herein, the algorithm that incorporates the contributions of co-correlated genes that is applied to the measured expression level values is algorithm A, as defined herein below.

Algorithm A consists of two main components: 1) a gene selection component based on correlation of expression and 2) an index score calculation component based on mean expression of selected genes. Specifically, given a genelist A and dataset B, algorithm A performs the following steps:

1) Define correlation-based anchor gene (AG) for A in B:
   a) Calculate Pearson or Spearman correlation (user-selected) of gene expression for every gene-gene pair in A across all samples in B.
   b) AG for AB is the gene x that maximizes the following:

$$AG_{AB} = \frac{\sum_{Nx} |R|}{n}$$

Where $AG_{AB}$ is the anchor gene for genelist A in dataset B, Nx is the set of all gene-gene pairs with gene x, n is the number of gene-gene pairs in Nx, and |R| is the absolute value of the Pearson (or Spearman) correlation coefficient for each gene-gene pair across all samples in B.

2) Select a subset of genes from the genelist ($A_{AG}$) that significantly correlate with AG:
   a) Rank all genes based on the Pvalue of their correlation to AG.
   b) $A_{AG}$ is defined as the subset of genes in A that correlate with AG across B, for which Pvalue≤c, where c is the user-specified significance cutoff (typically 0.01).

3) For each sample s in B, calculate a correlation-based expression index score (I) for genelist A:
   a) Define $I_{ABs}$ as:

$$I_{ABs} = \frac{\sum_{A_{AG}} e'_{sx}}{m}$$

Where $A_{AG}$ is the subset of genes in A that significantly correlate with the anchor gene AG, m is the number of genes in $A_{AG}$, and $e_{sx}'$ defined as the expression of gene x (from subset $A_{AG}$) in sample s of dataset B as follows:

$e_{sx}' = e_{sx}$ if $R_x > 0$ or $e_{sx}' = \mu_{Bx} - e_{sx}$ if $R_x < 0$

Where $e_{sx}$, is the expression of gene x in sample s, $\mu_{Bx}$ is the mean expression of gene x is dataset B, and $R_x$ is the correlation coefficient of gene x with the anchor gene AG.

EMTGS index scores must be calculated as part of a group or dataset in order to achieve statistical significance in the co-correlation analysis. The number of samples changes the value at which the correlation coefficient can achieve statistical significance. As the number of samples increases, the coefficient that achieves significance decreases. Thus, samples must be processed through the indexing algorithm as part of a group of about 25-30 samples or more. For clinical application, single patient samples may be analysed with a control group of samples, taken for example from a clinical trial where the relative indexes correlated with patient response.

As an alternative to any of the methods described herein, where a the user-specified significance cutoff (c) of 0.01 is typically chosen, a user-specified significance cutoff (c) of 1.0 may be chosen if one wishes to ensure that the contribution of all genes in a gene signature are used for calculating an index score. Comparison of different samples may thus be made using the data from all the genes in a signature, which may be of interest if, for example, the number of samples is very small.

As an alternative to any of the methods disclosed herein involving an EMTGS of 88 genes, wherein the EMTGS consists of, or consists essentially of, the 88 genes SERPINA3, ACTN1, AGR2, AKAP12, ALCAM, AP1M2, AXL, BSPRY, CCL2, CDH1, CDH2, CEP170, CLDN3, CLDN4, CNN3, CYP4X1, DNMT3A, DSG3, DSP, EFNB2, EHF, ELF3, ELF5, ERBB3, ETV5, FLRT3, FOSB, FOSL1, FOXC1, FXYD5, GPD1L, HMGA1, HMGA2, HOPX, IFI16, IGFBP2, IHH, IKBIP, IL-11, IL-18, IL6, IL8, ITGA5, ITGB3, LAMB1, LCN2, MAP7, MB, MMP7, MMP9, MPZL2, MSLN, MTA3, MTSS1, OCLN, PCOLCE2, PECAM1, PLAUR, PLXNB1, PPL, PPP1R9A, RASSF8, SCNN1A, SERPINB2, SERPINE1, SFRP1, SH3YL1, SLC27A2, SMAD7, SNAI1, SNAI2, SPARC, SPDEF, SRPX, STAT5A, TBX2, TJP3, TMEM125, TMEM45B, TWIST1, VCAN, VIM, VWF, XBP1, YBX1, ZBTB10, ZEB1 and ZEB2, the present invention also provides any of these methods where, rather than the 88 gene EMTGS, the EMTGS may consist of, or consist essentially of, a subset of these 88 genes selected from the gene signatures herein below (i.e. subsets A to Q; R1 to R17; any 54- or -greater gene subsets from 87 genes (i.e. as in Table 1 but not including MTA3) from the 88-gene EMTGS; and any 24- or -greater gene subsets from the 43 epithelial genes of the 87 genes from the from the 88 gene EMTGS). The present invention further provides for each of these subsets of the 88 genes, a PCR primer set consisting of a pair of primers for each of the genes of the subset. The present invention further provides for each of these subsets of the 88 genes, a DNA microarray chip consisting of a solid surface and a probe set, said probe set consisting of probes specific for each of the genes of the subset.

EMTGS subset A (i.e. without ITGA5): SERPINA3, ACTN1, AGR2, AKAP12, ALCAM, AP1M2, AXL, BSPRY, CCL2, CDH1, CDH2, CEP170, CLDN3, CLDN4, CNN3, CYP4X1, DNMT3A, DSG3, DSP, EFNB2, EHF, ELF3, ELF5, ERBB3, ETV5, FLRT3, FOSB, FOSL1, FOXC1, FXYD5, GPD1L, HMGA1, HMGA2, HOPX, IFI16, IGFBP2, IHH, IKBIP, IL-11, IL-18, IL6, IL8, ITGB3, LAMB1, LCN2, MAP7, MB, MMP7, MMP9, MPZL2, MSLN, MTA3, MTSS1, OCLN, PCOLCE2, PECAM1, PLAUR, PLXNB1, PPL, PPP1R9A, RASSF8, SCNN1A, SERPINB2, SERPINE1, SFRP1, SH3YL1, SLC27A2, SMAD7, SNAI1, SNAI2, SPARC, SPDEF, SRPX, STAT5A, TBX2, TJP3, TMEM125, TMEM45B, TWIST1, VCAN, VIM, VWF, XBP1, YBX1, ZBTB10, ZEB1, ZEB2.

EMTGS subset B (i.e. without VIM): SERPINA3, ACTN1, AGR2, AKAP12, ALCAM, AP1M2, AXL, BSPRY, CCL2, CDH1, CDH2, CEP170, CLDN3, CLDN4, CNN3, CYP4X1, DNMT3A, DSG3, DSP, EFNB2, EHF, ELF3, ELF5, ERBB3, ETV5, FLRT3, FOSB, FOSL1, FOXC1, FXYD5, GPD1L, HMGA1, HMGA2, HOPX, IFI16, IGFBP2, IHH, IKBIP, IL-11, IL-18, IL6, IL8, ITGA5, ITGB3, LAMB1, LCN2, MAP7, MB, MMP7, MMP9, MPZL2, MSLN, MTA3, MTSS1, OCLN, PCOLCE2, PECAM1, PLAUR, PLXNB1, PPL, PPP1R9A, RASSF8, SCNN1A, SERPINB2, SERPINE1, SFRP1, SH3YL1, SLC27A2, SMAD7, SNAI1, SNAI2, SPARC, SPDEF, SRPX, STAT5A, TBX2, TJP3, TMEM125, TMEM45B, TWIST1, VCAN, VWF, XBP1, YBX1, ZBTB10, ZEB1, ZEB2.

EMTGS subset C (i.e. without CDH1): SERPINA3, ACTN1, AGR2, AKAP12, ALCAM, AP1M2, AXL, BSPRY, CCL2, CDH2, CEP170, CLDN3, CLDN4, CNN3, CYP4X1, DNMT3A, DSG3, DSP, EFNB2, EHF, ELF3, ERBB3, ETV5, FLRT3, FOSB, FOSL1, FOXC1, FXYD5, GPD1L, HMGA1, HMGA2, HOPX, IFI16, IGFBP2, IHH, IKBIP, IL-11, IL-18, IL6, IL8, ITGA5, ITGB3, LAMB1, LCN2, MAP7, MB, MMP7, MMP9, MPZL2, MSLN, MTA3, MTSS1, OCLN, PCOLCE2, PECAM1, PLAUR, PLXNB1, PPL, PPP1R9A, RASSF8, SCNN1A, SERPINB2, SERPINE1, SFRP1, SH3YL1, SLC27A2, SMAD7, SNAI1, SNAI2, SPARC, SPDEF, SRPX, STAT5A, TBX2, TJP3, TMEM125, TMEM45B, TWIST1, VCAN, VIM, VWF, XBP1, YBX1, ZBTB10, ZEB1, ZEB2.

EMTGS subset D (i.e. without ERBB3): SERPINA3, ACTN1, AGR2, AKAP12, ALCAM, AP1M2, AXL, BSPRY, CCL2, CDH1, CDH2, CEP170, CLDN3, CLDN4, CNN3, CYP4X1, DNMT3A, DSG3, DSP, EFNB2, EHF, ELF3, ELF5, ETV5, FLRT3, FOSB, FOSL1, FOXC1, FXYD5, GPD1L, HMGA1, HMGA2, HOPX, IFI16, IGFBP2, IHH, IKBIP, IL-11, IL-18, IL6, IL8, ITGA5, ITGB3, LAMB1, LCN2, MAP7, MB, MMP7, MMP9, MPZL2, MSLN, MTA3, MTSS1, OCLN, PCOLCE2, PECAM1, PLAUR, PLXNB1, PPL, PPP1R9A, RASSF8, SCNN1A, SERPINB2, SERPINE1, SFRP1, SH3YL1, SLC27A2, SMAD7, SNAI1, SNAI2, SPARC, SPDEF, SRPX, STAT5A, TBX2, TJP3, TMEM125, TMEM45B, TWIST1, VCAN, VIM, VWF, XBP1, YBX1, ZBTB10, ZEB1, ZEB2.

EMTGS subset E (i.e. E only (only epithelial genes)): AGR2, AKAP12, AP1M2, BSPRY, CDH1, CLDN3, CLDN4, DNMT3A, DSG3, DSP, EHF, ELF3, ELF5, ERBB3, ETV5, FOXC1, GPD1L, HOPX, IGFBP2, IHH, LCN2, MAP7, MB, MMP7, MPZL2, MTA3, MTSS1, OCLN, PLXNB1, PPL, PPP1R9A, SCNN1A, SFRP1, SH3YL1, SLC27A2, SPDEF, STAT5A, TBX2, TJP3, TMEM125, TMEM45B, VWF, XBP1, ZBTB10.

EMTGS subset F (i.e. E-CDH1, epithelial genes without CDH1): AGR2, AKAP12, AP1M2, BSPRY, CLDN3, CLDN4, DNMT3A, DSG3, DSP, EHF, ELF3, ELF5, ERBB3, ETV5, FOXC1, GPD1L, HOPX, IGFBP2, IHH, LCN2, MAP7, MB, MMP7, MPZL2, MTA3, MTSS1, OCLN, PLXNB1, PPL, PPP1R9A, SCNN1A, SFRP1, SH3YL1, SLC27A2, SPDEF, STAT5A, TBX2, TJP3, TMEM125, TMEM45B, VWF, XBP1, ZBTB10.

EMTGS subset G (i.e. E-ERBB3, epithelial genes without ERBB3: AGR2, AKAP12, AP1M2, BSPRY, CDH1, CLDN3, CLDN4, DNMT3A, DSG3, DSP, EHF, ELF3, ELF5, ETV5, FOXC1, GPD1L, HOPX, IGFBP2, IHH, LCN2, MAP7, MB, MMP7, MPZL2, MTA3, MTSS1, OCLN, PLXNB1, PPL, PPP1R9A, SCNN1A, SFRP1, SH3YL1, SLC27A2, SPDEF, STAT5A, TBX2, TJP3, TMEM125, TMEM45B, VWF, XBP1, ZBTB10.

EMTGS subset H (80 genes): SERPINA3, ACTN1, AKAP12, ALCAM, AP1M2, AXL, BSPRY, CCL2, CDH2, CEP170, CLDN3, CNN3, CYP4X1, DNMT3A, DSG3, DSP, EFNB2, EHF, ELF5, ETV5, FLRT3, FOSB, FOSL1, FOXC1, FXYD5, GPD1L, HMGA1, HMGA2, HOPX, IFI16, IGFBP2, IHH, IL-11, IL-18, IL6, IL8, ITGA5, ITGB3, LAMB1, LCN2, MAP7, MB, MMP7, MMP9, MPZL2, MSLN, MTA3, MTSS1, PCOLCE2, PECAM1, PLAUR, PLXNB1, PPL, PPP1R9A, RASSF8, SCNN1A, SERPINB2, SERPINE1, SFRP1, SLC27A2, SMAD7, SNAI1, SNAI2, SPARC, SPDEF, SRPX, STAT5A, TBX2, TJP3, TMEM125, TMEM45B, TWIST1, VCAN, VIM, VWF, XBP1, YBX1, ZBTB10, ZEB1, ZEB2.

EMTGS subset I (8 genes): AGR2, CDH1, CLDN4, ELF3, ERBB3, IKBIP, OCLN, SH3YL1.

EMTGS subsets J, K, L, M, N, O, P and Q are the eight subsets of genes listed in FIG. 40 which were used by the correlation analysis software running algorithm A to generate an EMTGS index score (i.e. for each group, one anchor gene, plus those genes listed below the anchor gene).

EMTGS subsets R1 to R17 are the 17 groups of genes listed in Table 6 herein which passed the co-correlation cutoff and were used by the correlation analysis software running algorithm A to generate EMTGS index scores for the human tumor datasets indicated.

54-gene EMTGSs: Any 54- or -greater gene subsets from 87 genes selected from the 88-gene EMTGS, wherein the 87 genes are the genes of the 88-gene EMTGS but without MTA-3. The 87 genes (i.e. not including MTA-3) from the 88-gene EMTGS are thus: SERPINA3, ACTN1, AGR2, AKAP12, ALCAM, AP1M2, AXL, BSPRY, CCL2, CDH1, CDH2, CEP170, CLDN3, CLDN4, CNN3, CYP4X1, DNMT3A, DSG3, DSP, EFNB2, EHF, ELF3, ELF5, ERBB3, ETV5, FLRT3, FOSB, FOSL1, FOXC1, FXYD5, GPD1L, HMGA1, HMGA2, HOPX, IFI16, IGFBP2, IHH, IKBIP, IL-11, IL-18, IL6, IL8, ITGA5, ITGB3, LAMB1, LCN2, MAP7, MB, MMP7, MMP9, MPZL2, MSLN, MTSS1, OCLN, PCOLCE2, PECAM1, PLAUR, PLXNB1, PPL, PPP1R9A, RASSF8, SCNN1A, SERPINB2, SERPINE1, SFRP1, SH3YL1, SLC27A2, SMAD7, SNAI1, SNAI2, SPARC, SPDEF, SRPX, STAT5A, TBX2, TJP3, TMEM125, TMEM45B, TWIST1, VCAN, VIM, VWF, XBP1, YBX1, ZBTB10, ZEB1, ZEB2. Thus, for example, a signature comprising any 54 or more genes from these 87 genes can be used in the methods of the invention for determining whether a human tumor is likely to be responsive to treatment with an EGFR kinase inhibitor or an IGF-1R kinase inhibitor.

24-gene EMTGSs: Any 24- or -greater gene subsets from the 43 epithelial genes of the 87 genes (i.e. not including MTA-3) selected from the from the 88-gene EMTGS. The 43 epithelial genes are thus AGR2, AKAP12, AP1M2, BSPRY, CDH1, CLDN3, CLDN4, DNMT3A, DSG3, DSP, EHF, ELF3, ELF5, ERBB3, ETV5, FOXC1, GPD1L, HOPX, IGFBP2, IHH, LCN2, MAP7, MB, MMP7, MPZL2, MTSS1, OCLN, PLXNB1, PPL, PPP1R9A, SCNN1A, SFRP1, SH3YL1, SLC27A2, SPDEF, STAT5A, TBX2, TJP3, TMEM125, TMEM45B, VWF, XBP1, ZBTB10. Thus, for example, a signature comprising any 24 or more genes from these 43 genes can be used in the methods of the invention for determining whether a human tumor is likely to be responsive to treatment with an EGFR kinase inhibitor or an IGF-1R kinase inhibitor.

Indexes derived from each of these subsets of the 88 gene EMTGS all have predictive value for assessing EMT status, tumor cell sensitivity to EGFR kinase inhibitors or IGF-1R kinase inhibitors, or human tumors in patients as likely to be responsive or non-responsive to treatment with an EGFR kinase inhibitor or an IGF-1R kinase inhibitor. However, each of these may have specific advantages in given areas. For example, the indexes derived from only epithelial genes may have particular value when used with tumor samples that have a high content of stromal tissue. The indexes derived from R1 to R17 signatures will be most useful with the tumor types with which they are associated, as indicated in Table 6.

Additionally, as an alternative to any of the methods disclosed herein involving an EMTGS of 88 genes, the present invention also provides any of these methods where, rather than the 88 gene EMTGS, the gene signature may be the Choi signature, the Bunn gefitinib signature, the Yauch signature, or the SABiosciences signature as described herein below (see Tables 10-13). The present invention further provides for each of these signatures, a PCR primer set consisting of a pair of primers for each of the genes of the signature. The present invention further provides for each of these signatures, a DNA microarray chip consisting of a solid surface and a probe set, said probe set consisting of probes specific for each of the genes of the signature. Indexes derived from each of these signatures have predictive value for assessing EMT status, tumor cell sensitivity to EGFR kinase inhibitors or IGF-1R kinase inhibitors, or human tumors in patients as likely to be responsive or non-responsive to treatment with an EGFR kinase inhibitor or an IGF-1R kinase inhibitor. However, compared to indexes derived from the 88 gene EMTGS, or subsets thereof, there are limitations in their use. For example, none of these signatures was derived using multiple human tumor datasets, and thus they will lack the predictive power of the 88 gene EMTGS in human tumors in vivo. The Choi signature only has value for predicting results for breast tumor cells. The SABiosciences signature shows far fewer gene changes on EMT induction than the 88 gene EMTGS in several tumor cell EMT models, and thus will be an inferior tool for monitoring EMT in situations where only a small subset of genes is involved in the EMT or its inhibition, as in certain tumor types, or when certain EMT inhibitor compounds are used to prevent EMT. The Bunn gefitinib signature was developed as a gefitinib sensitivity signature for NSCLC tumors, not as an EMT status indicator, and thus is likely to have limitations in this area, particularly for tumor tissues other than lung, for which the signature was developed. Finally, it appears that the Yauch signature is unable to differentiate different types of human lung tumors (e.g. adenocarcinoma and squamous cell carcinoma) as effectively as the 88 gene EMTGS, likely due to the fact that human tumor datasets were not utilized in its generation.

The present invention further provides any of the methods disclosed herein, wherein the tumor cells are from a tumor of a patient with cancer. The present invention also provides any of the methods disclosed herein, comprising an additional step of obtaining a sample of cells of the tumor of the patient prior to the step of measuring gene expression levels. The present invention also provides any of the methods disclosed herein, wherein the tumor cells are derived from a tumor biopsy. The present invention also provides any of the methods disclosed herein, wherein the tumor cells are derived from a blood sample containing circulating tumor cells. The present invention also provides any of the methods disclosed herein, wherein the tumor cells are NSCL cancer, breast cancer, colorectal cancer, or pancreatic cancer tumor cells.

The present invention further provides a method of identifying a human tumor as likely to be responsive or non-responsive to treatment with an EGFR kinase inhibitor, comprising: measuring in a sample of the tumor cells the relative expression level of each gene of an EMT gene signature (EMTGS), wherein the EMTGS consists essentially of the following genes: SERPINA3, ACTN1, AGR2, AKAP12, ALCAM, AP1M2, AXL, BSPRY, CCL2, CDH1, CDH2, CEP170, CLDN3, CLDN4, CNN3, CYP4X1, DNMT3A, DSG3, DSP, EFNB2, EHF, ELF3, ELF5, ERBB3, ETV5, FLRT3, FOSB, FOSL1, FOXC1, FXYD5, GPD1L, HMGA1, HMGA2, HOPX, IFI16, IGFBP2, IHH, IKBIP, IL-11, IL-18, IL6, IL8, ITGA5, ITGB3, LAMB1, LCN2, MAP7, MB, MMP7, MMP9, MPZL2, MSLN, MTA3, MTSS1, OCLN, PCOLCE2, PECAM1, PLAUR, PLXNB1, PPL, PPP1R9A, RASSF8, SCNN1A, SERPINB2, SERPINE1, SFRP1, SH3YL1, SLC27A2, SMAD7, SNAI1, SNAI2, SPARC, SPDEF, SRPX, STAT5A, TBX2, TJP3, TMEM125, TMEM45B, TWIST1, VCAN, VIM, VWF, XBP1, YBX1, ZBTB10, ZEB1, ZEB2; calculating an EMTGS index score for said tumor cells by applying an algorithm to the measured expression level values that incorporates the contributions of co-correlated genes; and determining if the EMTGS index score is above a defined threshold that indicates that the tumor is likely to be responsive to an EGFR kinase inhibitor, or below said threshold and thus likely to be non-responsive to an EGFR kinase inhibitor.

The present invention further provides a method of identifying a human tumor as likely to be responsive or non-responsive to treatment with an IGF-1R kinase inhibitor, comprising: measuring in a sample of the tumor cells the relative expression level of each gene of an EMT gene signature (EMTGS), wherein the EMTGS consists essentially of the following genes: SERPINA3, ACTN1, AGR2, AKAP12, ALCAM, AP1M2, AXL, BSPRY, CCL2, CDH1, CDH2, CEP170, CLDN3, CLDN4, CNN3, CYP4X1, DNMT3A, DSG3, DSP, EFNB2, EHF, ELF3, ELF5, ERBB3, ETV5, FLRT3, FOSB, FOSL1, FOXC1, FXYD5, GPD1L, HMGA1, HMGA2, HOPX, IFI16, IGFBP2, IHH, IKBIP, IL-11, IL-18, IL6, IL8, ITGA5, ITGB3, LAMB1, LCN2, MAP7, MB, MMP7, MMP9, MPZL2, MSLN, MTA3, MTSS1, OCLN, PCOLCE2, PECAM1, PLAUR, PLXNB1, PPL, PPP1R9A, RASSF8, SCNN1A, SERPINB2, SERPINE1, SFRP1, SH3YL1, SLC27A2, SMAD7, SNAI1, SNAI2, SPARC, SPDEF, SRPX, STAT5A, TBX2, TJP3, TMEM125, TMEM45B, TWIST1, VCAN, VIM, VWF, XBP1, YBX1, ZBTB10, ZEB1, ZEB2; calculating an EMTGS index score for said tumor cells by applying an algorithm to the measured expression level values that incorporates the contributions of co-correlated genes; and determining if the EMTGS index score is above a defined threshold that indicates that the tumor is likely to be responsive to an IGF-1R kinase inhibitor, or below said threshold and thus likely to be non-responsive to an IGF-1R kinase inhibitor.

In one embodiment, an EMTGS index score above a defined threshold indicates that the tumor is likely to be responsive to an EGFR or IGF-1R kinase inhibitor, and an EMTGS score below a defined threshold indicates that the tumor is likely to be non-responsive to an EGFR or IGF-1R kinase inhibitor. The threshold value may be determined, for example, as described herein, using an ROC curve analysis, or by any comparable statistical methods.

Thus, for interpretation of EMTGS index scores with respect to a threshold EMTGS index score, in one embodiment of the present invention, using OCR for EMTGS measurements, EMTGS index scores higher than the threshold EMTGS index score will be interpreted as indicating a tumor likely to be non-responsive (resistant) to an EGFR kinase inhibitor or IGF-1R kinase inhibitor treatment. EMTGS index scores lower than the threshold EMTGS index score will be interpreted as indicating a tumor likely to be responsive (sensitive) to EGFR kinase inhibitor or IGF-1R kinase inhibitor treatment. It is contemplated that a given threshold EMTGS index score will vary depending on tumor type. In the context of the present invention, the term "tumor type" takes into account (a) species (human, mouse, dog etc.); and (b) organ or tissue of origin. Optionally, tumor type further takes into account tumor categorization based on gene expression characteristics, e.g., HER2-positive breast tumors, or non-small cell lung tumors expressing a particular EGFR mutation.

For any given tumor type, an optimum threshold EMTGS index score can be determined (or at least approximated) empirically by performing a threshold determination analysis. In many effective methods, threshold determination analysis includes receiver operator characteristic (ROC) curve analysis.

A "threshold determination analysis" as described herein means an analysis of a dataset representing a given tumor type (e.g. human NSCLC) to determine a threshold EMTGS index score, e.g., an optimum threshold EMTGS score, for that particular tumor type. In the context of a threshold determination analysis, the dataset representing a given tumor type includes (a) actual response data (response or non-response), and (b) an EMTGS score for each tumor from a group of tumor-bearing mice or humans. As used herein, "optimum threshold PGS score" means the threshold PGS score at which the classifier gives the most desirable balance between the cost of false negative calls and false positive calls.

ROC curve analysis is an established statistical technique, the application of which is within ordinary skill in the art. For a discussion of ROC curve analysis, see generally Zweig et al., 1993, "Receiver operating characteristic (ROC) plots: a fundamental evaluation tool in clinical medicine," Clin. Chem. 39:561-577; and Pepe, 2003, The statistical evaluation of medical tests for classification and prediction, Oxford Press, New York.

As used herein, "receiver operating characteristic" (ROC) curve means a graphical plot of false positive rate (sensitivity) versus true positive rate (specificity) for a binary classifier system. In construction of an ROC curve, the following definitions apply: False negative rate: FNR=1−TPR.

True positive rate: TPR=positive/(true positive+false negative).

False positive rate: FPR=false positive/(false positive+true negative).

EMTGS index scores and the optimum threshold EMTGS index score may vary from tumor type to tumor type. Therefore, a threshold determination analysis preferably is performed on one or more datasets representing any given tumor type to be tested using the present invention. The dataset used for threshold determination analysis includes: (a) actual response data (response or non-response), and (b) an EMTGS index score for each tumor sample from a group of human tumors or animal tumors. Once an EMTGS index score threshold is determined with respect to a given tumor type, that threshold can be applied to interpret EMTGS index scores from tumors of that tumor type.

The ROC curve analysis is performed essentially as follows. Any sample with an EMTGS index score greater than threshold is identified as a non-responder. Any sample with an EMTGS index score less than or equal to threshold is identified as responder. For every EMTGS index score from a tested set of samples, "responders" and "non-responders" (hypothetical calls) are classified using that EMTGS index score as the threshold. This process enables calculation of TPR (y vector) and FPR (x vector) for each potential threshold, through comparison of hypothetical calls against the actual response data for the data set. Then an ROC curve is constructed by making a dot plot, using the TPR vector, and FPR vector. If the ROC curve is above the diagonal from (0, 0) point to (1.0, 0.5) point, it shows that the EMTGS test result is a better test than random. EDIT The ROC curve can be used to identify the best operating point. The best operating point is the one that yields the best balance between the cost of false positives weighed against the cost of false negatives. These costs need not be equal. The average expected cost of classification at point x,y in the ROC space is denoted by the expression $C=(1-p)alpha*x+p*beta(1-y)$ wherein: alpha=cost of a false positive, beta=cost of missing a positive (false negative), and p=proportion of positive cases.

False positives and false negatives can be weighted differently by assigning different values for alpha and beta. For example, if it is decided to include more patients in the responder group at the cost of treating more patients who are non-responders, one can put more weight on alpha. In this case, it is assumed that the cost of false positive and false negative is the same (alpha equals to beta). Therefore, the average expected cost of classification at point x,y in the ROC space is: $C'=(1-p)*x+p*(1-y)$. The smallest C' can be calculated after using all pairs of false positive and false negative (x, y). The optimum EMTGS index score threshold is calculated as the EMTGS index score of the (x, y) at C'.

In addition to predicting whether a tumor will be responsive or resistant to treatment with an EGFR kinase inhibitor or IGF-1R kinase inhibitor, an EMTGS index score provides an approximate, but useful, indication of how likely a tumor is to be responsive or non-responsive. In general, when using qPCR for EMTGS measurements, the lower the EMTGS index score, the more likely a tumor is to be responsive to an EGFR kinase inhibitor or IGF-1R kinase inhibitor, and the higher the EMTGS index score, the more likely a tumor is to be resistant to an EGFR kinase inhibitor or IGF-1R kinase inhibitor.

The present invention further provides a method of treatment of a patient with cancer, comprising: determining whether the patient is likely to be responsive to an EGFR kinase inhibitor using any of the methods disclosed herein for identifying a human tumor as likely to be responsive or non-responsive to treatment with an EGFR kinase inhibitor, and administering to said patient a therapeutically effective amount of an EGFR kinase inhibitor if the patient is predicted to be responsive to an EGFR kinase inhibitor. In one embodiment of this method the EGFR kinase inhibitor comprises erlotinib.

The present invention further provides a method of treatment of a patient with cancer, comprising: administering to said patient a therapeutically effective amount of an EGFR kinase inhibitor if the patient is predicted to be responsive to an EGFR kinase inhibitor using any of the methods disclosed herein for identifying a human tumor as likely to be responsive or non-responsive to treatment with an EGFR kinase inhibitor. In one embodiment of this method the EGFR kinase inhibitor comprises erlotinib.

The present invention further provides a method of treatment of a patient with cancer, comprising: determining whether the patient is likely to be responsive to an IGF-1R kinase inhibitor using any of the methods disclosed herein for identifying a human tumor as likely to be responsive or non-responsive to treatment with an IGF-1R kinase inhibitor, and administering to said patient a therapeutically effective amount of an IGF-1R kinase inhibitor if the patient is predicted to be responsive to an IGF-1R kinase inhibitor. In one embodiment of this method the IGF-1R kinase inhibitor comprises OSI-906.

The present invention further provides a method of treatment of a patient with cancer, comprising: administering to said patient a therapeutically effective amount of an IGF-1R kinase inhibitor if the patient is predicted to be responsive to an IGF-1R kinase inhibitor using any of the methods disclosed herein for identifying a human tumor as likely to be responsive or non-responsive to treatment with an IGF-1R kinase inhibitor. In one embodiment of this method the IGF-1R kinase inhibitor comprises OSI-906.

The present invention further provides a method of predicting whether tumor cell growth, or tumor growth, will be inhibited synergistically by a combination of an EGFR kinase inhibitor and an IGF-1R kinase inhibitor, comprising: measuring in a sample of the tumor cells the relative expression level of each gene of an EMT gene signature (EMTGS), wherein the EMTGS consists essentially of the following genes: SERPINA3, ACTN1, AGR2, AKAP12, ALCAM, AP1M2, AXL, BSPRY, CCL2, CDH1, CDH2, CEP170, CLDN3, CLDN4, CNN3, CYP4X1, DNMT3A, DSG3, DSP, EFNB2, EHF, ELF3, ELF5, ERBB3, ETV5, FLRT3, FOSB, FOSL1, FOXC1, FXYD5, GPD1L, HMGA1, HMGA2, HOPX, IFI16, IGFBP2, IHH, IKBIP, IL-11, IL-18, IL6, IL8, ITGA5, ITGB3, LAMB1, LCN2, MAP7, MB, MMP7, MMP9, MPZL2, MSLN, MTA3, MTSS1, OCLN, PCOLCE2, PECAM1, PLAUR, PLXNB1, PPL, PPP1R9A, RASSF8, SCNN1A, SERPINB2, SERPINE1, SFRP1, SH3YL1, SLC27A2, SMAD7, SNAI1SNAI2, SPARC, SPDEF, SRPX, STAT5A, TBX2, TJP3, TMEM125, TMEM45B, TWIST1, VCAN, VIM, VWF, XBP1, YBX1, ZBTB10, ZEB1, ZEB2; calculating an EMTGS index score for said tumor cells by applying an algorithm to the measured expression level values that incorporates the contributions of co-correlated genes; and determining if said EMTGS index score is more similar to an EMTGS index score from a reference epithelial tumor cell which is inhibited synergistically by a combination of an EGFR kinase inhibitor and an IGF-1R kinase inhibitor, or an EMTGS index score from a reference mesenchymal-like tumor cell which is not inhibited synergistically by a combination of an EGFR kinase inhibitor and an IGF-1R kinase inhibitor, and thus predicting whether or not tumor growth will be inhibited synergistically by a combination of an EGFR kinase inhibitor and an IGF-1R kinase inhibitor. In one embodiment of this method the EGFR kinase inhibitor comprises erlotinib and the IGF-1R kinase inhibitor comprises OSI-906.

The present invention further provides a method of predicting whether tumor growth in a patient will be inhibited synergistically by a combination of an EGFR kinase inhibitor and an IGF-1R kinase inhibitor, comprising: measuring in a sample of the tumor cells the relative expression level of each gene of an EMT gene signature (EMTGS), wherein the EMTGS consists essentially of the following genes: SERPINA3, ACTN1, AGR2, AKAP12, ALCAM, AP1M2, AXL, BSPRY, CCL2, CDH1, CDH2, CEP170, CLDN3, CLDN4, CNN3, CYP4X1, DNMT3A, DSG3, DSP, EFNB2, EHF, ELF3, ELF5, ERBB3, ETV5, FLRT3, FOSB, FOSL1, FOXC1, FXYD5, GPD1L, HMGA1, HMGA2, HOPX, IFI16, IGFBP2, IHH, IKBIP, IL-11, IL-18, IL6, IL8, ITGA5, ITGB3, LAMB1, LCN2, MAP7, MB, MMP7, MMP9, MPZL2, MSLN, MTA3, MTSS1, OCLN, PCOLCE2, PECAM1, PLAUR, PLXNB1, PPL, PPP1R9A, RASSF8, SCNN1A, SERPINB2, SERPINE1, SFRP1, SH3YL1, SLC27A2, SMAD7, SNAI1, SNAI2, SPARC, SPDEF, SRPX, STAT5A, TBX2, TJP3, TMEM125, TMEM45B, TWIST1, VCAN, VIM, VWF, XBP1, YBX1, ZBTB10, ZEB1, ZEB2; calculating an EMTGS index score for said tumor cells by applying an algorithm to the measured expression level values that incorporates the contributions of co-correlated genes; and determining if said EMTGS index score is above a defined threshold that indicates that the tumor is likely to be inhibited synergistically by a combination of an EGFR kinase inhibitor and an IGF-1R kinase inhibitor, or below said threshold and thus likely to be not inhibited synergistically by a combination of an EGFR kinase inhibitor and an IGF-1R kinase inhibitor. In one embodiment of this method the EGFR kinase inhibitor comprises erlotinib and the IGF-1R kinase inhibitor comprises OSI-906. This method will assist physicians in determining whether patients with cancer may benefit from treatment with a combination of an EGFR kinase inhibitor and an IGF-1R kinase inhibitor, rather than these inhibitors as just single agents, and may be particularly useful in instances where a degree of resistance to a single agent has developed.

The present invention further provides a method of predicting the sensitivity of tumor cell growth to inhibition by a compound whose tumor growth-inhibiting properties are dependent on the EMT status of the tumor cells, comprising: identifying the EMT status of the tumor cells by any of the methods disclosed herein; and predicting the sensitivity of tumor cell growth to inhibition by the inhibitor compound, wherein if the tumor cell EMT status is epithelial, high sensitivity to inhibition by the inhibitor compound is predicted, and if the tumor cell EMT status is mesenchymal, low sensitivity to inhibition by the inhibitor compound is predicted. In one embodiment of this method the compound whose tumor growth-inhibiting properties are dependent on the EMT status of the tumor cells is an EGFR kinase inhibitor. In another embodiment of this method the compound whose tumor growth-inhibiting properties are dependent on the EMT status of the tumor cells is an EGFR kinase inhibitor.

The present invention further provides a method of identifying a compound that inhibits tumor cells from undergoing an epithelial to mesenchymal transition, comprising contacting a sample of cells of an epithelial tumor cell line with a test compound to be screened, contacting the sample with an agent that induces an epithelial-to-mesenchymal transition in the tumor cells, determining whether the test compound inhibits the tumor cells in the sample from undergoing an epithelial to mesenchymal transition, by comparing the EMT status of the sample tumor cells to the EMT status in an identical sample of tumor cells not contacted with the test compound, wherein the EMT status of the tumor cells is determined by any of the methods disclosed herein for that purpose, and thus determining whether the test compound is a compound that inhibits tumor cells from undergoing an epithelial to mesenchymal transition.

In the methods of this invention, an agent that induces an epithelial-to-mesenchymal transition in the tumor cells may be any agent known to induce EMT in the particular tumor cell type. Tumor cells vary in their sensitivity to such agents. Examples of such EMT-inducing agents include HGF, WNT pathway agonists, activators of the sonic hedgehog (SHH) pathway, TGF-beta (e.g. TGFβ1, TGFβ2, TGFβ3), TNF-alpha, oncostatin M (OSM), LPA (lysophosphatidic acid), and ILEI.

In the methods of this invention, when contacting epithelial tumor cells with a test compound to be screened for activity in inhibiting an epithelial-to-mesenchymal transition in the tumor cells, the compound may for example be one that has inhibitory activity against a protein (or the expression of the gene encoding it in the tumor cell) that is involved in one of the biological pathways whose activation is known to induce EMT, such as those described herein above. Examples of such proteins include the protein kinases PAK1 (GeneID: 5058), PAK2 (GeneID: 5062), Aurora A (GeneID: 6790), ACK1 (a.k.a. TNK2; GeneID: 10188), SRC (GeneID: 6714), TAK1 (GeneID: 7182) and MET (GeneID: 4233); histone deacetylase (HDAC; e.g. any of HDAC 1 to 10); LPA receptors; proteins that have activity in stimulating the SHH (sonic hedgehog) signalling pathway, proteins that have activity in stimulating the WNT signaling pathway, the SHH pathway receptor Smoothened (SMO; GeneID: 6608), the SHH pathway receptor Patched (PTCH1; GeneID: 5727); WNT pathway receptors (e.g. Frizzled receptors 1 to 10, LRP5, LRP6); Frizzled co-receptors; TGF-beta receptors; TNF-alpha receptors; and OSM receptors. Many compounds, or antibodies, are already known which inhibit the activity of these proteins, and additional compounds are readily identified in biochemical assays or screens, including high-throughput screens (HTS).

The methods disclosed herein, for identifying a compound that inhibits tumor cells from undergoing an epithelial to mesenchymal transition, are also useful in the identification of agents for the treatment of fibrotic disorders resulting in part from EMT transitions, including but not limited to renal fibrosis, hepatic fibrosis, pulmonary fibrosis, and mesotheliomas. In these diseases, normally functioning lung, kidney and liver cells may be transformed into myofibroblast cells. Thus any of the methods described herein for tumor cells, will also be applicable to other cell types involved in fibrotic diseases that undergo EMT. Similarly, any of the inventions described herein as being useful for the identification of anti-cancer agents, will also be useful in the identification of anti-fibrotic agents for treating diseases that involve fibrosis.

The present invention further provides a method of identifying a compound that stimulates mesenchymal-like tumor cells to undergo a mesenchymal to epithelial transition, comprising contacting a sample of cells of an epithelial tumor cell line with an agent to induce an epithelial-to-mesenchymal transition in the tumor cells, contacting the sample of cells with a test agent to be screened, determining whether the test compound stimulates the mesenchymal-like tumor cells in the sample to undergo a mesenchymal to epithelial transition, by comparing the EMT status of the sample tumor cells to the EMT status in an identical sample of tumor cells not contacted with the test compound, wherein the EMT status of the tumor cells is determined by any of the methods disclosed herein for that purpose, and thus determining whether the test compound is a compound that stimulates mesenchymal-like tumor cells to undergo a mesenchymal to epithelial transition.

The present invention further provides a method of identifying an agent that inhibits tumor cells that have undergone an epithelial to mesenchymal transition, comprising contacting a sample of cells of an epithelial tumor cell line with an agent to induce an epithelial-to-mesenchymal transition in the tumor cells, wherein the mesenchymal-like phenotype is determined by any of the methods disclosed herein for that purpose, contacting the sample of cells with a test agent to be screened, determining whether the test agent inhibits mesenchymal-like tumor cell growth, and thus determining whether it is an agent that inhibits the growth of tumor cells that have undergone an epithelial to mesenchymal transition. One embodiment of this method comprises, after the step of determining whether the test agent inhibits the growth of tumor cells that have undergone an epithelial to mesenchymal transition, the additional steps of determining whether an agent that inhibits mesenchymal-like tumor cell growth, also inhibits epithelial tumor cell growth, and thus determining whether it is an agent that specifically inhibits the growth of tumor cells that have undergone an epithelial to mesenchymal transition. In an additional embodiment of this method, for the step of determining whether the test agent inhibits mesenchymal-like tumor cell growth, it is determined that the test agent does so by stimulating apoptosis of said tumor cells. In a further embodiment of this method, for the step of determining whether the test agent inhibits mesenchymal-like tumor cell growth, it is determined that the test agent does so by inhibiting proliferation of said tumor cells.

The present invention further provides any of the methods of identifying agents disclosed herein, wherein the sample of cells of the epithelial tumor cell line is a xenograft growing in an animal (e.g. a nude mouse).

The present invention further provides a method of identifying patients with cancer who may benefit from treatment with a pharmaceutical composition comprising a compound that inhibits tumor cells from undergoing an epithelial to mesenchymal transition, comprising; obtaining a sample of tumor cells from a patient, measuring the expression levels of the RNA transcripts of SERPINA3, ACTN1, AGR2, AKAP12, ALCAM, AP1M2, AXL, BSPRY, CCL2, CDH1, CDH2, CEP170, CLDN3, CLDN4, CNN3, CYP4X1, DNMT3A, DSG3, DSP, EFNB2, EHF, ELF3, ELF5, ERBB3, ETV5, FLRT3, FOSB, FOSL1, FOXC1, FXYD5, GPD1L, HMGA1, HMGA2, HOPX, IFI16, IGFBP2, IHH, IKBIP, IL-11, IL-18, IL6, IL8, ITGA5, ITGB3, LAMB1, LCN2, MAP7, MB, MMP7, MMP9, MPZL2, MSLN, MTA3, MTSS1, OCLN, PCOLCE2, PECAM1, PLAUR, PLXNB1, PPL, PPP1R9A, RASSF8, SCNN1A, SERPINB2, SERPINE1, SFRP1, SH3YL1, SLC27A2, SMAD7, SNAI1, SNAI2, SPARC, SPDEF, SRPX, STAT5A, TBX2, TJP3, TMEM125, TMEM45B, TWIST1, VCAN, VIM, VWF, XBP1, YBX1, ZBTB10, ZEB1, and ZEB2, or their expression products in the sample; calculating an EMTGS index score for said tumor cells by applying an algorithm to the measured expression level values that incorporates the contributions of co-correlated genes; determining if said EMTGS index score is more similar to an EMTGS index score from a reference epithelial tumor cell or an EMTGS index score from a reference mesenchymal-like tumor cell, and identifying the patient as one who may benefit from treatment with a pharmaceutical composition comprising a compound that inhibits tumor cells from undergoing an epithelial to mesenchymal transition if the EMT index score is more similar to cells of a mesenchymal phenotype. In one embodiment of this method, the pharmaceutical composition comprising a compound that inhibits tumor, cells from undergoing an epithelial to mesenchymal transition, comprises in addition an inhibitor of EGFR kinase. In another embodiment of this method, the pharmaceutical composition comprising a compound that inhibits tumor cells from undergoing an epithelial to mesenchymal transition, comprises in addition an inhibitor of IGF-1R kinase.

The present invention further provides a method of monitoring patients with cancer who have been treated with the compound that inhibits tumor cells from undergoing an epithelial to mesenchymal transition (EMT) to determine whether the inhibitor is effective at inhibiting EMT of the tumor cells, comprising; (a) obtaining a sample of tumor cells from a patient, (b) measuring the expression levels of the RNA transcripts of SERPINA3, ACTN1, AGR2, AKAP12, ALCAM, AP1M2, AXL, BSPRY, CCL2, CDH1, CDH2, CEP170, CLDN3, CLDN4, CNN3, CYP4X1, DNMT3A, DSG3, DSP, EFNB2, EHF, ELF3, ELF5, ERBB3, ETV5, FLRT3, FOSB, FOSL1, FOXC1, FXYD5, GPD1L, FIMGA1, HMGA2, HOPX, IFI16, IGFBP2, IHH, IKBIP, IL-11, IL-18, IL6, IL8, ITGA5, ITGB3, LAMB1, LCN2, MAP7, MB, MMP1, MMP9, MPZL2, MSLN, MTA3, MTSS1, OCLN, PCOLCE2, PECAM1, PLAUR, PLXNB1, PPL, PPP1R9A, RASSF8, SCNN1A, SERPINB2, SERPINE1, SFRP1, SH3YL1, SLC27A2, SMAD7, SNAI1, SNAI2, SPARC, SPDEF, SRPX, STAT5A, TBX2, TJP3, TMEM125, TMEM45B, TWIST1, VCAN, VIM, VWF, XBP1, YBX1, ZBTB10, ZEB1, ZEB2, or their expression products in the sample; (c) calculating an EMTGS index score for said tumor cells by applying an algorithm to the measured expression level values that incorporates the contributions of co-correlated genes; (d) determining if said EMTGS index score is more similar to an EMTGS index score from a reference epithelial tumor cell or an EMTGS index score from a reference mesenchymal-like tumor cell, and identifying the patient as one who may benefit from treatment with a pharmaceutical composition comprising a compound that inhibits tumor cells from undergoing an epithelial to mesenchymal transition if the EMT index score is more similar to cells of a mesenchymal phenotype; (e) administering to said patient who may benefit from treatment a therapeutically effective amount of a pharmaceutical composition comprising a compound that inhibits tumor cells from undergoing an epithelial to mesenchymal transition; and (f) obtaining another sample of tumor cells from a patient, and determining if administration of the EMT inhibitor has increased the EMT index score from that measured in step (c) to one more similar to that of cells of an epithelial phenotype, and thus determining whether the compound is effective at inhibiting EMT of the tumor cells.

The present invention further provides a method for treating tumors or tumor metastases in a patient with cancer, comprising the steps of: diagnosing a patient's likely responsiveness to an EGFR kinase inhibitor by assessing whether the tumor cells have undergone an epithelial-mesenchymal transition using any of the methods disclosed herein for that purpose, and administering to said patient a therapeutically effective amount of an EGFR kinase inhibitor.

The present invention further provides a method for treating tumors or tumor metastases in a patient with cancer, comprising the steps of: diagnosing a patient's likely responsiveness to an IGF-1R kinase inhibitor by assessing whether the tumor cells have undergone an epithelial-mesenchymal transition using any of the methods disclosed herein for that purpose, and administering to said patient a therapeutically effective amount of an IGF-1R kinase inhibitor.

The present invention further provides a method for treating tumors or tumor metastases in a patient with cancer, comprising the steps of: identifying the patient as one who may benefit from treatment with an inhibitor of EMT using any of the methods described herein for that purpose, and administering to said patient a therapeutically effective amount of a pharmaceutical composition comprising a compound that inhibits tumor cells from undergoing an epithelial to mesenchymal transition. In one embodiment of this method, the pharmaceutical composition comprising a compound that inhibits tumor cells from undergoing an epithelial to mesenchymal transition, comprises in addition an inhibitor of EGFR kinase. In another embodiment of this method, the pharmaceutical composition comprising a compound that inhibits tumor cells from undergoing an epithelial to mesenchymal transition, comprises in addition an inhibitor of IGF-1R kinase.

Examples of EMT inhibitor compounds that may be used in the methods of this invention include antagonists of EMT inducing agents, TGF-beta antagonists or TGF-beta receptor antagonists (for example: anti-TGF-beta and anti-TGF-beta receptor antibodies, 4-(4-Fluorophenyl)-2-(4-methylsulfinylphenyl)-5-(4-pyridyl)-1H-imidazole (SB 203580); 4-[4-(3,4-Methylenedioxyphenyl)-5-(2-pyridyl)-1H-imidazol-2-yl]-benzamide (SB431542); and similarly or more active analogues or homologues of such compounds), inhibitors of MET, FAK, TAK1, ILK, SRC, FYN or YES protein kinases, and calpain inhibitors. Additional examples of such compounds include those in U.S. patent application Ser. No. 12/791,047, US published patent application US2009/197862, dasatinib (N-(2-chloro-6-methylphenyl)-2-[[6-[4-(2-hydroxyethyl)-1-piperazinyl]-2-methyl-4-pyrimidinyl]amino]-5-thiazole carboxamide monohydrate), AZD0530, PF 573228 (3,4-Dihydro-6-[[4-[[[3-(methylsulfonyl) phenyl]methyl]amino]-5-(trifluoromethyl)-2-pyrimidinyl]amino]-2(1H)-quinolinone), NVP-TAE226, NVP-TAC544, ARQ 197 (Arqule), PND-1186, PF2362376 (Pfizer), PF-562,271 (Pfizer), PF-2,341,066 (Pfizer), CE-355621 anti-c-MET antibody, PHA665752 (Pfizer), and PF-3,814,735 (Pfizer).

The present invention further provides a method of determining the EMT status of tumor cells in each of a plurality of tumor cell samples, comprising: measuring in each sample of tumor cells the relative expression level of each gene of an EMT gene signature (EMTGS), wherein the EMTGS consists essentially of the following genes: SERPINA3, ACTN1, AGR2, AKAP12, ALCAM, AP1M2, AXL, BSPRY, CCL2, CDH1, CDH2, CEP170, CLDN3, CLDN4, CNN3, CYP4X1, DNMT3A, DSG3, DSP, EFNB2, EHF, ELF3, ELF5, ERBB3, ETV5, FLRT3, FOSB, FOSL1, FOXC1, FXYD5, GPD1L, HMGA1, HMGA2, HOPX, IFI16, IGFBP2, IHH, IKBIP, IL-11, IL-18, IL6, IL8, ITGA5, ITGB3, LAMB1, LCN2, MAP7, MB, MMP7, MMP9, MPZL2, MSLN, MTA3, MTSS1, OCLN, PCOLCE2, PECAM1, PLAUR, PLXNB1, PPL, PPP1R9A, RASSF8, SCNN1A, SERPINB2, SERPINE1, SFRP1, SH3YL1, SLC27A2, SMAD7, SNAI1, SNAI2, SPARC, SPDEF, SRPX, STAT5A, TBX2, TJP3, TMEM125, TMEM45B, TWIST1, VCAN, VIM, VWF, XBP1, YBX1, ZBTB10, ZEB1, ZEB2; calculating an EMTGS index score for each sample of tumor cells by applying an algorithm to the measured expression level values that incorporates the contributions of co-correlated genes; and determining for each sample of tumor cells if said EMTGS index score is more similar to an EMTGS index score from a reference epithelial tumor cell or an EMTGS index score from a reference mesenchymal-like tumor cell, and thus determining the EMT status of each tumor cell sample. This method can be used, for example, in determining the relative numbers of epithelial and mesenchymal-like tumors in a patient population, and thus for predicting the likelihood that patients in this group will be effectively treated by an anti-cancer agent whose effectiveness is dependent on the EMT status of tumor cells (e.g. EGFR or IGF-1R kinase inhibitors, such as erlotinib, or OSI-906). In specific embodiments of this method the plurality of tumor cell samples may be for example any number in the range 1-10, 10-20, 20-30; 30-40; 40-50, 50-60, 60-70, 70-80, 80-90, 90-100, 100-1000, or 1000-10000.

The present invention further provides a PCR primer set consisting of a pair of primers for each of the following genes: SERPINA3, ACTN1, AGR2, AKAP12, ALCAM, AP1M2, AXL, BSPRY, CCL2, CDH1, CDH2, CEP170, CLDN3, CLDN4, CNN3, CYP4X1, DNMT3A, DSG3, DSP, EFNB2, EHF, ELF3, ELF5, ERBB3, ETV5, FLRT3, FOSB, FOSL1, FOXC1, FXYD5, GPD1L, HMGA1, HMGA2, HOPX, IFI16, IGFBP2, IHH, IKBIP, IL-11, IL-18, IL6, IL8, ITGA5, ITGB3, LAMB1, LCN2, MAP7, MB, MMP7, MMP9, MPZL2, MSLN, MTA3, MTSS1, OCLN, PCOLCE2, PECAM1, PLAUR, PLXNB1, PPL, PPP1R9A, RASSF8, SCNN1A, SERPINB2, SERPINE1, SFRP1, SH3YL1, SLC27A2, SMAD7, SNAI1, SNAI2, SPARC, SPDEF, SRPX, STAT5A, TBX2, TJP3, TMEM125, TMEM45B, TWIST1, VCAN, VIM, VWF, XBP1, YBX1, ZBTB10, ZEB1, and ZEB2.

The present invention further provides a DNA microarray chip consisting of a solid surface and a probe set, said probe set consisting of probes specific for each of the following genes: SERPINA3, ACTN1, AGR2, AKAP12, ALCAM, AP1M2, AXL, BSPRY, CCL2, CDH1, CDH2, CEP170, CLDN3, CLDN4, CNN3, CYP4X1, DNMT3A, DSG3, DSP, EFNB2, EHF, ELF3, ELF5, ERBB3, ETV5, FLRT3, FOSB, FOSL1, FOXC1, FXYD5, GPD1L, HMGA1, HMGA2, HOPX, IFI16, IGFBP2, IHH, IKBIP, IL-11, IL-18, IL6, IL8, ITGA5, ITGB3, LAMB1, LCN2, MAP7, MB, MMP7, MMP9, MPZL2, MSLN, MTA3, MTSS1, OCLN, PCOLCE2, PECAM1, PLAUR, PLXNB1, PPL, PPP1R9A, RASSF8, SCNN1A, SERPINB2, SERPINE1, SFRP1, SH3YL1, SLC27A2, SMAD7, SNAI1, SNAI2, SPARC, SPDEF, SRPX, STAT5A, TBX2, TJP3, TMEM125, TMEM45B, TWIST1, VCAN, VIM, VWF, XBP1, YBX1, ZBTB10, ZEB1, and ZEB2.

In the methods of this invention, a compound that inhibits tumor cells from undergoing an epithelial to mesenchymal transition may inhibit EMT or stimulate the reverse process of MET. "Inhibition of epithelial to mesenchymal transition" implies no particular mechanism, merely that the epithelial phenotype of the cells is maintained, or re-established, by such a compound.

In the methods of this invention, a "pharmaceutical composition comprising a compound that inhibits tumor cells from undergoing an epithelial to mesenchymal transition"

may comprise one or multiple compounds that inhibit tumor cells from undergoing an epithelial to mesenchymal transition. Multiple compounds may complement each other by modulating different EMT gene sets. For example one compound may modulate a subset of genes responsible for EMT, while a second may modulate others, such that the sum effect is a more effective inhibition of tumor cells from undergoing an epithelial to mesenchymal transition. The 88 EMTGS, and other EMTGS, disclosed herein may be used to determine the expression of which genes within the EMTGS are modulated by any given EMT inducer, and thus also the expression of what genes are affected by EMT inhibitor compounds. Thus it is possible to identify a subset of the EMTGS genes, modulation of the expression of which is critical to the action of the EMT inhibitor. Assessment of the expression of this subset of genes can be used to monitor effects of the compound on tumor cells, for example in a tumor biopsy, and can be quantified by derivation of an index score from the EMTGS for the tumor cell.

The present invention thus provides a method of monitoring the response of a human tumor to treatment with an inhibitor compound to determine whether the inhibitor is effective at inhibiting EMT in the tumor cells, comprising: measuring in a sample of the tumor cells from both before and after said treatment the relative expression level of each gene of an EMT gene signature (EMTGS) that consists of a group of genes that have been determined to be coordinately regulated when EMT is inhibited by an EMT inhibitor compound acting via a specific biological mechanism, and is characteristic of inhibition via that mechanism; calculating an EMTGS index score for said tumor cells from both before and after said treatment, by applying an algorithm to the measured expression level values that incorporates the contributions of co-correlated genes; and determining from the magnitude of the difference in the EMTGS index scores from both before and after said treatment, relative to EMTGS index scores from a reference epithelial tumor cell and a reference mesenchymal-like tumor cell, if treatment with the inhibitor compound has been effective at inhibiting EMT in the tumor cells. In one embodiment of this method the inhibitor compound is a MET kinase inhibitor, and the EMTGS consists essentially of the following genes: CYP4X1, FOSB, MMP9, VIM, CLDN3, EHF, ELF3, ERBB3, HOPX, MMP7, OCLN, PLXNB1, SCNN1A, TJP3, TMEM125, TMEM45B, and VWF. In another embodiment of this method the inhibitor compound is a FAK kinase inhibitor, and the EMTGS consists essentially of the following genes: AP1M2, BSPRY, CDH1, CLDN3, EHF, ELF3, ERBB3, MPZL2, MAP7, OCLN, PPL, PPP1R9A, SCNN1A, SLC27A2, SPDEF, TJP3, TMEM125, and TMEM45B. In an additional embodiment of this method method the inhibitor compound is a TAK1 kinase inhibitor, and the EMTGS consists essentially of the following genes: FOSB, IL8, ITGB3, MMP9, MSLN, SERPINE1, SNAI2, PPL, PPP1R9A, SCNN1A, TJP3, and XBP1. In any of these methods, the algorithm used to derive the EMTGS index score may be algorithm A or algorithm $A^1$, as defined herein below.

The present invention further provides a PCR primer set consisting of a pair of primers for each of the following genes: CYP4X1, FOSB, MMP9, VIM, CLDN3, EHF, ELF3, ERBB3, HOPX, MMP7, OCLN, PLXNB1, SCNN1A, TJP3, TMEM125, TMEM45B, and VWF.

The present invention further provides a DNA microarray chip consisting of a solid surface and a probe set, said probe set consisting of probes specific for each of the following genes: CYP4X1, FOSB, MMP9, VIM, CLDN3, EHF, ELF3, ERBB3, HOPX, MMP7, OCLN, PLXNB1, SCNN1A, TJP3, TMEM125, TMEM45B, and VWF.

The present invention further provides a PCR primer set consisting of a pair of primers for each of the following genes: AP1M2, BSPRY, CDH1, CLDN3, EHF, ELF3, ERBB3, MPZL2, MAP7, OCLN, PPL, PPP1R9A, SCNN1A, SLC27A2, SPDEF, TJP3, TMEM125, and TMEM45B.

The present invention further provides a DNA microarray chip consisting of a solid surface and a probe set, said probe set consisting of probes specific for each of the following genes: AP1M2, BSPRY, CDH1, CLDN3, EHF, ELF3, ERBB3, MPZL2, MAP7, OCLN, PPL, PPP1R9A, SCNN1A, SLC27A2, SPDEF, TJP3, TMEM125, and TMEM45B.

The present invention further provides a PCR primer set consisting of a pair of primers for each of the following genes: FOSB, IL8, ITGB3, MMP9, MSLN, SERPINE1, SNAI2, PPL, PPP1R9A, SCNN1A, TJP3, and XBP1.

The present invention further provides a DNA microarray chip consisting of a solid surface and a probe set, said probe set consisting of probes specific for each of the following genes: FOSB, IL8, ITGB3, MMP9, MSLN, SERPINE1, SNAI2, PPL, PPP1R9A, SCNN1A, TJP3, and XBP1.

In an embodiment of any of the methods of monitoring the response of a human tumor to treatment with an inhibitor compound to determine whether the inhibitor is effective at inhibiting EMT in the tumor cells s, the tumor cells may be from a tumor from a patient with cancer. In an embodiment of any of these methods, the samples of tumor cells are derived from a tumor biopsy, or are derived from a blood sample containing circulating tumor cells. The tumor cells may be for example NSCL cancer, breast cancer, colorectal cancer, or pancreatic cancer tumor cells.

In certain embodiments of the invention described herein, involving for example, identification of human tumors likely to be responsive or non-responsive to treatment with EGFR or IGF-1R kinase inhibitors, the EMTGS consists of, or consists essentially of, or is comprised of, the 88 genes listed in Table 1 by theit HUGO gene symbols. These genes are described in more detail in FIGS. 36 and 37.

Inclusion of any of the diagnostic methods described herein as part of treatment regimens to predict the effectiveness of treatment of a cancer patient with an EGFR kinase inhibitor or an IGF-1R kinase inhibitor provides an advantage over treatment regiments that do not include such a diagnostic step, in that only that patient population which derives most benefit from an EGFR kinase inhibitor or an IGF-1R kinase inhibitor need be treated, and in particular, patients who are predicted not to benefit from treatment with an EGFR kinase inhibitor or an IGF-1R kinase inhibitor need not be treated.

The present invention further provides a method for treating a patient with cancer, comprising the step of diagnosing a patient's likely responsiveness to an EGFR kinase inhibitor by any of the methods of the invention described herein for predicting effectiveness of an EGFR kinase inhibitor; and a step of administering the patient a therapeutically effective dose of an EGFR kinase inhibitor.

In one embodiment of any of the methods of treating a patient described herein, the step of administering the patient a therapeutically effective dose of an EGFR kinase inhibitor or an IGF-1R kinase inhibitor is conditional on the prior biomarker diagnostic step indicating that treatment will be more effective. In an alternative embodiment of any of the methods of treating a patient described herein, the patient is administered a therapeutically effective dose of an EGFR kinase inhibitor or an IGF-1R kinase inhibitor even when the prior biomarker diagnostic step predicts that treatment is not likely to be particularly effective. The latter embodiment may be pursued if, for example, in a physicians judgment some benefit may still be achieved by administration of an EGFR kinase inhibitor or an IGF-1R kinase inhibitor, and/or other options for the patient are limited or non-existent.

For the methods of treatment with an EGFR kinase inhibitor described herein, an example of a preferred EGFR kinase inhibitor is erlotinib, including pharmacologically acceptable salts or polymorphs thereof. One or more additional anti-cancer agents or treatments may also be co-administered simultaneously or sequentially with the EGFR kinase inhibitor, as judged to be appropriate by the administering physician given the prediction of the likely responsiveness of the patient to an EGFR kinase inhibitor, in combination with any additional circumstances pertaining to the individual patient.

For the methods of treatment with an IGF-1R kinase inhibitor described herein, an example of a preferred IGF-1R kinase inhibitor is OSI-906, including pharmacologically acceptable salts or polymorphs thereof. One or more additional anti-cancer agents or treatments may also be co-administered simultaneously or sequentially with the IGF-1R kinase inhibitor, as judged to be appropriate by the administering physician given the prediction of the likely responsiveness of the patient to an IGF-1R kinase inhibitor, in combination with any additional circumstances pertaining to the individual patient.

Thus, it will be appreciated by one of skill in the medical arts that the exact manner of administering to said patient a therapeutically effective amount of an EGFR kinase inhibitor or an IGF-1R kinase inhibitor following a diagnosis of a patient's likely responsiveness to an EGFR kinase inhibitor or an IGF-1R kinase inhibitor will be at the discretion of the attending physician. The mode of administration, including dosage, combination with other anti-cancer agents, timing and frequency of administration, and the like, may be affected by the diagnosis of a patient's likely responsiveness to an EGFR kinase inhibitor or an IGF-1R kinase inhibitor, as well as the patient's condition and history. Thus, even patients that are diagnosed to not respond well to EGFR kinase inhibitors or IGF-1R kinase inhibitors may still benefit from treatment with such inhibitors, particularly in combination with other anti-cancer agents, or agents that may alter a patient's response to EGFR kinase inhibitors or IGF-1R kinase inhibitors.

In any of the methods of the invention described herein, the step of "assessing the level of expression of a gene (e.g. E-cadherin, vimentin) expressed by cells of a tumor of the patient" may encompass additional steps, such as for example one or more of the following steps: 1. Obtaining a sample of the tumor from the cancer patient; 2. Contacting a sample of the tumor, or sample purified therefrom, with an anti-biomarker antibody, a biomarker probe, or PCR primers; and 3. Employing a detection method (e.g. chromogenic; fluorescent) to localize and quantify the sites of antibody or probe binding in the sample of the tumor.

Assessment of an EMTGS index score of a patient's tumor cells as more similar to an EMTGS index score of an epithelial or a mesenchymal-like tumor cell in any of the methods of this invention may be determined by comparison to the value of the index score of a reference or control tumor cell sample, wherein this control tumor cell score has been previously correlated with an epithelial or a mesenchymal-like phenotype. Alternatively, a panel of such reference tumor cell samples, representing a range of index scores, and thus a range of phenotypes, for example from 100% epithelial to 100% mesenchymal, can be used construct a standard curve from which the phenotype can be predicted from the index score of test tumor cell samples.

The term "more similar" as used herein has its usual meaning. Tumor cells from patients will have a range of index scores reflecting the phenotype of the cell, for example from tumor cells that are 100% epithelial to tumor cells that are 100% mesenchymal. Tumor cells from the extremes of such a range may be utilized as reference tumor cells for comparison to a sample of tumor cells that requires characterization with respect to EMT status. Thus, a tumor cell will be more similar to one or the other of these two phenotypes if its index score is much closer to the value for the epithelial or the mesenchymal cell (e.g. a reference cell index score plus or minus any value less than 10%, 20%, 30%, 40%, or 50% of the magnitude of the difference between the two reference cell index scores), and would be considered of intermediate phenotype if its index score falls in the middle of the range. Such an intermediate phenotype would be expected, for example, for a metastable tumor cell type, or tumor cells that are actively transitioning from epithelial to mesenchymal, or vice versa. Examples of epithelial or mesenchymal-like tumor cells that may be used as reference cells in the methods of this invention include tumor samples that have been characterized as epithelial or mesenchymal (e.g. as judged for example, by morphological, biomarker, and/or phenotypic status), or tumor cell lines that have been similarly characterized, including many of those described herein. For example, one of the tumor cell EMT models described herein (e.g. H358 NSCLC tumor cells; a.k.a. NCI-H358™ or CRL-5807) may be used to provide the reference cells, wherein the epithelial reference cell is the unstimulated tumor cell, and the mesenchymal-like reference cell is the tumor cell after EMT induction by an exogenous ligand, or induction of a transfected gene coding for an EMT inducer (e.g. activated TGF-beta, the transcription factor snai1). Reference tumor cells are preferably of the same or similar tissue type as the sample tumor cell that is being analyzed. Additional suitable reference tumor cells include, for example, the lung tumor cells H441, H322, and H292, which are all epithelial, and H1703, and H460, which are both mesenchymal-like; the breast tumor cells MCF7 and T47D, which are both epithelial, and BT-549 and MDA-MB-231, which are both mesenchymal-like; the pancreatic tumor cells CFPAC1, HPAC, and BxPC3, which are all epithelial, and A1165 and PANC1, which are both mesenchymal-like; and the CRC tumor cells HCT-15, SW480, HCT8, which are all epithelial, and SW620, which is mesenchymal-like. If the index score of sample tumor cells falls outside the range between sensitive and resistant reference cells, it will clearly be more similar to the reference cell on the side of the range where the sample score has fallen outside the range.

It will be appreciated by those of skill in the art that a reference tumor cell sample (e.g. epithelial or mesenchymal) need not be established for every assay while the assay is being performed, but rather, a baseline or reference can be established by referring to a form of stored information regarding a previously determined index score (or scores) to discriminate between epithelial and mesenchymal tumor cells (or patient responders and non-responders). Such a form of stored information can include, for example, but is not limited to, a reference chart, listing or electronic file of population or individual data regarding sensitive and resistant tumors or patients, or any other source of data regarding a cutoff level of EMT index value for tumor cell sensitivity or resistance that is useful for the patient or tumor cell to be evaluated.

The present invention further provides a method for treating a patient with cancer, comprising: a step of identifying patients with cancer who are most likely to benefit from treatment with an EGFR kinase inhibitor or an IGF-1R kinase inhibitor, by obtaining a sample of the patient's tumor, determining if tumor cells of the sample have an EMTGS index value that is predictive of sensitivity to an EGFR kinase inhibitor or an IGF-1R kinase inhibitor, and administering to the patient a therapeutically effective dose of an EGFR kinase inhibitor or an IGF-1R kinase inhibitor.

The NCBI GeneID numbers listed herein (e.g. in FIGS. 36 and 37) are unique identifiers of human genes from the NCBI Entrez Gene database record (National Center for Biotechnology Information (NCBI), U.S. National Library of Medicine, 8600 Rockville Pike, Building 38A, Bethesda, Md. 20894; Internet address http://www.ncbi.nlm.nih.gov/). They are used herein to unambiguously identify genes that are referred to in the application by names and/or acronyms. Gene products (e.g. mRNA, protein) expressed by genes thus identified represent products that may be used in the methods of this invention, and the sequences of these products, including different isoforms, as disclosed in NCBI database (e.g. GENBANK®) records are herein incorporated by reference. Similarly, Ensemble Gene ID numbers (e.g. in FIGS. 36 and 37) are unique identifiers of human genes used by the EMBL-EBI and Sanger Centre collaboration.

In the methods of this invention, the tumor cell of the cancer patient is preferably of a type known to, or expected to, express EGFR or IGF-1R kinase, as do most tumor cells from solid tumors derived from an epithelial cell linage. Such tumor cells include those from, for example, lung cancer tumors (e.g. non-small cell lung cancer (NSCLC)), pancreatic cancer tumors, breast cancer tumors, head and neck cancer tumors, gastric cancer tumors, colon cancer tumors, ovarian cancer tumors, or a tumor cell from any of a variety of other cancers as described herein below. The EGFR kinase of these tumor cells can be wild type or a mutant form.

In the methods of this invention, the EGFR kinase inhibitor can be any EGFR kinase inhibitor as described herein below. In one embodiment, the EGFR kinase inhibitor is 6,7-bis(2-methoxyethoxy)-4-quinazolin-4-yl]-(3-ethynyl-phenyl)amine (also known as erlotinib, OSI-774, or TARCEVA® (i.e. erlotinib HCl)), including pharmacologically acceptable salts or polymorphs thereof.

In the methods of this invention, the IGF-1R kinase inhibitor can be any IGF-1R kinase inhibitor as described herein below. In one embodiment the IGF-1R kinase inhibitor is cis-3-[8-amino-1-(2-phenyl-quinolin-7-yl)-imidazo[1,5-a]pyrazin-3-yl]-1-methyl-cyclobutanol (also known as OSI-906), including pharmacologically acceptable salts or polymorphs thereof.

In the methods of this invention, the expression level of a tumor cell gene is preferably assessed by assaying a tumor biopsy. However, in an alternative embodiment, expression level of the tumor cell genes can be assessed in bodily fluids or excretions containing detectable levels of tumor cells originating from the tumor. Bodily fluids or excretions useful in the present invention include blood, urine, saliva, stool, pleural fluid, lymphatic fluid, sputum, ascites, prostatic fluid, cerebrospinal fluid (CSF), or any other bodily secretion or derivative thereof. By blood it is meant to include whole blood, plasma, serum or any derivative of blood. Assessment of tumor cell genes in such bodily fluids or excretions can sometimes be preferred in circumstances where an invasive sampling method is inappropriate or inconvenient. For assessment of tumor cell gene expression, patient samples containing tumor cells, or proteins or nucleic acids produced by these tumor cells, may be used in the methods of the present invention. The cell sample can, of course, be subjected to a variety of well-known post-collection preparative and storage techniques (e.g., nucleic acid and/or protein extraction, fixation, storage, freezing, ultrafiltration, concentration, evaporation, centrifugation, etc.) prior to assessing gene expression in the sample. Likewise, tumor biopsies may also be subjected to post-collection preparative and storage techniques, e.g., fixation.

In the methods of this invention, gene expression in a tumor cell can be assessed by using any of the standard bioassay procedures known in the art for determination of the level of expression of a gene, including for example immunohistochemistry (IHC), enzyme-linked immunosorbent assay (ELISA), radioimmunoassay (RIA), immunoprecipitation, immunoblotting, immunofluorescence microscopy, real-time polymerase chain reaction (RT-PCR), in situ hybridization, cDNA microarray, in vitro transcription, or the like, as described in more detail below.

A general principle of diagnostic assays as described herein involves preparing a sample or reaction mixture that may contain an expressed gene product, and a probe, under appropriate conditions and for a time sufficient to allow the product and probe to interact and bind, thus forming a complex that can be removed and/or detected in the reaction mixture or sample. These assays can be conducted in a variety of ways. For example, one method to conduct such an assay would involve anchoring the expressed product or probe onto a solid phase support, also referred to as a substrate, and detecting target product/probe complexes anchored on the solid phase at the end of the reaction. In one embodiment of such a method, a sample from a subject, which is to be assayed for presence and/or concentration of a gene product, can be anchored onto a carrier or solid phase support. In another embodiment, the reverse situation is possible, in which the probe can be anchored to a solid phase and a sample from a subject can be allowed to react as an unanchored component of the assay.

There are many established methods for anchoring assay components to a solid phase. These include, without limitation, biomarker or probe molecules which are immobilized through conjugation of biotin and streptavidin. Such biotinylated assay components can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). In certain embodiments, the surfaces with immobilized assay components can be prepared in advance and stored.

Other suitable carriers or solid phase supports for such assays include any material capable of binding the class of molecule to which the biomarker or probe belongs. Well-known supports or carriers include, but are not limited to, glass, polystyrene, nylon, polypropylene, nylon, polyethylene, dextran, amylases, natural and modified celluloses, polyacrylamides, gabbros, and magnetite.

In order to conduct assays with the above mentioned approaches, the non-immobilized component is added to the solid phase upon which the second component is anchored. After the reaction is complete, uncomplexed components may be removed (e.g., by washing) under conditions such that any complexes formed will remain immobilized upon the solid phase. The detection of expressed product/probe complexes anchored to the solid phase can be accomplished in a number of methods outlined herein.

In one embodiment, the probe, when it is the unanchored assay component, can be labeled for the purpose of detection and readout of the assay, either directly or indirectly, with detectable labels discussed herein and which are well-known to one skilled in the art.

It is also possible to directly detect product/probe complex formation without further manipulation or labeling of either component (biomarker or probe), for example by utilizing the technique of fluorescence energy transfer (i.e. FET, see for example, Lakowicz et al., U.S. Pat. No. 5,631,169; Stavrianopoulos, et al., U.S. Pat. No. 4,868,103). A fluorophore label on the first, 'donor' molecule is selected such that, upon excitation with incident light of appropriate wavelength, its emitted fluorescent energy will be absorbed by a fluorescent label on a second 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, spatial relationships between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determination of the ability of a probe to recognize a biomarker can be accomplished without labeling either assay component (probe or biomarker) by utilizing a technology such as real-time Biomolecular Interaction Analysis (BIA) (see, e.g., Sjolander, S, and Urbanic-zky, C., 1991, Anal. Chem. 63:2338-2345 and Szabo et al., 1995, Curr. Opin. Struct. Biol. 5:699-705). As used herein, "BIA" or "surface plasmon resonance" is a technology for studying biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In a particular embodiment, the level of mRNA can be determined both by in situ and by in vitro formats in a biological sample using methods known in the art. The term "biological sample" is intended to include tissues, cells, biological fluids and isolates thereof, isolated from a subject, as well as tissues, cells and fluids present within a subject. Many expression detection methods use isolated RNA. For in vitro methods, any RNA isolation technique that does not select against the isolation of mRNA can be utilized for the purification of RNA from tumor cells (see, e.g., Ausubel et al., ed., Current Protocols in Molecular Biology, John Wiley & Sons, New York 1987-1999). Additionally, large numbers of tissue samples can readily be processed using techniques well known to those of skill in the art, such as, for example, the single-step RNA isolation process of Chomczynski (1989, U.S. Pat. No. 4,843,155).

The isolated mRNA can be used in hybridization or amplification assays that include, but are not limited to, Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to a mRNA or genomic DNA encoding a biomarker of the present invention. Other suitable probes for use in the diagnostic assays of the invention are described herein. Hybridization of an mRNA with the probe indicates that the biomarker in question is being expressed.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in an AFFYMETRIX® gene chip array. A skilled artisan can readily adapt known mRNA detection methods for use in detecting the level of mRNA encoded by the biomarkers of the present invention.

An alternative method for determining the level of mRNA in a sample involves the process of nucleic acid amplification, e.g., by RT-PCR (the experimental embodiment set forth in Mullis, 1987, U.S. Pat. No. 4,683,202), ligase chain reaction (Barany, 1991, Proc. Natl. Acad. Sci. USA, 88:189-193), self sustained sequence replication (Guatelli et al., 1990, Proc. Natl. Acad. Sci. USA 87:1874-1878), transcriptional amplification system (Kwoh et al., 1989, Proc. Natl. Acad. Sci. USA 86:1173-1177), Q-Beta Replicase (Lizardi et al., 1988, Bio/Technology 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the tumor cells prior to detection. In such methods, a cell or tissue sample is prepared/processed using known histological methods. The sample is then immobilized on a support, typically a glass slide, and then contacted with a probe that can hybridize to mRNA that encodes the biomarker.

A tissue sample from a tumor in a human patient or an animal model can be used as a source of RNA so that the EMT signature gene expression levels in the sample can be determined in accordance with the present invention. Generally, the tumor will be a carcinoma. The tissue sample can be obtained by using conventional tumor biopsy instruments and procedures. Endoscopic biopsy, excisional biopsy, incisional biopsy, fine needle biopsy or aspiration (FNA), core biopsy, punch biopsy, shave biopsy and skin biopsy are examples of recognized medical procedures that can be used by one of skill in the art to obtain tumor samples for use in practicing the invention. The tumor tissue sample should be large enough to provide sufficient RNA for measuring individual gene expression levels.

Macrodissection and/or microdisection methods (e.g. Laser Microdissection and Pressure Catapulting (LMPC) may be used to obtain a tissue sample from a tumor. For example, the PALM® Micro Beam microscope (P.A.L.M. Microlaser Technologies AG, Bernried, Germany); or SL-Microtest UV laser microdissection system (Molecular Machines & Industries, Glattbrugg, Switzerland)) may be used to enrich the tumor cell population of a tumor sample by removing normal tissue cells or stromal cells (e.g. de Bruin E C. et al. BMC Genomics. 2005 Oct. 14; 6:142; Dhal, E. et al. Clinical Cancer Research Jul. 2006 12; 3950; Funel, N. et al. Laboratory Investigation (2008) 88, 773-784, doi:10.1038/labinvest.2008.40, published online 19 May 2008). Primary tumor cell cultures may also be prepared from the sample in order to produce a pure tumor cell population.

The tumor tissue sample can be in any form that allows gene expression analysis, e.g., RNA extraction and quantitation. Accordingly, the tissue sample can be fresh, preserved through suitable cryogenic techniques, or preserved through non-cryogenic techniques. A standard process for handling clinical biopsy specimens is to fix the tissue sample in formalin and then embed it in paraffin. Samples in this form are commonly known as formalin-fixed, paraffin-embedded (FFPE) tissue. Suitable techniques of tissue preparation and tissue preservation for subsequent RNA extraction are well-known to those of skill in the art.

Individual gene expression levels for each gene in the EMT gene signature are the input values used to calculate the EMT index value. Once a tissue sample is obtained it is necessary to determine, i.e., measure, the expression levels of the individual genes in the EMT gene signature. Gene expression level can be determined by any suitable method. Two exemplary methods for measuring individual expression are DNA microarray analysis and qRT-PCR, which are discussed below. A prerequisite for either of these alternative methods is RNA isolation.

Methods for rapid and efficient extraction of eukaryotic mRNA, i.e., poly(a) RNA, from tissue samples or cultured cells are well established and known to those of skill in the art. See, e.g., Ausubel et al., 1997, Current Protocols of Molecular Biology, John Wiley & Sons. The tissue sample can be fresh, frozen or fixed paraffin-embedded (FFPE) clinical study tumor specimens. In general, RNA isolated from fresh or frozen tissue samples tends to be less fragmented than RNA from FFPE samples. FFPE samples of tumor material, however, are more readily available, and FFPE samples are suitable sources of RNA for use in methods of the present invention. For a discussion of FFPE samples as sources of RNA for gene expression profiling by RT-PCR, see, e.g., Clark-Langone et al., 2007, BMC Genomics 8:279. Also see, De Andres et al., 1995, Biotechniques 18:42044; and Baker et al., U.S. Patent Application Publication No. 2005/0095634. The use of commercially available kits with vendor's instructions for RNA extraction and preparation is widespread and common. Commercial vendors of various RNA isolation products and complete kits include Qiagen (Valencia, Calif.), Invitrogen (Carlsbad, Calif.), Ambion (Austin, Tex.) and Exiqon (Woburn, Mass.).

In general, RNA isolation begins with tissue/cell disruption. During tissue/cell disruption it is desirable to minimize RNA degradation by RNases. One approach to limiting RNase activity during the RNA isolation process is to ensure that a denaturant is in contact with cellular contents as soon as the cells are disrupted. Another common practice is to include one or more proteases in the RNA isolation process. Optionally, fresh tissue samples are immersed in an RNA stabilization solution, at room temperature, as soon as they are collected. The stabilization solution rapidly permeates the cells, stabilizing the RNA for storage at 4° C., for subsequent isolation. One such stabilization solution is available commercially as RNAlater®. (Ambion, Austin, Tex.).

In some protocols, total RNA is isolated from disrupted tumor material by cesium chloride density gradient centrifugation. In general, mRNA makes up approximately 1% to 5% of total cellular RNA. Immobilized Oligo(dT), e.g., oligo(dT) cellulose, is commonly used to separate mRNA from ribosomal RNA and transfer RNA. If stored after isolation, RNA must be stored in under RNase-free conditions. Methods for stable storage of isolated RNA are known in the art. Various commercial products for stable storage of RNA are available.

The mRNA expression level for multiple genes can be measured using conventional DNA microarray expression profiling technology. A DNA microarray is a collection of specific DNA segments or probes affixed to a solid surface or substrate such as glass, plastic or silicon, with each specific DNA segment occupying a known location in the array. Hybridization with a sample of labeled RNA, usually under stringent hybridization conditions, allows detection and quantitation of RNA molecules corresponding to each probe in the array. After stringent washing to remove non-specifically bound sample material, the microarray is scanned by confocal laser microscopy or other suitable detection method. Modern commercial DNA microarrays, often known as DNA chips, typically contain tens of thousands of probes, and thus can measure expression of tens of thousands of genes simultaneously. Such microarrays can be used in practicing the present invention. Alternatively, custom chips containing as few probes as those needed to measure expression of the genes of the EMT gene signature, plus necessary controls or standards (for data normalization, etc.), can be used in practicing the invention.

To facilitate data normalization, a two-color microarray reader can be used. In a two-color (two-channel) system, samples are labeled with a first fluorophore that emits at a first wavelength, while an RNA or cDNA standard is labeled with a second fluorophore that emits at a different wavelength. For example, Cy3 (570 nm) and Cy5 (670 nm) often are employed together in two-color microarray systems.

DNA microarray technology is well-developed, commercially available, and widely employed. Therefore, in performing methods of the invention, a person of ordinary skill in the art can use microarray technology to measure expression levels of genes in the EMT gene signature without undue experimentation. DNA microarray chips, reagents (such as those for RNA or cDNA preparation, RNA or cDNA labeling, hybridization and washing solutions), instruments (such as microarray readers) and protocols are well known in the art and available from various commercial sources. Commercial vendors of microarray systems include Agilent Technologies (Santa Clara, Calif.) and Affymetrix (Santa Clara, Calif.), but other systems can be used.

The level of mRNA representing individual genes in the EMT gene signature can be measured using conventional quantitative reverse transcriptase polymerase chain reaction (qRT-PCR) technology. Advantages of qRT-PCR include sensitivity, flexibility, quantitative accuracy, and ability to discriminate between closely related mRNAs. Guidance concerning the processing of tissue samples for quantitative PCR is available from various sources, including manufacturers and vendors of commercial products for qRT-PCR (e.g., Qiagen (Valencia, Calif.) and Ambion (Austin, Tex.)). Instrument systems for automated performance of qRT-PCR are commercially available and used routinely in many laboratories. An example of a well-known commercial system is the Applied Biosystems 7900HT Fast Real-Time PCR System (Applied Biosystems, Foster City, Calif.).

Once isolated mRNA is in hand, the first step in gene expression profiling by RT-PCR is the reverse transcription of the mRNA template into cDNA, which is then exponentially amplified in a PCR reaction. Two commonly used reverse transcriptases are avilo myeloblastosis virus reverse transcriptase (AMV-RT) and Moloney murine leukemia virus reverse transcriptase (MMLV-RT). The reverse transcription reaction typically is primed with specific primers, random hexamers, or oligo(dT) primers. Suitable primers are commercially available, e.g., GeneAmp® RNA PCR kit (Perkin Elmer, Waltham, Mass.). The resulting cDNA product can be used as a template in the subsequent polymerase chain reaction.

The PCR step is carried out using a thermostable DNA-dependent DNA polymerase. The polymerase most commonly used in PCR systems is a Thermus aquaticus (Taq) polymerase. The selectivity of PCR results from the use of primers that are complementary to the DNA region targeted for amplification, i.e., regions of the cDNAs reverse transcribed from the genes of the EMT gene signature. Therefore, when qRT-PCR is employed in the present invention, primers specific to each gene in the EMT gene signature are based on the cDNA sequence of the gene. Commercial technologies such as SYBR® green or TaqMan® (Applied Biosystems, Foster City, Calif.) can be used in accordance with the vendor's instructions. Messenger RNA levels can be normalized for differences in loading among samples by comparing the levels of housekeeping genes such as beta-actin or GAPDH. The level of mRNA expression can be expressed relative to any single control sample such as mRNA from normal, non-tumor tissue or cells. Alternatively, it can be expressed relative to mRNA from a pool of tumor samples, or tumor cell lines, or from a commercially available set of control mRNA.

Suitable primer sets for PCR analysis of expression levels of the genes in the EMT gene signature can be designed and synthesized by one of skill in the art, without undue experimentation. Alternatively, complete PCR primer sets for practicing the present invention can be purchased from commercial sources, e.g., Applied Biosystems, based on the identities of the genes in the EMT gene signature, as set forth herein in Table 1 and FIGS. 36-37. PCR primers preferably are about 17 to 25 nucleotides in length. Primers can be designed to have a particular melting temperature (Tm), using conventional algorithms for Tm estimation. Software for primer design and Tm estimation are available commercially, e.g., Primer Express™ (Applied Biosystems), and also are available on the internet, e.g., Primer3 (Massachusetts Institute of Technology). By applying established principles of PCR primer design, a large number of different primers can be used to measure the expression level of any given gene. Accordingly, the invention is not limited with respect to which particular primers are used for any given gene in the EMT gene signature.

In another embodiment of the present invention, an expressed protein is detected. A preferred agent for detecting an expressed protein in the invention is an antibody capable of binding to such a protein or a fragment thereof, preferably an antibody with a detectable label. Antibodies can be polyclonal, or more preferably, monoclonal. An intact antibody, or a fragment or derivative thereof (e.g., Fab or F(ab').sub.2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

Proteins from tumor cells can be isolated using techniques that are well known to those of skill in the art. The protein isolation methods employed can, for example, be such as those described in Harlow and Lane (Harlow and Lane, 1988, Antibodies: A Laboratory Manual, Cold Spring Harbor Laboratory Press, Cold Spring Harbor, N.Y.).

A variety of formats can be employed to determine whether a sample contains a protein that binds to a given antibody. Examples of such formats include, but are not limited to, enzyme immunoassay (EIA), radioimmunoassay (RIA), Western blot analysis and enzyme linked immunoabsorbant assay (ELISA). A skilled artisan can readily adapt known protein/antibody detection methods for use in determining whether tumor cells express a biomarker of the present invention.

In one format, antibodies, or antibody fragments or derivatives, can be used in methods such as Western blots or immunofluorescence techniques to detect the expressed proteins. In such uses, it is generally preferable to immobilize either the antibody or proteins on a solid support. Suitable solid phase supports or carriers include any support capable of binding an antigen or an antibody. Well-known supports or carriers include glass, polystyrene, polypropylene, polyethylene, dextran, nylon, amylases, natural and modified celluloses, polyacrylamides, gabbros, and magnetite.

One skilled in the art will know many other suitable carriers for binding antibody or antigen, and will be able to adapt such support for use with the present invention. For example, protein isolated from tumor cells can be run on a polyacrylamide gel electrophoresis and immobilized onto a solid phase support such as nitrocellulose. The support can then be washed with suitable buffers followed by treatment with the detectably labeled antibody. The solid phase support can then be washed with the buffer a second time to remove unbound antibody. The amount of bound label on the solid support can then be detected by conventional means.

For ELISA assays, specific binding pairs can be of the immune or non-immune type. Immune specific binding pairs are exemplified by antigen-antibody systems or hapten/anti-hapten systems. There can be mentioned fluorescein/anti-fluorescein, dinitrophenyl/anti-dinitrophenyl, biotin/anti-biotin, peptide/anti-peptide and the like. The antibody member of the specific binding pair can be produced by customary methods familiar to those skilled in the art. Such methods involve immunizing an animal with the antigen member of the specific binding pair. If the antigen member of the specific binding pair is not immunogenic, e.g., a hapten, it can be covalently coupled to a carrier protein to render it immunogenic. Non-immune binding pairs include systems wherein the two components share a natural affinity for each other but are not antibodies. Exemplary non-immune pairs are biotin-streptavidin, intrinsic factor-vitamin $B_{12}$, folic acid-folate binding protein and the like.

A variety of methods are available to covalently label antibodies with Members of specific binding pairs. Methods are selected based upon the nature of the member of the specific binding pair, the type of linkage desired, and the tolerance of the antibody to various conjugation chemistries. Biotin can be covalently coupled to antibodies by utilizing commercially available active derivatives. Some of these are biotin-N-hydroxy-succinimide which binds to amine groups on proteins; biotin hydrazide which binds to carbohydrate moieties, aldehydes and carboxyl groups via a carbodiimide coupling; and biotin maleimide and iodoacetyl biotin which bind to sulfhydryl groups. Fluorescein can be coupled to protein amine groups using fluorescein isothiocyanate. Dinitrophenyl groups can be coupled to protein amine groups using 2,4-dinitrobenzene sulfate or 2,4-dinitrofluorobenzene. Other standard methods of conjugation can be employed to couple monoclonal antibodies to a member of a specific binding pair including dialdehyde, carbodiimide coupling, homofunctional crosslinking, and heterobifunctional crosslinking. Carbodiimide coupling is an effective method of coupling carboxyl groups on one substance to amine groups on another. Carbodiimide coupling is facilitated by using the commercially available reagent 1-ethyl-3-(dimethyl-aminopropyl)-carbodiimide (EDAC).

Homobifunctional crosslinkers, including the bifunctional imidoesters and bifunctional N-hydroxysuccinimide esters, are commercially available and are employed for coupling amine groups on one substance to amine groups on another. Heterobifunctional crosslinkers are reagents which possess different functional groups. The most common commercially available heterobifunctional crosslinkers have an amine reactive N-hydroxysuccinimide ester as one functional group, and a sulfhydryl reactive group as the second functional group. The most common sulfhydryl reactive groups are maleimides, pyridyl disulfides and active halogens. One of the functional groups can be a photoactive aryl nitrene, which upon irradiation reacts with a variety of groups.

The detectably-labeled antibody or detectably-labeled member of the specific binding pair is prepared by coupling to a reporter, which can be a radioactive isotope, enzyme, fluorogenic, chemiluminescent or electrochemical materials. Two commonly used radioactive isotopes are $^{125}$I and $^{3}$H. Standard radioactive isotopic labeling procedures include the chloramine T, lactoperoxidase and Bolton-Hunter methods for $^{125}$I and reductive methylation for $^{3}$H. The term "detectably-labeled" refers to a molecule labeled in such a way that it can be readily detected by the intrinsic enzymic activity of the label or by the binding to the label of another component, which can itself be readily detected.

Enzymes suitable for use in this invention include, but are not limited to, horseradish peroxidase, alkaline phosphatase, β-galactosidase, glucose oxidase, luciferases, including firefly and renilla, β-lactamase, urease, green fluorescent protein (GFP) and lysozyme. Enzyme labeling is facilitated by using dialdehyde, carbodiimide coupling, homobifunctional crosslinkers and heterobifunctional crosslinkers as described above for coupling an antibody with a member of a specific binding pair.

The labeling method chosen depends on the functional groups available on the enzyme and the material to be labeled, and the tolerance of both to the conjugation conditions. The labeling method used in the present invention can be one of, but not limited to, any conventional methods currently employed including those described by Engvall and Pearlmann, Immunochemistry 8, 871 (1971), Avrameas and Ternynck, Immunochemistry 8, 1175 (1975), Ishikawa et al., J. Immunoassay 4(3):209-327 (1983) and Jablonski, Anal. Biochem. 148:199 (1985).

Labeling can be accomplished by indirect methods such as using spacers or other members of specific binding pairs. An example of this is the detection of a biotinylated antibody with unlabeled streptavidin and biotinylated enzyme, with streptavidin and biotinylated enzyme being added either sequentially or simultaneously. Thus, according to the present invention, the antibody used to detect can be detectably-labeled directly with a reporter or indirectly with a first member of a specific binding pair. When the antibody is coupled to a first member of a specific binding pair, then detection is effected by reacting the antibody-first member of a specific binding complex with the second member of the binding pair that is labeled or unlabeled as mentioned above.

Moreover, the unlabeled detector antibody can be detected by reacting the unlabeled antibody with a labeled antibody specific for the unlabeled antibody. In this instance "detectably-labeled" as used above is taken to mean containing an epitope by which an antibody specific for the unlabeled antibody can bind. Such an anti-antibody can be labeled directly or indirectly using any of the approaches discussed above. For example, the anti-antibody can be coupled to biotin which is detected by reacting with the streptavidin-horseradish peroxidase system discussed above.

In one embodiment of this invention biotin is utilized. The biotinylated antibody is in turn reacted with streptavidin-horseradish peroxidase complex. Orthophenylenediamine, 4-chloro-naphthol, tetramethylbenzidine (TMB), ABTS, BTS or ASA can be used to effect chromogenic detection.

In one immunoassay format for practicing this invention, a forward sandwich assay is used in which the capture reagent has been immobilized, using conventional techniques, on the surface of a support. Suitable supports used in assays include synthetic polymer supports, such as polypropylene, polystyrene, substituted polystyrene, e.g. aminated or carboxylated polystyrene, polyacrylamides, polyamides, polyvinylchloride, glass beads, agarose, or nitrocellulose.

The invention also encompasses kits for detecting the expression of the genes of an EMTGS in a biological sample. Such kits can be used to determine if a subject is suffering from or is at increased risk of developing a tumor that is less susceptible to inhibition by an EGFR kinase inhibitor or an IGF-1R kinase inhibitor. For example, the kit can comprise a labeled compound or agent capable of detecting multiple EMTGS proteins or nucleic acids in a biological sample, or primers for use in PCR amplification, and means for determining the amounts of the proteins or mRNAs in the sample (e.g., antibodies which binds the proteins or a fragment thereof, or oligonucleotide probes which binds to the mRNAs, or derived cDNAs). Kits can also include instructions for interpreting the results obtained using the kit.

For oligonucleotide-based kits, the kit can comprise, for example, for each EMTGS gene: (1) an oligonucleotide, e.g., a detectably labeled oligonucleotide, which hybridizes to a nucleic acid sequence encoding an EMTGS gene or (2) a pair of primers useful for amplifying a EMTGS nucleic acid molecule. The kit can also comprise, e.g., a buffering agent, a preservative, or a protein stabilizing agent. The kit can further comprise components necessary for detecting the detectable label (e.g., an enzyme or a substrate). The kit can also contain a control sample or a series of control samples which can be assayed and compared to the test sample. Each component of the kit can be enclosed within an individual container and all of the various containers can be within a single package, along with instructions for interpreting the results of the assays performed using the kit. The kit may also comprise a DNA microarray chip with oligonucleotide probes specific for each of the genes of the EMTGS.

The present invention further provides any of the methods disclosed herein for treating cancer, or tumors or tumor metastases in a patient with cancer, comprising administering to the patient a therapeutically effective amount of an EGFR kinase inhibitor or an IGF-1R kinase inhibitor and in addition, simultaneously or sequentially, one or more other cytotoxic, chemotherapeutic or anti-cancer agents, or compounds that enhance the effects of such agents. In the context of this invention, other anti-cancer agents includes, for example, other cytotoxic, chemotherapeutic or anti-cancer agents, or compounds that enhance the effects of such agents, anti-hormonal agents, angiogenesis inhibitors, agents that inhibit or reverse EMT (e.g. TGF-beta receptor inhibitors), tumor cell pro-apoptotic or apoptosis-stimulating agents, histone deacetylase (HDAC) inhibitors, histone demethylase inhibitors, DNA methyltransferase inhibitors, signal transduction inhibitors, anti-proliferative agents, anti-HER2 antibody (e.g. trastuzumab (Genentech)) or an immunotherapeutically active fragment thereof, anti-proliferative agents, COX II (cyclooxygenase II) inhibitors, and agents capable of enhancing antitumor immune responses.

In the context of this invention, additional other cytotoxic, chemotherapeutic or anti-cancer agents, or compounds that enhance the effects of such agents, include, for example: alkylating agents or agents with an alkylating action, such as cyclophosphamide (CTX; e.g. CYTOXAN®), chlorambucil (CHL; e.g. LEUKERAN®), cisplatin (CisP; e.g. PLATINOL®) busulfan (e.g. MYLERAN®), melphalan, carmustine (BCNU), streptozotocin, triethylenemelamine (TEM), mitomycin C, and the like; anti-metabolites, such as methotrexate (MTX), etoposide (VP16; e.g. VEPESID®), 6-mercaptopurine (6 MP), 6-thioguanine (6TG), cytarabine (Ara-C), 5-fluorouracil (5-FU), capecitabine (e.g.XELODA®), dacarbazine (DTIC), and the like; antibiotics, such as actinomycin D, doxorubicin (DXR; e.g. ADRIAMYCIN®), daunorubicin (daunomycin), bleomycin, mithramycin and the like; alkaloids, such as vinca alkaloids such as vincristine (VCR), vinblastine, and the like; and other antitumor agents, such as paclitaxel (e.g. TAXOL®) and pactitaxel derivatives, the cystostatic agents, glucocorticoids such as dexamethasone (DEX; e.g. DECADRON®) and corticosteroids such as prednisone, nucleoside enzyme inhibitors such as hydroxyurea, amino acid depleting enzymes such as asparaginase, leucovorin, pemetrexed, and other folic acid derivatives, and similar, diverse antitumor agents. The following agents may also be used as additional agents: arnifostine (e.g. ETHYOL®), dactinomycin, mechlorethamine (nitrogen mustard), streptozocin, cyclophosphamide, lomustine (CCNU), doxorubicin lipo (e.g. DOXIL®), gemcitabine (e.g. GEMZAR®), daunorubicin lipo (e.g. DAUNOXOME®), procarbazine, mitomycin, docetaxel (e.g. TAXOTERE®), aldesleukin, carboplatin, oxaliplatin, cladribine, camptothecin, CPT 11 (irinotecan), 10-hydroxy 7-ethyl-camptothecin (SN38), floxuridine, fludarabine, ifosfamide, idarubicin, mesna, interferon beta, interferon alpha, mitoxantrone, topotecan, leuprolide, megestrol, melphalan, mercaptopurine, plicamycin, mitotane, pegaspargase, pentostatin, pipobroman, plicamycin, tamoxifen, teniposide, testolactone, thioguanine, thiotepa, uracil mustard, vinorelbine, chlorambucil.

The present invention further provides the preceding methods for treating tumors or tumor metastases in a patient, comprising administering to the patient a therapeutically effective amount of an EGFR kinase inhibitor or an IGF-1R kinase inhibitor and in addition, simultaneously or sequentially, one or more anti-hormonal agents. As used herein, the term "anti-hormonal agent" includes natural or synthetic organic or peptidic compounds that act to regulate or inhibit hormone action on tumors.

Antihormonal agents include, for example: steroid receptor antagonists, anti-estrogens such as tamoxifen, raloxifene, aromatase inhibiting 4(5)-imiclazoles, other aromatase inhibitors, 42-hydroxytamoxifen, trioxifene, keoxifene, LY 117018, onapristone, and toremifene (e.g. FARESTON®); anti-androgens such as flutamide, nilutamide, bicalutamide, leuprolide, and goserelin; and pharmaceutically acceptable salts, acids or derivatives of any of the above; agonists and/or antagonists of glycoprotein hormones such as follicle stimulating hormone (FSH), thyroid stimulating hormone (TSH), and luteinizing hormone (LH) and LHRH (leuteinizing hormone-releasing hormone); the LHRH agonist goserelin acetate, commercially available as ZOLADEX® (AstraZeneca); the LHRH antagonist D-alaninamide N-acetyl-3-(2-naphthalenyl)-D-alanyl-4-chloro-D-phenylalanyl-3-(3-pyridinyl)-D-alanyl-L-seryl-N6-(3-pyridinylcarbonyl)-L-lysyl-N6-(3-pyridinylcarbonyl)-D-lysyl-L-leucyl-N6-(1-methylethyl)-L-lysyl-L-proline (e.g ANTIDE®, Ares-Serono); the LHRH antagonist ganirelix acetate; the steroidal anti-androgens cyproterone acetate (CPA) and megestrol acetate, commercially available as MEGACE® (Bristol-Myers Oncology); the nonsteroidal anti-androgen flutamide (2-methyl-N-[4,20-nitro-3-(trifluoromethyl)phenylpropanamide), commercially available as EULEXIN® (Schering Corp.); the non-steroidal anti-androgen nilutamide, (5,5-dimethyl-3-[4-nitro-3-(trifluoromethyl-4'-nitrophenyl)-4,4-dimethyl-imidazolidine-dione); and antagonists for other non-permissive receptors, such as antagonists for RAR, RXR, TR, VDR, and the like.

The use of the cytotoxic and other anti-cancer agents described above in chemotherapeutic regimens is generally well characterized in the cancer therapy arts, and their use herein falls under the same considerations for monitoring tolerance and effectiveness and for controlling administration routes and dosages, with some adjustments. For example, the actual dosages of the cytotoxic agents may vary depending upon the patient's cultured cell response determined by using histoculture methods. Generally, the dosage will be reduced compared to the amount used in the absence of additional other agents.

Typical dosages of an effective cytotoxic agent can be in the ranges recommended by the manufacturer, and where indicated by in vitro responses or responses in animal models, can be reduced by up to about one order of magnitude concentration or amount. Thus, the actual dosage will depend upon the judgment of the physician, the condition of the patient, and the effectiveness of the therapeutic method based on the in vitro responsiveness of the primary cultured malignant cells or histocultured tissue sample, or the responses observed in the appropriate animal models.

The present invention further provides the preceding methods for treating tumors or tumor metastases in a patient, comprising administering to the patient a therapeutically effective amount of an EGFR kinase inhibitor or an IGF-1R kinase inhibitor and in addition, simultaneously or sequentially, one or more angiogenesis inhibitors.

Anti-angiogenic agents include, for example: VEGFR inhibitors, such as SU-5416 and SU-6668 (Sugen Inc. of South San Francisco, Calif., USA), or as described in, for example International Application Nos. WO 99/24440, WO 99/62890, WO 95/21613, WO 99/61422, WO 98/50356, WO 99/10349, WO 97/32856, WO 97/22596, WO 98/54093, WO 98/02438, WO 99/16755, and WO 98/02437, and U.S. Pat. Nos. 5,883,113, 5,886,020, 5,792,783, 5,834,504 and 6,235,764; VEGF inhibitors such as IM862 (Cytran Inc. of Kirkland, Wash., USA); sunitinib (Pfizer); angiozyme, a synthetic ribozyme from Ribozyme (Boulder, Colo.) and Chiron (Emeryville, Calif.); and antibodies to VEGF, such as bevacizumab (e.g. AVASTIN™, Genentech, South San Francisco, Calif.), a recombinant humanized antibody to VEGF; integrin receptor antagonists and integrin antagonists, such as to $\alpha_v\beta_3$, $\alpha_v\beta_5$ and $\alpha_v\beta_6$ integrins, and subtypes thereof, e.g. cilengitide (EMD 121974), or the anti-integrin antibodies, such as for example $\alpha_v\beta_3$ specific humanized antibodies (e.g. VITAXIN®); factors such as IFN-alpha (U.S. Pat. Nos. 41,530,901, 4,503,035, and 5,231,176); angiostatin and plasminogen fragments (e.g. kringle 1-4, kringle 5, kringle 1-3 (O'Reilly, M. S. et al. (1994) Cell 79:315-328; Cao et al. (1996) J. Biol. Chem. 271: 29461-29467; Cao et al. (1997) J. Biol. Chem. 272:22924-22928); endostatin (O'Reilly, M. S. et al. (1997) Cell 88:277; and International Patent Publication No. WO 97/15666); thrombospondin (TSP-1; Frazier, (1991) Curr. Opin. Cell Biol. 3:792); platelet factor 4 (PF4); plasminogen activator/urokinase inhibitors; urokinase receptor antagonists; heparinases; fumagillin analogs such as TNP-4701; suramin and suramin analogs; angiostatic steroids; bFGF antagonists; flk-1 and flt-1 antagonists; anti-angiogenesis agents such as MMP-2 (matrix-metalloproteinase 2) inhibitors and MMP-9 (matrix-metalloproteinase 9) inhibitors. Examples of useful matrix metalloproteinase inhibitors are described in International Patent Publication Nos. WO 96/33172, WO 96/27583, WO 98/07697, WO 98/03516, WO 98/34918, WO 98/34915, WO 98/33768, WO 98/30566, WO 90/05719, WO 99/52910, WO 99/52889, WO 99/29667, and WO 99/07675, European Patent Publication Nos. 818,442, 780,386, 1,004,578, 606,046, and 931,788; Great Britain Patent Publication No. 9912961, and U.S. Pat. Nos. 5,863,949 and 5,861,510. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

The present invention further provides the preceding methods for treating tumors or tumor metastases in a patient, comprising administering to the patient a therapeutically effective amount of an EGFR kinase inhibitor or an IGF-1R kinase inhibitor and in addition, simultaneously or sequentially, one or more tumor cell pro-apoptotic or apoptosis-stimulating agents.

The present invention further provides the preceding methods for treating tumors or tumor metastases in a patient, comprising administering to the patient a therapeutically effective amount of an EGFR kinase inhibitor or an IGF-1R kinase inhibitor and in addition, simultaneously or sequentially, one or more histone deacetylase (HDAC) inhibitors.

HDAC inhibitors include, for example: SB939, CHR-3996, CRA-024781, ITF2357, JNJ-26854165, JNJ-26481585 (Ortho Biotech), Vorinostat (suberoylanilide hydroxamic acid, SAHA; Merck), FK-228 (depsipeptide/FR-901228, Fujisawa, Osaka, Japan), Phenylbutyrate (Elan Pharmaceuticals, Dublin), LAQ824 and LBH589 (Novartis), PXD101 (TopoTarget, Copenhagen), MS-275 (Schering AG), Pyroxamide (Aton Pharma, Tarrytown, N.Y.), MGCD0103 (MethylGene, Montreal), NBM-HD-1 (Nature-Wise Biotech & Medicals Corporation), CI-994 (Pfizer Inc), Pivanex (Titan Pharmaceuticals Inc), Romidepsin (Gloucester Pharmaceuticals), and Entinostat (SNDX-275; Syndax Pharmaceuticals), The present invention further provides the preceding methods for treating tumors or tumor metastases in a patient, comprising administering to the patient a therapeutically effective amount of an EGFR kinase inhibitor or an IGF-1R kinase inhibitor and in addition, simultaneously or sequentially, one or more histone demethylase inhibitors.

The present invention further provides the preceding methods for treating tumors or tumor metastases in a patient, comprising administering to the patient a therapeutically effective amount of an EGFR kinase inhibitor or an IGF-1R kinase inhibitor and in addition, simultaneously or sequentially, one or more DNA methyltransferase inhibitors. DNA methyltransferase inhibitors include, for example: S-110 (Supergen, Dublin, Calif.), Zebularine, Procaine, (−) epigallocatechin-3-gallate (EGCG), and Psammaplins.

The present invention further provides the preceding methods for treating tumors or tumor metastases in a patient, comprising administering to the patient a therapeutically effective amount of an EGFR kinase inhibitor or an IGF-1R kinase inhibitor and in addition, simultaneously or sequentially, one or more signal transduction inhibitors.

Signal transduction inhibitors include, for example: erbB2 receptor inhibitors, such as organic molecules, or antibodies that bind to the erbB2 receptor, for example, trastuzumab (e.g. HERCEPTIN®); inhibitors of other protein tyrosine-kinases, e.g. imitinib (e.g. GLEEVEC®); ras inhibitors; raf inhibitors; MEK inhibitors; PAK1 and PAK2 kinase inhibitors; mTOR inhibitors, such as, for example, rapamycin and its analogues (e.g. CCI-779, RAD001 and AP23573), including mTOR inhibitors that bind to and directly inhibits both mTORC1 and mTORC2 kinases (e.g. OSI-027, OSI Pharmaceuticals); mTOR inhibitors that are dual PI3K/mTOR kinase inhibitors, such as for example the compound PI-103 as described in Fan, Q-W et al (2006) Cancer Cell 9:341-349 and Knight, Z. A. et al. (2006) Cell 125:733-747; mTOR inhibitors that are dual inhibitors of mTOR kinase and one or more other PIKK (or PIK-related) kinase family members. Such members include MEC1, TEL1, RAD3, ME1-41, DNA-PK, ATM, ATR, TRRAP, PI3K, and PI4K kinases; cyclin dependent kinase inhibitors; protein kinase C inhibitors; PI-3 kinase inhibitors; and PDK-1 inhibitors (see Dancey, J. and Sausville, E. A. (2003) Nature Rev. Drug Discovery 2:92-313, for a description of several examples of such inhibitors, and their use in clinical trials for the treatment of cancer).

ErbB2 receptor inhibitors include, for example: ErbB2 receptor inhibitors, such as lapatinib or GW-282974 (both Glaxo Wellcome plc), monoclonal antibodies such as AR-209 (Aronex Pharmaceuticals Inc. of The Woodlands, Tex., USA) and 2B-1 (Chiron), and erbB2 inhibitors such as those described in International Publication Nos. WO 98/02434, WO 99/35146, WO 99/35132, WO 98/02437, WO 97/13760, and WO 95/19970, and U.S. Pat. Nos. 5,587,458, 5,877,305, 6,465,449 and 6,541,481.

As used herein, an mTOR inhibitor includes any mTOR inhibitor that is currently known in the art, and includes any chemical entity that, upon administration to a patient, results in inhibition of mTOR in the patient. An mTOR inhibitor can inhibit mTOR by any biochemical mechanism, including competition at the ATP binding site, competition elsewhere at the catalytic site of mTOR kinase, non-competitive inhibition, irreversible inhibition (e.g. covalent protein modification), or modulation of the interactions of other protein subunits or binding proteins with mTOR kinase in a way that results in inhibition of mTOR kinase activity (e.g. modulation of the interaction of mTOR with FKBP12, GβL, (mLST8), RAPTOR (mKOG1), or RICTOR (mAVO3)). Specific examples of mTOR inhibitors include: rapamycin; other rapamycin macrolides, or rapamycin analogues, derivatives or prodrugs; RAD001 (also known as Everolimus, RAD001 is an alkylated rapamycin (40-O-(2-hydroxyethyl)-rapamycin), disclosed in U.S. Pat. No. 5,665,772; Novartis); CCI-779 (also known as Temsirolimus, CCI-779 is an ester of rapamycin (42-ester with 3-hydroxy-2-hydroxymethyl-2-methylpropionic acid), disclosed in U.S. Pat. No. 5,362,718; Wyeth); AP23573 or AP23841 (Ariad Pharmaceuticals); ABT-578 (40-epi-(tetrazolyl)-rapamycin; Abbott Laboratories); KU-0059475 (Kudus Pharmaceuticals); and TAFA-93 (a rapamycin prodrug; Isotechnika). Examples of rapamycin analogs and derivatives known in the art include those compounds described in U.S. Pat. Nos. 6,329,386; 6,200,985; 6,117,863; 6,015,815; 6,015,809; 6,004,973; 5,985,890; 5,955,457; 5,922,730; 5,912,253; 5,780,462; 5,665,772; 5,637,590; 5,567,709; 5,563,145; 5,559,122; 5,559,120; 5,559,119; 5,559,112; 5,550,133; 5,541,192; 5,541,191; 5,532,355; 5,530,121; 5,530,007; 5,525,610; 5,521,194; 5,519,031; 5,516,780; 5,508,399; 5,508,290; 5,508,286; 5,508,285; 5,504,291; 5,504,204; 5,491,231; 5,489,680; 5,489,595; 5,488,054; 5,486,524; 5,486,523; 5,486,522; 5,484,791; 5,484,790; 5,480,989; 5,480,988; 5,463,048; 5,446,048; 5,434,260; 5,411,967; 5,391,730; 5,389,639; 5,385,910; 5,385,909; 5,385,908; 5,378,836; 5,378,696; 5,373,014; 5,362,718; 5,358,944; 5,346,893; 5,344,833; 5,302,584; 5,262,424; 5,262,423; 5,260,300; 5,260,299; 5,233,036; 5,221,740; 5,221,670; 5,202,332; 5,194,447; 5,177,203; 5,169,851; 5,164,399; 5,162,333; 5,151,413; 5,138,051; 5,130,307; 5,120,842; 5,120,727; 5,120,726; 5,120,725; 5,118,678; 5,118,677; 5,100,883; 5,023,264; 5,023,263; and 5,023,262; all of which are incorporated herein by reference. Rapamycin derivatives are also disclosed for example in WO 94/09010, WO 95/16691, WO 96/41807, or WO 99/15530, which are incorporated herein by reference. Such analogs and derivatives include 32-deoxorapamycin, 16-pent-2-ynyloxy-32-deoxorapamycin, 16-pent-2-ynyloxy-32 (S or R)-dihydrorapamycin, 16-pent-2-ynyloxy-32 (S or R)-dihydro-40O-(2-hydroxyethyl)-rapamycin, 40-O-(2-hydroxyethyl)-rapamycin, 32-deoxorapamycin and 16-pent-2-ynyloxy-32 (S)-dihydro-rapamycin. Rapamycin derivatives may also include the so-called rapalogs, e.g. as disclosed in WO 98/02441 and WO01/14387 (e.g. AP23573, AP23464, AP23675 or AP23841). Further examples of a rapamycin derivative are those disclosed under the name biolimus-7 or biolimus-9 (BIOLIMUS A9™) (Biosensors International, Singapore). Any of the above rapamycin analogs or derivatives may be readily prepared by procedures as described in the above references.

As used herein, the term "mTOR inhibitor that binds to and directly inhibits both mTORC1 and mTORC2 kinases" refers to any mTOR inhibitor that binds to and directly inhibits both mTORC1 and mTORC2 kinases, and includes any chemical entity that, upon administration to a patient, binds to and results in direct inhibition of both mTORC1 and mTORC2 kinases in the patient. Examples of mTOR inhibitors useful in the invention described herein include those disclosed and claimed in U.S. patent application Ser. No. 11/599,663, filed Nov. 15, 2006, a series of compounds that inhibit mTOR by binding to and directly inhibiting both mTORC1 and mTORC2 kinases.

The present invention further provides the preceding methods for treating tumors or tumor metastases in a patient, comprising administering to the patient a therapeutically effective amount of an EGFR kinase inhibitor or an IGF-1R kinase inhibitor and in addition, simultaneously or sequentially, an anti-HER2 antibody (e.g. trastuzumab (Genentech)) or an immunotherapeutically active fragment thereof.

The present invention further provides the preceding methods for treating tumors or tumor metastases in a patient, comprising administering to the patient a therapeutically effective amount of an EGFR kinase inhibitor or an IGF-1R kinase inhibitor and in addition, simultaneously or sequentially, one or more additional anti-proliferative agents.

Additional antiproliferative agents include, for example: Inhibitors of the enzyme farnesyl protein transferase, platelet-derived growth factor receptor (PDGFR) kinase inhibitors, including the compounds disclosed and claimed in U.S. Pat. Nos. 6,080,769, 6,194,438, 6,258,824, 6,586,447, 6,071,935, 6,495,564, 6,150,377, 6,596,735 and 6,479,513, and International Patent Publication WO 01/40217. Antiproliferative agents also include IGF-1R kinase inhibitors and fibroblast growth factor receptor (FGFR) kinase inhibitors.

As used herein, the term "PDGFR kinase inhibitor" includes any PDGFR kinase inhibitor that is currently known in the art, and includes any chemical entity that, upon administration to a patient, results in inhibition of a biological activity associated with activation of the PDGFR in the patient, including any of the downstream biological effects otherwise resulting from the binding to PDGFR of its natural ligand. Such PDGFR kinase inhibitors include any agent that can block PDGFR activation or any of the downstream biological effects of PDGFR activation that are relevant to treating cancer in a patient. Such an inhibitor can act by binding directly to the intracellular domain of the receptor and inhibiting its kinase activity. Alternatively, such an inhibitor can act by occupying the ligand binding site or a portion thereof of the PDGFR, thereby making the receptor inaccessible to its natural ligand so that its normal biological activity is prevented or reduced. Alternatively, such an inhibitor can act by modulating the dimerization of PDGFR polypeptides, or interaction of PDGFR polypeptide with other proteins, or enhance ubiquitination and endocytotic degradation of PDGFR. PDGFR kinase inhibitors include but are not limited to small molecule inhibitors, antibodies or antibody fragments, antisense constructs, small inhibitory RNAs (i.e. RNA interference by dsRNA; RNAi), and ribozymes. PDGFR kinase inhibitors include anti-PDGF (anti-platelet-derived growth factor) or anti-PDGFR aptamers, anti-PDGF or anti-PDGFR antibodies, or soluble PDGF receptor decoys that prevent binding of a PDGF to its cognate receptor. In a preferred embodiment, the PDGFR kinase inhibitor is a small organic molecule or an antibody that binds specifically to the human PDGFR. The ability of a compound or agent to serve as a PDGFR kinase inhibitor may be determined according to the methods known in art and, further, as set forth in, e.g., Dai et al., (2001) *Genes & Dev.* 15: 1913-25; Zippel, et al., (1989) *Eur. J. Cell Biol.* 50(2):428-34; and Zwiller, et al., (1991) *Oncogene* 6: 219-21.

The invention includes PDGFR kinase inhibitors known in the art as well as those supported below and any and all equivalents that are within the scope of ordinary skill to create. For example, inhibitory antibodies directed against PDGF are known in the art, e.g., those described in U.S. Pat. Nos. 5,976,534, 5,833,986, 5,817,310, 5,882,644, 5,662, 904, 5,620,687, 5,468,468, and PCT WO 2003/025019, the contents of which are incorporated by reference in their entirety. In addition, the invention includes N-phenyl-2- pyrimidine-amine derivatives that are PDGFR kinase inhibitors, such as those disclosed in U.S. Pat. No. 5,521,184, as well as WO2003/013541, WO2003/078404, WO2003/099771, WO2003/015282, and WO2004/05282 which are hereby incorporated in their entirety by reference.

Small molecules that block the action of PDGF are known in the art, e.g., those described in U.S. Pat. No. 6,528,526 (PDGFR tyrosine kinase inhibitors), U.S. Pat. No. 6,524,347 (PDGFR tyrosine kinase inhibitors), U.S. Pat. No. 6,482,834 (PDGFR tyrosine kinase inhibitors), U.S. Pat. No. 6,472,391 (PDGFR tyrosine kinak inhibitors), U.S. Pat. Nos . 6,949,563, 6,696,434, 6,331,555, 6,251,905, 6,245,760, 6,207,667, 5,990,141, 5,700,822, 5,618,837, 5,731,326, and 2005/0154014, and International Published Application Nos. WO 2005/021531, WO 2005/021544, and WO 2005/021537, the contents of which are incorporated by reference in their entirety.

Proteins and polypeptides that block the action of PDGF are known in the art, e.g., those described in U.S. Pat. No. 6,350,731 (PDGF peptide analogs), U.S. Pat. No. 5,952,304, the contents of which are incorporated by reference in their entirety.

Bis mono- and bicyclic aryl and heteroaryl compounds which inhibit EGF and/or PDGF receptor tyrosine kinase are known in the art, e.g., those described in, e.g. U.S. Pat. Nos. 5,476,851, 5,480,883, 5,656,643, 5,795,889, and 6,057,320, the contents of which are incorporated by reference in their entirety.

Antisense oligonucleotides for the inhibition of PDGF are known in the art, e.g., those described in U.S. Pat. Nos. 5,869,462, and 5,821,234, the contents of each of which are incorporated by reference in their entirety.

Aptamers (also known as nucleic acid ligands) for the inhibition of PDGF are known in the art, e.g., those described in, e.g., U.S. Pat. Nos. 6,582,918, 6,229,002, 6,207,816, 5,668,264, 5,674,685, and 5,723,594, the contents of each of which are incorporated by reference in their entirety.

Other compounds for inhibiting PDGF known in the art include those described in U.S. Pat. Nos. 5,238,950, 5,418,135, 5,674,892, 5,693,610, 5,700,822, 5,700,823, 5,728,726, 5,795,910, 5,817,310, 5,872,218, 5,932,580, 5,932,602, 5,958,959, 5,990,141, 6,358,954, 6,537,988 and 6,673,798, the contents of each of which are incorporated by reference in their entirety.

A number of types of tyrosine kinase inhibitors that are selective for tyrosine kinase receptor enzymes such as PDGFR are known (see, e.g., Spada and Myers ((1995) *Exp. Opin. Ther. Patents*, 5: 805) and Bridges ((1995) *Exp. Opin. Ther. Patents*, 5: 1245). Additionally Law and Lydon have summarized the anti-cancer potential of tyrosine kinase inhibitors ((1996) *Emerging Drugs: The Prospect For Improved Medicines*, 241-260). For example, U.S. Pat. No. 6,528,526 describes substituted quinoxaline compounds that selectively inhibit platelet-derived growth factor-receptor (PDGFR) tyrosine kinase activity. The known inhibitors of PDGFR tyrosine kinase activity includes quinoline-based inhibitors reported by Maguire et al., ((1994) *J. Med. Chem.*, 37: 2129), and by Dolle, et al., ((1994) *J. Med. Chem.*, 37: 2627). A class of phenylamino-pyrimidine-based inhibitors was recently reported by Traxler, et al., in EP 564409 and by Zimmerman et al., ((1996) *Biorg. Med. Chem. Lett.*, 6: 1221-1226) and by Buchdunger, et al., ((1995) *Proc. Nat. Acad. Sci. (USA)*, 92: 2558). Quinazoline derivatives that are useful in inhibiting PDGF receptor tyrosine kinase activity include bismono- and bicyclic aryl compounds and heteroaryl compounds (see, e.g., WO 92/20642), quinoxaline derivatives (see (1994) *Cancer Res.*, 54: 6106-6114), pyrimidine derivatives (Japanese Published Patent Application No. 87834/94) and dimethoxyquinoline derivatives (see *Abstracts of the* 116*th Annual Meeting of the Pharmaceutical Society of Japan (Kanazawa)*, (1996), 2, p. 275, 29(C2) 15-2).

Specific preferred examples of small molecule PDGFR kinase inhibitors that can be used according to the present invention include Imatinib (GLEEVEC®; Novartis); SU-12248 (sunitinib malate, SUTENT®; Pfizer); Dasatinib (SPRYCEL®; BMS; also known as BMS-354825); Sorafenib (NEXAVAR®; Bayer; also known as Bay-43-9006); AG-13736 (Axitinib; Pfizer); RPR127963 (Sanofi-Aventis); CP-868596 (Pfizer/OSI Pharmaceuticals); MLN-518 (tandutinib; Millennium Pharmaceuticals); AMG-706 (Motesanib; Amgen); ARAVA® (leflunomide; Sanofi-Aventis; also known as SU101), and OSI-930 (OSI Pharmaceuticals); Additional preferred examples of small molecule PDGFR kinase inhibitors that are also FGFR kinase inhibitors that can be used according to the present invention include XL-999 (Exelixis); SU6668 (Pfizer); CHIR-258/TKI-258 (Chiron); RO4383596 (Hoffmann-La Roche) and BIBF-1120 (Boehringer Ingelheim).

As used herein, the term "FGFR kinase inhibitor" includes any FGFR kinase inhibitor that is currently known in the art, and includes any chemical entity that, upon administration to a patient, results in inhibition of a biological activity associated with activation of FGFR in the patient, including any of the downstream biological effects otherwise resulting from the binding to FGFR of its natural ligand. Such FGFR kinase inhibitors include any agent that can block FGFR activation or any of the downstream biological effects of FGFR activation that are relevant to treating cancer in a patient. Such an inhibitor can act by binding directly to the intracellular domain of the receptor and inhibiting its kinase activity. Alternatively, such an inhibitor can act by occupying the ligand binding site or a portion thereof of the FGF receptor, thereby making the receptor inaccessible to its natural ligand so that its normal biological activity is prevented or reduced. Alternatively, such an inhibitor can act by modulating the dimerization of FGFR polypeptides, or interaction of FGFR polypeptide with other proteins, or enhance ubiquitination and endocytotic degradation of FGFR. FGFR kinase inhibitors include but are not limited to small molecule inhibitors, antibodies or antibody fragments, antisense constructs, small inhibitory RNAs (i.e. RNA interference by dsRNA; RNAi), and ribozymes. FGFR kinase inhibitors include anti-FGF (anti-fibroblast growth factor) or anti-FGFR aptamers, anti-FGF or anti-FGFR antibodies, or soluble FGFR receptor decoys that prevent binding of a FGFR to its cognate receptor. In a preferred embodiment, the FGFR kinase inhibitor is a small organic molecule or an antibody that binds specifically to the human FGFR. Anti-FGFR antibodies include FR1-H7 (FGFR-1) and FR3-D11 (FGFR-3) (Imclone Systems, Inc.).

FGFR kinase inhibitors also include compounds that inhibit FGFR signal transduction by affecting the ability of heparan sulfate proteoglycans to modulate FGFR activity. Heparan sulfate proteoglycans in the extracellular matrix can mediate the actions of FGF, e.g., protection from proteolysis, localization, storage, and internalization of growth factors (Faham, S. et al. (1998) Curr. Opin. Struct. Biol., 8:578-586), and may serve as low affinity FGF receptors that act to present FGF to its cognate FGFR, and/or to facilitate receptor oligomerization (Galzie, Z. et al. (1997) Biochem. Cell. Biol., 75:669-685).

The invention includes FGFR kinase inhibitors known in the art (e.g. PD173074) as well as those supported below and any and all equivalents that are within the scope of ordinary skill to create.

Examples of chemicals that may antagonize fibroblast growth factor (FGF) action, and can thus be used as FGFR kinase inhibitors in the methods described herein, include suramin, structural analogs of suramin, pentosan polysulfate, scopolamine, angiostatin, sprouty, estradiol, carboxymethylbenzylamine dextran (CMDB7), suradista, insulin-like growth factor binding protein-3, ethanol, heparin (e.g., 6-O-desulfated heparin), small molecule heparin, protamine sulfate, cyclosporin A, or RNA ligands for bFGF.

Other agents or compounds for inhibiting FGFR kinase known in the art include those described in U.S. Pat. No. 7,151,176 (Bristol-Myers Squibb Company; Pyrrolotriazine compounds); U.S. Pat. No. 7,102,002 (Bristol-Myers Squibb Company; pyrrolotriazine compounds); U.S. Pat. No. 5,132,408 (Salk Institute; peptide FGF antagonists); and U.S. Pat. No. 5,945,422 (Warner-Lambert Company; 2-amino-substituted pyrido[2,3-d]pyrimidines); U.S. published Patent application Nos. 2005/0256154 (4-amino-thieno[3,2-c]pyridine-7-carboxylic acid amide compounds); and 2004/0204427 (pyrimidino compounds); and published International Patent Applications WO-2007019884 (Merck Patent GmbH; N-(3-pyrazolyl)-N'-4-(4-pyridinyloxy)phenyl)urea compounds); WO-2007009773 (Novartis AG; pyrazolo[1,5-a]pyrimidin-7-yl amine derivatives); WO-2007014123 (Five Prime Therapeutics, Inc.; FGFR fusion proteins); WO-2006134989 (Kyowa Hakko Kogyo Co., Ltd.; nitrogenous heterocycle compounds); WO-2006112479 (Kyowa Hakko Kogyo Co., Ltd.; azaheterocycles); WO-2006108482 (Merck Patent GmbH; 9-(4-ureidophenyl)purine compounds); WO-2006105844 (Merck Patent GmbH; N-(3-pyrazolyl)-N'-4-(4-pyridinyloxy)phenyl)urea compounds); WO-2006094600 (Merck Patent GmbH; tetrahydropyrroloquinoline derivatives); WO-2006050800 (Merck Patent GmbH; N,N'-diarylurea derivatives); WO-2006050779 (Merck Patent GmbH; N,N'-diarylurea derivatives); WO-2006042599 (Merck Patent GmbH; phenylurea derivatives); WO-2005066211 (Five Prime Therapeutics, Inc.; anti-FGFR antibodies); WO-2005054246 (Merck Patent GmbH; heterocyclyl amines); WO-2005028448 (Merck Patent GmbH; 2-amino-1-benzyl-substituted benzimidazole derivatives); WO-2005011597 (Irm Lie; substituted heterocyclic derivatives); WO-2004093812 (Irm Llc/Scripps; 6-phenyl-7H-pyrrolo[2,3-d]pyrimidine derivatives); WO-2004046152 (F. Hoffmann La Roche A G; pyrimido[4,5-e]oxadiazine derivatives); WO-2004041822 (F. Hoffmann La Roche A G; pyrimido[4,5-d]pyrimidine derivatives); WO-2004018472 (F. Hoffmann La Roche A G; pyrimido[4,5-d]pyrimidine derivatives); WO-2004013145 (Bristol-Myers Squibb Company; pyrrolotriazine derivatives); WO-2004009784 (Bristol-Myers Squibb Company; pyrrolo[2,1-f][1,2,4]triazin-6-yl compounds); WO-2004009601 (Bristol-Myers Squibb Company; azaindole compounds); WO-2004001059 (Bristol-Myers Squibb Company; heterocyclic derivatives); WO-02102972 (Prochon Biotech Ltd./Morphosys AG; anti-FGFR antibodies); WO-02102973 (Prochon Biotech Ltd.; anti-FGFR antibodies); WO-00212238 (Warner-Lambert Company; 2-(pyridin-4-ylamino)-6-dialkoxyphenyl-pyrido[2,3-d]pyrimidin-7-one derivatives); WO-00170977 (Amgen, Inc.; FGFR-L and derivatives); WO-00132653 (Cephalon, Inc.; pyrazolone derivatives); WO-00046380 (Chiron Corporation; FGFR-Ig fusion proteins); and WO-00015781 (Eli Lilly; polypeptides related to the human SPROUTY-1 protein).

Specific preferred examples of small molecule FGFR kinase inhibitors that can be used according to the present invention include RO-4396686 (Hoffmann-La Roche); CHIR-258 (Chiron; also known as TKI-258); PD 173074 (Pfizer); PD 166866 (Pfizer); ENK-834 and ENK-835 (both Enkam Pharmaceuticals A/S); and SU5402 (Pfizer). Additional preferred examples of small molecule FGFR kinase inhibitors that are also PDGFR kinase inhibitors that can be used according to the present invention include XL-999 (Exelixis); SU6668 (Pfizer); CHIR-258/TKI-258 (Chiron); RO4383596 (Hoffmann-La Roche), and BIBF-1120 (Boehringer Ingelheim).

As used herein, the term "IGF-1R kinase inhibitor" includes any IGF-1R kinase inhibitor that is currently known in the art, and includes any chemical entity that, upon administration to a patient, results in inhibition of a biological activity associated with activation of the IGF-1 receptor in the patient, including any of the downstream biological effects otherwise resulting from the binding to IGF-1R of its natural ligand. Such IGF-1R kinase inhibitors include any agent that can block IGF-1R activation or any of the downstream biological effects of IGF-1R activation that are relevant to treating cancer in a patient. Such an inhibitor can act by binding directly to the intracellular domain of the receptor and inhibiting its kinase activity. Alternatively, such an inhibitor can act by occupying the ligand binding site or a portion thereof of the IGF-1 receptor, thereby making the receptor inaccessible to its natural ligand so that its normal biological activity is prevented or reduced. Alternatively, such an inhibitor can act by modulating the dimerization of IGF-1R polypeptides, or interaction of IGF-1R polypeptide with other proteins, or enhance ubiquitination and endocytotic degradation of IGF-1R. An IGF-1R kinase inhibitor can also act by reducing the amount of IGF-1 available to activate IGF-1R, by for example antagonizing the binding of IGF-1 to its receptor, by reducing the level of IGF-1, or by promoting the association of IGF-1 with proteins other than IGF-1R such as IGF binding proteins (e.g. IGFBP3). IGF-1R kinase inhibitors include but are not limited to low molecular weight inhibitors, antibodies or antibody fragments, antisense constructs, small inhibitory RNAs (i.e. RNA interference by dsRNA; RNAi), and ribozymes. In a preferred embodiment, the IGF-1R kinase inhibitor is a small organic molecule or an antibody that binds specifically to the human IGF-1R.

IGF-1R kinase inhibitors include, for example imidazopyrazine IGF-1R kinase inhibitors, azabicyclic amine inhibitors, quinazoline IGF-1R kinase inhibitors, pyrido-pyrimidine IGF-1R kinase inhibitors, pyrimido-pyrimidine IGF-1R kinase inhibitors, pyrrolo-pyrimidine IGF-1R kinase inhibitors, pyrazolo-pyrimidine IGF-1R kinase inhibitors, phenylamino-pyrimidine IGF-1R kinase inhibitors, oxindole IGF-1R kinase inhibitors, indolocarbazole IGF-1R kinase inhibitors, phthalazine IGF-1R kinase inhibitors, isoflavone IGF-1R kinase inhibitors, quinalone IGF-1R kinase inhibitors, and tyrphostin IGF-1R kinase inhibitors, and all pharmaceutically acceptable salts and solvates of such IGF-1R kinase inhibitors.

Examples of IGF-1R kinase inhibitors include those in International Patent Publication No. WO 05/097800, that describes azabicyclic amine derivatives, International Patent Publication No. WO 05/037836, that describes imidazopyrazine IGF-1R kinase inhibitors, International Patent Publication Nos. WO 03/018021 and WO 03/018022, that describe pyrimidines for treating IGF-1R related disorders, International Patent Publication Nos. WO 02/102804 and WO 02/102805, that describe cyclolignans and cyclolignans as IGF-1R inhibitors, International Patent Publication No. WO 02/092599, that describes pyrrolopyrimidines for the treatment of a disease which responds to an inhibition of the IGF-1R tyrosine kinase, International Patent Publication No. WO 01/72751, that describes pyrrolopyrimidines as tyrosine kinase inhibitors, and in International Patent Publication No. WO 00/71129, that describes pyrrolotriazine inhibitors of kinases, and in International Patent Publication No. WO 97/28161, that describes pyrrolo[2,3-d]pyrimidines and their use as tyrosine kinase inhibitors, Parrizas, et al., which describes tyrphostins with in vitro and in vivo IGF-1R inhibitory activity (Endocrinology, 138:1427-1433 (1997)), International Patent Publication No. WO 00/35455, that describes heteroaryl-aryl ureas as IGF-1R inhibitors, International Patent Publication No. WO 03/048133, that describes pyrimidine derivatives as modulators of IGF-1R, International Patent Publication No. WO 03/024967, WO 03/035614, WO 03/035615, WO 03/035616, and WO 03/035619, that describe chemical compounds with inhibitory effects towards kinase proteins, International Patent Publication No. WO 03/068265, that describes methods and compositions for treating hyperproliferative conditions, International Patent Publication No. WO 00/17203, that describes pyrrolopyrimidines as protein kinase inhibitors, Japanese Patent Publication No. JP 07/133,280, that describes a cephem compound, its production and antimicrobial composition, Albert, A. et al., Journal of the Chemical Society, 11: 1540-1547 (1970), which describes pteridine studies and pteridines unsubstituted in the 4-position, and A. Albert et al., Chem. Biol. Pteridines Proc. Int. Symp., 4th, 4: 1-5 (1969) which describes a synthesis of pteridines (unsubstituted in the 4-position) from pyrazines, via 3-4-dihydropteridines.

Additional, specific examples of IGF-1R kinase inhibitors that can be used according to the present invention include h7C10 (Centre de Recherche Pierre Fabre), an IGF-1 antagonist; EM-164 (ImmunoGen Inc.), an IGF-1R modulator; CP-751871 (Pfizer Inc.), an IGF-1 antagonist; lanreotide (Ipsen), an IGF-1 antagonist; IGF-1R oligonucleotides (Lynx Therapeutics Inc.); IGF-1 oligonucleotides (National Cancer Institute); IGF-1R protein-tyrosine kinase inhibitors in development by Novartis (e.g. NVP-AEW541, Garcia-Echeverria, C. et al. (2004) Cancer Cell 5:231-239; or NVP-ADW742, Mitsiades, C. S. et al. (2004) Cancer Cell 5:221-230); IGF-1R protein-tyrosine kinase inhibitors (Ontogen Corp); OSI-906 (OSI Pharmaceuticals); AG-1024 (Camirand, A. et al. (2005) Breast Cancer Research 7:R570-R579 (DOI 10.1186/bcr1028); Camirand, A. and Pollak, M. (2004) Brit. J. Cancer 90:1825-1829; Pfizer Inc.), an IGF-1 antagonist; the tyrphostins AG-538 and I-OMe-AG 538; BMS-536924, a small molecule inhibitor of IGF-1R; PNU-145156E (Pharmacia & Upjohn SpA), an IGF-1 antagonist; BMS 536924, a dual IGF-1R and IR kinase inhibitor (Bristol-Myers Squibb); AEW541 (Novartis); GSK621659A (Glaxo Smith-Kline); INSM-18 (Insmed); and XL-228 (Exelixis).

Antibody-based IGF-1R kinase inhibitors include any anti-IGF-1R antibody or antibody fragment that can partially or completely block IGF-1R activation by its natural ligand. Antibody-based IGF-1R kinase inhibitors also include any anti-IGF-1 antibody or antibody fragment that can partially or completely block IGF-1R activation. Non-limiting examples of antibody-based IGF-1R kinase inhibitors include those described in Larsson, O. et al (2005) Brit. J. Cancer 92:2097-2101 and Ibrahim, Y. H. and Yee, D. (2005) Clin. Cancer Res. 11:944s-950s; or being developed by Imclone (e.g. IMC-A12), or AMG-479, an anti-IGF-1R antibody (Amgen); R1507, an anti-IGF-1R antibody (Genmab/Roche); AVE-1642, an anti-IGF-1R antibody (Immunogen/Sanofi-Aventis); MK 0646 or h7C10, an anti-IGF-1R antibody (Merck); or antibodies being develop by Schering-Plough Research Institute (e.g. SCH 717454 or 19D12; or as described in US Patent Application Publication Nos. US 2005/0136063 A1 and US 2004/0018191 A1). The IGF-1R kinase inhibitor can be a monoclonal antibody, or an antibody or antibody fragment having the binding specificity thereof.

In another embodiment of any of the methods described herein the IGF-1R kinase inhibitor may be an IGF-1R kinase inhibitor approved by a government regulatory authority (e.g. US Food and Drug Administration (FDA); European Medicines Agency; Japanese Ministry of Health, Labour & Welfare; UK Medicines and Healthcare Products Regulatory Agency (MHRA)) (e.g. any of the IGF-1R kinase inhibitors disclosed herein that have been so approved). Similarly, in another embodiment of any of the methods described herein the EGFR kinase inhibitor may be an EGFR kinase inhibitor approved by a government regulatory authority (e.g. any of the EGFR kinase inhibitors disclosed herein that have been so approved). Additionally, in another embodiment of any of the methods described herein the EMT inhibitor may be an EMT inhibitor approved by a government regulatory authority (e.g. any of the EMT inhibitors disclosed herein that have been so approved).

The present invention further provides the preceding methods for treating tumors or tumor metastases in a patient, comprising administering to the patient a therapeutically effective amount of an EGFR kinase inhibitor or an IGF-1 kinase inhibitor and in addition, simultaneously or sequentially, a COX II (cyclooxygenase II) inhibitor. Examples of useful COX-II inhibitors include alecoxib (e.g. CELEBREX™), valdecoxib, and rofecoxib.

The present invention further provides the preceding methods for treating tumors or tumor metastases in a patient, comprising administering to the patient a therapeutically effective amount of an EGFR kinase inhibitor or an IGF-1R kinase inhibitor and in addition, simultaneously or sequentially, treatment with radiation or a radiopharmaceutical.

The source of radiation can be either external or internal to the patient being treated. When the source is external to the patient, the therapy is known as external beam radiation therapy (EBRT). When the source of radiation is internal to the patient, the treatment is called brachytherapy (BT). Radioactive atoms for use in the context of this invention can be selected from the group including, but not limited to, radium, cesium-137, iridium-192, americium-241, gold-198, cobalt-57, copper-67, technetium-99, iodine-123, iodine-131, and indium-111. Where the EGFR kinase inhibitor or an IGF-1R kinase inhibitor according to this invention is an antibody, it is also possible to label the antibody with such radioactive isotopes.

Radiation therapy is a standard treatment for controlling unresectable or inoperable tumors and/or tumor metastases. Improved results have been seen when radiation therapy has been combined with chemotherapy. Radiation therapy is based on the principle that high-dose radiation delivered to a target area will result in the death of reproductive cells in both tumor and normal tissues. The radiation dosage regimen is generally defined in terms of radiation absorbed dose (Gy), time and fractionation, and must be carefully defined by the oncologist. The amount of radiation a patient receives will depend on various considerations, but the two most important are the location of the tumor in relation to other critical structures or organs of the body, and the extent to which the tumor has spread. A typical course of treatment for a patient undergoing radiation therapy will be a treatment schedule over a 1 to 6 week period, with a total dose of between 10 and 80 Gy administered to the patient in a single daily fraction of about 1.8 to 2.0 Gy, 5 days a week. In a preferred embodiment of this invention there is synergy when tumors in human patients are treated with the combination treatment of the invention and radiation. In other words, the inhibition of tumor growth by means of the agents comprising the combination of the invention is enhanced when combined with radiation, optionally with additional chemotherapeutic or anti-cancer agents. Parameters of adjuvant radiation therapies are, for example, contained in International Patent Publication WO 99/60023.

The present invention further provides the preceding methods for treating tumors or tumor metastases in a patient, comprising administering to the patient a therapeutically effective amount of an EGFR kinase inhibitor or an IGF-1R kinase inhibitor and in addition, simultaneously or sequentially, treatment with one or more agents capable of enhancing antitumor immune responses.

Agents capable of enhancing antitumor immune responses include, for example: CTLA4 (cytotoxic lymphocyte antigen 4) antibodies (e.g. MDX-CTLA4, ipilimumab, MDX-010), and other agents capable of blocking CTLA4. Specific CTLA4 antibodies that can be used in the present invention include those described in U.S. Pat. No. 6,682,736.

In the context of this invention, an "effective amount" of an agent or therapy is as defined above. A "sub-therapeutic amount" of an agent or therapy is an amount less than the effective amount for that agent or therapy, but when combined with an effective or sub-therapeutic amount of another agent or therapy can produce a result desired by the physician, due to, for example, synergy in the resulting efficacious effects, or reduced side effects.

As used herein, the term "patient" preferably refers to a human in need of treatment with an EGFR kinase inhibitor or an IGF-1R kinase inhibitor for cancer. However, the term "patient" can also refer to non-human animals, preferably mammals such as dogs, cats, horses, cows, pigs, sheep and non-human primates, among others, that are in need of treatment with an EGFR kinase inhibitor or an IGF-1R kinase inhibitor.

In a preferred embodiment, the patient is a human in need of treatment for cancer. The cancer of the patient is preferably any cancer treatable, either partially or completely, by administration of an EGFR kinase inhibitor or an IGF-1R kinase inhibitor. The cancer may be, for example, lung cancer, non-small cell lung cancer, bronchioloalviolar cell lung cancer, bone cancer, pancreatic cancer, skin cancer, cancer of the head and neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, colorectal cancer, cancer of the small intestine, cancer of the endocrine system, cancer of the thyroid gland, cancer of the parathyroid gland, cancer of the adrenal gland (e.g. adrenocortical carcinoma), sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, chronic or acute leukemia, lymphocytic lymphomas, neoplasms of the central nervous system (CNS), spinal axis tumors, brain stem glioma, glioblastoma multiforme, astrocytomas, schwannomas, ependymomas, medulloblastomas, meningiomas, squamous cell carcinomas, pituitary adenomas, including refractory versions of any of the above cancers, or a combination of one or more of the above cancers.

For purposes of the present invention, "co-administration of" and "co-administering" an EGFR kinase inhibitor or an IGF-1R kinase inhibitor with an additional anti-cancer agent (both components referred to hereinafter as the "two active agents") refer to any administration of the two active agents, either separately or together, where the two active agents are administered as part of an appropriate dose regimen designed to obtain the benefit of the combination therapy. Thus, the two active agents can be administered either as part of the same pharmaceutical composition or in separate pharmaceutical compositions. The additional agent can be administered prior to, at the same time as, or subsequent to administration of the EGFR kinase inhibitor or an IGF-1R kinase inhibitor, or in some combination thereof. Where the EGFR kinase inhibitor or an IGF-1R kinase inhibitor is administered to the patient at repeated intervals, e.g., during a standard course of treatment, the additional agent can be administered prior to, at the same time as, or subsequent to, each administration of the EGFR kinase inhibitor or an IGF-1R kinase inhibitor, or some combination thereof, or at different intervals in relation to the EGFR kinase inhibitor or an IGF-1R kinase inhibitor treatment, or in a single dose prior to, at any time during, or subsequent to the course of treatment with the EGFR kinase inhibitor or an IGF-1R kinase inhibitor.

The EGFR kinase inhibitor or IGF-1R kinase inhibitor will typically be administered to the patient in a dose regimen that provides for the most effective treatment of the cancer (from both efficacy and safety perspectives) for which the patient is being treated, as known in the art, and as disclosed, e.g. in International Patent Publication No. WO 01/34574. In conducting the treatment method of the present invention, the inhibitor can be administered in any effective manner known in the art, such as by oral, topical, intravenous, intra-peritoneal, intramuscular, intra-articular, subcutaneous, intranasal, intra-ocular, vaginal, rectal, or intradermal routes, depending upon the type of cancer being treated, the type of EGFR kinase inhibitor or an IGF-1R kinase inhibitor being used (for example, small molecule, antibody, RNAi, ribozyme or antisense construct), and the medical judgement of the prescribing physician as based, e.g., on the results of published clinical studies.

The amount of EGFR kinase inhibitor or IGF-1R kinase inhibitor administered and the timing of inhibitor administration will depend on the type (species, gender, age, weight, etc.) and condition of the patient being treated, the severity of the disease or condition being treated, and on the route of administration. For example, small molecule EGFR kinase inhibitors or IGF-1R kinase inhibitors can be administered to a patient in doses ranging from 0.001 to 100 mg/kg of body weight per day or per week in single or divided doses, or by continuous infusion (see for example, International Patent Publication No. WO 01/34574). In particular, erlotinib HCl can be administered to a patient in doses ranging from 5-200 mg per day, or 100-1600 mg per week, in single or divided doses, or by continuous infusion. A preferred dose is 150 mg/day. Antibody-based EGFR kinase inhibitors or IGF-1R kinase inhibitors, or antisense, RNAi or ribozyme constructs, can be administered to a patient in doses ranging from 0.1 to 100 mg/kg of body weight per day or per week in single or divided doses, or by continuous infusion. In some instances, dosage levels below the lower limit of the aforesaid range may be more than adequate, while in other cases still larger doses may be employed without causing any harmful side effect, provided that such larger doses are first divided into several small doses for administration throughout the day.

The EGFR kinase inhibitor or IGF-1R kinase inhibitors and other additional agents can be administered either separately or together by the same or different routes, and in a wide variety of different dosage forms. For example, the inhibitor is preferably administered orally or parenterally. Where the EGFR kinase inhibitor is erlotinib HCl (TARCEVA®), oral administration is preferable. Where the IGF-1R kinase inhibitor is OSI-906, oral administration is preferable. Both the EGFR kinase inhibitor or IGF-1R kinase inhibitor and other additional agents can be administered in single or multiple doses.

The EGFR kinase inhibitor or IGF-1R kinase inhibitor can be administered with various pharmaceutically acceptable inert carriers in the form of tablets, capsules, lozenges, troches, hard candies, powders, sprays, creams, salves, suppositories, jellies, gels, pastes, lotions, ointments, elixirs, syrups, and the like. Administration of such dosage forms can be carried out in single or multiple doses. Carriers include solid diluents or fillers, sterile aqueous media and various non-toxic organic solvents, etc. Oral pharmaceutical compositions can be suitably sweetened and/or flavored.

The EGFR kinase inhibitor or IGF-1R kinase inhibitor can be combined together with various pharmaceutically acceptable inert carriers in the form of sprays, creams, salves, suppositories, jellies, gels, pastes, lotions, ointments, and the like. Administration of such dosage forms can be carried out in single or multiple doses. Carriers include solid diluents or fillers, sterile aqueous media, and various non-toxic organic solvents, etc. All formulations comprising proteinaceous EGFR kinase inhibitors or IGF-1R kinase inhibitors should be selected so as to avoid denaturation and/or degradation and loss of biological activity of the inhibitor.

Methods of preparing pharmaceutical compositions comprising an EGFR kinase inhibitor are known in the art, and are described, e.g. in International Patent Publication No. WO 01/34574. In view of the teaching of the present invention, methods of preparing pharmaceutical compositions comprising an EGFR kinase inhibitor or IGF-1R kinase inhibitor will be apparent from the above-cited publications and from other known references, such as Remington's Pharmaceutical Sciences, Mack Publishing Company, Easton, Pa., 18$^{th}$ edition (1990).

For oral administration of EGFR kinase inhibitors or IGF-1R kinase inhibitors, tablets containing one or both of the active agents are combined with any of various excipients such as, for example, micro-crystalline cellulose, sodium citrate, calcium carbonate, dicalcium phosphate and glycine, along with various disintegrants such as starch (and preferably corn, potato or tapioca starch), alginic acid and certain complex silicates, together with granulation binders like polyvinyl pyrrolidone, sucrose, gelatin and acacia. Additionally, lubricating agents such as magnesium stearate, sodium lauryl sulfate and talc are often very useful for tableting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the EGFR kinase inhibitor or IGF-1R kinase inhibitor may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration of either or both of the active agents, solutions in either sesame or peanut oil or in aqueous propylene glycol may be employed, as well as sterile aqueous solutions comprising the active agent or a corresponding water-soluble salt thereof. Such sterile aqueous solutions are preferably suitably buffered, and are also preferably rendered isotonic, e.g., with sufficient saline or glucose. These particular aqueous solutions are especially suitable for intravenous, intramuscular, subcutaneous and intraperitoneal injection purposes. The oily solutions are suitable for intra-articular, intramuscular and subcutaneous injection purposes. The preparation of all these solutions under sterile conditions is readily accomplished by standard pharmaceutical techniques well known to those skilled in the art. Any parenteral formulation selected for administration of proteinaceous EGFR kinase inhibitors or IGF-1R kinase inhibitors should be selected so as to avoid denaturation and loss of biological activity of the inhibitor.

Additionally, it is possible to topically administer either or both of the active agents, by way of, for example, creams, lotions, jellies, gels, pastes, ointments, salves and the like, in accordance with standard pharmaceutical practice. For example, a topical formulation comprising an EGFR kinase inhibitor or IGF-1R kinase inhibitor in about 0.1% (w/v) to about 5% (w/v) concentration can be prepared.

For veterinary purposes, the active agents can be administered separately or together to animals using any of the forms and by any of the routes described above. In a preferred embodiment, the EGFR kinase inhibitor or IGF-1R kinase inhibitor is administered in the form of a capsule, bolus, tablet, liquid drench, by injection or as an implant. As an alternative, the EGFR kinase inhibitor or IGF-1R kinase inhibitor can be administered with the animal feedstuff, and for this purpose a concentrated feed additive or premix may be prepared for a normal animal feed. Such formulations are prepared in a conventional manner in accordance with standard veterinary practice.

As used herein, the term "EGFR kinase inhibitor" includes any EGFR kinase inhibitor that is currently known in the art, and includes any chemical entity that, upon administration to a patient, results in inhibition of a biological activity associated with activation of the EGFR in the patient, including any of the downstream biological effects otherwise resulting from the binding to EGFR of its natural ligand. Such EGFR kinase inhibitors include any agent that can block EGFR activation or any of the downstream biological effects of EGFR activation that are relevant to treating cancer in a patient. Such an inhibitor can act by binding directly to the intracellular domain of the receptor and inhibiting its kinase activity. Alternatively, such an inhibitor can act by occupying the ligand binding site or a portion thereof of the EGFR, thereby making the receptor inaccessible to its natural ligand so that its normal biological activity is prevented or reduced. Alternatively, such an inhibitor can act by modulating the dimerization of EGFR polypeptides, or interaction of EGFR polypeptide with other proteins, or enhance ubiquitination and endocytotic degradation of EGFR. EGFR kinase inhibitors include but are not limited to low molecular weight inhibitors, antibodies or antibody fragments, antisense constructs, small inhibitory RNAs (i.e. RNA interference by dsRNA; RNAi), and ribozymes. In a preferred embodiment, the EGFR kinase inhibitor is a small organic molecule or an antibody that binds specifically to the human EGFR.

EGFR kinase inhibitors that include, for example quinazoline EGFR kinase inhibitors, pyrido-pyrimidine EGFR kinase inhibitors, pyrimido-pyrimidine EGFR kinase inhibitors, pyrrolo-pyrimidine EGFR kinase inhibitors, pyrazolo-pyrimidine EGFR kinase inhibitors, phenylamino-pyrimidine EGFR kinase inhibitors, oxindole EGFR kinase inhibitors, indolocarbazole EGFR kinase inhibitors, phthalazine EGFR kinase inhibitors, isoflavone EGFR kinase inhibitors, quinalone EGFR kinase inhibitors, and tyrphostin EGFR kinase inhibitors, such as those described in the following patent publications, and all pharmaceutically acceptable salts and solvates of said EGFR kinase inhibitors: International Patent Publication Nos. WO 96/33980, WO 96/30347, WO 97/30034, WO 97/30044, WO 97/38994, WO 97/49688, WO 98/02434, WO 97/38983, WO 95/19774, WO 95/19970, WO 97/13771, WO 98/02437, WO 98/02438, WO 97/32881, WO 98/33798, WO 97/32880, WO 97/3288, WO 97/02266, WO 97/27199, WO 98/07726, WO 97/34895, WO 96/31510, WO 98/14449, WO 98/14450, WO 98/14451, WO 95/09847, WO 97/19065, WO 98/17662, WO 99/35146, WO 99/35132, WO 99/07701, and WO 92/20642; European Patent Application Nos. EP 520722, EP 566226, EP 787772, EP 837063, and EP 682027; U.S. Pat. Nos. 5,747,498, 5,789,427, 5,650,415, and 5,656,643; and German Patent Application No. DE 19629652. Additional non-limiting examples of low molecular weight EGFR kinase inhibitors include any of the EGFR kinase inhibitors described in Traxler, P., 1998, Exp. Opin. Ther. Patents 8(12):1599-1625.

Specific preferred examples of low molecular weight EGFR kinase inhibitors that can be used according to the present invention include [6,7-bis(2-methoxyethoxy)-4-quinazolin-4-yl]-(3-ethynylphenyl)amine (also known as OSI-774, erlotinib, or TARCEVA® (erlotinib HCl); OSI Pharmaceuticals/Genentech/Roche) (U.S. Pat. No. 5,747,498; International Patent Publication No. WO 01/34574, and Moyer, J. D. et al. (1997) Cancer Res. 57:4838-4848); canertinib (also known as CI-1033, and formerly known as PD183805; Pfizer) (Sherwood et al., 1999, Proc. Am. Assoc. Cancer Res. 40:723); PD-158780 (Pfizer); AG-1478 (University of California); CGP-59326 (Novartis); PKI-166 (Novartis); EKB-569 (Wyeth); GW-2016 (also known as GW-572016 or lapatinib ditosylate; GSK); vandetanib (ZD6474; Astrazeneca), PF00299804 (Pfizer), and gefitinib (also known as ZD1839 or IRESSA™; Astrazeneca) (Woodburn et al., 1997, Proc. Am. Assoc. Cancer Res. 38:633). A particularly preferred low molecular weight EGFR kinase inhibitor that can be used according to the present invention is [6,7-bis(2-methoxyethoxy)-4-quinazolin-4-yl]-(3-ethynylphenyl)amine (i.e. erlotinib), its hydrochloride salt (i.e. erlotinib HCl, TARCEVA®), or other salt forms (e.g. erlotinib mesylate).

Antibody-based EGFR kinase inhibitors include any anti-EGFR antibody or antibody fragment that can partially or completely block EGFR activation by its natural ligand. Non-limiting examples of antibody-based EGFR kinase inhibitors include those described in Modjtahedi, H., et al., 1993, Br. J. Cancer 67:247-253; Teramoto, T., et al., 1996, Cancer 77:639-645; Goldstein et al., 1995, Clin. Cancer Res. 1:1311-1318; Huang, S. M., et al., 1999, Cancer Res. 15:59(8):1935-40; and Yang, X., et al., 1999, Cancer Res. 59:1236-1243. Thus, the EGFR kinase inhibitor can be the monoclonal antibody Mab E7.6.3 (Yang, X. D. et al. (1999) Cancer Res. 59:1236-43), or Mab C225 (ATCC Accession No. HB-8508), or an antibody or antibody fragment having the binding specificity thereof. Suitable monoclonal antibody EGFR kinase inhibitors include, but are not limited to, IMC-C225 (also known as cetuximab or ERBITUX™; Imclone Systems), panitumumab (also known as ABX-EGF; Abgenix), matuzumab (also known as EMD 72000; Merck KgaA, Darmstadt), RH3 (York Medical Bioscience Inc.), MDX-447 (Medarex/Merck KgaA), nimotuzumab (h-R3), zalutumumab, and ch806 (targeting mutant EGFRvIII).

Additional antibody-based EGFR kinase inhibitors can be raised according to known methods by administering the appropriate antigen or epitope to a host animal selected, e.g., from pigs, cows, horses, rabbits, goats, sheep, and mice, among others. Various adjuvants known in the art can be used to enhance antibody production.

Although antibodies useful in practicing the invention can be polyclonal, monoclonal antibodies are preferred. Monoclonal antibodies against EGFR can be prepared and isolated using any technique that provides for the production of antibody molecules by continuous cell lines in culture. Techniques for production and isolation include but are not limited to the hybridoma technique originally described by Kohler and Milstein (Nature, 1975, 256: 495-497); the human B-cell hybridoma technique (Kosbor et al., 1983, Immunology Today 4:72; Cote et al., 1983, Proc. Natl. Acad. Sci. USA 80: 2026-2030); and the EBV-hybridoma technique (Cole et al, 1985, Monoclonal Antibodies and Cancer Therapy, Alan R. Liss, Inc., pp. 77-96).

Alternatively, techniques described for the production of single chain antibodies (see, e.g., U.S. Pat. No. 4,946,778) can be adapted to produce anti-EGFR single chain antibodies. Antibody-based EGFR kinase inhibitors useful in practicing the present invention also include anti-EGFR antibody fragments including but not limited to F(ab').sub.2 fragments, which can be generated by pepsin digestion of an intact antibody molecule, and Fab fragments, which can be generated by reducing the disulfide bridges of the F(ab').sub.2 fragments. Alternatively, Fab and/or scFv expression libraries can be constructed (see, e.g., Huse et al., 1989, Science 246: 1275-1281) to allow rapid identification of fragments having the desired specificity to EGFR.

Techniques for the production and isolation of monoclonal antibodies and antibody fragments are well-known in the art, and are described in Harlow and Lane, 1988, Antibodies: A Laboratory Manual, Cold Spring Harbor Laboratory, and in J. W. Goding, 1986, Monoclonal Antibodies: Principles and Practice, Academic Press, London. Humanized anti-EGFR antibodies and antibody fragments can also be prepared according to known techniques such as those described in Vaughn, T. J. et al., 1998, Nature Biotech. 16:535-539 and references cited therein, and such antibodies or fragments thereof are also useful in practicing the present invention.

EGFR kinase inhibitors for use in the present invention can alternatively be based on antisense oligonucleotide constructs. Anti-sense oligonucleotides, including anti-sense RNA molecules and anti-sense DNA molecules, would act to directly block the translation of EGFR mRNA by binding thereto and thus preventing protein translation or increasing mRNA degradation, thus decreasing the level of EGFR kinase protein, and thus activity, in a cell. For example, antisense oligonucleotides of at least about 15 bases and complementary to unique regions of the mRNA transcript sequence encoding EGFR can be synthesized, e.g., by conventional phosphodiester techniques and administered by e.g., intravenous injection or infusion. Methods for using antisense techniques for specifically inhibiting gene expression of genes whose sequence is known are well known in the art (e.g. see U.S. Pat. Nos. 6,566,135; 6,566,131; 6,365, 354; 6,410,323; 6,107,091; 6,046,321; and 5,981,732).

Small inhibitory RNAs (siRNAs) can also function as EGFR kinase inhibitors for use in the present invention. EGFR gene expression can be reduced by contacting the tumor, subject or cell with a small double stranded RNA (dsRNA), or a vector or construct causing the production of a small double stranded RNA, such that expression of EGFR is specifically inhibited (i.e. RNA interference or RNAi). Methods for selecting an appropriate dsRNA or dsRNA-encoding vector are well known in the art for genes whose sequence is known (e.g. see Tuschi, T., et al. (1999) Genes Dev. 13(24):3191-3197; Elbashir, S. M. et al. (2001) Nature 411:494-498; Hannon, G. J. (2002) Nature 418:244-251; McManus, M. T. and Sharp, P. A. (2002) Nature Reviews Genetics 3:737-747; Bremmelkamp, T. R. et al. (2002) Science 296:550-553; U.S. Pat. Nos. 6,573,099 and 6,506, 559; and International Patent Publication Nos. WO 01/36646, WO 99/32619, and WO 01/68836).

Ribozymes can also function as EGFR kinase inhibitors for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of EGFR mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Both antisense oligonucleotides and ribozymes useful as EGFR kinase inhibitors can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

In the context of the methods of treatment of this invention, EGFR kinase inhibitors or IGF-1R kinase inhibitors are used as a composition comprised of a pharmaceutically acceptable carrier and a non-toxic therapeutically effective amount of an EGFR kinase inhibitor compound (including pharmaceutically acceptable salts thereof).

The term "pharmaceutically acceptable salts" refers to salts prepared from pharmaceutically acceptable non-toxic bases or acids. When a compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (cupric and cuprous), ferric, ferrous, lithium, magnesium, manganese (manganic and manganous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylameine, trimethylamine, tripropylamine, tromethamine and the like.

When a compound used in the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric and tartaric acids.

Pharmaceutical compositions used in the present invention comprising an EGFR kinase inhibitor or IGF-1R kinase inhibitor compound (including pharmaceutically acceptable salts thereof) as active ingredient, can include a pharmaceutically acceptable carrier and optionally other therapeutic ingredients or adjuvants. Other therapeutic agents may include those cytotoxic, chemotherapeutic or anti-cancer agents, or agents which enhance the effects of such agents, as listed above. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the EGFR kinase inhibitor or IGF-1R kinase inhibitor compounds (including pharmaceutically acceptable salts thereof) of this invention can be combined as the active ingredient in intimate admixture with a pharmaceutical carrier according to conventional pharmaceutical compounding techniques. The carrier may take a wide variety of forms depending on the form of preparation desired for administration, e.g. oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, an EGFR kinase inhibitor or IGF-1R kinase inhibitor compound (including pharmaceutically acceptable salts of each component thereof) may also be administered by controlled release means and/or delivery devices. The combination compositions may be prepared by any of the methods of pharmacy. In general, such methods include a step of bringing into association the active ingredients with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

An EGFR kinase inhibitor or IGF-1R kinase inhibitor compound (including pharmaceutically acceptable salts thereof) used in this invention, can also be included in pharmaceutical compositions in combination with one or more other therapeutically active compounds. Other therapeutically active compounds may include those cytotoxic, chemotherapeutic or anti-cancer agents, or agents which enhance the effects of such agents, as listed above.

Thus in one embodiment of this invention, the pharmaceutical composition can comprise an EGFR kinase inhibitor or IGF-1R kinase inhibitor compound in combination with an anti-cancer agent, wherein said anti-cancer agent is a member selected from the group consisting of alkylating drugs, antimetabolites, microtubule inhibitors, podophyllotoxins, antibiotics, nitrosoureas, hormone therapies, kinase inhibitors, activators of tumor cell apoptosis, and antiangiogenic agents.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition used for this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably contains from about 0.05 mg to about 5 g of the active ingredient.

For example, a formulation intended for the oral administration to humans may contain from about 0.5 mg to about 5 g of active agent, compounded with an appropriate and convenient amount of carrier material that may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Pharmaceutical compositions used in the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions used in the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions for the present invention can be in a form suitable for topical use such as, for example, an aerosol, cream, ointment, lotion, dusting powder, or the like. Further, the compositions can be in a form suitable for use in transdermal devices. These formulations may be prepared, utilizing an EGFR kinase inhibitor or IGF-1R kinase inhibitor compound (including pharmaceutically acceptable salts thereof), via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions for this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing an EGFR kinase inhibitor or IGF-1R kinase inhibitor compound (including pharmaceutically acceptable salts thereof) may also be prepared in powder or liquid concentrate form.

Dosage levels for the compounds used for practicing this invention will be approximately as described herein, or as described in the art for these compounds. It is understood, however, that the specific dose level for any particular patient will depend upon a variety of factors including the age, body weight, general health, sex, diet, time of administration, route of administration, rate of excretion, drug combination and the severity of the particular disease undergoing therapy.

Many alternative experimental methods known in the art may be successfully substituted for those specifically described herein in the practice of this invention, as for example described in many of the excellent manuals and textbooks available in the areas of technology relevant to this invention (e.g. Using Antibodies, A Laboratory Manual, edited by Harlow, E. and Lane, D., 1999, Cold Spring Harbor Laboratory Press, (e.g. ISBN 0-87969-544-7); Roe B. A. et. al. 1996, DNA Isolation and Sequencing (Essential Techniques Series), John Wiley & Sons. (e.g. ISBN 0-471-97324-0); Methods in Enzymology: Chimeric Genes and Proteins", 2000, ed. J. Abelson, M. Simon, S. Emr, J. Thorner. Academic Press; Molecular Cloning: a Laboratory Manual, 2001, $3^{rd}$ Edition, by Joseph Sambrook and Peter MacCallum, (the former Maniatis Cloning manual) (e.g. ISBN 0-87969-577-3); Current Protocols in Molecular Biology, Ed. Fred M. Ausubel, et. al. John Wiley & Sons (e.g. ISBN 0-471-50338-X); Current Protocols in Protein Science, Ed. John E. Coligan, John Wiley & Sons (e.g. ISBN 0-471-11184-8); and Methods in Enzymology: Guide to protein Purification, 1990, Vol. 182, Ed. Deutscher, M. P., Acedemic Press, Inc. (e.g. ISBN 0-12-213585-7)), or as described in the many university and commercial websites devoted to describing experimental methods in molecular biology.

This invention will be better understood from the Experimental Details that follow. However, one skilled in the art will readily appreciate that the specific methods and results discussed are merely illustrative of the invention as described more fully in the claims which follow thereafter, and are not to be considered in any way limited thereto.

EXPERIMENTAL DETAILS

Materials and Methods:
Compounds:
The selective EGFR kinase inhibitor, erlotinib, was synthesized by OSI Pharmaceuticals, Farmingdale, N.Y., USA, as the hydrochloride salt, erlotinib HCl (TARCEVA®).

The selective IGF-1R kinase inhibitor OSI-906 has the formula cis-3-[8-amino-1-(2-phenyl-quinolin-7-yl)-imidazo[1,5-a]pyrazin-3-yl]-1-methyl-cyclobutanol. Its preparation is described in detail in US Published Patent Application US 2006/0235031. It has the structure as follows:

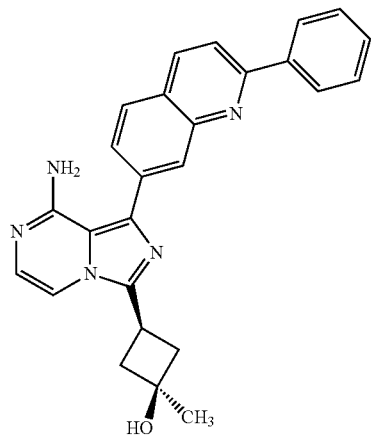 [SMILES: C[C@]1(O)C[C@@H](c2nc(-c3ccc4ccc(-c5ccccc5)nc4c3)c3c(N)nccn32)C1]

The selective FAK kinase inhibitor, Compound F, was synthesized by OSI Pharmaceuticals, Farmingdale, N.Y., USA, using methods. It represents a compound according to formula 1 in U.S. patent application Ser. No. 12/791,047, and is synthesized by methods described therein.

The selective MET kinase inhibitor, Compound M, was synthesized by OSI Pharmaceuticals, Farmingdale, N.Y., USA. It represents a compound according to formula I in US published patent application US2009/197862, and is synthesized by methods described therein.

General cell culture conditions: The human tumor cell lines NCI-H358™ [a.k.a. H-358; H358], NCI-H1650 [a.k.a. H1650; CRL-5883™], NCI-H292™ [a.k.a. CRL-1848™; H292], and CFPAC-1 [a.k.a. CRL-1918™] were cultured in the appropriate ATCC recommended supplemented media, unless indicated otherwise herein. Growth factors and cytokines, including HGF, TGFβ1, and Oncostatin M were obtained from commercial sources.

Additionally, the following human cancer cell lines were obtained from American Type Culture Collection (ATCC, Manassas, Va.), or the additional indicated sources, and cultured in media as described. Tumor types are also indicated: H295R (adrenocortical carcinoma; ATCC), NCI-H322 (NSCLC; ECACC), NCI-H460 (NSCLC; ATCC), SW1573 (NSCLC; ATCC), H1703 (NSCLC; ATCC), BxPC3 (pancreatic; ATCC), OVCAR5 (ovarian; NCI;), MDAH-2774 (ovarian; ATCC), Igrov1 (ovarian; NCI), GEO (colon; Roswell Park Cancer Institute (RPCC)), HT-29 (colon; ATCC), RKO (colon; ATCC), H226 (NSCLC; ATCC), 8226 (myeloma; ATCC), H929 (myeloma; ATCC), U266 (myeloma; ATCC), SKES1 (Ewings sarcoma; ATCC), RDES (Ewings sarcoma; ATCC), RD (rhabdomyosarcoma; ATCC), DU4475 (breast; ATCC), SKNAS (neuroblastoma; ATCC), 2650 (nasal SCC; ATCC), OVCAR4 (ovarian; NCI), A673 (Ewings sarcoma; ATCC), BT474 (breast; ATCC), 1386 (oral SCC; MSKCC, NY), 1186 (SCCHN; MSKCC, NY), Colo205 (colon; ATCC), HCT-15 (colon; ATCC), Fadu (oral SCC; ATCC), SKBR3 (breast; ATCC), 1483 (FINSCC; MSKCC, NY), HSC-2 (HNSCC; RIKEN BioResource Center, Tsukuba, Ibaraki, 305-0074, Japan). Cells were maintained at 37° C. in an incubator under an atmosphere containing 5% $CO_2$. The cells were routinely screened for the presence of mycoplasma (MycoAlert, Cambrex Bio Science, Baltimore, Md.).

Measurement of Cell Proliferation: Cell proliferation was determined using the Cell Titer Glo assay (Promega Corporation, Madison, Wis.). Cell lines were seeded at a density of 3000 cells per well in a 96-well plate. For assessment of drug effects on proliferation, 24 hours after plating, cells were dosed with varying concentrations of drug, either as a single agent or in combination. The signal for Cell Titer Glo was determined 72 hours after dosing.

Generation of TET-inducible target gene cell lines: Plasmids containing full length cDNAs encoding Snai1, Zeb1, or TGFbeta (constitutively active) (Snai1 mRNA sequence, Genbank NM_005985, product of GeneID: 6615; Zeb1 mRNA sequence, Genbank NM_030751, product of GeneID: 6935; TGFbeta sequence encoding constitutively active Ser223/S225 human TGF-beta-1 (i.e. Genbank NP_000651 (product of GeneID: 7040), with cysteines 223 and 225 mutated to serine) under the control of a Tet-regulated promoter (pTRE2; Invitrogen) were constructed using standard methods. The TET-ON cell lines were plated and transfected with a pTRE2-Snai1, pTRE2-Zeb1, or pTRE2-TGFbeta plasmid as described above. Once plated into 150 mm dishes the single cells were selected using puromycin (0.5 µg/ml). Colonies were selected over a 3-4 weeks period with puromycin concentration being reduced to a final concentration of 0.1 μg/ml. Colonies were picked using colony filters and screened for TET-dependent expression of the target gene by western blot analysis. In some cases multiple cDNAs were cotransfected into a given cell line. These methods enable the generation of cell lines which undergo EMT in response to tetracycline or analogs thereof, driven by the cDNAs listed above.

EMT cell model protocols: EMT cell models used are essentially as described herein, or in more detail in U.S. patent application Ser. Nos. 12/381,082, 12/660,443, 12/660,444 and PCT application PCT/US2010/25137.

Ligand-driven EMT models: NCI-H358 cells were cultured in RPMI medium (Gibco #21870) with 10% fetal bovine serum (Sigma), 1 mM sodium pyruvate (Gibco #11360), 2 mM L-glutamine (Gibco #25030) and 10 mM HEPES (Gibco #15630). For ligand treatment, cells were seeded in normal growth medium and stimulated the following day (Day 0) with 100 ng/ml HGF (Peprotech #100-39), 100 ng/ml OSM (R and D systems, 295-OM), 2.5 ng/ml TGFβ1 (EMD Biosciences #616450) or combinations of the three. Medium was changed and fresh ligand was added on day 4 and day 6 after stimulation, such that samples were stimulated with fresh ligand 24 hrs prior to RNA isolation. For analysis containing drug treatments, DMSO or Drug was added to the samples at time of ligand treatments. Samples were taken for RNA Day 1, Day 4 and Day 7. NCI-H1650 and NCI-H292 cells were grown in RPM medium (Gibco #21870) with 10% fetal bovine serum (Sigma), 1 mM sodium pyruvate (Gibco #11360), 2 mM L-glutamine (Gibco #25030) and 10 mM HEPES (Gibco #15630). CFPAC1 cells (ATCC #CRL-1918) were cultured in DMEM (Gibco #11960) supplemented with 10% FBS (Sigma), 2 mM L-glutamine (Gibco #25030). A549 cells were cultured in MEM with 10% fetal bovine serum, 2 mM L-glutamine and 1 mM sodium pyruvate. Cells were treated with ligand for 7 days and harvested as described for NCI-H358 cells in [249] unless otherwise noted.

H358Tet ON Snail, aTGFβ and zeb model protocols: H358 cells stably expressing either Snail, aTGFβ, Zeb or empty Vector under the tetracycline/doxycycline inducible promoter were cultured in RPMI medium (Gibco #21870) with 10% Certified Tetracycline Free fetal bovine serum (Clontech), 1 mM sodium pyruvate (Gibco #11360), 2 mM L-glutamine (Gibco #25030) and 10 mM HEPES (Gibco #15630), 10 μg/ml Blasticidin (InvivoGen, San Diego) and 0.5 μg/ml puromycin. For stimulation, cells were seeded in normal growth medium and a stimulated the next day (Day 0) with 0.5 μg/ml Doxycycline. Medium was changed and fresh Doxycycline was added on day 4. Cells were harvested for RNA or protein on day 7.

3D Matrigel culture: Cold Growth Factor Reduced Matrigel (80 μl; BD Biosciences #354230) was plated in 8 well chamber slides (Labtek II, Nunc #154534) and solidified at 37° C. Cells were diluted in complete medium containing 2% Matrigel, to give 5000 cells for every 300 μl. 300 μl was plated into each well and incubated at 37° C., 5% CO$_2$ overnight. Medium was aspirated and replaced with 120 μl per well of medium containing 2% Matrigel and ligand treatments. Cells were grown for 14 days, feeding every 3-4 days. Cells were imaged by phase contrast.

TAK1 siRNA: Cells were plated at approximately 50% confluence. The following day, the cells were transfected with 25 ng/ml siRNA to TAK1 (Ambion). Transfection medium was removed after 8 hours. After 48 hours, medium was changed to MEM with 1% FBS and treated with ligand for 4 hours. Cells were harvested for RNA 24 hours later for qPCR analysis.

qPCR: At Day 1 (ligand models only), Day 4 (ligand models only), Day 7 & Day 14 (H358Tet On models only), cells were trypsinized, washed twice in PBS and RNA was isolated using RNAaqueous 4-PCR Kit (Ambion, AM1914). Samples were then DNase treated using the Turbo DNA-Free kit (Ambion, AM1907) and reverse transcribed using Superscript III (Invitrogen, 18080-044) for qPCR analysis. Taqman primers and Locked-Nucleic Acid probes were designed using ProbeFinder software (Universal Probe library, Roche). For mRNA analysis, real time PCR was performed using the ABI 7900HT series PCR machine. Thermocycle conditions were as follows: 50° C. for 2 min, 95° C. for 10 min, 95° C. for 15 sec, 50° C. for 10 sec, 60° C. for 1 min. Data was collected over 45 cycles and then normalized to GAPDH and further normalized to the untreated control sample.

Normalization genes used with 88 gene EMTGS for RT-PCR Analysis: The genes GTF2B, GAPDH, SDHA, and ACTB were chosen as normalization genes in qPCR analysis. They were used to calculate the geometric mean (Geometric Mean=n-th root of (X1)(X2) . . . (Xn)) of all normalization genes for a particular sample. The geometric mean indicates the central tendency of a given set of numbers. The Delta Ct is then calculated as follows:

Delta $Ct$=($Ct$ value of Gene $X$)−(Geometric mean of all normalization genes)

For calculation of fold change between a control sample and a treated sample:

Control sample=2^(−Delta $Ct$)

Treated sample=2^(−Delta $Ct$)

Fold change=Treated sample/Control sample

Values below 1 (ratios) are converted to fold change by multiplying by −(1/X)

Western blots: Cells were washed with PBS, scraped into RIPA buffer (Sigma #R0278) containing 200 μM sodium vanadate and protease and phosphatase inhibitor cocktails (Sigma P2850, P8340, P5726), and centrifuged. Standard western blotting protocols were followed. Primary antibody sources are as follows: E-Cadherin (Santa Cruz #sc21791), vimentin (BD Pharmingen #550513), ErbB3 (Santa Cruz #sc285), Zeb1 (Santa Cruz #sc25388), Snail (Cell Signaling #4719), GAPDH (Santa Cruz #sc25778). Western blots were developed with Pierce Supersignal Femto substrate using the Kodak Image Station 4000mM or Alpha Innotech Fluorchem™ SP.

Zymograms: Cell lysated were run on Novex Zymogram Gelatin gels according to the manufacturer's protocol. Gels were stained with GelCode Blue and imaged on the Alpha Innotech Fluorchem™ SP.

Immunofluorescence/Confocal microscopy: Cells were plated on glass coverslips and treated as described. Standard immuno-fluorescence staining protocols were followed. Primary antibody sources are as follows: E-cadherin: Santa Cruz #sc21791 and vimentin: Chemicon #AB5733. Stained cells were captured on a Leica DMRXE microscope/SP2 scanner using Leica Confocal Software (LCS).

Migration/invasion: Cells were stimulated with ligand in the presence of serum for 6 days. On day 6, medium was changed to serum-free medium with ligand. On day 7, cells were plated in modified Boyden chambers (Trevigen Cultrex #3458-096-K) in serum-free medium in the upper chamber and 3× ligand/10% FBS in the lower chamber. For invasion assays, membranes were coated with type IV collagen (included in the assay kit). After 24 (migration) or 48 (invasion) hours, cells attached to the underside of the membrane were quantified using calcein-AM stain read on a fluorescent plate reader (Wallac). Significance was determined by unpaired T-test with cutoff value of p<0.05.

Xenografts: Female SCID mice (Charles River Laboratories; 7-8 weeks old) were implanted subcutaneously with $1\times10^7$ H358 TET-ON pTre2-SNAIL, pTRE2-ZEB or pTRE2-aTGFb cells suspended in normal growth medium in a 1:1 ratio with Matrigel (100 μL final volume). Tumors were allowed to grow for 7 days prior to induction of transgenes. Doxycycline was administered in the drinking water at a final concentration of 0.5 mg/ml for two weeks. Tumor volume was calculated from bidirectional tumor measurements taken by Vernier calipers on day 7, 14, and 21 post implantation (V=[length×(width)2]/2). Mice were sacrificed on day 21 by $CO_2$ asphyxiation according to IACUC guidelines. Tumors were removed and either snap frozen in liquid nitrogen or fixed in neutral buffered formalin overnight.

Immunohistochemistry: Formalin fixed tumors were paraffin embedded and sectioned in-house according to standard protocols. Slides were deparaffinized with Hemo-De (Scientific Safety Solvents, Keller, Tex.) and rehydrated through graded alcohols. Heat Induced Epitope Retrieval (HIER) was performed in citrate buffer pH 6.0 in a steamer. Vector Elite ABC (Vector Laboratories, Burlingame, Calif.) detection system protocols were followed for all immunostaining. Sections were counterstained with Hematoxylin (vendor), dehydrated through graded alcohols and Hemo-De and then mounted. Antibody sources and incubations are as follows: E-Cadherin (24E10), Cell Signaling #31195, 1:50 for 1 hour; Vimentin, Millipore/Chemicon #AB5733 chicken 1:6400 for 30 minutes; SNAIL, ABCAM #17732 rabbit pAB 1:1600 for 1 hour; Zeb-1 (E-20) Santa Cruz #10572 goat 1:400 for 1 hour; Cyto-keratin (Wide spectrum) Dako #Z0622 rabbit p-AB 1:500 for 1 hour.

Affymetrix arrays: On experimental day 7, the cells were trypsinized, washed, pelleted, and snap frozen. Cell pellets were sent to Genome Explorations (Memphis, Tenn.) or Expression Analysis (Durham, N.C.) for isolation of RNA. mRNA was then processed to cDNA, amplified and labeled for hybridization to Affymetrix U133 Plus 2.0 mRNA microarrays. After hybridization and washing, the microarrays were scanned and the data processed into signal intensities for each probeset. The raw data is normalized using the Affymetrix MAS 5 software, and each probeset is given a detection call of present (P) absent (A) or marginal (M) based on proprietary algorithms. To determine which genes were differentially regulated between untreated and treated cells, probe sets were filtered for a fold change of at least 2, and also for a detection call of P in at least one of the compared samples.

Bioinformatics:

Analysis for co-correlation of genes to generate a gene index was performed using custom proprietary software developed by AVEO Pharmaceuticals for co-correlation analysis. Parameter settings for bioinformatics used Pearson correlation with p-values set to 0.01, random gene selection for statistics, either a median centered or non-median centered method, and were auto-anchored. For calculation of the EMTGS index, negatively correlated genes were flipped for calculating the overall gene index score.

The software used for this analysis is based on the concept that genes in a biological pathway are regulated together and that many genes in the same pathway show correlated expression. It calculates an index score based on the cumulative expression of correlated and anti-correlated genes in a list that represents a biologically meaningful pathway.

The software algorithm (referred to herein as algorithm $A^1$) consists of two main components: 1) agene selection component based on correlation of expression and 2) an index score calculation component based on mean expression of selected genes. Specifically, given a genelist A and dataset B the algorithm functions as follows:

1) Define correlation-based anchor gene (AG) for A in B:
   a) Calculate Pearson or Spearman correlation (user-selected) or gene expression for every gene-gene pair in A across all samples in B.
   b) AG for AB is the gene x that maximizes the following:

$$AG_{AB} = \frac{\sum_{Nx} |R|}{n}$$

Where $AG_{AB}$ is the anchor gene for genelist A in dataset B, Nx is the set of all gene-gene pairs with gene x, n is the number of gene-gene pairs in Nx, and |R| is the absolute value of the Pearson (or Spearman) correlation coefficient for each gene-gene pair across all samples in B.

2) Select a subset of genes from the genelist ($A_{AG}$) that significantly correlate with AG:
   a) Rank all genes based on the Pvalue of their correlation to AG.
   b) $A_{AG}$ is defined as the subset of genes in A that correlate with AG across B, for which Pvalue≤c, where c is the user-specified significance cutoff (typically 0.01).

3) For each sample s in B, calculate a correlation-based expression index score (I) for genelist A:
   a) Define $I_{ABs}$ as:

$$I_{ABs} = \frac{\sum_{A_{AG}} e'_{sx}}{m}$$

Where $A_{AG}$ is the subset of genes in A that significantly correlate with the anchor gene AG, m is the number of genes in $A_{AG}$, and $e_{sx}'$ defined as the expression of gene x (from subset $A_{AG}$) in sample s of dataset B as follows:

$e_{sx}'=e_{sx}$ if $R_x>0$ or $e_{sx}'=2\mu_{Bx}-e_{sx}$ if $R_x<0$

Where $e_{sx}$ is the expression of gene x in sample s, $\mu_{Bx}$ is the mean expression of gene x is dataset B, and $R_x$ is the correlation coefficient of gene x with the anchor gene AG.

Algorithm $A^1$, was used to calculate index scores for FIGS. 45-51. Index scores for all other data was calculated using algorithm A, which is identical to algorithm $A^1$ described herein, with the exception that $e_{sx}'=\mu_{Bx}-e_{sx}$ if $R_x<0$.

The indexing platform computes the correlation coefficients (R-values from −1 to 1) for each pair of genes on the gene list for all samples being evaluated. For each gene, the average R-value is calculated across the absolute value of all correlations and anti-correlations. An anchor gene is defined as the gene with the highest average R-value. A heatmap of correlation is plotted for each gene pair, based on correlation to the anchor. Genes that pass the user-specified p-value cutoff for correlation to the anchor gene are used in calculating the index score. The index score is the mean expression value of the genes that passed the p-value cutoff when the genes are positively correlated with the anchor gene. For anti-correlated genes, the expression value is subtracted from the mean expression value for that gene and then calculated as part of the mean with the positively correlated genes. The index scores for all samples are then plotted in a waterfall plot in increasing order.

To determine whether an index score for a given gene list is significantly different than a score for a random gene list, a method was developed that compares the calculated index score to the average index score from 1000 random gene lists (Significance assessment via randomized re-sampling or "bootstrapping method"). The random index statistics are displayed on the waterfall plot as a box and whiskers plot for each sample with the minimum, maximum, mean, $25^{th}$ and $75^{th}$ percentiles displayed. The index value is overlaid on the box and whiskers, and any index in the top or bottom 5 percentiles was considered significantly different from random.

Bootstrapping Method for Determining the Significance of Signature Index Score.

A bootstrapping method was developed to determine the statistical significance for the EMTGS index score from each sample. It calculates an index score based on an N-gene signature with the following 3-step procedure for each sample. It first identifies the anchor gene among the signature that has the highest average Pearson correlation to the other genes in the signature among samples. Subsequently, the expression value of each gene is adjusted. For genes in the signature that negatively correlate with the anchor, their expression value is inverted around the average expression value across samples. For genes that positively correlate with the anchor, the average expression value across samples is deducted from their expression value. Finally, the average of adjusted expression values from all genes in the signature is computed and constitutes the index score for that sample.

In order to assess the significance of the index score in each sample, a random N-gene list is selected in each sample and the index score based on this random genelist is calculated following the same aforementioned procedure. This process is repeated for 1000 times and 1000 index scores from random N-gene lists are generated. If the sample has an index score based on the signature that falls in the bottom P (the significance level defined by users) quantile of those 1000 index scores based on random genelists, this sample is determined to have significantly low index score at the significance level of P. Conversely, if a sample has a signature index score that falls in the top P quantile, it is determined to have significantly high index score at the significance level of P. This bootstrapping method is iterated through each sample to determine whether the index score is significantly low or high. The advantage of this bootstrapping method for index score significance determination are two fold. First, it takes into account the sample to sample variability of the expression level for the signature. The significance level assigned by this method measures how the expression index from the signature differs from what is expected by chance (the background) within each sample, rather than comparing the signature index scores across samples, for example. Secondly, by including exactly the same number of genes as in the signature and calculating the index score with the same procedure for random genelists as for the signature, an unbiased distribution of index scores is established to assess the significance level of index score based on the signature. Thus, this bootstrapping method provides an objective way to measure the statistical significance of a signature index score in each sample, and facilitates assessing the prevalence of particular EMTGS index scores in human tumors.

Laser Capture Microdissection (LCM) Micro-array Data:

Affymetrix U133-AB chip expression data for matched laser capture microdissected tumor, stroma, and undissected from ten patients (seven ovarian and three breast tumors) were purchased from GeneLogic. CEL files were RMA normalized together and mean-centered before using the bootstrapping algorithm for index significance scoring.

Results/Discussion

An 88 gene EMT signature was derived using a gene set obtained initially from four H358 EMT cell models, that has been refined through bioinformatics comparisons to 1] tumor models, 2] EMT cell models and 3] publicly available human tumor patient micro-array datasets. Analysis indicates that this new EMT gene signature has many potential uses, including, for example, diagnosing and/or monitoring a patient's susceptibility to treatment with certain anti-cancer drugs, identifying new targets of interest for drug discovery, and monitoring changes to the EMT process in various EMT models upon compound treatment. Furthermore, an EMT index derived from this EMT signature allows for qualitative and quantitative characterization of tumor cells regarding their status as more epithelial or more mesenchymal. This will be an invaluable tool in both research and the clinic as a means to broadly examine EMT at the molecular level.

The 88 gene EMT signature described herein (see Table 1) consists of 44 genes that are expressed in epithelial tumor cells and 44 genes that are expressed in mesenchymal-like tumor cells (see FIGS. 36-37 for description of genes). The expression pattern of the genes as measured, for example, by qPCR or mRNA microarray, characterizes tumor cells or tumor tissue sections along a spectrum of epithelial to mesenchymal states. AVEO software running algorithm A or algorithm $A^1$ is used to convert the expression values of the best co-correlating genes in the signature to calculate a numerical EMT index for each sample analyzed. The EMT index correlates with tumor cell sensitivity to the EGFR kinase inhibitor erlotinib and the IGF-1R kinase inhibitor OSI-906, and may be used to predict patient response to these compounds in the clinic.

TABLE 1

Genes in the 88 gene EMT Gene Signature.

| Epithelial Genes | | | | Mesenchymal Genes | | | |
|---|---|---|---|---|---|---|---|
| AGR2 | ELF3 | MB | SH3YL1 | ACTN1 | FOSL1 | ITGB3 | SERPINE1 |
| AKAP12 | ELF5 | MMP7 | SLC27A2 | ALCAM | FXYD5 | LAMB1 | SMAD7 |
| AP1M2 | ERBB3 | MTA3 | SPDEF | AXL | HMGA1 | MMP9 | SNAI1 |
| BSPRY | ETV5 | MAP7 | STAT5A | CCL2 | HMGA2 | MSLN | SNAI2 |
| CDH1 | EVA1 | MTSS1 | TBX2 | CEP170 | SPARC | PCOLCE2 | ITGA5 |
| CLDN3 | FOXC1 | OCLN | TJP3 | CNN3 | FLRT3 | PECAM1 | TWIST1 |
| CLDN4 | GPD1L | PLXNB1 | TMEM125 | CYP4X1 | IFI16 | PLAUR | VCAN |
| DNMT3A | IGFBP2 | PPL | TMEM45B | IL11 | IKBIP | RASSF8 | VIM |
| DSG3 | IHH | PPP1R9A | VWF | SRPX | IL18 | CDH2 | YBX1 |
| DSP | LCN2 | SCNN1A | XBP1 | EFNB2 | IL6 | SERPINA3 | ZEB1 |
| EHF | HOP | SFRP1 | ZBTB10 | FOSB | IL8 | SERPINB2 | ZEB2 |

Since the 88 gene EMT signature disclosed herein was developed using genes that are co-regulated during EMT in different in vitro models, as well as genes that showed good co-correlation with these genes in multiple human tumor micro-array databases (see Material and Methods section), this has resulted in a gene signature, and corresponding gene index, that is widely applicable to different tumor types, that has the power to characterize not only cell culture models, but also tumor tissue from in vivo samples, or clinical biopsies.

Human tumor databases were used in developing the gene signature in order to represent gene expression as it occurs in vivo. In other, publicly available EMT signatures, none have used tumor data to refine the genelists. While cell lines are cleaner systems to develop gene signatures, they are also incomplete for developing a signature that will be relevant in vivo, and in clinical situations, where tumor and stroma interactions impact gene expression.

Derivation of 88 Gene EMT Signature and Index

Significant genes identified by Affymetrix microarray analysis that were up regulated or down regulated in H358 tumor cell EMT models treated with 1] dual ligands HGF+OSM, 2] TGFβ, 3] doxycycline to induce expression of vector-encoded snai1, or 4] doxycycline to induce expression of vector-encoded zeb1, were compared by Venn analysis using a 4-way Venn diagram generator (FIG. 1). 101 genes were identified that were common in all four cell models induced to undergo an epithelial to mesenchymal transition (see Table 2). Of the 101 genes in Table 2, the ten that are italicized were omitted from initial bioinformatics analysis for eventual generation of the 88 EMT gene signature. Eight of these genes were omitted because they were unknown genes. CGB5 and 7 were eliminated when they did not validate in other EMT models.

TABLE 2

101 Genes Up or Down regulated in all four H358 EMT cell models.

| GENE | Description |
|---|---|
| AGPAT3 | 1-acylglycerol-3-phosphate O-acyltransferase 3 |
| AGR2 | anterior gradient homolog 2 (*Xenopus laevis*) |
| BSPRY | B-box and SPRY domain containing |
| C10orf116 | |
| C10orf81 | |
| C11orf17 | |
| C20orf102 | |
| C8orf55 | |
| C8orf57 | |
| CELSR2 | cadherin, EGF LAG seven-pass G-type receptor 2 (flamingo homolog, *Drosophila*) |
| CEP170 | centrosomal protein 170 kDa |
| CGB | chorionic gonadotropin, beta polypeptide /// chorionic gonadotropin, beta polypeptide 5 /// chorionic gonadotropin, beta polypeptide 7 |
| CGB5 | |
| CGB7 | |
| CHST2 | carbohydrate (N-acetylglucosamine-6-O) sulfotransferase 2 |
| CLDN3 | claudin 3 |
| CNN3 | calponin 3, acidic |
| COBLL1 | COBL-like 1 |
| COL6A2 | collagen, type VI, alpha 2 |
| CTGF | connective tissue growth factor |
| CYB5A | cytochrome b5 type A (microsomal) |
| CYP4X1 | cytochrome P450, family 4, subfamily X, polypeptide 1 |
| DMPK | dystrophia myotonica-protein kinase |
| DOCK9 | dedicator of cytokinesis 9 |
| EFNB2 | ephrin-B2 |
| EHF | ets homologous factor |
| ELF3 | E74-like factor 3 (ets domain transcription factor, epithelial-specific) |
| ERBB3 | v-erb-b2 erythroblastic leukemia viral oncogene homolog 3 (avian) |
| FA2H | fatty acid 2-hydroxylase |
| FAM84A | family with sequence similarity 84, member A /// hypothetical LOC653602 |
| FBN1 | fibrillin 1 |
| FLJ20273 | RNA-binding protein |
| FLRT3 | fibronectin leucine rich transmembrane protein 3 |
| G0S2 | G0/G1switch 2 |
| GALNT2 | UDP-N-acetyl-alpha-D-galactosamine: polypeptide N-acetylgalactosaminyltransferase 2 (GalNAc-T2) |
| GATM | glycine amidinotransferase (L-arginine: glycine amidinotransferase) |
| GPC6 | Glypican 6 |
| GPD1L | glycerol-3-phosphate dehydrogenase 1-like |
| GPR110 | G protein-coupled receptor 110 |
| GPR157 | G protein-coupled receptor 157 |
| GRTP1 | growth hormone regulated TBC protein 1 |
| HIST1H2AG | histone cluster 1, H2ag |
| HMGA1 | high mobility group AT-hook 1 |
| HOP | homeodomain-only protein |
| HPGD | hydroxyprostaglandin dehydrogenase 15-(NAD) |
| IBRDC2 | IBR domain containing 2 |
| IFI16 | interferon, gamma-inducible protein 16 |
| IGFBP2 | insulin-like growth factor binding protein 2, 36 kDa |
| IKBIP | IKK interacting protein |
| IL11 | interleukin 11 |
| IL18 | interleukin 18 (interferon-gamma-inducing factor) |
| IMPA2 | inositol(myo)-1(or 4)-monophosphatase 2 |
| INHBB | inhibin, beta B (activin AB beta polypeptide) |
| KRT15 | keratin 15 |
| LAMB1 | laminin, beta 1 |
| LIMA1 | LIM domain and actin binding 1 |
| LLGL2 | lethal giant larvae homolog 2 (*Drosophila*) |

TABLE 2-continued

101 Genes Up or Down regulated in all four H358 EMT cell models.

| GENE | Description |
|---|---|
| LOC388743 | |
| LOC653602 | |
| LUM | lumican |
| MB | myoglobin |
| MUC1 | mucin 1, cell surface associated |
| MYO5C | myosin VC |
| NAIP | occludin /// similar to Occludin |
| NBEAL2 | neurobeachin-like 2 |
| NKD2 | naked cuticle homolog 2 (*Drosophila*) |
| NOTCH3 | Notch homolog 3 (*Drosophila*) |
| NR4A2 | nuclear receptor subfamily 4, group A, member 2 |
| NUAK2 | chromosome 11 open reading frame 17 /// NUAK family, SNF1-like kinase, 2 |
| NUP210 | nucleoporin 210 kDa |
| OCLN | occludin /// similar to Occludin |
| PCOLCE2 | procollagen C-endopeptidase enhancer 2 |
| PPP1R9A | protein phosphatase 1, regulatory (inhibitor) subunit 9A |
| PRSS8 | protease, serine, 8 |
| PTGES | prostaglandin E synthase |
| RASSF8 | Ras association (RalGDS/AF-6) domain family 8 |
| RBMS3 | RNA binding motif, single stranded interacting protein |
| RHPN1 | rhophilin, Rho GTPase binding protein 1 |
| RNF208 | ring finger protein 208 |
| SCNN1A | sodium channel, nonvoltage-gated 1 alpha |
| SEPP1 | selenoprotein P, plasma, 1 |
| SH3BGRL2 | SH3 domain binding glutamic acid-rich protein like 2 |
| SH3GLB2 | SH3-domain GRB2-like endophilin B2 |
| SH3YL1 | SH3 domain containing, Ysc84-like 1 (*S. cerevisiae*) |
| SLC27A2 | solute carrier family 27 (fatty acid transporter), member 2 |
| SLCO4A1 | solute carrier organic anion transporter family, member 4A1 |
| SMPDL3B | sphingomyelin phosphodiesterase, acid-like 3B |
| SNAI2 | snail homolog 2 (*Drosophila*) |
| SORL1 | sortilin-related receptor, L(DLR class) A repeats-containing |
| SPTBN2 | spectrin, beta, non-erythrocytic 2 |
| SRPX | sushi-repeat-containing protein, X-linked |
| TFPI2 | tissue factor pathway inhibitor 2 |
| TJP3 | tight junction protein 3 (zona occludens 3) |
| TMC4 | transmembrane channel-like 4 |
| TMEM125 | transmembrane protein 125 |
| TMEM45B | transmembrane protein 45B |
| TMPRSS4 | transmembrane protease, serine 4 |
| TNC | tenascin C (hexabrachion) |
| UCP2 | uncoupling protein 2 (mitochondrial, proton carrier) |
| VCAN | versican |
| ZNF569 | zinc finger protein 569 |

The H358 EMT model system is a robust model of reversible EMT. After 7 day treatment with either ligands or stable expression of transcription factors Snai1 or Zeb1, the cells undergo morphological, marker, and phenotypic changes consistent with EMT (FIG. 8). Furthermore, ligand- and snai1-induced EMT in 14358 cells results in a decreased sensitivity to erlotinib. It was hypothesized that an EMT signature that incorporated some of the gene changes associated with this system would predict erlotinib sensitivity.

The subsequent 91 gene set obtained from the four H358 EMT cell models was refined through iterative bioinformatics comparisons (FIG. 2) to 1] AVEO tumor models (Table 3); additional EMT cell models (Table 4); and 3] publicly available human tumor patient micro-array datasets (Table 3) to generate the final 88 gene EMT signature (Table 1). FIGS. 3 and 4 illustrate the increases in the correlation index of the gene signature versus a breast tumor archive that was achieved by this iterative process by comparing the initial gene signature to the final 88 gene signature obtained. This analysis assumes that co-expression of genes in the same pathway means the pathway is active.

TABLE 3

Tumor Microarray Databases used in EMTGS Development.

| Source | Tumor | Number of Samples |
|---|---|---|
| Gene Logic | Breast (U133 Plus 2.0) | 101 |
| | Breast (U133AB) | 112 |
| | Colon (U133 Plus 2.0) | 75 |
| | Kidney (U133 Plus 2.0) | 71 |
| | Kidney (U133AB) | 111 |
| | Liver (U133 Plus 2.0) | 16 |
| | Liver (U133AB) | 25 |
| | Lung (U133 Plus 2.0) | 112 |
| | Lung (U133AB) | 133 |
| | Lymphoma and Multiple Myeloma (U133 Plus 2.0) | 157 |
| | Lymphoma and Multiple Myeloma (U133AB) | 160 |
| | Pancreas (U133 Plus 2.0) | 64 |
| | Pancreas (U133AB) | 86 |
| | Prostate (U133 Plus 2.0) | 8 |
| | Prostate (U133AB) | 8 |
| | Stomach and Esophagus (U133 Plus 2.0) | 42 |
| | Stomach and Esophagus (U133AB) | 43 |
| | NCI60 (U133 Plus 2.0) | 4 |
| | NCI60 (U133AB) | 60 |
| TCGA | GBM (U133A) | 386 |
| | Ovarian (U133A) | 431 |
| Van't Veer et al 2002 | Breast (Custom) | 295 |
| Neve et al. 2006 | Breast (U133A) | 54 |
| Jacobson et al. 2008 | Lung (U133A) | 464 |
| BH Archive (mouse) | Breast | 107 |

TABLE 4

Additional tumor cell EMT models used in EMTGS Development

| Cell line | Tissue | Ligands (7 day treatments) |
|---|---|---|
| CFPAC1 | Pancreas | HGF, OSM, HGF + OSM |
| NCI-H1650 | Lung | HGF, OSM, TGFb, EGF and combinations thereof |
| NCI-H292 | Lung | HGF, OSM, TGFb and combinations thereof |
| NCI-H441 | Lung | OSM, TGFb and OSM + TGFb |
| MDA-MB-468 | Breast | Amphiregulin |

The overall strategy for refining the signature was to exclude or include genes based on their behavior in both the tumor datasets and the EMT models. The original list of EMT genes was derived from microarray datasets from 1-1358 models. These genes were evaluated for changes in the CFPAC1, H1650 and H292 EMT models, and also for co-correlation in the tumor datasets. Genes that did not change in any model were eliminated. New genes were also introduced into the signature from several additional sources (literature, proteomic datasets, AVEO tumor models, other EMT models) and evaluated in the same way. Refining the signature was an iterative process with multiple rounds of adding genes, evaluating, and then removing genes that did not change. To illustrate this process, Table 5 contains 4 progressive versions of the EMT signature, and FIGS. 9-10 demonstrate the improvement in the co-correlation plots through these four versions in the GeneLogic lung (U133AB) and pancreas (U133 Plus 2.0) datasets.

TABLE 5

Progression of the EMT Gene Signature.

| Gene category | Version 1 | Version 2 | Version 3 | Version 4 Final |
|---|---|---|---|---|
| E | ACTN1 | AGR2 | AGR2 | AGR2 |
| E | CDH11 | AKAP12 | AKAP12 | AKAP12 |
| E | CDH1 | AP1M2 | AP1M2 | AP1M2 |
| E | CDH3 | BSPRY | BSPRY | BSPRY |
| E | CDH4 | CDH1 | CDH1 | CDH1 |
| E | CLDN4 | CLDN3 | CLDN3 | CLDN3 |
| E | CTNNG | CLDN4 | CLDN4 | CLDN4 |
| E | DSP | DNMT3A | DNMT3A | DNMT3A |
| E | ELF3 | DSG3 | DSG3 | DSG3 |
| E | Ep-CAM | DSP | DSP | DSP |
| E | EVA1 | EHF | EHF | EHF |
| E | Fos-B | ELF3 | ELF3 | ELF3 |
| E | Grb7 | ELF5 | ELF5 | ELF5 |
| E | Id2 | ERBB3 | ERBB3 | ERBB3 |
| E | KRT8 | ETV5 | ETV5 | ETV5 |
| E | MAP7 | Mpzl2 | Mpzl2 | Mpzl2 |
| E | MMP7 | FOXC1 | FOXC1 | FOXC1 |
| E | Msx2 | GPD1L | GPD1L | GPD1L |
| E | PCDH7 | IGFBP2 | IGFBP2 | IGFBP2 |
| E | PECAM1 | IHH | IHH | IHH |
| E | PPL | LCN2 | LCN2 | LCN2 |
| E | SCEL | LLGL2 | HOP | HOP |
| E | SELL | MB | MB | MB |
| E | SLC9A1 | MMP7 | MMP7 | MMP7 |
| E | TIAM1 | MTA3 | MTA3 | MTA3 |
| E | TIMP3 | MAP7 | MAP7 | MAP7 |
| E | TIS11 | MTSS1 | MTSS1 | MTSS1 |
| E | TMTM30B | OCLN | OCLN | OCLN |
| E | | PLXNB1 | PLXNB1 | PLXNB1 |
| E | | PPL | PPL | PPL |
| E | | PPP1R9A | PPP1R9A | PPP1R9A |
| E | | SCNN1A | SCNN1A | SCNN1A |
| E | | SFRP1 | SFRP1 | SFRP1 |
| E | | SH3YL1 | SH3YL1 | SH3YL1 |
| E | | SLC27A2 | SLC27A2 | SLC27A2 |
| E | | SPDEF | SPDEF | SPDEF |
| E | | STAT5A | STAT5A | STAT5A |
| E | | TBX2 | TBX2 | TBX2 |
| E | | TJP3 | TJP3 | TJP3 |
| E | | TMEM125 | TMEM125 | TMEM125 |
| E | | TMEM45B | TMEM45B | TMEM45B |
| E | | VWF | VWF | VWF |
| E | | XBP1 | XBP1 | XBP1 |
| E | | ZBTB10 | ZBTB10 | ZBTB10 |
| M | ALCAM | ACTN1 | ACTN1 | ACTN1 |
| M | AXL | ALCAM | ALCAM | ALCAM |
| M | C/EBP-beta | AXL | AXL | AXL |
| M | CCK | CCL2 | CCL2 | CCL2 |
| M | CDH2 | CEP170 | CEP170 | CEP170 |
| M | COL3A1 | CNN3 | CNN3 | CNN3 |
| M | COL4A1 | CYP4X1 | CYP4X1 | CYP4X1 |
| M | COL5A2 | DBN1 | DBN1 | IL11 |
| M | c-Rel | E2F1 | E2F1 | SPRX |
| M | CTGF | EFNB2 | EFNB2 | EFNB2 |
| M | CutL1 | FOSB | FOSB | FOSB |
| M | Dab2 | FOSL1 | FOSL1 | FOSL1 |
| M | DCN | FXYD5 | FXYD5 | FXYD5 |
| M | DDX3 | HMGA1 | HMGA1 | HMGA1 |
| M | DDX5 | HMGA2 | HMGA2 | HMGA2 |
| M | EMP1 | HOP | SPARC | SPARC |
| M | ESX | HSPG2 | HSPG2 | FLRT3 |
| M | Ets1 | IFI16 | IFI16 | IFI16 |
| M | Fra1 | IKBIP | IKBIP | IKBIP |
| M | Fra2 | IL6 | IL6 | IL6 |
| M | GAS1 | IL8 | IL8 | IL8 |
| M | Glis2 | IL18 | IL18 | IL18 |
| M | GSC | ITGB3 | ITGB3 | ITGB3 |
| M | Hes1 | LAMB1 | LAMB1 | LAMB1 |
| M | Hey1 | MMP9 | MMP9 | MMP9 |
| M | HIF1A | MSLN | MSLN | MSLN |
| M | HIF2A | PCOLCE2 | PCOLCE2 | PCOLCE2 |
| M | HMGA2 | PECAM1 | PECAM1 | PECAM1 |
| M | hnRNP-A/B | PLAUR | PLAUR | PLAUR |
| M | hnRNP-G | RASSF8 | RASSF8 | RASSF8 |
| M | hnRNP-H3 | S100A4 | S100A4 | CDH2 |
| M | HoxA11 | SERPINA3 | SERPINA3 | SERPINA3 |
| M | HoxB13 | SERPINB2 | SERPINB2 | SERPINB2 |
| M | HoxB7 | SERPINE1 | SERPINE1 | SERPINE1 |
| M | HoxD10 | SMAD7 | SMAD7 | SMAD7 |
| M | HSPG2 | Snai1 | Snai1 | Snai1 |
| M | ILK | SNAI2 | SNAI2 | SNAI2 |
| M | ISG15 | SPP1 | ITGA5 | ITGA5 |
| M | ITGB1 | TWIST1 | TWIST1 | TWIST1 |
| M | ITGB3 | VCAN | VCAN | VCAN |
| M | LOXL2 | VIM | VIM | VIM |
| M | MMP9 | YBX1 | YBX1 | YBX1 |
| M | MRP8 | ZEB1 | ZEB1 | ZEB1 |
| M | MTA1 | ZEB2 | ZEB2 | ZEB2 |
| M | MTA3 | | | |
| M | PLAUR | | | |
| M | RelB | | | |
| M | SNAI1 | | | |
| M | SNAI2 | | | |
| M | SPARC | | | |
| M | TCF3 | | | |
| M | THBS3 | | | |
| M | Thy1 | | | |
| M | TJP1 | | | |
| M | TNC | | | |
| M | Twist1 | | | |
| M | Twist2 | | | |
| M | Vim | | | |
| M | Zeb1 | | | |
| M | Zeb2 | | | |

FIG. 5 shows co-correlation analysis in human tumor datasets for the 88 EMT gene signature genes. When all tumors are normalized together and viewed as a waterfall plot where each tumor type is arranged according to EMT index score, relative differences in EMT index expression between tumors become apparent. For example, breast tumors are evenly distributed between epithelial and mesenchymal index scores while colon tumors tend to have more epithelial (low score) than mesenchymal (high score) index scores. This demonstrates that the 88 gene EMT signature is able to identify EMT in multiple human tumor types.

The translation of the expression values of genes in the EMT signature into a numerical EMT index is done using AVEO software running algorithm A or algorithm $A^1$. Briefly, co-correlation coefficients (R-values) for each pair of genes in the signature are calculated for each sample, and plotted in a heat map sorted by strength of correlation to the gene with the highest average R-value (anchor gene). Positive correlations are indicated in purple and negative correlations are indicated in blue. The genes with p-values passing the user-specified cutoff are chosen to calculate the index. All gene expression values that are negatively correlated with the anchor gene are flipped around the mean for that gene. The index score is then calculated as the mean expression value of each gene that passed the p-value cutoff for the correlation plot.

In vitro, index values are translated into EMT status by using reference tumor cell lines for which the EMT status is known, or can be deduced, from morphology and EMT biomarkers. Reference tumor cells of known epithelial or mesenchymal phenotype are included with test or sample tumor cells in order to discriminate epithelial from mesenchymal-like cells using EMTGS index values. These are preferably of the same tissue type as the test or sample tumor cells (e.g. breast, NSCLC, pancreatic etc).

To discriminate predicted drug responders from non-responders using the EMTGS index score (e.g. for erlotinib, OSI-906, etc.), a threshold determination analysis (e.g. a receiver operator characteristic (ROC) curve analysis) can be performed to determine what index value cutpoint gives the optimal separation between true positives and false positives. Analysis of the EMTGS index values of cell lines for which the erlotinib sensitivity is known, indicates that there is a good, but not perfect, correlation between EMT index and drug sensitivity (FIG. 19).

Figure 4B:
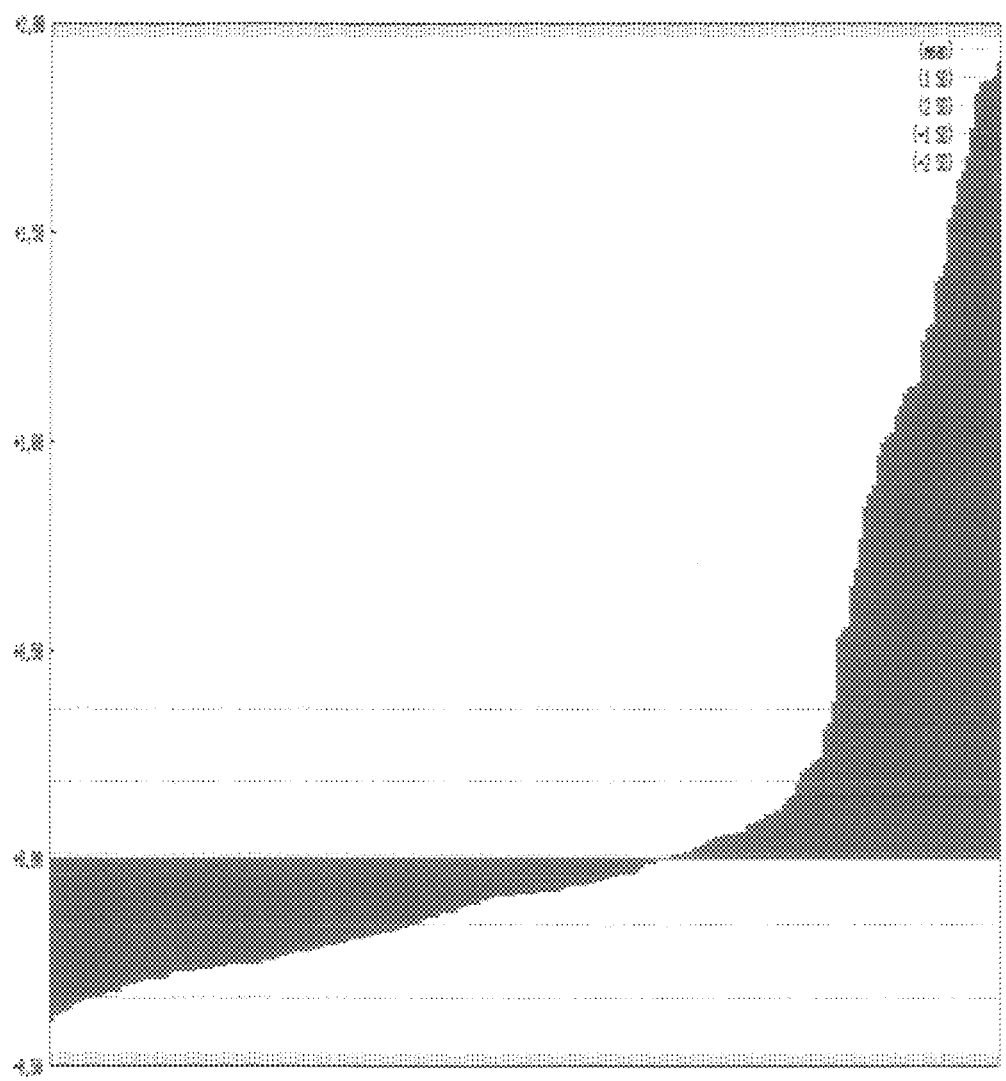
Figure 5A:
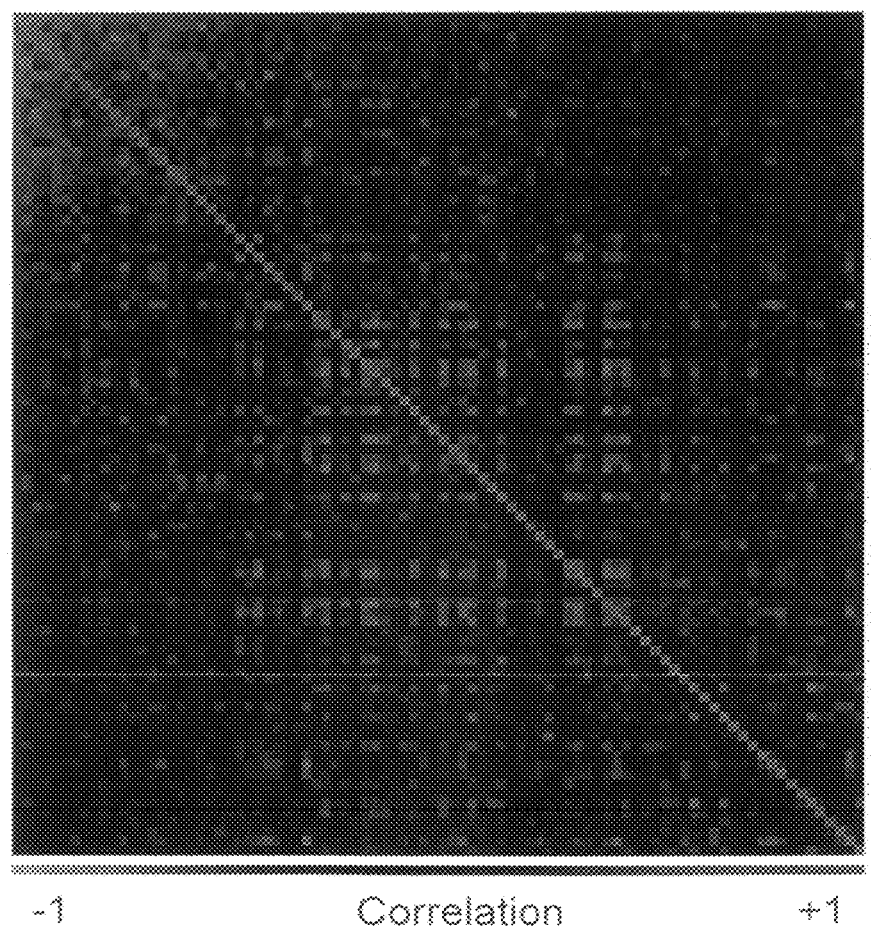
Figure 5B:
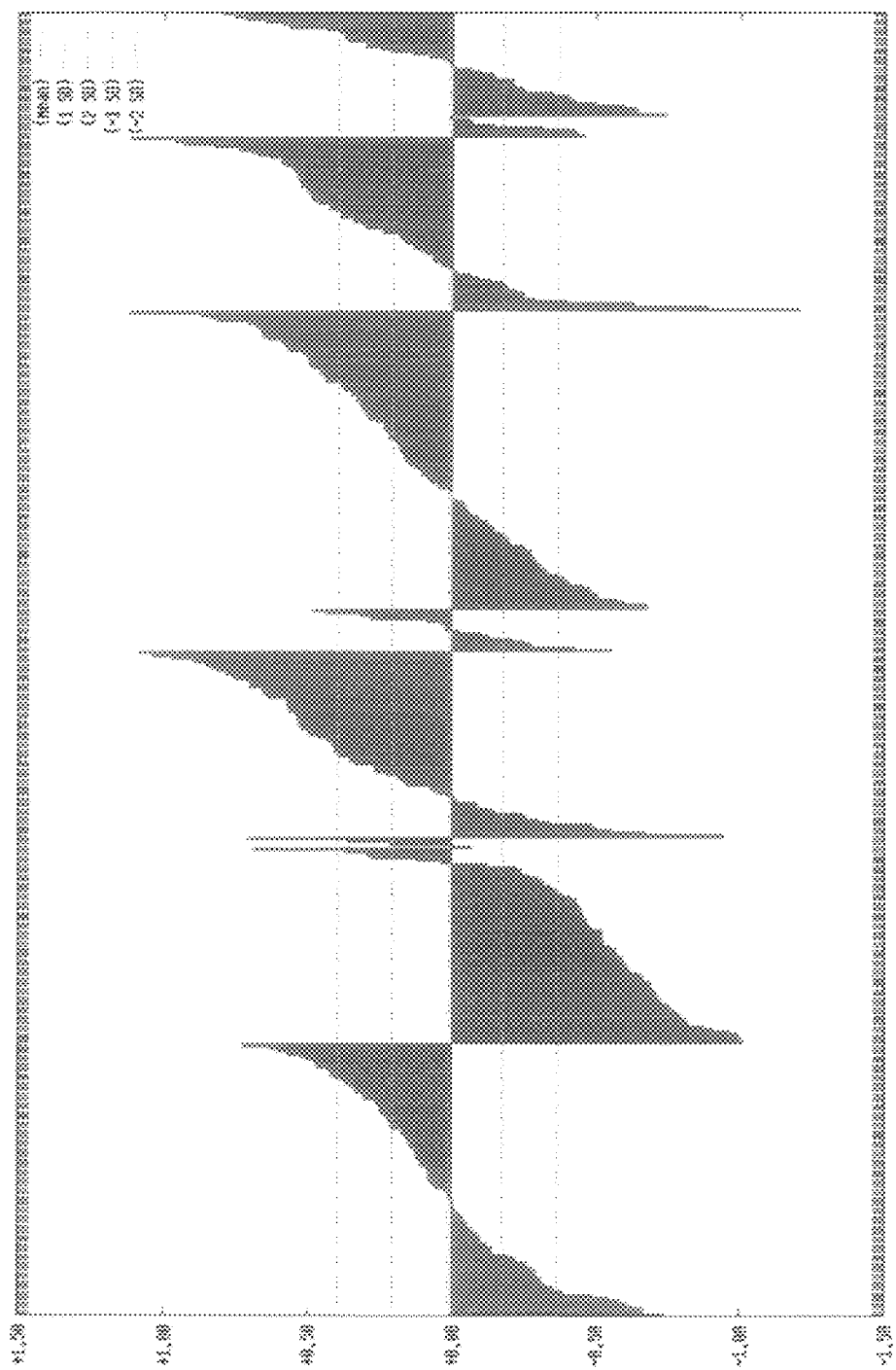
Figure 5C:
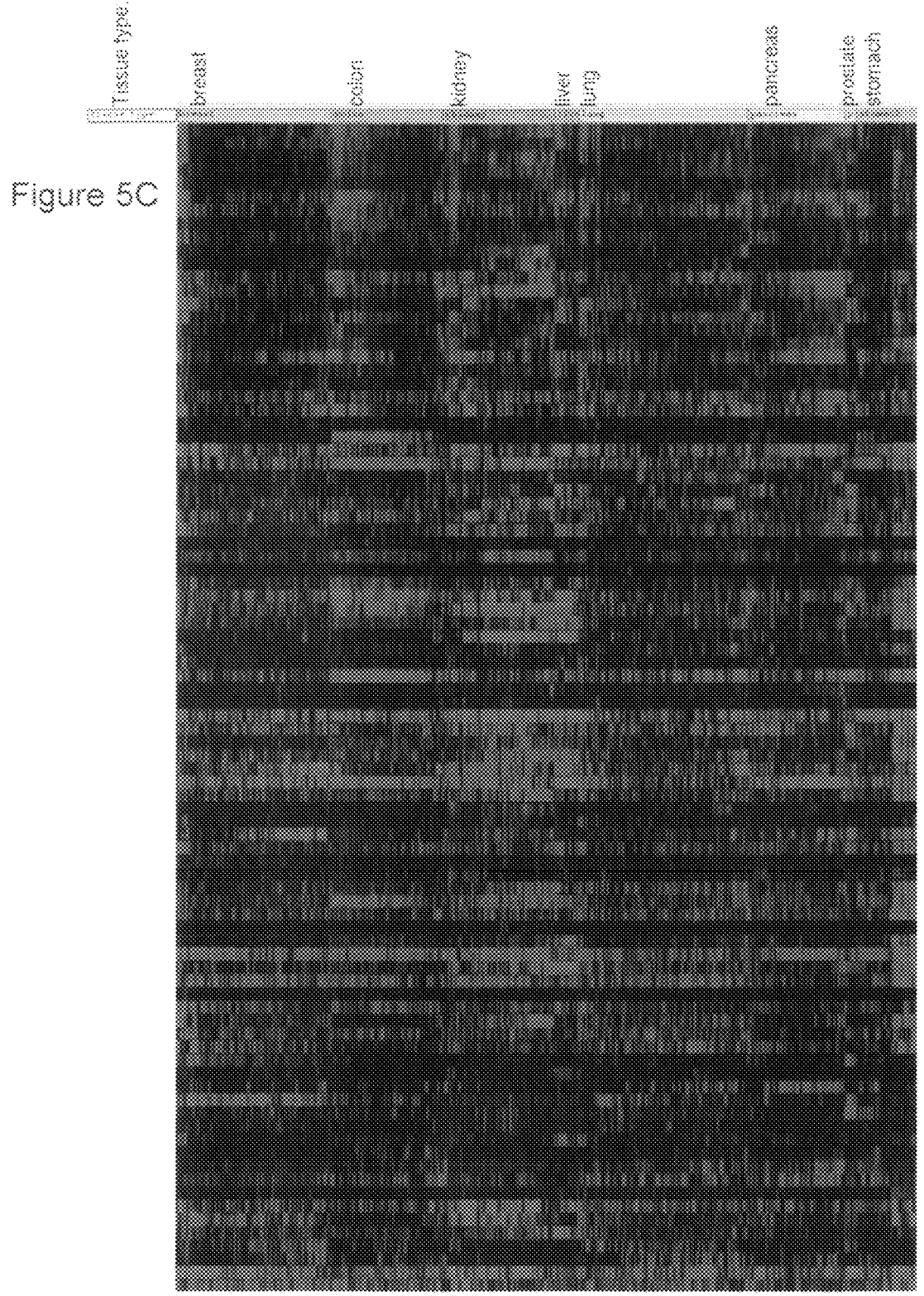
Figure 5D:
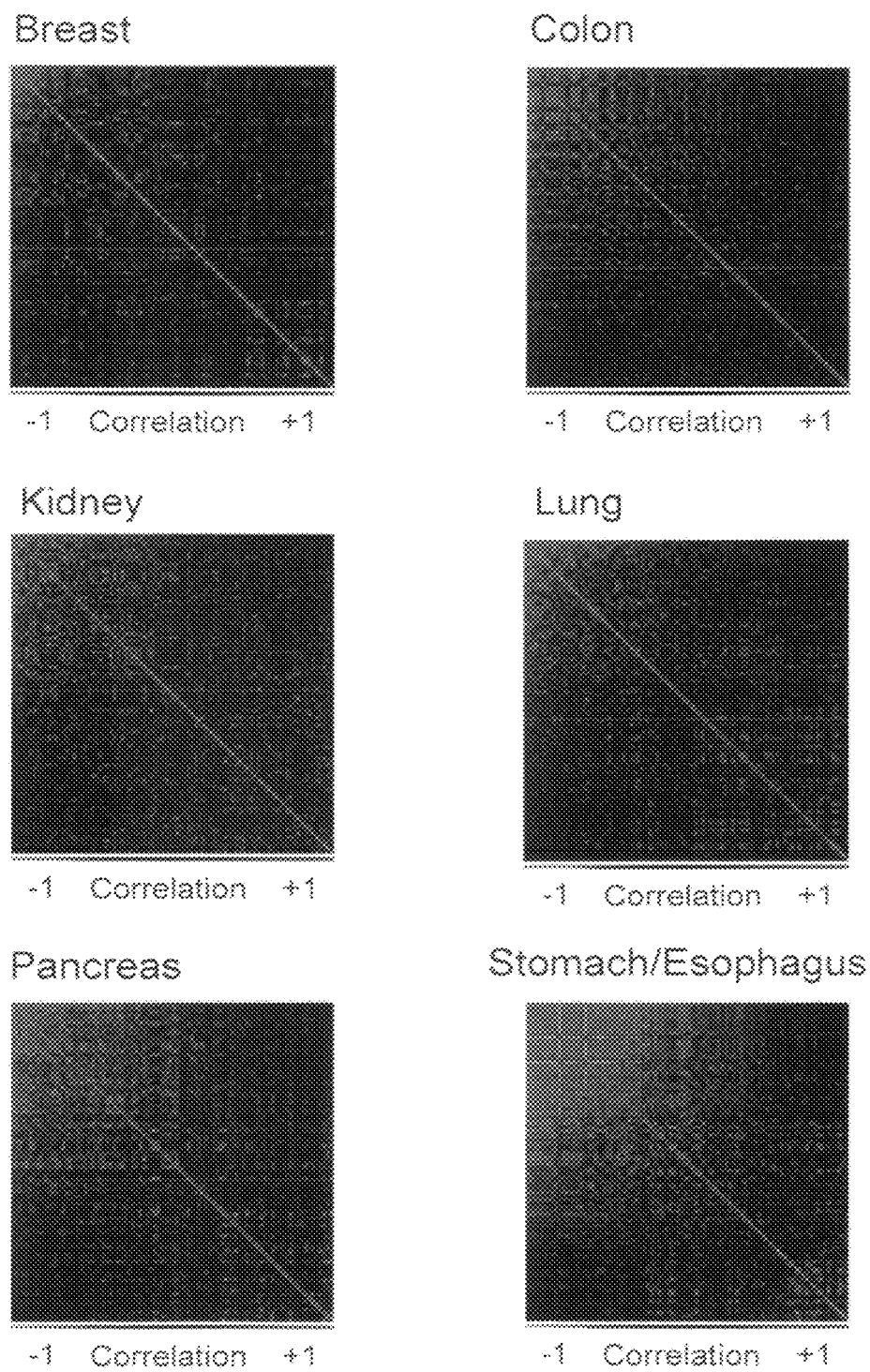

The EMTGS index scores for all samples may be plotted in increasing order on a waterfall plot, and indicate relative states of EMT (see FIG. 4B). When expression values are calculated from microarray data anchored on an epithelial gene, a high index score reflects an epithelial phenotype. When expression values are calculated from qPCR data anchored on an epithelial gene, a low index score reflects an epithelial phenotype. Microarray data reflects mRNA abundance, and therefore a high score will reflect a higher abundance of mRNA of genes co-correlating with the anchor gene. qPCR delta Ct data reflects amplification, and therefore a low score will reflect amplification at an earlier round of PCR, and thus a higher pre-amplification abundance of mRNA of genes co-correlating with the anchor gene.

EMTGS index scores must be calculated as part of a group in order to achieve statistical significance in the co-correlation plot. The number of samples changes the value at which the correlation coefficient can achieve statistical significance. As the number of samples increases, the coefficient that achieves significance decreases. Additionally, the significance assessment via randomized re-sampling (bootstrapping) method requires at least 25 to 30 samples for proper calculations. For these reasons, samples must be processed through the indexing algorithm as part of a group of 30 samples or more. For clinical application, single patient samples may be analysed with a group of samples taken for example from a phase 2 clinical trial where the relative indexes correlated with patient response.

Listed below (i.e. Table 6) are the groups of genes that passed the co-correlation cutoff and were therefore included in the index calculations for the indicated tumor datasets.

TABLE 6

| GeneLogic Breast AB | Gene Logic Breast Plus2 | GeneLogic Lung AB | GeneLogic Lung Plus2 | GeneLogic Pancreas AB | GeneLogic Pancreas Plus2 |
|---|---|---|---|---|---|
| XBP1 | SPARC | SNAI2 | VIM | IFI16 | IFI16 |
| AGR2 | VCAN | DSG3 | SPARC | AXL | AXL |
| ERBB3 | LAMB1 | BSPRY | PECAM1 | SNAI2 | FXYD5 |
| GPD1L | CNN3 | IFI16 | CCL2 | SPARC | SNAI2 |
| FOXC1 | ACTN1 | CLDN3 | AXL | CNN3 | ZEB1 |
| ALCAM | VIM | LAMB1 | PLAUR | VIM | PLAUR |
| CYP4X1 | PECAM1 | AP1M2 | VCAN | FXYD5 | MMP7 |
| YBX1 | AXL | TJP3 | LAMB1 | SRPX | CNN3 |
| ELF5 | SH3YL1 | TWIST1 | VWF | VCAN | SRPX |
| IL8 | SNAI2 | ERBB3 | CNN3 | MMP7 | TWIST1 |
| SPDEF | HMGA2 | SPDEF | SMAD7 | PLAUR | FOXC1 |
| LCN2 | TWIST1 | VCAN | SERPINE1 | ITGA5 | ITGA5 |
| HMGA1 | SRPX | SERPINB2 | FXYD5 | IKBIP | SERPINE1 |
| MPZL2 | DSP | SERPINE1 | ACTN1 | SERPINE1 | SPARC |
| SNAI1 | PLAUR | IKBIP | EFNB2 | ACTN1 | LCN2 |
| MTA3 | XBP1 | TMEM125 | FOSB | CEP170 | SNAI1 |
| FOSL1 | SMAD7 | SRPX | IFI16 | ZEB1 | CCL2 |
| SFRP1 | EFNB2 | OCLN | YBX1 | CCL2 | PPP1R9A |
| MSLN | ZEB1 | PPP1R9A | IL18 | PECAM1 | IL8 |
| PLAUR | ITGA5 | TMEM45B | STAT5A | ZEB2 | DSP |
| FXYD5 | VWF | SPARC | ZEB2 | LCN2 | PECAM1 |
| SERPINA3 | BSPRY | MB | SRPX | DSP | MMP9 |
| MMP7 | SERPINA3 | MMP7 | MMP7 | IL8 | ZEB2 |
| DSG3 | ST13 | HMGA2 | GPD1L | TWIST1 | IL18 |
| SMAD7 | GPD1L | CLDN4 | CEP170 | PPP1R9A | FOSL1 |
| TMEM125 | IGFBP2 | ACTN1 | ITGA5 | EFNB2 | VIM |
| SLC27A2 | CLDN4 | IL8 | MMP9 | HMGA1 | ACTN1 |
| IGFBP2 | STAT5A | ITGA5 | ALCAM | YBX1 | CEP170 |
| TJP3 | MMP9 | SERPINA3 | IL6 | SMAD7 | SERPINB2 |
| PCOLCE2 | CCL2 | SCNN1A | XBP1 | MMP9 | IKBIP |
| MB | IFI16 | ELF3 | MPZL2 | FOSB | VCAN |
| HMGA2 | AKAP12 | FOSL1 | SH3YL1 | AKAP12 | SLC27A2 |
| MTSS1 | CYP4X1 | MSLN | IKBIP | PLXNB1 | SERPINA3 |
| ITGA5 | PPL | EFNB2 | FLRT3 | BSPRY | STAT5A |
| CDH2 | ZEB2 | SLC27A2 | SNAI2 | LAMB1 | SMAD7 |
| SPARC | SERPINE1 | IHH | SERPINA3 | CLDN4 | CLDN4 |
| ST13 | YBX1 | CDH1 | PPL | FOSL1 | IL6 |
| ITGB3 | CEP170 | GPD1L | ZEB1 | IL6 | PLXNB1 |
| EFNB2 | IL11 | CEP170 | MTA3 | IL18 | HMGA1 |
| DNMT3A | OCLN | YBX1 | SNAI1 | SLC27A2 | ELF3 |
| MMP9 | IL18 | ITGB3 | HMGA2 | IGFBP2 | MSLN |
| IL11 | AP1M2 | AXL | IL8 | SERPINA3 | BSPRY |
|  | ELF3 | ZEB2 | ETV5 | ELF3 | PCOLCE2 |
|  | MB | IL6 | ST13 | VWF | FOSB |
|  | ALCAM | DSP | PLXNB1 | CLDN3 | LAMB1 |
|  | AGR2 | IGFBP2 | ZBTB10 | MSLN | AKAP12 |
|  | SCNN1A | ELF5 | PPP1R9A | SNAI1 | CYP4X1 |
|  | CLDN3 | DNMT3A | MTSS1 | SERPINB2 | GPD1L |
|  | MTSS1 | PLAUR | TMEM125 | STAT5A | AGR2 |
|  | ZBTB10 |  |  | MTSS1 |  |

TABLE 6-continued

PCOLCE2
AGR2
MPZL2
FOXC1
SPDEF
ST13
RASSF8

| GeneLogic Colon AB | GeneLogic Colon Plus2 | GeneLogic Kidney AB | GeneLogic Kidney Plus2 | GeneLogic Stomach/ Esophagus Plus2 |
|---|---|---|---|---|
| SERPINE1 | CEP170 | ITGA5 | VIM | HMGA1 |
| VCAN | ZEB2 | SERPINE1 | ZEB2 | AP1M2 |
| ITGA5 | AXL | ACTN1 | AXL | ELF3 |
| AXL | SERPINE1 | PECAM1 | IKBIP | DSP |
| SNAI2 | TJP3 | AXL | EHF | AGR2 |
| SPARC | SPARC | SPARC | SPARC | CLDN4 |
| VIM | VCAN | VWF | TJP3 | TMEM45B |
| CCL2 | AKAP12 | VIM | AKAP12 | CDH1 |
| TWIST1 | VIM | PPP1R9A | ACTN1 | PLAUR |
| PECAM1 | RASSF8 | IFI16 | GPD1L | ZEB1 |
| AKAP12 | IKBIP | FXYD5 | PECAM1 | LCN2 |
| CEP170 | MAP7 | ZEB2 | IFI16 | TMEM125 |
| IL6 | ZEB1 | GPD1L | ITGA5 | OCLN |
| ACTN1 | PECAM1 | OCLN | BSPRY | EHF |
| IKBIP | SNAI2 | ZEB1 | CDH2 | BSPRY |
| AP1M2 | IHH | DSP | ZEB1 | PPL |
| VWF | AP1M2 | IL6 | HMGA1 | SFRP1 |
| SRPX | CCL2 | PLXNB1 | CEP170 | FOSL1 |
| GPD1L | LAMB1 | CCL2 | PCOLCE2 | IL8 |
| ZEB1 | TWIST1 | CDH1 | VCAN | TJP3 |
| TJP3 | TMEM125 | AP1M2 | CDH1 | CLDN3 |
| PLAUR | CLDN3 | BSPRY | CCL2 | MAP7 |
| IHH | SLC27A2 | PLAUR | OCLN | PLXNB1 |
| ERBB3 | ITGA5 | SRPX | DSP | SERPINA3 |
| TMEM45B | IFI16 | IKBIP | SCNN1A | SLC27A2 |
| IFI16 | ELF3 | CLDN4 | PPP1R9A | MPZL2 |
| BSPRY | GPD1L | CLDN3 | PLXNB1 | XBP1 |
| SLC27A2 | TMEM45B | TJP3 | TMEM45B | FLRT3 |
| ZEB2 | SRPX | VCAN | SERPINE1 | IL18 |
| LAMB1 | BSPRY | SNAI1 | AP1M2 | MMP9 |
| MAP7 | OCLN | HMGA1 | VWF | MMP7 |
| DSP | IL6 | FLRT3 | ELF5 | ERBB3 |
| ELF3 | CDH1 | SNAI2 | CLDN4 | ETV5 |
| SNAI1 | DSP | PCOLCE2 | AGR2 | VCAN |
| FOSB | ACTN1 | LCN2 | SPDEF | ZEB2 |
| CDH2 | YBX1 | AKAP12 | CNN3 | IHH |
| TMEM125 | CDH2 | IL18 | FXYD5 | ITGA5 |
| RASSF8 | ERBB3 | FOXC1 | SERPINB2 | FOXC1 |
| FXYD5 | SCNN1A | FOSB | ELF3 | LAMB1 |
| IL8 | MMP9 | ELF3 | SRPX | PECAM1 |
| SERPINA3 | EHF | CEP170 | MTSS1 | IFI16 |
| CYP4X1 | FOXC1 | FOSL1 | IL6 | SPDEF |
| SH3YL1 | ETV5 | SCNN1A | STAT5A | MSLN |
| CNN3 | VWF | TBX2 | | SH3YL1 |
| MMP9 | LCN2 | MMP9 | | CEP170 |
| MB | CLDN4 | SERPINA3 | | PPP1R9A |
| EHF | STAT5A | MPZL2 | | SERPINE1 |
| CDH1 | ALCAM | | | FXYD5 |
| | HMGA1 | | | RASSF8 |
| | PLAUR | | | YBX1 |
| | PCOLCE2 | | | SERPINB2 |
| | CYP4X1 | | | IL11 |
| | CNN3 | | | SCNN1A |
| | AGR2 | | | DSG3 |
| | IL8 | | | CYP4X1 |
| | | | | IL6 |
| | | | | ELF5 |
| | | | | FOSB |
| | | | | EFNB2 |
| | | | | SNAI1 |

| GeneLogic Lymphoma/ MM Plus2 | TCGA Ovarian Plus2 | TCGA GBM Plus2 | All GeneLogic Plus2 Data | All GeneLogic Solid tumor Plus2 data | GeneLogic Lung AB E-only gene index |
|---|---|---|---|---|---|
| IHH | SNAI2 | VIM | LAMB1 | VIM | ERBB3 |
| AP1M2 | VCAN | SPARC | SPARC | SPARC | TJP3 |
| TJP3 | SPARC | YBX1 | CNN3 | PECAM1 | TMEM125 |

TABLE 6-continued

| | | | | | |
|---|---|---|---|---|---|
| CLDN4 | ZEB1 | ACTN1 | VCAN | ZEB2 | AGR2 |
| IL11 | SRPX | CNN3 | AXL | AXL | SH3YL1 |
| ELF3 | LAMB1 | IGFBP2 | ACTN1 | VCAN | OCLN |
| SPDEF | ITGA5 | SERPINA3 | EFNB2 | CCL2 | CLDN4 |
| SNAI1 | SERPINE1 | SRPX | SNAI2 | CEP170 | TMEM45B |
| SCNN1A | TWIST1 | ITGA5 | CCL2 | CNN3 | ELF3 |
| HMGA2 | VIM | LAMB1 | DSP | IKBIP | CLDN3 |
| ELF5 | ZEB2 | SERPINE1 | SRPX | VWF | GPD1L |
| TMEM45B | PECAM1 | IFI16 | VWF | SERPINE1 | BSPRY |
| MPZL2 | AXL | AKAP12 | SERPINE1 | AKAP12 | AP1M2 |
| TBX2 | PLAUR | SLC27A2 | ITGA5 | LAMB1 | DSG3 |
| FOSL1 | IL6 | BSPRY | PPL | IFI16 | CDH1 |
| ERBB3 | SFRP1 | SCNN1A | IGFBP2 | ITGA5 | SPDEF |
| CEP170 | PPP1R9A | DSG3 | CDH1 | ZEB1 | SLC27A2 |
| ITGB3 | CNN3 | SPDEF | ELF3 | SRPX | EHF |
| CLDN3 | SPDEF | TJP3 | AKAP12 | SMAD7 | XBP1 |
| MSLN | PLXNB1 | OCLN | CLDN4 | ACTN1 | LCN2 |
| IFI16 | ACTN1 | AP1M2 | MPZL2 | FOSB | SFRP1 |
| PLXNB1 | AP1M2 | CLDN4 | OCLN | SNAI2 | HOPX |
| RASSF8 | CCL2 | ELF3 | FLRT3 | STAT5A | PPP1R9A |
| TMEM125 | FXYD5 | EHF | MMP7 | IHH | MTSS1 |
| DSG3 | CLDN3 | MAP7 | AP1M2 | MMP7 | IGFBP2 |
| AGR2 | SERPINB2 | CDH2 | PLAUR | TMEM45B | PPL |
| IL18 | SMAD7 | ST13 | PLXNB1 | IL6 | MTA3 |
| MAP7 | SCNN1A | ZEB1 | SH3YL1 | FXYD5 | MPZL2 |
| ST13 | MSLN | MTSS1 | MAP7 | PCOLCE2 | |
| ZEB1 | FOSB | XBP1 | TMEM125 | FOXC1 | |
| LCN2 | VWF | ELF5 | TWIST1 | PLAUR | |
| SERPINB2 | BSPRY | CCL2 | AGR2 | ERBB3 | |
| MB | PCOLCE2 | CLDN3 | CLDN3 | TJP3 | |
| STAT5A | HMGA1 | VCAN | PPP1R9A | HMGA2 | |
| IL8 | AKAP12 | ERBB3 | SERPINA3 | MAP7 | |
| PPL | GPD1L | PCOLCE2 | EHF | SLC27A2 | |
| PPP1R9A | IL8 | MB | FOXC1 | EHF | |
| IKBIP | TJP3 | EFNB2 | SMAD7 | AP1M2 | |
| BSPRY | FOSL1 | SFRP1 | TBX2 | CDH2 | |
| PLAUR | ALCAM | PLAUR | TJP3 | ETV5 | |
| FLRT3 | DSP | MSLN | TMEM45B | YBX1 | |
| EHF | MMP9 | SMAD7 | LCN2 | CLDN3 | |
| FOSB | ZBTB10 | IL11 | CYP4X1 | SNAI1 | |
| SPARC | | ALCAM | ETV5 | RASSF8 | |
| VIM | | VWF | FOSL1 | AGR2 | |
| ITGA5 | | PECAM1 | RASSF8 | MMP9 | |
| MMP9 | | IL8 | SFRP1 | HMGA1 | |
| ZEB2 | | FXYD5 | VIM | BSPRY | |
| EFNB2 | | SNAI2 | IKBIP | TWIST1 | |
| ALCAM | | ZBTB10 | IL8 | SERPINA3 | |
| ETV5 | | FOSL1 | MSLN | CDH1 | |
| SH3YL1 | | PPP1R9A | STAT5A | TBX2 | |
| SFRP1 | | ETV5 | HMGA1 | ST13 | |
| | | MMP9 | FXYD5 | SFRP1 | |
| | | LCN2 | SNAI1 | IL18 | |
| | | CDH1 | BSPRY | MTA3 | |
| | | ITGB3 | MTSS1 | PPP1R9A | |
| | | HMGA2 | IFI16 | OCLN | |
| | | CEP170 | ALCAM | ELF3 | |
| | | TBX2 | GPD1L | PPL | |
| | | DSP | PECAM1 | ITGB3 | |
| | | STAT5A | CDH2 | CLDN4 | |
| | | PLXNB1 | XBP1 | LCN2 | |
| | | FOXC1 | ST13 | TMEM125 | |
| | | IHH | ERBB3 | FLRT3 | |
| | | FOSB | SLC27A2 | SCNN1A | |
| | | | MTA3 | EFNB2 | |
| | | | PCOLCE2 | DSP | |
| | | | MB | ALCAM | |
| | | | MMP9 | | |
| | | | YBX1 | | |
| | | | DSG3 | | |
| | | | ZEB1 | | |
| | | | IL11 | | |
| | | | ELF5 | | |
| | | | FOSB | | |
| | | | SERPINB2 | | |
| | | | IHH | | |
| | | | IL6 | | |
| | | | IL18 | | |

For each of the groups, the number of genes that overlap with any other group varies from 22 to 38, as shown in Table 7 below. There is only one gene that is common to all 15 lists: ITGA5. The contribution of any individual gene to the calculation of the gene index varies with the number of genes in the signature and whether that gene passes the p-value cutoff. ITGA5 by itself does not significantly impact the index values of the GeneLogic Lung AB dataset (FIGS. 11-12).

TABLE 7

| | GL Breast AB (44) | GL Breast Plus2 (50) | GL St/ES AB (50) | GL St/Es Plus2 (60) | GL Lung AB (49) | GL Lung Plus2 (49) | GL Colon AB (48) | GL Colon Plus2 (55) |
|---|---|---|---|---|---|---|---|---|
| GL Breast AB (44) | 44 | 19 | 22 | 28 | 23 | 21 | 16 | 19 |
| GL Breast Plus2 (50) | 19 | 50 | 27 | 29 | 29 | 35 | 31 | 36 |
| GL St/ES AB (50) | 22 | 27 | 50 | 48 | 30 | 25 | 32 | 37 |
| GL St/Es Plus2 (60) | 28 | 29 | 48 | 60 | 36 | 30 | 33 | 38 |
| GL Lung AB (49) | 23 | 29 | 30 | 36 | 49 | 24 | 31 | 34 |
| GL Lung Plus2 (49) | 21 | 35 | 25 | 30 | 24 | 49 | 30 | 29 |
| GL Colon AB (48) | 16 | 31 | 32 | 33 | 31 | 30 | 48 | 42 |
| GL Colon Plus2 (55) | 19 | 36 | 37 | 38 | 34 | 29 | 42 | 55 |
| GL IGd AB (47) | 15 | 30 | 28 | 34 | 28 | 30 | 32 | 36 |
| GL IGd Plus2 (43) | 12 | 28 | 24 | 28 | 27 | 24 | 43 | 36 |
| GL Panc AB (57) | 25 | 37 | 33 | 39 | 33 | 38 | 34 | 39 |
| GL Panc Plus2 (49) | 20 | 31 | 29 | 34 | 29 | 33 | 34 | 37 |
| GL Lym/MM Plus2 (53) | 25 | 26 | 34 | 43 | 30 | 27 | 26 | 30 |
| TCGA Ovar Plus2 (43) | 16 | 29 | 24 | 27 | 26 | 28 | 29 | 32 |
| TCGA GBM Plus2 (66) | 32 | 41 | 37 | 44 | 38 | 35 | 36 | 43 |
| Average | 22.47 | 31.87 | 32.00 | 36.73 | 31.13 | 30.53 | 33.13 | 36.20 |
| Fraction | 0.511 | 0.637 | 0.640 | 0.612 | 0.635 | 0.623 | 0.690 | 0.658 |

| | GL IGd AB (47) | GL IGd Plus2 (43) | GL Panc AB (57) | GL Panc Plus2 (49) | GL Lym/MM Plus2 (53) | TCGA Ovar Plus2 (43) | TCGA GBM Plus2 (66) |
|---|---|---|---|---|---|---|---|
| GL Breast AB (44) | 15 | 12 | 25 | 20 | 25 | 16 | 32 |
| GL Breast Plus2 (50) | 30 | 28 | 37 | 31 | 26 | 29 | 40 |
| GL St/ES AB (50) | 28 | 24 | 33 | 29 | 34 | 24 | 37 |
| GL St/Es Plus2 (60) | 34 | 28 | 39 | 34 | 43 | 27 | 44 |
| GL Lung AB (49) | 28 | 27 | 33 | 29 | 30 | 26 | 38 |
| GL Lung Plus2 (49) | 30 | 24 | 38 | 33 | 27 | 28 | 35 |
| GL Colon AB (48) | 32 | 43 | 34 | 34 | 26 | 29 | 36 |
| GL Colon Plus2 (55) | 36 | 36 | 39 | 37 | 30 | 32 | 43 |
| GL IGd AB (47) | | 47 | 33 | 39 | 37 | 27 | 32 | 37 |
| GL IGd Plus2 (43) | 33 | 43 | 33 | 31 | 23 | 29 | 34 |
| GL Panc AB (57) | 39 | 33 | 57 | 47 | 31 | 36 | 44 |
| GL Panc Plus2 (49) | 37 | 31 | 47 | 49 | 34 | 25 | 36 |
| GL Lym/MM Plus2 (53) | 27 | 23 | 31 | 34 | 53 | 22 | 40 |
| TCGA Ovar Plus2 (43) | 32 | 29 | 36 | 25 | 22 | 43 | 36 |

TABLE 7-continued

| | | | | | | | |
|---|---|---|---|---|---|---|---|
| TCGA GBM Plus2 (66) | 37 | 34 | 44 | 36 | 40 | 36 | 66 |
| Average | 32.33 | 29.87 | 37.67 | 33.73 | 31.40 | 28.93 | 39.87 |
| Fraction | 0.688 | 0.695 | 0.661 | 0.688 | 0.592 | 0.673 | 0.604 |

In contrast, when only the 44 epithelial genes are used to generate an index score in the same dataset, 28 genes pass the p-value cutoff of 0.1 (see Table 6, last column). The index scores generated from this list are quite different from the index scores generated from the 49 genes of the original 88 gene signature that passed the p-value cutoff for this dataset (FIGS. 11-12).

Clinically, it may be desirable to use only the epithelial genes to calculate an EMT index due to the potential for contamination of the mesenchymal genes by stromal cells when evaluating material from patient tumors. Analysis of the index using only the epithelial genes shows the mesenchymal genes do impact the index (FIGS. 11-13). In in vitro lung and pancreatic tumor models, index scores calculated from epithelial genes were able to differentiate erlotinib sensitive from insensitive cell lines (FIG. 14), albeit with less statistical significance compared to index scores calculated using both epithelial and mesenchymal genes for lung tumor cell lines.

Analysis of an EMT gene signature on clinical material will be done using formalin fixed paraffin embedded (FFPE) tissue, due to likely limitations in availability of tumor material. RNA that is of suitable quality for qPCR analysis can be extracted from FFPE tissue using commercially available RNA isolation kits. We have determined that the 88 genes in the EMT signature can be analyzed by qPCR using amplified RNA from tumor sections.

In vitro models of EMT were used during the development of the EMT index to evaluate and refine the final gene list. The ligand induced and engineered H358 models are both metastable models in which EMT characteristics that are induced by the EMT drivers are reversed when the drivers are withdrawn. As the H358 models undergo EMT, sensitivity to erlotinib decreases. FIG. 8 summarizes the morphological, marker and phenotype changes of the metastable H358 EMT models. Included in the tables are the EC50 values for erlotinib on proliferation for each model after induction of EMT, as well as the EMT index values calculated from qPCR data. For most models, EMT correlates with a decrease in erlotinib sensitivity and an increase in index. The two exceptions are the HGF and Zeb1 models. Given the low EMTGS index score of the HGF treated H358 cells, HGF would not have been expected to protect cells from erlotinib inhibition, however it does. This protection is most likely due to survival signaling via the HGF-cMet pathway, rather than EMT induction. Conversely, EMT driven by induced expression of Zeb1 would have been predicted to protect cells from erlotinib, but it does not, suggesting aspects of EMT that are not influenced by Zeb1 may be necessary for erlotinib protection in this instance.

Through iterative rounds of bioinformatics, we refined the EMT signature with the intention of strengthening the association of the genes within one tumor type and also broadening the application of the signature to multiple tumor types. This is illustrated in co-correlation plots of an early version and the final version of the EMT signature in the mouse BH tumor archive (FIGS. 3-4) where the co-correlation of the genes improves after refinement. FIG. 18 shows waterfall plots of an early EMT signature, comprised of genes reported to regulate EMT in the literature (Table 5, Version 1), an intermediate signature which includes genes from in vitro H358 EMT models (Version 2), and the final 88 gene EMT signature (Version 4) across all solid tumors in our GeneLogic database. Note there are differences in the percentage of tumors scored as more M-like and more E-like for each of the signatures.

Validation of 88 Gene EMTGS and Index as EMT Status Indicators.

FIG. 19 shows the E-cadherin status (top panel) and EMT index (lower panel) for tumor cell lines plotted against relative erlotinib sensitivity. The vertical line midway along the horizontal axis indicates a division between sensitive and insensitive cell lines, where the cutoff for sensitivity was 50% inhibition of growth at 10 µM erlotinib. Note the correlation of low (epithelial) index score with high E-cadherin expression and, conversely, high (mesenchymal) index score with low or non-functional E-cadherin expression.

H358 cells engineered to inducibly express activated TGFbeta, Snai1 or Zeb1 upon treatment with doxycycline undergo EMT in vivo. Immunohistochemistry and histology for the aTGFbeta model are shown in FIG. 24. Induction of TGFbeta results in decreased E-cadherin expression, increased vimentin expression and an overall change in architecture characterized by stromal infiltration and invading tumor cells. qPCR analysis of changes in EMT genes in vivo show qualitatively similar changes to those observed in vitro as illustrated in heat maps (FIG. 26). Changes in EMT index upon induction of transgenes aTGFb, Snai1 or Zeb1 in vitro are reported in the table in FIG. 26. It was not possible to determine EC50 values for erlotinib in the engineered models in vivo due to toxicity of treatment with the combination of doxycycline and erlotinib.

Gene changes in the EMT signature that occur in vitro and in vivo were compared for the three engineered models (Table 8 below) using a 2.5 fold cutoff. We identified more gene changes in vitro compared to in vivo in all three models. The genes regulated both in vitro and in vivo in each models are listed in Table 9 below.

TABLE 8

| In vivo (2.5 fold) | | | In vitro (2.5 fold) | | |
|---|---|---|---|---|---|
| aTGFb | Snail | Zeb1 | aTGFb | Snail | Zeb1 |
| SPARC | SPARC | SPARC | SPARC | SPARC | SPARC |
| LCN2 | LCN2 | ZEB1 | LCN2 | LCN2 | LCN2 |
| ITGB3 | MMP9 | LCN2 | MMP9 | MMP9 | SRPX |
| MMP9 | TMEM45B | CDH2 | TMEM45B | TMEM45B | AGR2 |
| TMEM45B | TBX2 | FLRT3 Var2 | SRPX | SRPX | TMEM125 |

TABLE 8-continued

| In vivo (2.5 fold) | | | In vitro (2.5 fold) | | |
|---|---|---|---|---|---|
| aTGFb | Snail | Zeb1 | aTGFb | Snail | Zeb1 |
| TBX2 | SRPX | ITGB3 | AGR2 | AGR2 | BSPRY |
| GPD1L | AGR2 | MMP9 | TMEM125 | TMEM125 | ZEB1 |
| VWF | TMEM125 | TMEM45B | BSPRY | BSPRY | FLRT Var2 |
| SRPX | BSPRY | IGFBP2 | Snal1 | Snal1 | IKBIP |
| AGR2 | IL6 | TBX2 | ITGA5 | ITGA5 | ITGB3 |
| TMEM125 | Snal1 | ZBTB10 | CYP4X1 | CYP4X1 | VIM |
| BSPRY | ITGA5 | SERPINB2 | CLDN3 | CLDN3 | ERBB3 |
| VIM | CYP4X1 | PCOLCE2 | ZEB1 | ZEB1 | MMP7 |
| ERBB3 | CLDN3 | GPD1L | CDH2 | CDH2 | MB |
| MMP7 | LAMB1 | DSG3 | FLRT Var2 | FLRT Var2 | SERPINE1 |
| MB | MSLN | VWF | SERPINB2 | IKBIP | VCAN |
| SERPINE1 | CCL2 | MTA3 | PCOLCE2 | RASSF8 | IL8 |
| VCAN | AACT | | IKBIP | ITGB3 | ZEB2 |
| IL8 | ELF5 | | RASSF8 | IL-11 | EHF |
| ZEB2 | ZEB | | IL-11 | VIM | ELF3 |
| EHF | CDH2 | | PLXNB1 | ERBB3 | PPL |
| ELF3 | FLRT3 Var2 | | CEP170 | MMP7 | HOP |
| PPL | ZBTB10 | | ITGB3 | MB | AXL |
| HOP | SERPINB2 | | GPD1L | SERPINE1 | AP1M2 |
| SPDEF | PCOLCE2 | | VIM | VCAN | CDH1 |
| SLC27A2 | DSG3 | | ERBB3 | IL8 | IL6 |
| TJP3 | IKBIP | | MMP7 | ZEB2 | DSP |
| IL6 | RASSF8 | | MB | EHF | HMGA1 |
| PECAM1 | DSP | | SERPINE1 | ELF3 | TJP3 |
| Snal1 | SFRP1 | | VCAN | PPL | Mpzl2 |
| ITGA5 | IL-11 | | IL8 | HOP | SFRP1 |
| CYP4X1 | PLXNB1 | | ZEB2 | SPDEF | |
| CLDN3 | CEP170 | | EHF | SLC27A2 | |
| LAMB1 | DNMT3A | | ELF3 | CNN3 | |
| CNN3 | FOSL1 | | PPL | SCNN1A | |
| SCNN1A | FOSB | | HOP | IGFBP2 | |
| MSLN | TWIST1 | | SPDEF | OCLN | |
| CLDN4 | IHH | | SLC27A2 | AXL | |
| CCL2 | IFI16 | | TJP3 | AP1M2 | |
| PLAUR | ETV5 | | PECAM1 | MAP7 | |
| AACT | STAT5A | | CNN3 | CDH1 | |
| ELF5 | | | SCNN1A | SH3YL1 | |
| | | | PLAUR | IL-18 | |
| | | | IGFBP2 | EFNB2 | |
| | | | Mpzl2 | SMAD7 | |
| | | | OCLN | TBX2 | |
| | | | AXL | IL6 | |
| | | | AP1M2 | LAMB1 | |
| | | | MAP7 | MSLN | |
| | | | CDH1 | DSP | |
| | | | SH3YL1 | CLDN4 | |
| | | | IL-18 | HMGA1 | |
| | | | EFNB2 | YBX1 | |
| | | | PPP1R9A | ALCAM | |
| | | | SMAD7 | | |
| | | | AKAP12 | | |
| | | | SNAI2 | | |
| | | | FOXC1 | | |

TABLE 9

| Genes in common, in vitro and in vivo | | |
|---|---|---|
| aTGFb (33) | Snail (21) | Zeb1 (4) |
| AGR2 | AGR2 | ITGB3 |
| BSPRY | BSPRY | LCN2 |
| CLDN3 | CDH2 | SPARC |
| CNN3 | CLDN3 | ZEB1 |
| CYP4X1 | CYP4X1 | |
| EHF | DSP | |
| ELF3 | IKBIP | |
| ERBB3 | IL-11 | |
| GPD1L | IL6 | |
| HOP | ITGA5 | |
| IL8 | LAMB1 | |
| ITGA5 | LCN2 | |
| ITGB3 | MMP9 | |
| LCN2 | MSLN | |
| MB | RASSF8 | |
| MMP7 | SPARC | |
| MMP9 | SRPX | |
| PECAM1 | SNAI1 | |
| PLAUR | TBX2 | |
| PPL | TMEM125 | |
| SCNN1A | TMEM45B | |
| SERPINE1 | | |
| SLC27A2 | | |
| SPARC | | |
| SPDEF | | |
| SRPX | | |

TABLE 9-continued

| Genes in common, in vitro and in vivo | | |
|---|---|---|
| aTGFb (33) | Snail (21) | Zeb1 (4) |
| SNAI1 | | |
| TJP3 | | |
| TMEM125 | | |
| TMEM45B | | |
| VCAN | | |
| VIM | | |
| ZEB2 | | |

Molecular Characterization of In Vitro EMT Models Using the 88 Gene EMTGS.

Figure 6A:
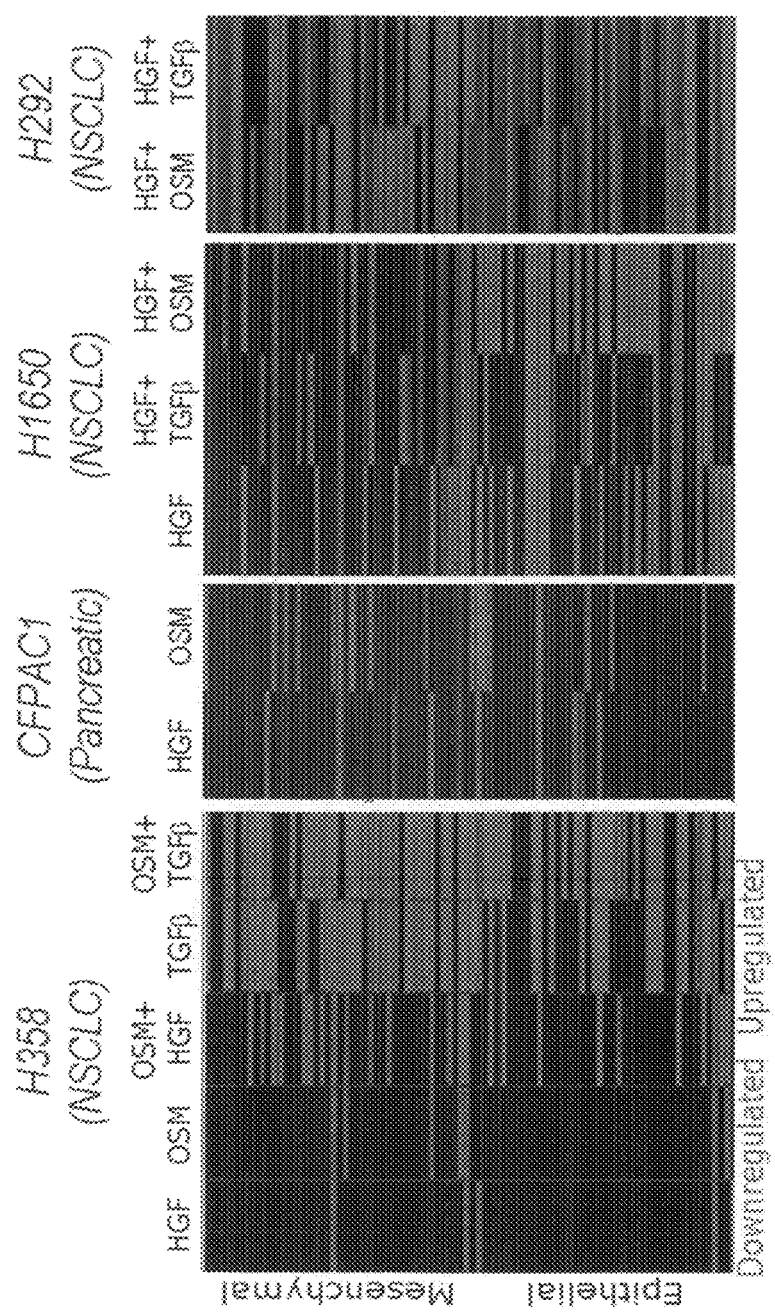

Changes to genes of the 88 gene EMT signature were profiled in four in vitro EMT cell models to evaluate the usefulness of the signature in understanding the molecular changes cells undergo during EMT. Cells were stimulated for 7 days with hepatocyte growth factor (HGF), oncostatin M (OSM), transforming growth factor β (TGFβ), or combinations thereof to induce EMT. RNA was harvested and converted to cDNA for analysis of the gene changes by qPCR. Raw Ct values were normalized to GAPDH and then converted to fold change values relative to untreated cells. A fold change cutoff of three was used to identify differentially expressed genes during EMT. The results are summarized in heat maps as shown in FIG. 6, where the 44 mesenchymal genes are listed first and the 44 epithelial genes second. In the H358 model, HGF and OSM each cause a partial EMT, and HGF+OSM, TGFβ, and TGFβ+OSM stimulate a more advanced EMT as characterized by morphology, biomarker, and phenotypic changes. This is reflected in the heat map where HGF and OSM caused few changes to EMT-related genes over 7 days (FIG. 6A). HGF+OSM, TGFβ and TGFβ+OSM, in contrast, caused a marked change to genes of the 88 gene EMT signature. Thus, the 88 gene EMT signature accurately assessed EMT status in this NSCL tumor EMT model.

The 88 gene EMTGS has a broader application than individual EMT biomarkers. No single epithelial or mesenchymal biomarker is able to reflect the phenotypic changes associated with all cell models, and by extension, all tumors. In particular, the mesenchymal biomarkers vary significantly. By using multiple genes to characterize EMT status, we are able to more accurately characterize the EMT status of cells and tumors.

Changes in CFPAC1, H1650 and H292 tumor cell EMT models after 7 day ligand stimulation were also profiled (FIG. 6A). Similar to what was observed in the H358 models, all showed variable changes to the signature, depending on the stimulus used. The differences in the profiles between and within cell lines illustrate a spectrum of EMT states, consistent with what is observed in tumors. The CFPAC1 pancreatic EMT model underwent fewer gene changes than the lung models. H1650 cells regulated the epithelial profile more robustly than the mesenchymal profile, and the reverse was true for H292 cells. Here again, the 88 gene EMT signature accurately reflects changes in EMT status in these NSCLC and pancreatic tumor EMT models.

Morphological, marker and phenotypic changes for each of the models are illustrated in FIGS. 28-30. Changes consistent with EMT occur in each model upon ligand stimulation, but each model is distinct in its ability to shift to a more mesenchymal state. CFPAC1 cells undergo EMT readily with single ligand stimulation, while H1650 cells and H292 cells undergo more subtle changes and require stimulation with two ligands.

The 88 gene EMTGS adds another dimension to the characterization of these in vitro models. Where we observed the CFPAC1 model underwent EMT with minimal stimulation, the 88 gene EMTGS showed fewer gene changes than the other models. This could be interpreted as fewer gene changes being necessary for these cells to undergo EMT compared to the other models. The H1650 model showed more subtle morphological changes. The 88 gene EMTGS showed clear downregulation of epithelial genes and more modest increase in mesenchymal genes. This suggests that the morphological changes indicate a less advanced mesenchymal phenotype. This is corroborated by a lack of consistent changes in migration and invasion assays. The H292 cells underwent convincing morphological and phenotypic changes as illustrated by the migration assay. Extensive exploration of mesenchymal biomarker expression identified few that were upregulated during EMT. MMP9 was the most pronounced. The 88 gene EMTGS, however showed a strong regulation of mesenchymal genes, suggesting that there was a transcriptional shift to a more mesenchymal state. Such data indicates that had we relied solely on conventional EMT biomarkers to characterize these models, we would have developed an incomplete understanding of their EMT states.

Figure 6B:
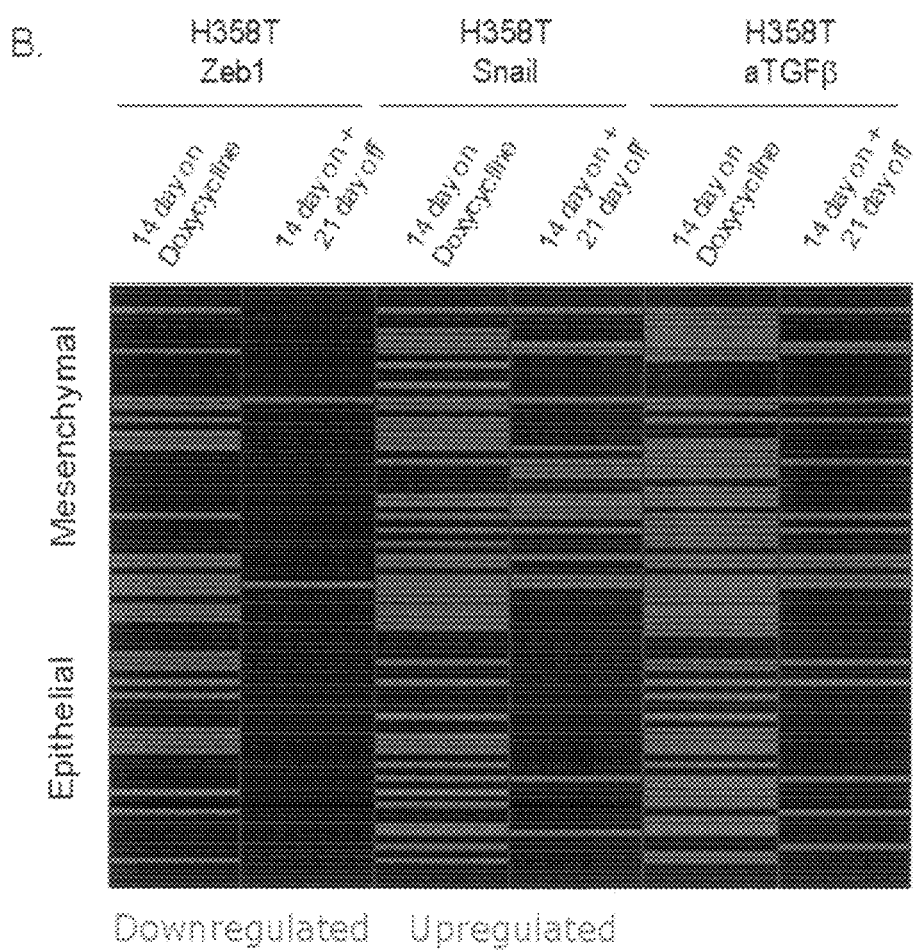

The 88 gene EMT signature also characterizes the extent of mesenchymal to epithelial (MET) reversion in vitro. Using H358 cells engineered to inducibly express activated TGFβ (aTGFβ), Snail or Zeb1, we identified gene changes observed after 14 days of transgene expression. Doxycycline was then withdrawn to eliminate expression of the transgenes, and the cells were cultured for 21 days in order to induce reversion of EMT. FIG. 6B shows the profiles after 14 day stimulation and 21 day reversion, each relative to untreated cells. Zeb1 transgenic cells were able revert to a profile consistent with untreated cells, whereas cells induced to express Snail and aTGFβ only partially reverted.

The 88 gene EMTGS can be used to characterize the extent to which an in vitro EMT model has reverted, thus defining whether a model is metastable (reversible) or epigenetically fixed. Knowing the reversibility of the model determines its usefulness as a model to investigate the role of EMT and MET in metastasis, where metastasized tumor cells must revert to a more epithelial state in order to proliferate and form a cohesive tumor.

As described above, growth of the H358 engineered EMT models in subcutaneous and orthotopic settings in vivo serves as a model for EMT in NSCLC tumors. In each case, induction of the transgenes results in loss of E-cadherin, increased expression of vimentin and slowed tumor growth (see FIGS. 21-25). Snail and Zeb1 did not have an invasive tumor phenotype, but TGFb showed clear invasion of the tumor cells into the stroma.

As shown in FIG. 26, there is qualitative agreement of the models in the in vitro and in vivo settings as judged by the heat maps of the 88 gene EMTGS. TGFbeta and Snail show similar numbers of gene changes, while Zeb1 has less of an impact on the 88 gene EMTGS. Growth of the models in 3D matrix predicts the growth rate and aggressiveness of the xenografts. FIG. 27 shows decreased growth of all models as determined by colony size, with Snail colonies nearly growth arrested after induction of the transgene. Neither Snail nor Zeb1 colonies invade into the matrix, but aTGFb shows protrusions from the colony into the matrix. These phenotypes are recapitulated in vivo both in growth rate and invasiveness.

As shown in tables 8 and 9, there is variable commonality in gene changes between the in vitro and in vivo settings for each model (see FIG. 31). aTGFb shows the best overlap, and Zeb1 the least. It was expected that there would be differences between the two settings since the growth environment contributes to signaling and therefore transcriptional profile in the cells. This includes input from the extracellular matrix and stromal cells.

The 88 gene EMTGS captures cells/tumors that do not express the "classical" EMT markers but may be classified by less common markers. EMTGS index scores are not dominated by any one marker and therefore are still useful in models where the classical markers may not be expressed. We have also shown that the 88 gene EMT signature/index is applicable across multiple solid tumor types, unlike other EMT signatures (e.g. the Choi EMT signature; see herein below), which only perform well in certain tumor types. These features illustrate the advantages of the 88 gene EMTGS and index versus classical EMT biomarker analyses.

EMTGS index values represent relative states of EMT as shown in FIG. 20. The H358 engineered models of EMT, Zeb1, Snai1, and aTGFb all show changes in index scores upon induction of the transgenes. The relative values of the index scores after two weeks of induction reflect what we observe as EMT status, as judged by morphological, marker and phenotypic status. When the transgenes are turned off, the index scores decrease to represent more epithelial states. The final scores correlate with the extent of reversion we observe in the cells: Zeb1 reverts completely, Snai1 less completely, and TGFb only partially. Index scores in the H358 ligand-driven models also reflect relative states of EMT. OSM or HGF stimulation results in only a partial EMT state, while TGFb, HGF+OSM and TGFb+OSM all drive a more complete EMT change, as reflected in the increasing index scores. Thus, EMT index scores can distinguish differences in EMT state within the same cell line across the entire spectrum from 100% epithelial to 100% mesenchymal. FIG. 19 shows that the 88 gene EMTGS index can distinguish EMT states across unrelated cell lines in vitro.

Comparison of 88 Gene EMT Signature to Other EMT Gene Signatures

In the scientific literature, many conclusions regarding EMT have relied on a few established markers (e.g. E-cadherin, vimentin) to characterize the cells in question as either epithelial or mesenchymal-like. Due to the complex phenotypes of epithelial and mesenchymal-like cells, this has undoubtedly led to mischaracterization of cell populations. In moving away from this method and toward development of an 88 gene EMT signature and index, one can improve the molecular classification of EMT status, and thus the ability to qualitatively and quantitatively study the spectrum of EMT states observed in human tumors. In the clinic, use of the 88 gene EMT signature and EMT index may improve patient care by effectively predicting whether tumors will respond to erlotinib, allowing for more tailored cancer therapy.

Several EMT gene signatures have been published, and one is sold as a research tool. The 88 gene EMT signature disclosed herein was compared to two published EMT signatures, one developed in Ras transformed EpH4 cells (Jechlinger, 2003; 54 genes) and one in non-transformed MDCK cells (Moreno-Bueno, 2006; 189 genes), as well as a disease recurrence signature developed from HNSCC tumor tissue that was shown to be enriched with genes involved in EMT (Chung, 2006; 42 genes). Little overlap was found between the 88 gene EMT signature disclosed herein and these three EMT-based signatures that were experimentally derived from in vitro models or from tumor biopsies (gene overlap: Jechlinger, 5 genes; Moreno-Bueno, 5 genes; Chung, 1 gene).

Four additional signatures were compared in evaluating the OSI EMT signature for predicting erlotinib sensitivity. They were the Choi EMT signature, the SABiosciences EMT signature, the Yauch erlotinib signature and the Bunn gefitinib signature and (Choi, 2010; Coldren, 2006; Yauch, 2005, Tables 10-12). The Choi EMT signature (Table 10) was developed experimentally by comparing expression patterns between three cell types: epithelial breast tumor cells, mesenchymal breast tumor cells and fibroblasts. The top 100 genes with at least 2 fold higher expression in the epithelial tumor cells compared to the mesenchymal tumor cells and the fibroblasts were designated the epithelial genes. The top 100 genes with at least 2 fold higher expression in the mesenchymal tumor cells compared to the epithelial tumor cells and the fibroblasts were designated the mesenchymal genes. The genes are listed below. There are 11 genes common to the OSI EMT gene signature and the Choi EMT gene signature (i.e. AGR2, CDH1, CLDN3, CLDN4, ELF3, ERBB3, HMGA2, IKBIP, OCLN, SH3YL1, SPDEF).

TABLE 10

| Choi EMT signature genes: |
|---|
| 7A5 |
| ABCA12 |
| ABCC4 |
| ACSL4 |
| AGPAT5 |
| AGR2 |
| AIM1 |
| ANLN |
| ANP32E |
| ANXA1 |
| ANXA9 |
| AP1S2 |
| ARL4A |
| ARSJ |
| ATAD4 |
| ATCAY |
| BIRC3 |
| C10orf58 |
| C17orf28 |
| C1orf172 |
| C20orf151 |
| C2orf44 |
| C6orf150 |
| C6orf173 |
| C7orf24 |
| C9orf140 |
| C9orf58 |
| CAMK4 |
| CCDC82 |
| CCDC88A |
| CCDC99 |
| CD24 |
| CD83 |
| CDH1 |
| CEBPA |
| CELSR1 |
| CHN1 |
| CKMT1A |
| CKMT1B |
| CKS2 |
| CLDN3 |
| CLDN4 |
| CLDN7 |
| CLDND1 |
| CLSPN |
| COMMD8 |
| CTNNAL1 |
| DCBLD2 |

TABLE 10-continued

Choi EMT signature genes:

DDX60
DDX60L
DKFZp586I1420
DMN
DNAJB4
DNER
DPH3
E2F7
ECHDC1
EFNA1
ELF3
ERBB3
EST_AA233823
EST_AA411685
EST_AA598828
EST_AA629908
EST_AI192452
EVPL
FABP5
FAM40B
FAM92A1
FLJ32810
FLJ36445
FXYD3
GALNT1
GALNT3
GBP1
GCA
GNAI1
GRHL1
GRHL2
GULP1
HCAP-G
HDAC9
HJURP
HMGA2
ICA1
IFI44
IFIT2
IGF2BP3
IGSF3
IGSF9
IKBIP
IMPA1
KIAA0020
KIAA1524
KIAA1598
KIF21A
KRT8
L2HGDH
LACTB
LAD1
LIFR
LLGL2
LNX2
LOC124220
LOC126987
LOC149501
LOC202451
LOC344595
LOC344787
LOC388116
LOC389695
LOC392335
LOC401584
LOC440281
LOC92497
LRRC1
LYN
LYST
MAK16
MAL2
MAP3K1
MAP7D3
MARVELD2
MCAM
MGAT5B
MLPH

TABLE 10-continued

Choi EMT signature genes:

MPZL3
MREG
MSX2
MYB
MYBL1
MYH14
NOL8
OCLN
OSTM1
PAG1
PBK
PIK3R3
PKP3
PLEKHF2
PMAIP1
PNMA2
POLK
POT1
PPARG
PPM1L
PPM2C
PREX1
PRKCH
PROM2
PRSS22
PTTG1
PTTG3
RAB25
RAD18
RB1CC1
RBM35A
RBM35B
RBM47
RND3
RP2
RP6-213H19.1
S100A14
SACS
SAMD9
SCML1
SCYL1BP1
SELENBP1
SH3YL1
SLC29A2
SLC9A3R1
SMC5
SOAT1
SPDEF
SPINT1
SPINT2
ST14
SUSD5
SYNE2
TACSTD1
TACSTD2
TBC1D30
TOM1L1
TPD52
TSPAN1
TSPAN13
TSPAN15
TTC27
TTK
UBLCP1
USP33
VAMP8
WDR19
WDR47
XM_165511
XM_374637
XM_496852
YBX2
ZMYM1
ZNF788

Since the 88 gene EMT signature disclosed herein was evaluated for its ability to predict erlotinib sensitivity, the commonality between this EMT signature and two gene signatures developed in cell lines for prediction of sensitivity to the EGFR kinase inhibitors, erlotinib (Yauch, 2005, Table xx) and gefitinib (Coldren, 2006, Table 11), was determined. Here again we observed limited overlap of the genes of the 88EMTGS and the erlotinib sensitivity (5 gene overlap) gefitinib sensitivity (15 gene overlap) signatures.

The Yauch erlotinib sensitivity signature was developed from genes differentially expressed between lung tumor lines characterized as sensitive or insensitive to erlotinib in vitro. A panel of 42 NSCLC cell lines of known erlotinib sensitivity was profiled by Affymetrix microarray, and the 19,592 most variably expressed probesets between the sensitive and insensitive lines were identified. The 50 probesets that showed highest expression in the sensitive cell lines and the 50 probesets with highest expression in the mesenchymal cell lines were combined to make the signature. Of the 62 known genes in this signature (Table 11), 5 overlapped with the 88EMTGS (AP1M2, CDH1, MAP7, VIM and ZEB1).

TABLE 11

Yauch erlotinib sensitivity signature:

| | | | | |
|---|---|---|---|---|
| ST6GALNAC6 | TRPC1 | SMURF2 | TUBB | FLJ31952 |
| LAMA5 | LARGE | TTC28 | NFATC3 | FLJ20171 |
| DKK3 | MAP7 | B4GALT1 | MARVELD3 | KIAA0470 |
| C16orf45 | GALNT3 | AP1S2 | SERPINB5 | LOC58489 |
| ZFP37 | PRAF2 | ANXA6 | ST14 | C14ORF159 |
| DYRK3 | KLC3 | GJB3 | DZIP1 | C12ORF75 |
| EPN3 | ZNF682 | INSIG1 | FAM83H | DKFZp762F237 |
| MAPK13 | SPINT2 | DMKN | ALDH1A3 | FLJ26472 |
| SFN | DTX3 | ARAP2 | UCHL1 | C19ORF21 |
| AP1M2 | P2RY2 | TUBA1A | MAL2 | C5ORF13 |
| CDH1 | KCNMA1 | VIM | RBM47 | |
| PAK6 | GPR176 | ASAP3 | STX2 | |
| FLJ10357 | KCNK1 | INSR | EMP3 | |
| ZEB1 | ELMO3 | TFAP2C | ZNF702P | |
| SPINT1 | CHN1 | PTK6 | | |
| TACSTD2 | CDS1 | SDCCAG8 | | |

The Bunn gefitinib signature (Table 12) was also developed experimentally to predict sensitivity to gefitinib, rather than as an EMT status indicator. Five gefitinib sensitive and six insensitive cell lines were compared by mRNA microarray. All genes that were differentially expressed as determined by a two-sample t-test with a p-value cutoff of 0.001 were included in the signature (415 probesets, 333 genes). There are 15 genes common to the Bunn gefitinib signature and the 88 gene EMT gene signature (i.e. AGR2, AP1M2, BSPRY, CDH1, CDH2, CLDN4, EHF, ELF3, ERBB3, IKBIP, OCLN, PPL, SH3YL1, TJP3, TMEM45B).

TABLE 12

The Bunn Gefitinib sensitivity signature:

AA573901
AA675917
AA772172
AA991267
ACPP
ACTR1A
ADAM28
ADK
AF1Q
AGR2
AI038402
AI051046
AI146812
AI28209
AI458439

TABLE 12-continued

The Bunn Gefitinib sensitivity signature:

AI493046
AI675682
AI797017
AI830823
AI857788
AI916284
AI928513
AIG1
AIM1
AIM1L
AL359055
ALDH1A1
ALDH1A3
ALDH1B1
ANKRD22
ANXA9
AP1M2
ARD1

TABLE 12-continued

The Bunn Gefitinib sensitivity signature:

ARHGDIB
ARL3
ARS2
ATPIF1
AV724325
AV741130
AW135306
AW242997
AW263497
AW302207
AW305300
B3GNT3
BCLP
BE883167
BF224444
BF433219
BF445865
BG231548
BIK
BLNK
BMS1L
BSPRY
C10ORF32
C10ORF76
C16ORF45
C18ORF21
C19ORF14
C19ORF28
C1ORF21
C20ORF27

TABLE 12-continued

The Bunn Gefitinib sensitivity signature:

C20ORF55
CAB39
CAPS
CCNG2
CDC42
CDH1
CDH2
CDH3
CDK5RAP2
CDS1
CEBPG
CENTA1
CENTD1
CGI-30
CGN
CLDN4
CLDN7
CLDN9
CNKSR1
COBLL1
COMT
COX15
CRTAP
CST6
CTPS
CYP2J2
DAPP1
DDR1
DKFZP434C0328
DKFZP761B107
DLX1
DST
DZIP1
EHF
ELF3
ELMO3
EMB
ENPP4
ENPP5
EPHA1
EPLIN
EPN3
EPPK1
EPS8L1
EPS8L2
ERBB3
EVA1
FAM3C
FAM55C
FBXO30
FGD4
FGFBP1
FLJ10156
FLJ10847
FLJ12644
FLJ20160
FLJ20244
FLJ20298
FLJ21918
FLJ23091
FLJ23867
FLJ32115
FLJ33718
FLJ34633
FLJ36445
FLJ46385
FOXA1
FRMD4B
FTS
FXYD3
GAB1
GALNACT-2
GALNT3
GAS5
GCA
GCNT2
GNAS
GOT1
GPR110
GPR160
GPR87
GUCY1B3
GUK1
H07986
HMGCL
HS3ST1
HSA272196
HSD17B7
IARS
ID3
IDE
IKBIP
IRF6
ITGB6
JAM3
KCNMB4
KCTD15
KIAA0040
KIAA0703
KIAA0830
KIAA1522
KIAA1754
KIAA1833
KIAA1946
KLC2L
KLHL15
KLK6
KRT15
KRT19
LAD1
LAMC2
LEMD1
LEPRE1
LGALS9
LIPH
LISCH7
LIX1L
LMO7
LNX
LOC146439
LOC202451
LOC255743
LOC284307
LOC339745
LOC389389
LOC57228
LRG1
LRRC16
MAL2
MAP1B
MAPK13
MCART1
MDM4
MGC11242
MGC12981
MGC16471
MGC17299
MGC17330
MGC42367
MGC45474
MGC45871
MLF1IP
MLL4
MPP7
MST1R
MTAC2D1
MYH14
MYO1D
MYO6
NAP1L1
NOL8
NSE2
NSMAF
OACT1
OCLN
OLFM1

TABLE 12-continued

The Bunn Gefitinib sensitivity signature:

OVOL1
PARVB
PCGF6
PDCD11
PDE5A
PDHA1
PEG10
PEO1
PLEKHA7
PLEKHF2
POLRMT
PORIMIN
PPIF
PPL
PPP2R1B
PRKCD
PRRG2
PRRG4
PRSS22
PRSS8
PSD4
PTK6
PTPRG
PVRL4
PX19
QPCT
RAB11FIP4
RAB25
RAB38
RAB9P40
RAD50
RAP2B
RASEF
RASGEF1B
RECQL5
REPS2
RFK
RHOD
RHOQ
RIPK4
RIS1
RNF141
S100A14
S100A16
SACS
SARG
SCAMP2
SCEL
SELM
SERPINB5
SESTD1
SH3BGRL2
SH3YL1
SLAC2-B
SLC1A1
SLC2A12
SLC35A3
SLC39A14
SLC7A1
SMPDL3B
SOX12
SPINK2
SPINT1
SPTLC2L
SRCAP
SRPX2
ST14
STAP2
STARD10
STK39
SUPV3L1
SVIL
SYTL1
TACSTD2
TBL1X
TCF8
TFCP2L2
TFCP2L3
TFCP2L4
TIMM50
TJP2
TJP3
TMC4
TMC5
TMEM30B
TMEM40
TMEM45B
TMPRSS4
TRAD
TRAF5
TRNT1
TSPAN1
TTL
TUB
UBA2
UBE2M
UCHL1
UNC13D
USP36
USP44
VAMP8
VAV3
WDFY1
WEE1
WFDC3
ZDHHC21
ZNF258
ZNF313
ZNF339
ZNF43
ZNF468
ZNF506
ZNF600
ZNF91

The 88 gene EMT signature disclosed herein was also compared to the 84 genes in a commercially available (SABiosciences; Table 13) EMT OCR array. It is not known how this signature was developed. Only 15 of the genes were found to be common to both lists (i.e. CDH1, CDH2, DSP, ERBB3, ITGA5, MMP9, OCLN, SERPINE1, SNAI2, SPARC, TWIST1, VCAN, VIM, ZEB1, ZEB2). When samples from EMT cell models were compared using either the 88EMTGS or the SABiosciences EMT array, both showed gene changes consistent with EMT, but the 88EMTGS showed approximately twice as many gene changes with each cell model (FIG. 7), illustrating a more comprehensive molecular classification of EMT with the 88EMTGS.

TABLE 13

SABiosciences EMT gene list:

AHNAK
AKT1
BMP1
BMP7
CALD1
CAMK2N1
CAV2
CDH1
CDH2
COL1A2
COL3A1
COL5A2
CTNNB1
DSC2
DSP
EGFR
ERBB3

TABLE 13-continued

SABiosciences EMT gene list:

ESR1
F11R
FGFBP1
FN1
FOXC2
FZD7
GNG11
GSC
GSK3B
IGFBP4
IL1RN
ILK
ITGA5
ITGAV
ITGB1
JAG1
KRT14
KRT19
KRT7
MAP1B
MITF
MMP2
MMP3
MMP9
MSN
MST1R
NODAL
NOTCH1
NUDT13
OCLN
PDGFRB
PLEK2
PPPDE2
PTK2
PTP4A1
RAC1
RGS2
SERPINE1
SIP1
SMAD2
SNAI1
SNAI2
SNAI3
SOX10
SPARC
SPP1
STAT3
STEAP1
TCF3
TCF4
TFPI2
TGFB1
TGFB2
TGFB3
TIMP1
TMEFF1
TMEM132A
TSPAN13
TWIST1
VCAN
VIM
VPS13A
WNT11
WNT5A
WNT5B
ZEB1
ZEB2

Waterfall plots of index score prevalence using different EMT signatures showed different profiles across different lung tumors (FIG. 44). The OSI EMT signature and the SABiosciences signature were more similar than the Choi or the Yauch erlotinib signatures. The Choi signature may be biased toward breast tumors since it was developed from breast tumor cell lines. Interestingly, the Yauch signature was developed from lung tumor line microarray data, but did not differentiate adenocarcinoma and squamous cell carcinoma as well as the 88EMTGS that was refined in human tumor datasets.

Derivation of index scores using the 88 gene EMTGS, the Choi signature, the SABiosciences signature, the Yauch erlotinib signature and the Bunn gefitinib signature, in a variety of tumor cell lines (FIG. 43) indicates that an index score derived from any of these gene signatures is significantly different in erlotinib sensitive and erlotinib resistant tumor cells lines, and thus can be used as a predictor of erlotinib sensitivity.

There are eight genes that are common to the 88 gene EMTGS, the Choi signature, and the Bunn gefitinib signature (i.e. AGR2, CDH1, CLDN4, ELF3, ERBB3, IKIP, OCLN, and SH3YL1). Derivation of an index score using these eight genes in a variety of tumor cell lines (FIG. 35) indicates that an index score derived from this eight gene signature is significantly different in erlotinib sensitive and erlotinib resistant tumor cells lines, and thus can be used as a predictor of erlotinib sensitivity.

Subset Analysis of 88 Gene EMTGS: 10,000 Different 54-Gene Subsets

The 88 gene PGS in its entirety predicts for sensitivity to erlotinib or OSI-906 in cell lines. To determine whether subsets of the 88 PGS would also predict, subsets of the 88PGS were randomly generated and then tested for the predictive power of the resulting gene indexes generated from qPCR data from 40 cell lines of known erlotinib or OSI-906 sensitivity. The qPCR dataset was limited to 87 of the 88 genes because one of the genes, MTA3, was never above the level of detection in any of the cell lines. 60 genes were first randomly drawn 10,000 times from the 87 gene list, and determined that each list predicted accurately using the response prediction test. Through an iterative process of generating smaller and smaller subsets of genes and then applying the response prediction test, it was determined that of the original 87 genes in the PGS, at least 54 are required to predict sensitivity in vitro. The optimum threshold for each of the 10,000 different scores was determined empirically. A separately calculated optimum threshold for each of the 10,000 subsets was applied. False positive and false negative rates were determined to assess whether each subset yielded satisfactory test accuracy when used as a PGS. Fisher's exact test was used to estimate p value of the enrichment. The biggest p value of all the 10,000 Fisher's exact test was 0.0069. This means that in the worst-performing 54-gene subset out of the 10,000 such 54-gene subsets tested, the probability of obtaining the observed result due to chance alone was 0.0069, which is approximately 3.6-fold better than the conventional cut-off for statistical significance, i.e., p=0.05. This analysis suggests that any subset of at least 54 genes selected from any of the 88 genes listed Table 1 except MTA3 (i.e. 87 genes) can be employed in practicing the invention.

It was also tested whether the epithelial genes alone were sufficient to predict erlotinib sensitivity using the same data set for the response prediction test. As a whole, the 43 epithelial gene list (i.e. excluding MTA3) was able to predict as well as the entire list of 87 genes. The iterative subset analysis showed that any 24 of the epithelial genes were sufficient to predict.

The computer program described below was written and used to automate the testing of 10,000 different 54-gene subsets.

```
# This function takes a matrix as input and calculates Fisher's
exact test p value for enrichment of # responders in the called responder
group.
    myROC <- function(index)
        {index=index[order(index[,7]),]
        b=index[,7]
        i=0
        fpr=NULL
        tpr=NULL
        th=NULL
        for(ab in b)
        { i=i+1
            tpr[i]=sum(index[index[,4]=="resp",7]<=
ab)/length(index[index[,4]=="resp",7])
            fpr[i]=sum(index[index[,4]=="nonresp",7]<=
ab)/length(index[index[,4]=="nonresp",7])
            th[i]=fpr[i]+(1-tpr[i])}
        fisher=fisher.test(matrix(c(sum(index[1:which(th==min(th)),
4]=="resp"),10- sum(index[1:which(th==min(th)),4]=="resp"),
sum(index[1:which(th==min(th)),4]==" nonresp"),
sum(index[(which(th==min(th))+1):26,4]=="nonresp")),ncol=2))
        resp=gsub("nonresp",0,index.ann[,4])
        resp=gsub("resp",1,resp)
        pearson=cor.test(as.numeric(resp),index.ann[,7])
        return(list(fpr=fpr[which(th==min(th))],fnr=(1-
tpr[which(th==min(th))]),fisher.pval=fisher$p.val,
pearson.pval=pearson$p.val))}
        #The script which does the 10,000 permutation test. The
pathway Score function is not
        #included here, nor is the input data file,
        #" Tarceva.cell.txt ".
    source("pathwayScore.R")
    source("ROC.functions.R")
    inputfile="Tarceva.cell.txt"
    ann=read.delim(file="ann.txt",sep="\t",header=TRUE,as.is=TRUE)
    ann[,1]=gsub("-",".",ann[,1])
    input=read.delim(file=inputfile,sep="\t",row.names=1,
    header=TRUE,as.is=TRUE)
    input=input-rowMeans(input)
    data=cbind(c(1:nrow(input)),row.names(input),input)
    all=NULL
    N=54
    perm=100000
    index=rownames(input)
    #max=7.214923e16
    for(i in c(.1:perm))
        {tt=sample(index,N)
        all=rbind(all,sort(tt))}
    all.u=unique(all)
    fnr=NULL
    fpr=NULL
    fisher.pval=NULL
    pearson.pval=NULL
    for(i in c(1:nrow(all.u)))
        {tt=pathwayScore(genelist=all.u[i,],dataset=data,pval=0.01)
        ind=match(tt$samples,ann[,1])
        index.ann=cbind(ann[ind,],tt$index)
        temp=myROC(index=index.ann)
        fnr=c(fnr,temp$fnr)
        fpr=c(fpr,temp$fpr)
        fisher.pval=c(fisher.pval,temp$fisher.pval)
        pearson.pval=c(pearson.pval,temp$pearson.pval)}
```

Use of 88 Gene EMT Gene Signature and Index to Identify New Drug Targets, and to Predict or Monitor Drug Effects.

To determine if the EMT index can predict sensitivity to erlotinib, we calculated the EMT index scores of 39 tumor cell lines derived from lung, colon, pancreas and breast tumors, and plotted them versus erlotinib sensitivity for each cell line (FIG. 19). A low EMT index score (more epithelial state) correlated with sensitivity to erlotinib and high index score (more mesenchymal state) correlated with erlotinib insensitivity. The ability of the EMT index to predict sensitivity in cultured cells was comparable to E-cadherin status (FIG. 19; N.B. Classification of E-cadherin status is based on relative expression on a western blot). Furthermore, an index based only on the 44 epithelial genes predicted sensitivity as well as an index based on all 88 genes (FIG. 14) in the models we tested. The EMT index scores from the samples used in FIG. 6 also indicated a strong correlation between higher index values and erlotinib insensitivity (see FIG. 20; N.B. Sensitive is defined here as having more than 50% maximal inhibition of proliferation at a concentration of 10 µM erlotinib).

Interestingly, in the H1650 model, gene changes consistent with EMT were reflected in the heat map (FIG. 28), but erlotinib sensitivity was only predicted by the index (i.e. H1650 cells were not sensitive to erlotinib in vitro, before or after EMT induction), thus illustrating the different applications of the index and the signature. The H1650 model serves as an example of a tumor cell line for which classical EMT biomarkers suggest it would respond to erlotinib prior to EMT induction, but the 88 gene EMTGS index correctly predicts it does not.

In addition to the EGFR kinase inhibitor erlotinib, index scores from the 88 gene EMTGS correlate with sensitivity to the IGF-1R kinase inhibitor OSI-906. FIG. 32 shows cell lines with EMT index scores and corresponding OSI-906 EC50 values. There is a good correlation between low (epithelial) index score and sensitivity to OSI-906. Of the cell lines where EMT index does not predict sensitivity, most are ER positive, suggesting they are protected from OSI-906 by survival signaling from the estrogen receptor. The EMT index score also predicts synergy between the two compounds OSI-906 and erlotinib. FIG. 33 shows the EMT index scores and corresponding synergy between OSI-906 and erlotinib, expressed as the ratio of maximal inhibition to experimental BLISS value. For those cell lines with lower EMT index score, the synergy is higher and conversely, cell lines with higher index scores show little or no synergy. This data demonstrates the usefulness for the 88 gene EMT signature in predicting sensitivity not only for erlotinib, but also for other compounds.

The EMT index score tracks with E-cadherin status as shown in the cell line data in FIG. 19. In vivo, we examined tumors in the AVEO BH breast tumor archive for agreement between the EMT index and E-cadherin score. FIG. 34 shows good agreement, however there were few tumors that showed a strong mesenchymal index. When we looked at E-cadherin mRNA levels compared to EMT index in the human tumor datasets we noted most tumor types showed good, but not perfect agreement (FIG. 17). However, in some cases E-cadherin levels were unable to differentiate epithelial from mesenchymal tumors (breast for example). The EMT index would be of particular use in such an indication to predict response to a drug that shows clear preference for the epithelial or mesenchymal phenotype.

As shown in FIG. 9, the EMT index is not significantly impacted by the absence of a single gene. We believe this contributes to its robustness across different tumor types. FIGS. 38-39, show that changes in index scores upon elimination of the individual genes indicated (i.e. ITGA5, VIM, CDH1, and ERBB3) do not significantly affect their ability to effectively predict erlotinib sensitivity, further demonstrating this important characteristic of the 88 gene EMTGS index, and the 44 gene epithelial subset derived therefrom. FIG. 40 lists the genes that contributed to the index score calculations of FIG. 39. These groups of genes, and indexes derived therefrom, may be used in lieu of the complete 88 or 44 gene EMTGS from which they were derived, for prediction of EMT status or sensitivity to EGFR or IGF-1R kinase inhibitors (e.g. erlotinib, OSI-906).

The mesenchymal genes do not offer predictive value by themselves with respect to erlotinib sensitivity (FIG. 15), in contrast to the epithelial genes. However, when included in the index score, they do improve the p-value in distinguishing sensitive from insensitive lung tumor cell lines (FIG. 14): Furthermore, in vivo or clinical diagnostic situations, including the mesenchymal genes will likely improve the ability of the index score to classify tumors that typically do not lose epithelial markers, such as was shown with breast cancer in FIG. 17. However, it is also likely that including the mesenchymal genes will confound some classifications due to stromal contamination of the tumor biopsy, and thus the 44 epithelial gene EMTGS index should prove invaluable in such situations.

Prevalence of Tumors with High or Low 88EMT Index Valuex in Human Tumor Populations Human solid tumor microarray datasets were examined for the prevalence of tumors with high or low index values relative to indexes from random gene lists (FIG. 18, bottom panel. For each tumor type, we were able to identify tumors that exhibit epithelial and mesenchymal index scores. In vitro data suggests that patients with more epithelial index scores may respond better to erlotinib therapy. This suggests that EMTGS index scores may be a valuable clinical tool to select patients for therapy.

FIG. 16 (bottom panel) shows prevalence data for EMTGS index scores in different lung tumor subtypes. Adenocarcinoma shows a higher population of epithelial-like tumors than squamous cell carcinoma as determined by the index scores. This characterization is reflected in the clinical response rates, where adenocarcinoma patients respond better to erlotinib than squamous cell carcinoma patients.

Figure 42A:
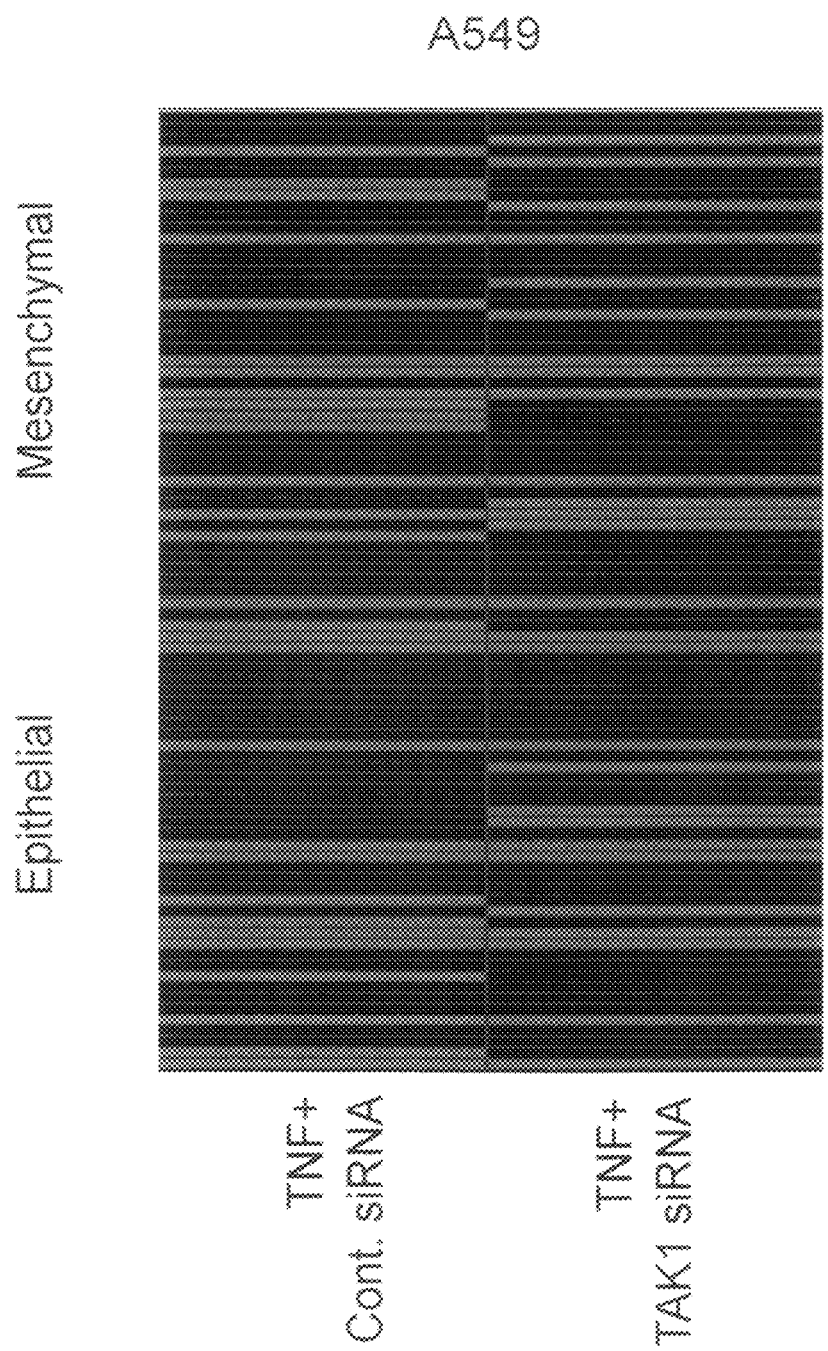
Figure 42B:
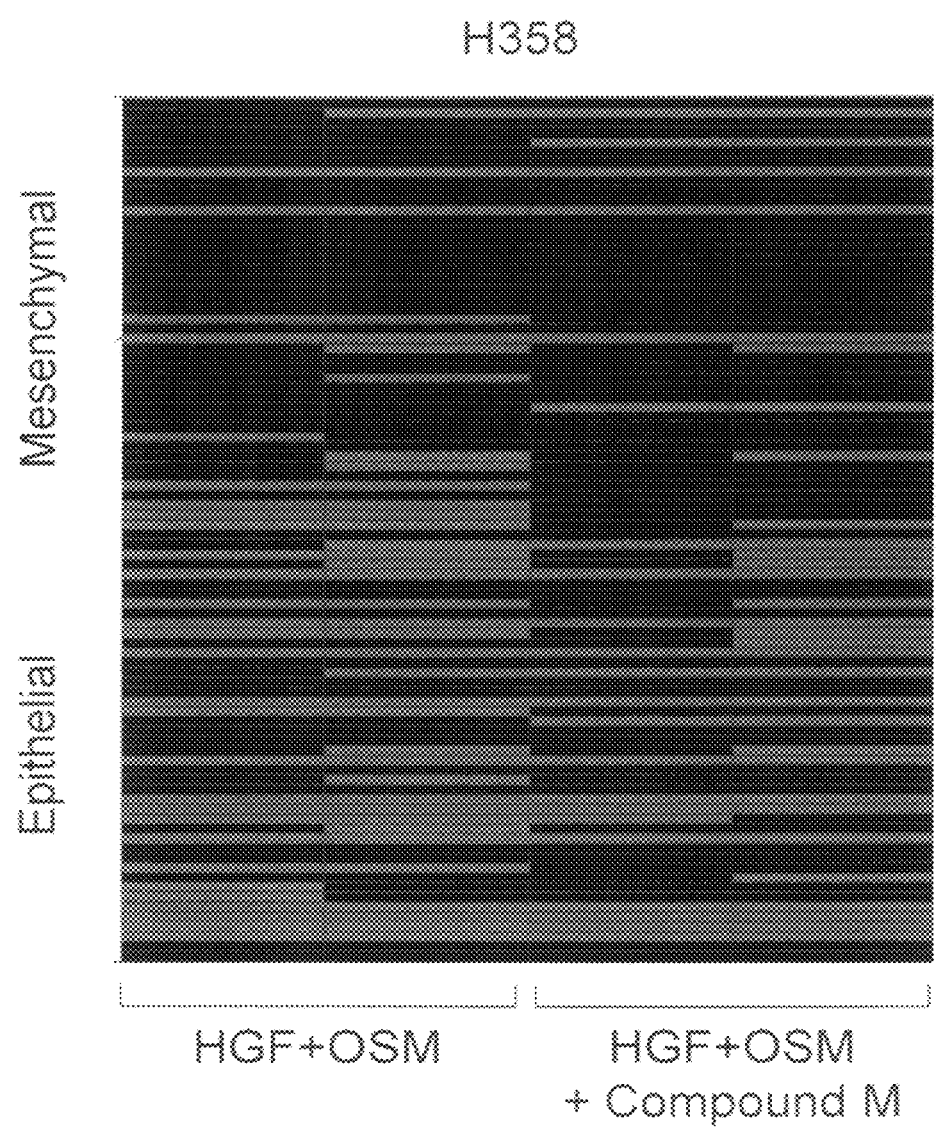
Figure 42C:
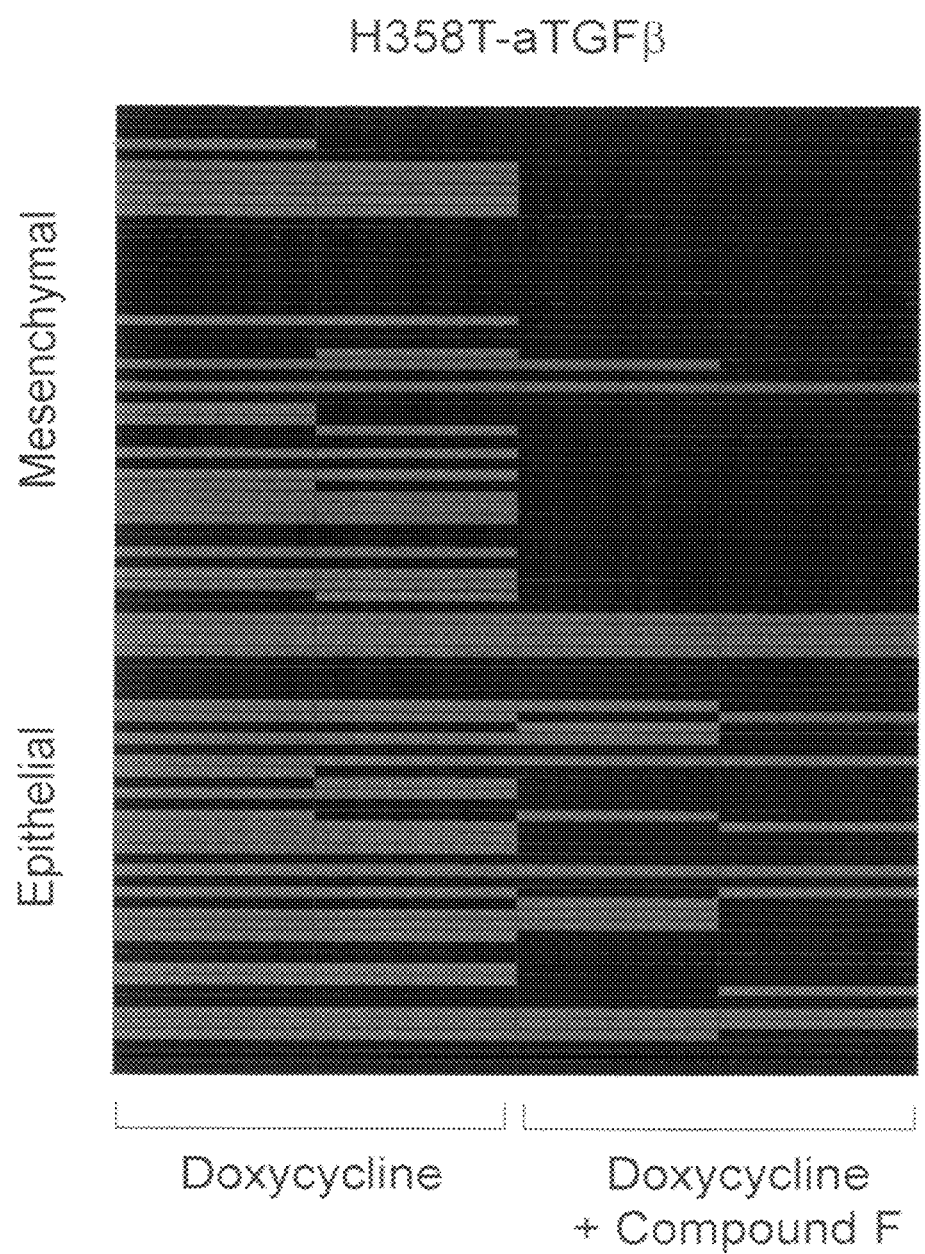

The 88EMTGS is also being used to identify new drug targets that regulate EMT. 88EMTGS qPCR analysis of A549 cells showed TNFa stimulation caused downregulation of epithelial genes and upregulation of mesenchymal genes relative to untreated cells (FIG. 42A). When TAK1 was knocked down in TNFa treated cells, mesenchymal genes were downregulated and epithelial genes were upregulated relative to TNFa treated cells, showing reversal of TNF-induced EMT gene transcription. In the H358 HGF+OSM model, inhibiton of HGF-cMET signaling by Compound M reversed the downregulation of epithelial genes and some of the effects on mesenchymal genes (FIG. 42B). In the H358T-aTGFb doxycycline-inducible model, inhibition of FAK, a downstream signaling component of TGFb-mediated EMT, by the selective FAK inhibitor Compound F, reversed the transcriptional downregulation of epithelial genes (FIG. 42C). However, inhibition of FAK had no effect on the upregulation of mesenchymal genes. These experiments demonstrate the value of the 88 gene EMTGS in identifying new drug targets that may be important regulators of the EMT process, and also individual epithelial or mesenchymal genes that may be important biomarkers for induction with any given EMT inducer.

Genes that were modulated by the EMT-inducing ligands and then reversed (more than 2.5 fold) after FAK or MET inhibitor compound, or TAK1siRNA, are listed in Table 14. Each of these gene lists represents an EMTGS specific to FAK, MET, or TAK1 inhibition of EMT in the tumor cells, and can be used to monitor treatment with compounds that inhibit EMT via these proteins (i.e. FAK, MET, TAK1). Furthermore, the algorithm used to generate an index score from the 88 gene EMTGS can be used in a similar fashion here to quantify the effects on these signatures, and more readily monitor the magnitude of inhibitory effects in vitro or in vivo.

Analysis using the 88 gene EMTGS index can also identify potential drug targets of interest by comparing the expression pattern of a gene of interest against the 88 gene EMT index. For example, in BH3 breast tumor archive cells AXL has low expression in tumors that are more epithelial and is more highly expressed in tumors that are more mesenchymal-like, suggesting AXL as a potential gene that is important for mesenchymal tumors (FIG. 41).

TABLE 14

EMTGS specific to FAK, MET, or TAK1 inhibition.

| FAK inhibitor (Compound F) | MET inhibitor (Compound M) | TAK1 inhibitor (TAK1 siRNA) |
|---|---|---|
| AP1M2 | CYP4X1 | FOSB |
| BSPRY | FOSB | IL8 |
| CDH1 | MMP9 | ITGB3 |
| CLDN3 | VIM | MMP9 |
| EHF | CLDN3 | MSLN |
| ELF3 | EHF | SERPINE1 |
| ERBB3 | ELF3 | SNAI2 |
| MPZL2 | ERBB3 | PPL |
| MAP7 | HOPX | PPP1R9A |
| OCLN | MMP7 | SCNN1A |
| PPL | OCLN | TJP3 |
| PPP1R9A | PLXNB1 | XBP1 |
| SCNN1A | SCNN1A | |
| SLC27A2 | TJP3 | |
| SPDEF | TMEM125 | |
| TJP3 | TMEM45B | |
| TMEM125 | VWF | |
| TMEM45B | | |

Prediction of Drug Responses in the Clinic.

The following prophetic example illustrates in detail how one could use the present invention to predict human response to an EGFR kinase inhibitor (e.g. erlotinib) or IGF-1R kinase inhibitor (e.g. OSI-906), using qPCR (e.g. TAQMAN®) data.

With regard to a given tumor type (e.g., NSCLC, ACC, hepatic cell carcinoma), tumor samples (archival FFPE blocks, fresh samples or frozen samples) are obtained from human patients (indirectly through a hospital or clinical laboratory) prior to treatment of the patients with EGFR kinase inhibitor or IGF-1R kinase inhibitor. Fresh or frozen tumor samples are placed in 10% neutral-buffered formalin for 5-10 hours before being alcohol dehydrated and embedded in paraffin, according to standard histology procedures.

RNA is extracted from 10 µm FFPE sections. Paraffin is removed by xylene extraction followed by ethanol washing. RNA is isolated using a commercial RNA preparation kit. RNA is quantitated using a suitable commercial kit, e.g., the RIBOGREEN® fluorescence method (Molecular Probes, Eugene, Oreg.). RNA size is analyzed by conventional methods.

Reverse transcription is carried out using the SUPERSCRIPT™. First-Strand Synthesis Kit for qRT-PCR (Invitrogen). Total RNA and pooled gene-specific primers are present at 10-50 ng/µl and 100 nM (each) respectively.

For each gene in the EMTGS, qRT-PCR primers are designed using a suitable commercial software, e.g., PRIMER EXPRESS® software (Applied Biosystems, Foster City, Calif.). The oligonucleotide primers are synthesized using a commercial synthesizer instrument and appropriate reagents, as recommended by the instrument manufacturer or vendor. Probes are labeled using a suitable commercial labeling kit.

TAQMAN® reactions are performed in 384-well plates, using an Applied Biosystems 7900HT instrument according to the manufacturer's instructions. Expression of each gene in the EMTGS is measured in duplicate 5 µl reactions, using cDNA synthesized from 1 ng of total RNA per reaction well. Final primer and probe concentrations are 0.9 µM (each primer) and 0.2 µM, respectively. PCR cycling is carried out according to a standard operating procedure. To verify that the qRT-PCR signal is due to RNA rather than contaminating DNA, for each gene tested, a no RT control is run in parallel. The threshold cycle for a given amplification curve during qRT PCR occurs at the point the fluorescent signal from probe cleavage grows beyond a specified fluorescence threshold setting. Test samples with greater initial template exceed the threshold value at earlier amplification cycles.

To compare gene expression levels across all the samples, normalization based on five reference genes (housekeeping genes whose expression level is assumed to be similar across all samples) is used to correct for differences arising from variation in RNA quality, and total quantity of RNA, in each assay well. A reference $C_T$ (threshold cycle) for each sample is defined as the average measured $C_T$ of the reference genes. Normalized mRNA levels of test genes are defined as $\Delta C_T + 10$, where $\Delta C_T$=reference gene $C_T$ minus test gene $C_T$.

The EMTGS index score for each tumor sample is calculated from the gene expression levels, according to an algorithm as set forth above. The actual response data associated with tumor sample tested are obtained from the hospital or clinical laboratory supplying the tumor samples. Clinical response is typically is defined in terms of tumor shrinkage, e.g., 30% shrinkage, as determined by suitable imaging technique, e.g. CT scan. In some cases, human clinical response is defined in terms of time, e.g., progression free survival time. The optimal threshold EMTGS index score for the given tumor type is calculated, as described above. Subsequently, this optimal threshold EMTGS index score is used to predict whether newly-tested human tumors of the same tumor type will be responsive or non-responsive to treatment with an EGFR kinase inhibitor or IGF-1R kinase inhibitor.

Effective Use of an EMTGS in Patient Tumor Samples.

To determine the extent to which infiltrating stromal tissue expressing mesenchymal genes might affect the index score of the 88-gene EMTGS in a tumor we made use of microarray expression data from a matched set of ten patient laser capture microdissection patient samples. For each patient sample, expression of the 88-gene EMTGS in matching tumor, stroma, and undissected cells was compared (FIG. 53). Across the patient samples, there was an overall higher level of M-gene expression seen in the stromal tissue as compared to the matched tumor tissue. Conversely, a higher level of E-gene expression was observed overall in the tumor tissue compared to the stromal tissue. The undissected patient samples displayed an intermediate pattern of gene expression across the 88-gene EMTGS. Additionally, a subset of 27 genes from the 88-gene EMTGS were found to have statistically differential expression between matched tumor and stroma (FIG. 53; FDR-corrected T-test<0.01).

Figure 54A:
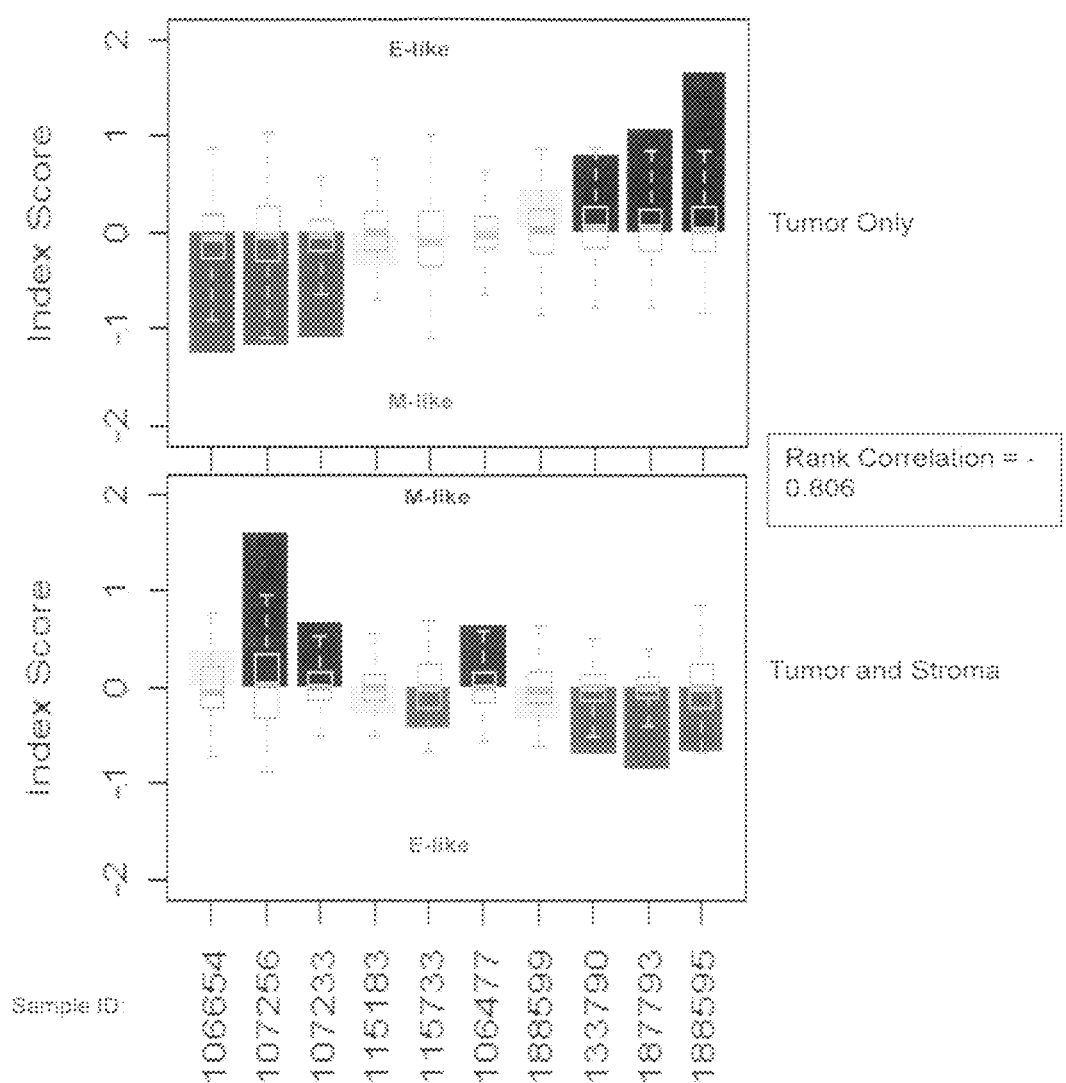

While the overall pattern of E- and M-gene expression across the EMTGS showed significant elevations in tumor and stroma, respectively, we sought to determine the impact of those expression patterns on the ability of the EMTGS index scores to rank samples. Using the bootstrapping algorithm to determine significance of index scores generated by the Expresso indexing platform we calculated EMTGS index scores for the matched tumor-only and tumor plus stroma LCM patient samples (FIG. 54A). The 88-gene EMTGS produced a very similar ranking of patients by index score in the tumor-only and tumor plus stroma matched sample sets (absolute value of Spearman rank correlation, |R|=0.806) indicating that the impact of infiltrating stromal cells on the EMTGS index scoring was minimal.

Despite the fact that the presence of M-genes in the EMTGS did not seem to greatly alter the function of the signature in a sample with mixed tumor and stromal cells, we sought to determine if an E-only signature would be even less affected by stromal infiltration. Using the 44-E-gene EMTGS, we compared index score ranking for the matched set of tumor-only and tumor plus stroma LCM samples (FIG. 54B). While the 44-E-gene EMTGS also produced a very similar ranking of samples (absolute value of Spearman rank correlation, |R|=0.673) there was no increase in rank correlation between the tumor-only and tumor plus stroma samples indicating that the presence of M-genes in the 88-gene EMTGS did not produce a confounding effect on the index score calculation in tumor samples with infiltrating stroma.

REFERENCES

Buck, E., A. et al. (2007) Molecular Cancer Therapeutics. 6(2): 532-541.
Chung, C. H., et al. (2006) Cancer research 66(16): 8210-8218.
Coldren, et al. (2006) Mol Cancer Res 4(8): 521-528.
Jechlinger, M., et al. (2003) Oncogene 22(46): 7155-7169.
Moreno-Bueno, G., et al. (2006) Cancer research 66(19): 9543-9556.
Thomson, S., et al. (2005) Cancer research 65(20): 9455-9462.
Yauch, R. L., et al. (2005). Clin Cancer Res 11(24 Pt 1): 8686-8698.
Choi, Y. L., et al. (2010) Cancer Research 70(6): 2296-2306.
Coldren, C. D., et al. (2006) Mol Cancer Res 4(8): 521-528.

ABBREVIATIONS

EMTGS, EMT gene signature; HR, hazard ratio; PFS, progression free survival; OS, overall survival; CI, confidence interval; E, erlotinib; P, placebo; H, high; L, low; EGF, epidermal growth factor; EMT, epithelial to mesenchymal transition; MET, mesenchymal to epithelial transition; NSCLC, non-small cell lung carcinoma; HNSCC, head and neck squamous cell carcinoma; CRC, colorectal cancer; MBC, metastatic breast cancer; EGFR, epidermal growth factor receptor; ErbB3, "v-erb-b2 erythroblastic leukemia viral oncogene homolog 3", also known as HER-3; pHER3, phosphorylated HER3; LC, liquid chromatography; IHC, immunohistochemistry; MS, mass spectrometry; IGF-1, insulin-like growth factor-1; IGF-2, insulin-like growth factor-2; IGF-1R or IGFR, insulin-like growth factor-1 receptor; RTK, receptor-tyrosine kinase; MET, met proto-oncogene (a.k.a. hepatocyte growth factor receptor); FAK, PTK2 protein tyrosine kinase 2; TAK1, TGF-beta activated kinase 1 (a.k.a. MAP3K7 or mitogen-activated protein kinase kinase kinase 7); LPA, lysophosphatidic acid; TGFα, transforming growth factor alpha; HB-EGF, heparin-binding epidermal growth factor; TGFβ or TGFbeta or TGFb, transforming growth factor beta; aTGFβ or aTGFbeta or aTGFb, activated transforming growth factor beta; OSM, oncostatin M; HGF, hepatocyte growth factor; TNF, tumor necrosis factor; $IC_{50}$, half maximal inhibitory concentration; EC50, half-maximal effective concentration; pY, phosphotyrosine; wt, wild-type; PI3K, phosphatidyl inositol-3 kinase; GAPDH, Glyceraldehyde 3-phosphate dehydrogenase, HUGO, The Human Genome Organisation; PMID, PubMed Unique Identifier; NCBI, National Center for Biotechnology Information; NCI, National Cancer Institute; MSKCC, Memorial Sloan Kettering Cancer Center; ECACC, European Collection of Cell Cultures; ATCC, American Type Culture Collection; LCM, laser capture microdissection; FDR, false discovery rate; FPR, false positive rate; TPR, true positive rate; FNR, false negative rate; ROC, receiver operating characteristic.

INCORPORATION BY REFERENCE

All patents, published patent applications and other references disclosed herein are hereby expressly incorporated herein by reference.

EQUIVALENTS

Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A method comprising:
   a) obtaining a biological sample from a human patient; and
   b) measuring mRNA expression of each gene in the set of genes consisting of SERPINA3, ACTN1, AGR2, AKAP12, ALCAM, AP1M2, AXL, BSPRY, CCL2, CDH1, CDH2, CEP170, CLDN3, CLDN4, CNN3, CYP4X1, DNMT3A, DSG3, DSP, EFNB2, EHF, ELF3, ELF5, ERBB3, ETV5, FLRT3, FOSB, FOSL1, FOXC1, FXYD5, GPD1L, HMGA1, HMGA2, HOPX, IF116, IGFBP2, IHH, IKBIP, IL-11, IL-18, IL6, IL8, ITGA5, ITGB3, LAMB1, LCN2, MAP7, MB, MMP7, MMP9, MPZL2, MSLN, MTA3, MTSS1, OCLN, PCOLCE2, PECAM1, PLAUR, PLXNB1, PPL, PPP1R9A, RASSF8, SCNN1A, SERPINB2, SERPINE1, SFRP1, SH3YL1, SLC27A2, SMAD7, SNAI1, SNAI2, SPARC, SPDEF, SRPX, STAT5A, TBX2, TJP3, TMEM125, TMEM45B, TWIST1, VCAN, VIM, VWF, XBP1, YBX1, ZBTB10, ZEB1, and ZEB2 by contacting the biological sample with a probe set consisting of probes that specifically hybridize to mRNA of each gene in the set of genes and detecting binding of mRNAs to the probes.

2. The method of claim 1, wherein the biological sample comprises tumor cells.

3. The method of claim 1, wherein the biological sample comprises a tumor tissue.

4. The method of claim 2, wherein the tumor cells are selected from the group consisting of non-small cell lung cancer (NSCLC) tumor cells, breast cancer tumor cells, ovarian cancer tumor cells, colorectal cancer tumor cells, and pancreatic cancer tumor cells.

5. The method of claim 1, wherein either the probes or the mRNAs are anchored to a substrate.

6. The method of claim 5, wherein the substrate is selected from the group consisting of glass, polystyrene, nylon, polypropylene, polyethylene, dextran, amylases, natural celluloses, modified celluloses, polyacrylamides, gabbros, and magnetite.

7. The method of claim 1, wherein the detecting is performed by quantitative polymerase chain reaction (qPCR).

8. The method of claim 1, wherein the detecting is performed by mRNA microarray.

9. A method comprising:
   a) obtaining a biological sample from a human patient; and
   b) measuring protein expression of each gene in the set of genes consisting of SERPINA3, ACTN1, AGR2, AKAP12, ALCAM, AP1M2, AXL, BSPRY, CCL2, CDH1, CDH2, CEP170, CLDN3, CLDN4, CNN3, CYP4X1, DNMT3A, DSG3, DSP, EFNB2, EHF, ELF3, ELF5, ERBB3, ETV5, FLRT3, FOSB, FOSL1, FOXC1, FXYD5, GPD1L, HMGA1, HMGA2, HOPX, IF116, IGFBP2, IHH, IKBIP, IL-11, IL-18, IL6, IL8, ITGA5, ITGB3, LAMB1, LCN2, MAP7, MB, MMP7, MMP9, MPZL2, MSLN, MTA3, MTSS1, OCLN, PCOLCE2, PECAM1, PLAUR, PLXNB1, PPL, PPP1R9A, RASSF8, SCNN1A, SERPINB2, SERPINE1, SFRP1, SH3YL1, SLC27A2, SMAD7, SNAI1, SNAI2, SPARC, SPDEF, SRPX, STAT5A, TBX2, TJP3, TMEM125, TMEM45B, TWIST1, VCAN, VIM, VWF, XBP1, YBX1, ZBTB10, ZEB1, and ZEB2 by contacting the biological sample with a set of antibodies or antibody fragments consisting of antibodies or antibody fragments that specifically bind to proteins of each gene in the set of genes and detecting binding of proteins to the antibodies or antibody fragments.

10. The method of claim 9, wherein the biological sample comprises tumor cells.

11. The method of claim 9, wherein the biological sample comprises a tumor tissue.

12. The method of claim 9, wherein the tumor cells are selected from the group consisting of non-small cell lung cancer (NSCLC) tumor cells, breast cancer tumor cells, ovarian cancer tumor cells, colorectal cancer tumor cells, and pancreatic cancer tumor cells.

13. The method of claim 9, wherein either the proteins or the antibodies or the antibody fragments are anchored to a substrate.

14. The method of claim 13, wherein the substrate is selected from the group consisting of glass, polystyrene, nylon, polypropylene, polyethylene, dextran, amylases, natural celluloses, modified celluloses, polyacrylamides, gabbros, and magnetite.

15. The method of claim 9, wherein the detecting is performed by a western blot.

16. The method of claim 9, wherein the detecting is performed by an enzyme-linked immunosorbent (ELISA) assay.

* * * * *